US012478616B2

(12) United States Patent
Fushimi et al.

(10) Patent No.: US 12,478,616 B2
(45) Date of Patent: Nov. 25, 2025

(54) PI3K INHIBITORS AND USES THEREOF

(71) Applicants: Sloan-Kettering Institute for Cancer Research, New York, NY (US); Tri-Institutional Therapeutics Discovery Institute, Inc., New York, NY (US)

(72) Inventors: Makoto Fushimi, Harrison, NY (US); Maurizio Scaltriti, New York, NY (US); Daniel Alan Heller, New York, NY (US); Carles Monterrubio Martinez, Boston, MA (US); Amaia Arruabarrena Aristorena, New York, NY (US); Peter T. Meinke, Scotch Plains, NJ (US); Michael Andrew Foley, New York, NY (US); Yasutomi Asano, Chigasaki (JP); Kazuyoshi Aso, Yokohama (JP); Hiroki Takahagi, Yokohama (JP); Yosef Shamay, Zichron Yaakov (IL); Jose Manuel Baselga Torres, New York, NY (US); Yusuke Sasaki, Yokohamashi (JP); Mayako Michino, New York, NY (US)

(73) Assignees: Sloan-Kettering Institute for Cancer Research, New York, NY (US); Tri-Institutional Therapeutics Discovery Institute, Inc., New York, NY (US)

( * ) Notice: Subject to any disclaimer, the term of this patent is extended or adjusted under 35 U.S.C. 154(b) by 1100 days.

(21) Appl. No.: 17/282,657

(22) PCT Filed: Oct. 4, 2019

(86) PCT No.: PCT/US2019/054679
§ 371 (c)(1),
(2) Date: Apr. 2, 2021

(87) PCT Pub. No.: WO2020/072892
PCT Pub. Date: Apr. 9, 2020

(65) Prior Publication Data

US 2021/0353607 A1 Nov. 18, 2021

Related U.S. Application Data

(60) Provisional application No. 62/742,163, filed on Oct. 5, 2018.

(51) Int. Cl.
*C07D 417/14* (2006.01)
*A61K 9/16* (2006.01)
(Continued)

(52) U.S. Cl.
CPC ........ *A61K 31/4439* (2013.01); *A61K 9/1652* (2013.01); *A61K 9/1658* (2013.01);
(Continued)

(58) Field of Classification Search
CPC .............. C07D 417/14; A61K 31/4439; A61K 31/4429; A61K 9/1652; A61K 9/1658;
(Continued)

(56) References Cited

U.S. PATENT DOCUMENTS

2014/0186469 A1 7/2014 Fairhurst et al.
2018/0147232 A1 5/2018 Castel et al.

FOREIGN PATENT DOCUMENTS

WO WO 2009/080694 A1 7/2009
WO WO 2010/029082 A1 3/2010
(Continued)

OTHER PUBLICATIONS

Partial Supplementary European Search Report, mailed Apr. 12, 2022, in connection with Application No. EP 19868787.3.
(Continued)

*Primary Examiner* — Jared Barsky
(74) *Attorney, Agent, or Firm* — Wolf, Greenfield & Sacks, P.C.

(57) ABSTRACT

The development of a new, targeted drug delivery paradigm coupled to improved PI3K inhibitors (e.g., PI3Kα inhibitors) represents a significant advance in cancer therapy. Provided herein are compounds, such as compounds of Formula (I) and (II), and pharmaceutically acceptable salts, hydrates, solvates, polymorphs, co-crystals, tautomers, stereoisomers, isotopically labeled derivatives, and prodrugs thereof. The compounds provided herein are PI3K (e.g., PI3Kα) inhibitors and are therefore useful for the treatment and/or prevention of various diseases (e.g., proliferative diseases such as cancer). Also provided herein are nanoparticles and nanogels (e.g., P-selectin targeting nanoparticles) comprising PI3K inhibitors, such a compound described herein. In certain embodiments, a nanoparticle or nanogel described herein encapsulates a compound described herein for targeting delivery to cancer cells or tumors.

(I)

(Continued)

-continued (II)

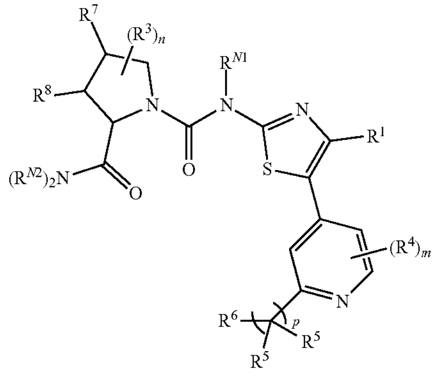

25 Claims, 24 Drawing Sheets

(51) Int. Cl.

| | |
|---|---|
| ***A61K 31/427*** | (2006.01) |
| ***A61K 31/4439*** | (2006.01) |
| ***A61K 49/00*** | (2006.01) |
| ***A61P 35/00*** | (2006.01) |

(52) U.S. Cl.
CPC ........ *A61K 31/427* (2013.01); *A61K 49/0032* (2013.01); *A61K 49/0034* (2013.01); *A61K 49/0065* (2013.01); *A61P 35/00* (2018.01); *C07D 417/14* (2013.01)

(58) Field of Classification Search
CPC ................ A61K 31/427; A61K 9/0032; A61K 49/0034; A61K 49/0065; A61P 35/00
See application file for complete search history.

(56) References Cited

FOREIGN PATENT DOCUMENTS

| | | |
|---|---|---|
| WO | WO 2011/000905 A1 | 1/2011 |
| WO | WO 2015/161192 A1 | 10/2015 |

OTHER PUBLICATIONS

Extended European Search Report, mailed Jul. 14, 2022, in connection with Application No. EP 19868787.3.
Invitation to Pay Additional Fees for Application No. PCT/US2019/054679, mailed Nov. 18, 2019.
International Search Report and Written Opinion for Application No. PCT/US2019/054679, mailed Jan. 23, 2020.
International Preliminary Report on Patentability for Application No. PCT/US2019/054679, mailed Apr. 15, 2021.
[No Author Listed], PubChem Compound Summary for Alpelisib. PubChem CID: 56649450. Created Mar. 5, 2012. 33 pages.
Chandarlapaty et al., AKT inhibition relieves feedback suppression of receptor tyrosine kinase expression and activity. Cancer Cell. Jan. 18, 2011;19(1):58-71. doi: 10.1016/j.ccr.2010.10.031. Epub Jan. 6, 2011.
Engelman, Targeting PI3K signalling in cancer: opportunities, challenges and limitations. Nat Rev Cancer. Aug. 2009;9(8):550-62. doi: 10.1038/nrc2664.
Fruman et al., PI3K and cancer: lessons, challenges and opportunities. Nat Rev Drug Discov. Feb. 2014;13(2):140-56. doi: 10.1038/nrd4204.
Furet et al., Discovery of NVP-BYL719 a potent and selective phosphatidylinositol-3 kinase alpha inhibitor selected for clinical evaluation. Bioorg Med Chem Lett. Jul. 1, 2013;23(13):3741-8. doi: 10.1016/j.bmcl.2013.05.007. Epub May 14, 2013. Erratum in: Bioorg Med Chem Lett. Aug. 15, 2013;23(16):4723.
Mayer et al., The PI3K/AKT Pathway as a Target for Cancer Treatment. Annu Rev Med. 2016;67:11-28. doi: 10.1146/annurev-med-062913-051343. Epub Oct. 14, 2015.
Mizrachi et al., Tumour-specific PI3K inhibition via nanoparticle-targeted delivery in head and neck squamous cell carcinoma. Nat Commun. Feb. 13, 2017;8:14292. doi: 10.1038/ncomms14292.
Rodon et al., Development of PI3K inhibitors: lessons learned from early clinical trials. Nat Rev Clin Oncol. Mar. 2013;10(3):143-53. doi: 10.1038/nrclinonc.2013.10. Epub Feb. 12, 2013.
Serra et al., PI3K inhibition results in enhanced HER signaling and acquired ERK dependency in HER2-overexpressing breast cancer. Oncogene. Jun. 2, 2011;30(22):2547-57. doi: 10.1038/onc.2010.626. Epub Jan. 31, 2011.
Shamay et al., P-selectin is a nanotherapeutic delivery target in the tumor microenvironment. Sci Transl Med. Jun. 29, 2016;8(345):345ra87. doi: 10.1126/scitranslmed.aaf7374. Author Manuscript. 28 pages.
Vanhaesebroeck et al., PI3K signalling: the path to discovery and understanding. Nat Rev Mol Cell Biol. Feb. 23, 2012;13(3):195-203. doi: 10.1038/nrm3290.

Compound (14)

Compound (14)

PI3K INHIBITORS AND USES THEREOF

RELATED APPLICATIONS

This application is a national stage filing under 35 U.S.C. § 371 of International PCT Application, PCT/US2019/054679, filed Oct. 4, 2019, which claims priority under 35 U.S.C. § 119(e) to U.S. Provisional Patent Application, U.S. Ser. No. 62/742,163, filed Oct. 5, 2018; the entire contents of each of which is incorporated herein by reference.

BACKGROUND OF THE INVENTION

Personalized medicine, based on the genomic context of a patient's disease, is becoming a leading strategy to treat cancer, often using agents targeting signaling pathways.[1,2] Kinase inhibitors still represent the majority of the current targeted agents even in the face of recent and dramatic breakthroughs in immuno-oncology. Typically, small molecule kinase inhibitors are hydrophobic molecules, often administrated orally. In addition, some of these drugs require administration with high frequency to achieve a sufficient tumor concentration. Despite their specific effects on cancer cells, some of these ligands exert undesirable effects, modulating the same signaling pathways in non-cancerous cells and thereby leading to dose-limiting, on-target toxicities. As an additional complication, therapeutic resistance often develops, prompting the use of drug combinations that result in increased toxicities.

The PI3K-AKT-mTOR pathway plays a central role in tumor biology and is involved in cancers carrying mutations in PTEN, AKT, and PI3K. As a result, PI3K inhibition is a preferred therapeutic strategy for these malignancies and, as such, its discovery, the development of clinically relevant inhibitors, and their utility have been extensively reviewed.[3,4,5,6] Due to its pivotal role, this pathway has been the focus of intense interest with drug discovery efforts culminating in the invention of over 50 new drugs inhibiting the PI3K/AKT/mTOR pathway advancing to different stages of development in this highly validated pathway.[7]

Unfortunately, however, it is well established that some PI3Kα inhibitors can carry a significant toxicity profile that limits their therapeutic window, specifically in patients who develop fatigue and intractable hyperglycemia.[8] Pre-clinical data established that hyperglycemia is caused by inhibition of PI3K leading to loss of insulin signaling in peripheral tissue and pancreatic β cells through phosphorylation of insulin receptors.[9,10,11] Clinical investigations have also found evidence of acquired resistance to some PI3Kα inhibitors, leading to disease relapse over time.[12] Therapeutic combinations with mTOR inhibitors or anti-endocrine therapies have been shown to obviate both intrinsic and acquired resistance to BYL719,[13] a PI3Kα inhibitor, although co-administration is predicted to produce intolerable side effects.[14] To improve the utility of targeted therapeutics such as PI3K inhibitors, there is a need to mitigate dose-limiting side effects.

Scientists have worked in recent decades to develop strategies to deliver therapeutic agents safely and selectively to dysfunctional tissues, such as cancer by exploiting advances in nanoparticle generation and nanoformulation. These efforts culminated in key advances leading to clinical candidate nanoparticles, including CRLX101[15] and AZD2811.[16] Nanoparticles have the ability to confer, in a clinical arena, improved oncologic efficacy coupled to a superior therapeutic indices.[17,18,19,20,21,54]

SUMMARY OF THE INVENTION

Recent advances have provided a potential path to expand the therapeutic index (TI) of certain kinase inhibitors, including PI3K inhibitors.[22] P-selectin, a protein commonly upregulated in many cancers including head and neck squamous cell carcinoma (HNSCC), actively transports fucoidan polysaccharides into tumor cells. In addition, it has long been recognized that P-selectin is upregulated approximately 4-fold by irradiation, a common adjunct to chemotherapy. It was recently established that P-selectin targeting nanoparticles could be generated that encapsulate certain small molecule inhibitors and selectively deliver them to the tumor vasculature. This encapsulation protects the patient from systemic exposure to mechanism-based adverse effects from the kinase inhibitor and increases, through targeted delivery and the enhanced permeability and retention (EPR) effect, drug concentrations in the tumor. The net result of this process is an increased TI relative to free drug. Current P-selectin targeting nanoparticles useful in the present invention can be found in International Application Publication No. WO 2015/161192, published Oct. 22, 2015, the entire contents of which is incorporated herein by reference.

The development of a new, targeted drug delivery paradigm coupled to improved PI3K inhibitors (e.g., PI3Kα inhibitors) represents a significant advance in cancer therapy. Provided herein are compounds, such as compounds of Formula (I) and (II), and pharmaceutically acceptable salts, hydrates, solvates, polymorphs, co-crystals, tautomers, stereoisomers, isotopically labeled derivatives, and prodrugs thereof. The compounds provided herein are PI3K (e.g., PI3Kα) inhibitors and are therefore useful for the treatment and/or prevention of various diseases (e.g., proliferative diseases, such as cancer). Also, provided herein are nanoparticles and nanogels (e.g., P-selectin targeting nanoparticles) comprising a compound described herein. In certain embodiments, a nanoparticle described herein encapsulates a compound described herein for targeted delivery to cancer cells and/or tumors.

In one aspect, provided herein are compounds of Formula (I):

(I)

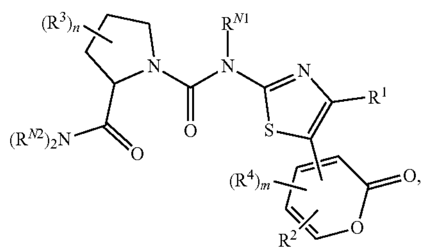

and pharmaceutically acceptable salts, hydrates, solvates, polymorphs, co-crystals, tautomers, stereoisomers, isotopically labeled derivatives, and prodrugs thereof, wherein $R^1$, $R^2$, $R^3$, $R^4$, $R^{N1}$, $R^{N2}$, m, and n are as defined herein.

In certain embodiments, for example, a compound of Formula (I) is selected from the group consisting of:

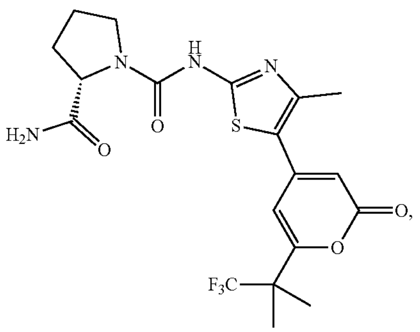

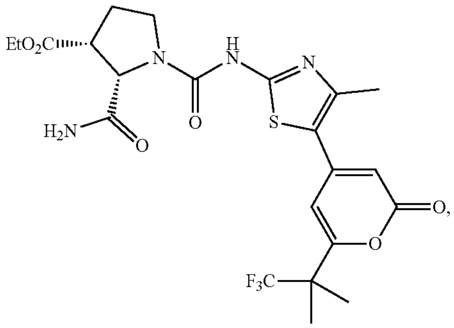

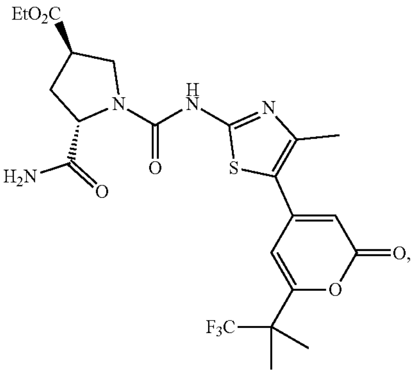

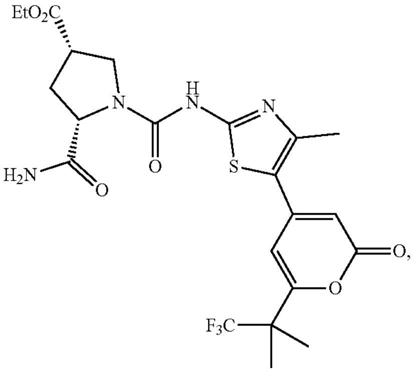

-continued

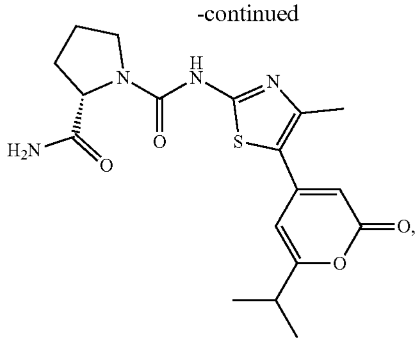

and

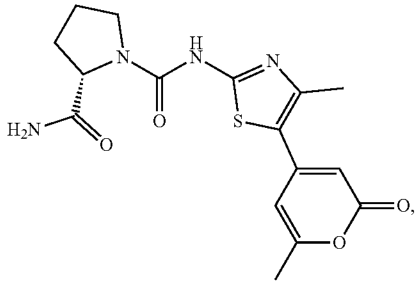

and pharmaceutically acceptable salts, hydrates, solvates, polymorphs, co-crystals, tautomers, stereoisomers, isotopically labeled derivatives, and prodrugs thereof.

In another aspect, provided herein are compounds of Formula (II):

(II)

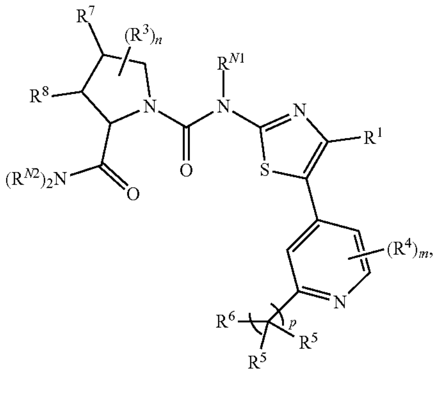

and pharmaceutically acceptable salts, hydrates, solvates, polymorphs, co-crystals, tautomers, stereoisomers, isotopically labeled derivatives, and prodrugs thereof, wherein $R^1$, $R^3$, $R^4$, $R^5$, $R^6$, $R^7$, $R^8$, $R^{N1}$, $R^{N2}$, m, n, and p are as defined herein. As described herein, in certain embodiments, when $R^6$ is $—CF_3$, $R^8$ is hydrogen or optionally substituted acyl; and at least one of $R^7$ or $R^8$ is not hydrogen. In certain embodiments, when $R^6$ is $—CF_3$, $R^7$ and $R^8$ are independently hydrogen or optionally substituted acyl; and at least one of $R^7$ or $R^8$ is not hydrogen.

In certain embodiments, for example, a compound of Formula (II) is selected from the group consisting of:

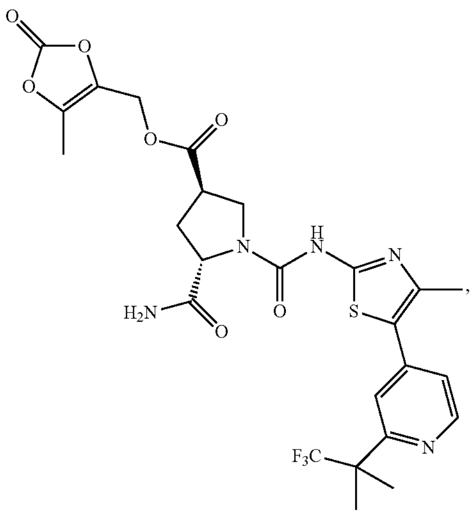

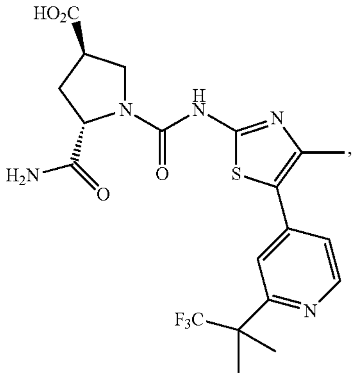

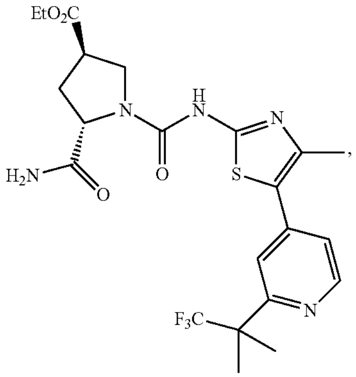

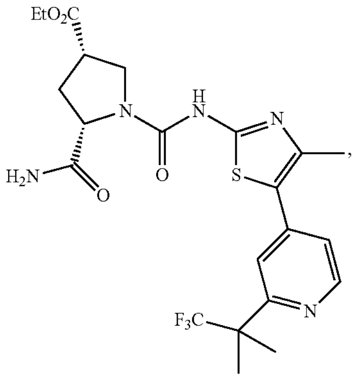

and

-continued

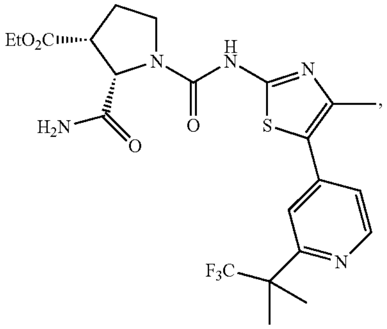 [SMILES: CCOC(=O)[C@@H]1CCN(C(=O)Nc2nc(C)c(-c3ccnc(C(C)(C)C(F)(F)F)c3)s2)[C@@H]1C(N)=O]

and pharmaceutically acceptable salts, hydrates, solvates, polymorphs, co-crystals, tautomers, stereoisomers, isotopically labeled derivatives, and prodrugs thereof.

In certain embodiments, as a further example, a compound of Formula (II) is selected from the group consisting of:

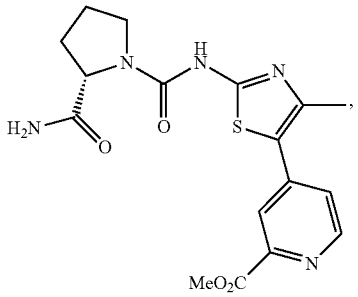

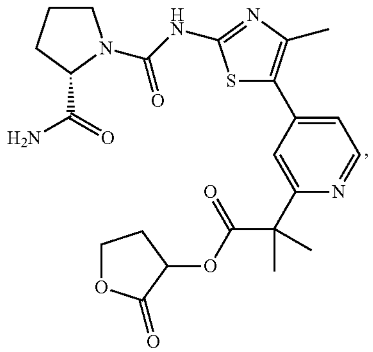

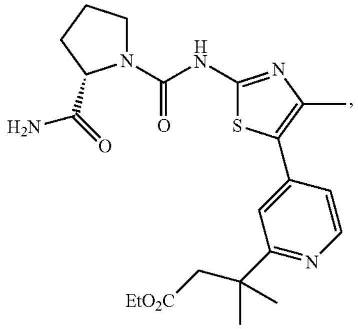

-continued

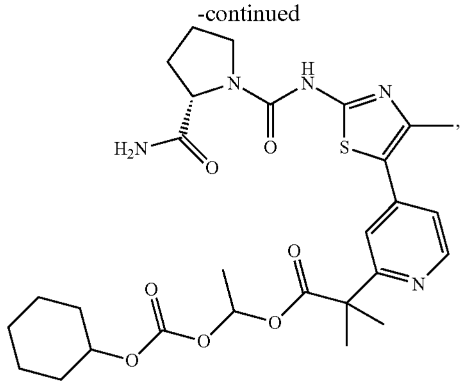,

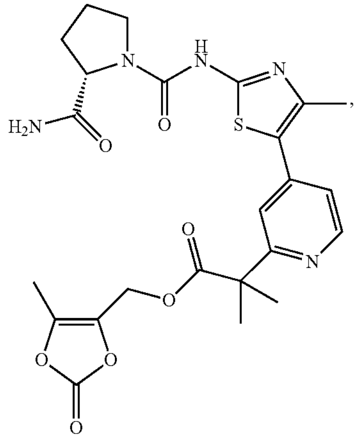,

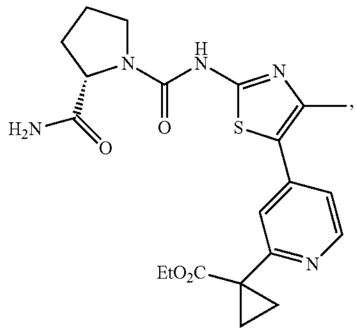,

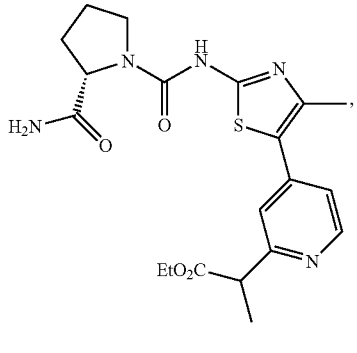,

-continued

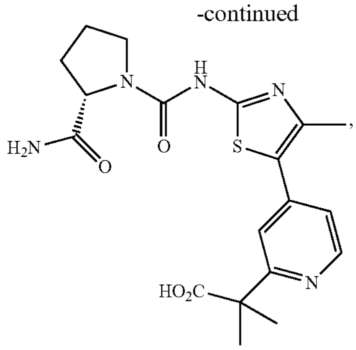, and

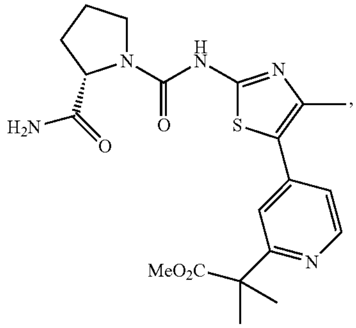, and pharmaceutically acceptable salts, hydrates, solvates, polymorphs, co-crystals, tautomers, stereoisomers, isotopically labeled derivatives, and prodrugs thereof.

In another aspect, the present invention provides pharmaceutical compositions comprising a compound of Formula (I) or (II), or a pharmaceutically acceptable salt, hydrate, solvate, polymorph, co-crystal, tautomer, stereoisomer, isotopically labeled derivative, or prodrug thereof, and optionally a pharmaceutically acceptable excipient. In certain embodiments, the pharmaceutical composition described herein includes a therapeutically and/or prophylactically effective amount of a compound of Formula (I) or (II), or a pharmaceutically acceptable salt, solvate, hydrate, polymorph, co-crystal, tautomer, stereoisomer, isotopically labeled derivative, or prodrug thereof. The pharmaceutical compositions described herein may be useful for treating and/or preventing a disease (e.g., a proliferative disease, such as cancer) in a subject.

In another aspect, provided herein are nanoparticles comprising a compound of Formula (I) or (II), or a pharmaceutically acceptable salt, solvate, hydrate, polymorph, co-crystal, tautomer, stereoisomer, isotopically labeled derivative, or prodrug thereof. In certain embodiments, the nanoparticles provided herein have an affinity for P-selectin and can therefore be used to treat diseases associated with P-selectin (e.g., proliferative diseases such as cancer). In certain embodiments, nanoparticles provided herein target cells (e.g., cancer cells) expressing P-selectin. In certain embodiments, the nanoparticles comprise a sulfated polymer comprising free hydroxyl moieties and sulfate moieties capable of targeting P-selectin. In certain embodiments, the sulfated polymer is a fucoidan polymer (e.g., a sulfated polysaccharide comprising sulfated ester moieties of fucose).

In other aspects, provided herein are pharmaceutical compositions comprising a nanogel or a plurality of nanoparticles described herein.

In another aspect, provided herein are methods for treating and/or preventing a disease in a subject. The method may comprise administering to a subject in need thereof a therapeutically effective amount of a compound of Formula (I) or (II), or a pharmaceutically acceptable salt, hydrate, solvate, polymorph, co-crystal, tautomer, stereoisomer, isotopically labeled derivative, or prodrug thereof, or a pharmaceutical composition thereof. In certain embodiments, the method comprises administering to the subject a nanoparticle or nanogel described herein, or a pharmaceutical composition thereof. In certain embodiments, the disease is a P-selectin associated disease. In certain embodiments, the disease is associated with a PI3K enzyme (e.g., PI3Kα). In certain embodiments, the disease is associated with overexpression and/or aberrant activity of PI3K (e.g., PI3Kα). In certain embodiments, the disease is an inflammatory disease. In certain embodiments, the disease is a proliferative disease (e.g., cancer). In certain embodiments, the disease is a cancer associated with P-selectin and/or PI3Kα. Examples of cancers associated with P-selectin and/or PI3Kα include, but are not limited to, head and neck cancer (e.g., head and neck squamous cell carcinoma (HNSCC)), brain cancer (e.g., glioblastoma), breast cancer, ovarian cancer, cervical cancer, lung cancer, kidney cancer, bladder cancer, liver cancer, sarcoma, and hematological cancers (e.g., leukemias, lymphomas, myelomas).

Also provided herein are methods of preparing compounds of Formula (I) or (II), or pharmaceutically acceptable salts, hydrates, solvates, polymorphs, co-crystals, tautomers, stereoisomers, isotopically labeled derivatives, or prodrugs thereof. Also provided herein are methods of preparing nanoparticles and nanogels described herein.

Another aspect of the present disclosure relates to kits comprising a compound, or a pharmaceutically acceptable salt, hydrate, solvate, polymorph, co-crystal, tautomer, stereoisomer, isotopically labeled derivative, or prodrug thereof, or pharmaceutical composition of the invention. In another aspect, the present disclosure provides kits comprising nanoparticles and nanogels described herein, or pharmaceutical compositions thereof. The kits described herein may include a single dose or multiple doses of the compound, nanoparticle, nanogel, or pharmaceutical composition thereof. The provided kits may be useful in a method of the invention (e.g., a method of treating and/or preventing a disease in a subject). A kit of the invention may further include instructions for using the kit (e.g., instructions for using the compound, nanoparticle, nanogel, or composition included in the kit).

The details of certain embodiments of the invention are set forth in the Detailed Description of Certain Embodiments, as described below. Other features, objects, and advantages of the invention will be apparent from the Definitions, Examples, Figures, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, ∿∿ is a single bond where the stereochemistry of the moieties immediately attached thereto is not specified, - - - is absent or a single bond, and ═ ‑ ‑ or ‑ ‑ ═ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (i-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═$CHCH_3$ or

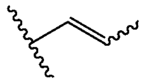

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl").

In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracenyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_3$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(=O)(OR^{cc})_2$—$OP(=O)(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{cc})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, =$NN(R^{bb})_2$, =$NNR^{bb}C(=O)R$—, =$NNR^{bb}C(=O)OR^{aa}$, =$NNR^{bb}S(=O)_2R^{aa}$, =$NR^{bb}$, or =$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{aa}$, —$SO_2OR^{cc}$, —$SOR^{aa}$, —$C(=S)N(R^{cc})_2$, —$C(=O)SR^{cc}$, —$C(=S)SR^{cc}$, —$P(=O)(R^{aa})_2$, —$P(=O)(OR^{cc})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of R is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NRC(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)(OR^{ee})_2$, —$P(=O)(R^{ee})_2$, —$OP(=O)(R^{ee})_2$, —$OP(=O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+X^-$, —$NH_3^+X^-$, —$N(OC_{1-6}$ alkyl$)(C_{1-6}$ alkyl$)$, —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2$H, —$CO_2$($C_{1-6}$ alkyl), —OC(═O)($C_{1-6}$ alkyl), —$OCO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(═NH)NH($C_{1-6}$ alkyl), —OC(═NH)$NH_2$, —NHC(═NH)N($C_{1-6}$ alkyl)$_2$, —NHC(═NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2$($C_{1-6}$ alkyl), —$SO_2$O($C_{1-6}$ alkyl), —$OSO_2$($C_{1-6}$ alkyl), —SO($C_{1-6}$ alkyl), —Si($C_{1-6}$ alkyl)$_3$, —OSi($C_{1-6}$ alkyl)$_3$, —C(═S)N($C_{1-6}$ alkyl)$_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)($OC_{1-6}$ alkyl)$_2$, —P(═O)($C_{1-6}$ alkyl)$_2$, —OP(═O)($C_{1-6}$ alkyl)$_2$, —OP(═O)($OC_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{99}$ substituents can be joined to form ═O or ═S; wherein $X^-$ is a counterion.

In certain embodiments, exemplary substituents include, but are not limited to, halogen, —CN, —$NO_2$, —$N_3$, —$SO_2$H, —$SO_3$H, —OH, —$OR^{aa}$, —N($R^{bb}$)$_2$, —N($R^{bb}$)$_3^+X^-$, —SH, —$SR^{aa}$, —C(═O)$R^{aa}$, —$CO_2$H, —CHO, —$CO_2R^{aa}$, —OC(═O)$R^{aa}$, —$OCO_2R^{aa}$, —C(═O)N($R^{bb}$)$_2$, —OC(═O)N($R^{bb}$)$_2$, —$NR^{bb}$C(═O)$R^{aa}$, —$NR^{bb}CO_2R^{aa}$, —$NR^{bb}$C(═O)N($R^{bb}$)$_2$, —$NR^{bb}SO_2R^{aa}$, —$SO_2$N($R^{bb}$)$_2$, —$SO_2R^{aa}$, —$SO_2$OR, —$OSO_2R^{aa}$, —S(═O)$R^{aa}$, —OS(═O)$R^{aa}$, —Si($R^{aa}$)$_3$, —OSi($R^{aa}$)$_3$, —P(═O)($R^{aa}$)$_2$, —P(═O)($OR^{cc}$)$_2$, —OP(═O)($R^{aa}$)$_2$, —OP(═O)($OR^{cc}$)$_2$, —P(═O)(N($R^{bb}$)$_2$)$_2$, —OP(═O)(N($R^{bb}$)$_2$)$_2$, —$NR^{bb}$P(═O)($R^{aa}$)$_2$, —$NR^{bb}$P(═O)($OR^{cc}$)$_2$, —$NR^{bb}$P(═O)(N($R^{bb}$)$_2$)$_2$, —B($R^{aa}$)$_2$, —B($OR^{cc}$)$_2$, —$BR^{aa}$($OR^{cc}$), $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl; wherein $X^-$ is a counterion;

or two geminal hydrogens on a carbon atom are replaced with the group ═O, ═S, ═NN($R^{bb}$)$_2$, ═$NNR^{bb}$C(═O)$R^{aa}$, ═$NNR^{bb}$C(═O)$OR^{aa}$, ═$NNR^{bb}$S(═O)$_2R^{aa}$, ═$NR^{bb}$, or ═$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring;

each instance of $R^{bb}$ is, independently, selected from hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —P(═O)($R^{aa}$)$_2$, —P(═O)($OR^{cc}$)$_2$, —P(═O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring; and each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(═O)$SR^{aa}$, —OC(═O)$R^{aa}$, —$OCO_2R^{aa}$, —OC(═O)N($R^{bb}$)$_2$, —OC(═$NR^{bb}$)$R^{aa}$, —OC(═$NR^{bb}$)$OR^{aa}$, —OC(═$NR^{bb}$)N($R^{bb}$)$_2$, —OS(═O)$R^{aa}$, —$OSO_2R^{aa}$, —OSi($R^{aa}$)$_3$, —OP($R^{cc}$)$_2$, —OP($R^{cc}$)$_3^+X^-$, —OP($OR^{cc}$)$_2$, —OP($OR^{cc}$)$_3^+X^-$, —OP(═O)($R^{aa}$)$_2$, —OP(═O)($OR^{cc}$)$_2$, and —OP(═O)(N($R^{bb}$)$_2$)$_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(═O)$R^{aa}$, —$NHCO_2R^{aa}$, —NHC(═O)N($R^{bb}$)$_2$, —NHC(═$NR^{bb}$)N($R^{bb}$)$_2$, —$NHSO_2R^{aa}$, —NHP(═O)($OR^{cc}$)$_2$, and —NHP(═O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(═O)R—, —$NR^{bb}CO_2$R—, —$NR^{bb}$C(═O)N($R^{bb}$)$_2$, —$NR^{bb}$C(═$NR^{bb}$)N($R^{bb}$)$_2$, —$NR^{bb}SO_2R^{aa}$, —$NR^{bb}$P(═O)($OR^{cc}$)$_2$, and —$NR^{bb}$P(═O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

The term "sulfonyl" refers to a group selected from —$SO_2$N($R^{bb}$)$_2$, —$SO_2R^{aa}$, and —$SO_2OR^{aa}$, wherein $R^{aa}$ and $R^{bb}$ are as defined herein.

The term "sulfinyl" refers to the group —S(═O)$R^{aa}$, wherein $R^{aa}$ is as defined herein.

The term "acyl" refers to a group having the general formula —C(═O)$R^{X1}$, —C(═O)$OR^{X1}$, —C(═O)—O—C(═O)$R^{X1}$, —C(═O)$SR^{X1}$, —C(═O)N($R^{X1}$)$_2$, —C(═S)$R^{X1}$, —C(═S)N($R^{X1}$)$_2$, —C(═S)O($R^{X1}$), —C(═S)S($R^{X1}$), —C(═$NR^{X1}$)$R^{X1}$, —C(═$NR^{X1}$)$OR^{X1}$, —C(═$NR^{X1}$)$SR^{X1}$, and —C(═$NR^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (e.g., —C(═O)$R^{aa}$), carboxylic acids (e.g., —$CO_2H$), aldehydes (—CHO), esters (e.g., —$CO_2R^{aa}$, —C(═O)$SR^{aa}$, —C(═S)$SR^{aa}$), amides (e.g., —C(═O)$N(R^{bb})_2$, —C(═O)$NR^{bb}SO_2R^{aa}$, —C(═S)$N(R^{bb})_2$), and imines (e.g., —C(═$NR^{bb}$)$R^{aa}$, —C(═$NR^{bb}$)$OR^{aa}$), —C(═$NR^{bb}$)$N(R^{bb})_2$), wherein $R^{aa}$ and $R^{bb}$ are as defined herein.

The term "silyl" refers to the group —$Si(R^{aa})_3$, wherein $R^{aa}$ is as defined herein.

The term "oxo" refers to the group ═O, and the term "thiooxo" refers to the group ═S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(OR^{cc})_2$, —P(═O)$(R^{aa})_2$, —P(═O)$(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —C(═O)$R^{aa}$, —C(═O)$N(R^{cc})_2$—$CO_2R^{aa}$, —$SO_2R^{aa}$, —C(═$NR^{cc}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl- 2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —$S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-fluorenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7α-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisopropylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $P_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

Other Definitions

The following definitions are more general terms used throughout the present application.

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^{+}(C_{1-4}\ alkyl)_4^{-}$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "nanoparticle" refers to a particle having an average (e.g., mean) dimension (e.g., diameter) of between about 1 nanometer (nm) and about 1 micrometer (μm), inclusive. In certain embodiments, the nanoparticle is between about 1 nm and about 300 nm, between about 1 nm and about 100 nm, between about 1 nm and about 30 nm, between about 1 nm and about 10 nm, or between about 1 nm and about 3 nm, inclusive. Nanoparticles can be compromised of polymers, lipids, and other molecules that self-assemble into particle form. Nanoparticles can be comprised of synthetic polymers or biopolymers (e.g., fucoidan polymers). Nanoparticles can be loaded with drugs by entrapment, covalent conjugation, etc. Examples of types of nanoparticles include, but are not limited to, polymeric particles, lipid nanoparticles, liposomes, micelles, dendrimers, amphiphilic particles, liquid-filled particles, solid particles, ceramic particles, carbon-based particles and nanotubes, metal particles, metal oxide particles, silica particles, quantum dots, layered particles, and composite or hybrid particles.

"Nanogels" are porous nanoscale polymer networks comprised of crosslinked polymer chains. The polymers in the network may be covalently or non-covalently crosslinked. Nanogels are intrinsically porous and can be loaded with small or large molecules by physical entrapment, covalent conjugation, or controlled self-assembly. Nanogels can be comprised of synthetic polymers or biopolymers (e.g., fucoidan polymers) which are chemically or physically crosslinked.

"Fucoidan polymers" refers to a class of sulfated, fucose-rich polymers. As described herein, a fucoidan polymer is a sulfated polysaccharide that can be found in various species of brown algae and brown seaweed, for example, brown macroalgae. Fucoidans have been reported to have anticoagulant, antiviral, anti-inflammatory, and anticancer activities, as well as high affinity to P-selectin. It can be obtained and purified from natural sources, or it may be synthesized. In general, fucoidan has an average molecular weight of from about 10,000 to about 30,000 (e.g., about 20,000), but other molecular weights may be found as well. Naturally—occurring fucoidan includes F-fucoidan, which has a high content of sulfated esters of fucose (e.g., no less than 95 wt. %), and U-fucoidan, which contains sulfates esters of fucose but is about 20% glucuronic acid. The fucoidan used in various embodiments described herein contains no less than 50 wt. %, no less than 60 wt. %, no less than 70 wt. %, no less than 80 wt. %, no less than 90 wt. %, or no less than 95 wt. % sulfate esters of fucose.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" may refer to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue comprises cancer cells. In certain embodiments, the target tissue is a tumor. In certain embodiments, the target tissue is a tissue with cells expressing P-selectin. A "non-target tissue" is any biological tissue of a subject (including a group of cells, a body part, or an organ) or a part thereof, including blood and/or lymph vessels, which is not a target tissue.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein the term "inhibit" or "inhibition" in the context of enzymes, for example, in the context of PI3K (e.g., PI3Kα), refers to a reduction in the activity of the enzyme. In some embodiments, the term refers to a reduction of the level of enzyme activity (e.g., PI3K activity, e.g., PI3Kα activity) to a level that is statistically significantly lower than an initial level, which may, for example, be a baseline level of enzyme activity. In some embodiments, the term refers to a reduction of the level of enzyme activity (e.g., PI3K activity, e.g., PI3Kα activity) to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

As defined herein, "PI3K" refers to phosphatidylinositol-4,5-bisphosphate 3-kinase enzymes (sometimes also called phosphatidylinositide 3-kinases, phosphatidylinositol-3-kinases, PI 3-kinases, PI(3)Ks, PI3Ks, or PI3K(s)). PI3K enzymes are a family of enzymes involved in cellular functions including, but not limited to, cell growth, proliferation, differentiation, motility, survival, and intracellular trafficking. PI3K enzymes are therefore often involved in proliferative diseases, such as cancer.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chrondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma, a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hay fever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

"Anti-cancer agents" encompass biotherapeutic anti-cancer agents as well as chemotherapeutic agents. Exemplary biotherapeutic anti-cancer agents include, but are not limited to, interferons, cytokines (e.g., tumor necrosis factor, interferon $\alpha$, interferon $\gamma$), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN® (trastuzumab), T-DM1, AVASTIN® (bevacizumab), ERBITUX® (cetuximab), VECTIBIX® (panitumumab), RITUXAN® (rituximab), BEXXAR® (tositumomab)).

Exemplary chemotherapeutic agents include, but are not limited to, anti-estrogens (e.g. tamoxifen, raloxifene, and megestrol), LHRH agonists (e.g. goserelin and leuprolide), anti-androgens (e.g. flutamide and bicalutamide), photodynamic therapies (e.g. verteporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (ABRAXANE®), docosahexaenoic acid bound-paclitaxel (DHA-paclitaxel, TAXOPREXIN®), polyglutamate bound-paclitaxel (PG-paclitaxel, paclitaxel poliglumex, CT-2103, XYOTAX®), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, raltitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (GLEEVEC®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (LUCENTIS®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE®)), mTOR inhibitors (e.g., rapamycin, temsirolimus (CCI-779), everolimus (RAD-001), ridaforolimus, AP23573 (ARIAD®), AZD8055 (ASTRAZENECA®), BEZ235 (NOVARTIS®), BGT226 (NOVARTIS®), XL765 (SANOFI AVENTIS®), PF-4691502 (PFIZER®), GDC0980 (Genetech), SF1126 (Semafoe), and OSI-027 (OSI)), oblimersen, gemcitabine, carminomycin, leucovorin, pemetrexed, cyclophosphamide, dacarbazine, procarbazine, prednisolone, dexamethasone, campothecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

These and other exemplary substituents are described in more detail in the Detailed Description, Examples, and Claims. The invention is not intended to be limited in any manner by the above exemplary listing of substituents.

BRIEF DESCRIPTION OF THE DRAWINGS

The accompanying drawings, which constitute a part of this specification, illustrate several embodiments of the invention and together with the description, serve to explain the principles of the invention.

FIG. 2A) Percentage of positively stained samples from tumor microarrays. FIG. 2B) The Cancer Genome Atlas (TCGA) for P-selectin (SELP) RNA expression (RNASeq Version 2) in patients from TCGA. A threshold for high expression was set at the highest expression of the lowest expressing cancer.[22] Abbreviations: ALL=acute lymphoblastic leukemia; SCC=squamous cell carcinoma.

FIG. 3A) Nanoparticle biodistribution in organs and tumor, calculated from ex vivo fluorescence images as total fluorescence efficiency (TFE) divided by organ weight (n=3). FIG. 3B) Quantification of double-staining positive endothelial cells per tumor shown in response to RT (unit=Gy) (n=3). FIG. 3C) Quantification of total fluorescence efficiency of tumors from in vivo fluorescence imaging of Cal-33 xenograft-bearing mice 24 hours after treatment with Fi(BYL719) or 4 Gy RT followed by Fi(BYL719) (n=10).[23]

FIG. 4A) Western blot of pS6 and pERK in Cal-33 xenograft tissues following treatment with BYL719 (25 mg/kg) or Fi(BYL719) (25 mg/kg), n=3. FIG. 4B) Box plots of cleaved caspase 3, pERK, or pS6 from a stained Cal-33 xenograft section 24 hours after treatment with either BYL719 (50 mg/kg) or Fi(BYL719) (25 mg/kg) comparing the volume of positive staining (% of total tissue volume) (n=2).[23]

FIG. 5A) Tumor growth curves of Cal-33 xenografts treated with oral administration of either 50 mg/kg/week BYL719 or 7 mg/kg BYL719 daily for 7 days, or IV injection of 25 mg/kg Fi(BYL719) bi-weekly (n=10). FIG. 5B) Tumor growth curves of H22 patient-derived xenografts treated with oral administration of either 50 or 7 mg/kg BYL719 daily, or bi-weekly IV injections of 25 mg/kg Fi(BYL719) (n=10). FIG. 5C) Survival curve of mice engrafted with orthotopic tongue cal-33 xenografts treated with oral administration of either 50 mg/kg/week BYL719 or 7 mg/kg BYL719 daily for 7 days or IV injections of 25 mg/kg Fi(BYL719) bi-weekly (n=5). In FIGS. 5A-5B, error bars indicate mean±s.e.m. *P<0.05, P<0.01, P<0.0001; by one-way ANOVA with post hoc Tukey test. In FIG. 5**C, the P-value was calculated by using the log-rank test.[23]

FIG. 6A) Quantification of γH2AX staining (foci per cell) presented in nuclear γH2AX foci and DAPI in H22 patient-derived xenografts 24 hours post treatment with RT (4 Gy) or RT followed by 50 mg/kg BYL719 or 25 mg/kg Fi(BYL719) (n=3). FIG. 6B) Tumor growth curves of H22 patient-derived xenografts treated for 5 days with daily oral administration of either 50 or 7 mg/kg BYL719 daily, or with IV injections of 25 mg/kg Fi(BYL719) administered bi-weekly, combined with fractionated RT of 4 Gy, 5 doses, on Days 1-5 (n=10). Error bars indicate mean±s.e.m.*P<0.05, *P<0.001, **P<0.0001; by one-way ANOVA with post hoc Tukey test.[23]

FIG. 20A) Quantification of nanoparticle emission in tumor spheres. Bars show means±SD of n=6 spheres; P=0.0042. FIG. 20B) Nanoparticle-mediated cytotoxicity of bEnd.3 cells activated by TNFα or 6 Gy, as measured by MTT (4,5-dimethylthiazol-2-yl)-2,5-diphenyltetrazolium bromide) cell viability assay.[22]

FIG. 21A): Diagram of assay to test penetration of nanoparticles into an activated endothelial monolayer barrier and infiltration into non-P-selectin-expressing tumor spheroids, LX33, composed of primary human small cell lung cancer (SCLC) cells. (FIG. 21B, 21C) Targeted (FiPAX) and control (DexPAX) nanoparticle emission in the upper and lower chambers of a Transwell system. Plots show means±SD (n=4).[22]

FIG. 24A) Survival data following the IV injection of B16F10 melanoma cells. The antitumor effects of fucoidan-encapsulated doxorubicin (FiDOX) nanoparticles were compared to the passively targeted DexDOX nanoparticle control and drug-polymer conjugate, DPD, at equivalent doxorubicin doses of 8 mg/kg in the B16F10 model. FIG. 24B) Survival data following the IV injection of B16F10 melanoma cells. Three different doses of FiDOX were administered. Mice bearing lung metastases were treated with a single dose of free doxorubicin (6 mg/kg), fucoidan (30 mg/kg) as a vehicle control, or FiDOX nanoparticles with several different doses of encapsulated doxorubicin (1, 5, and 30 mg/kg).[22]

FIG. 26A) P(A375)= 0.0048, FIG. 26B) P(SW620,FiMEK)=0.0071; P(SW620,MEK)=0.0055.[22]

FIG. 27A) P=0.0089 and FIG. 27B) P=0.0053, respectively.[22]

DETAILED DESCRIPTION OF CERTAIN EMBODIMENTS

Figure 1:
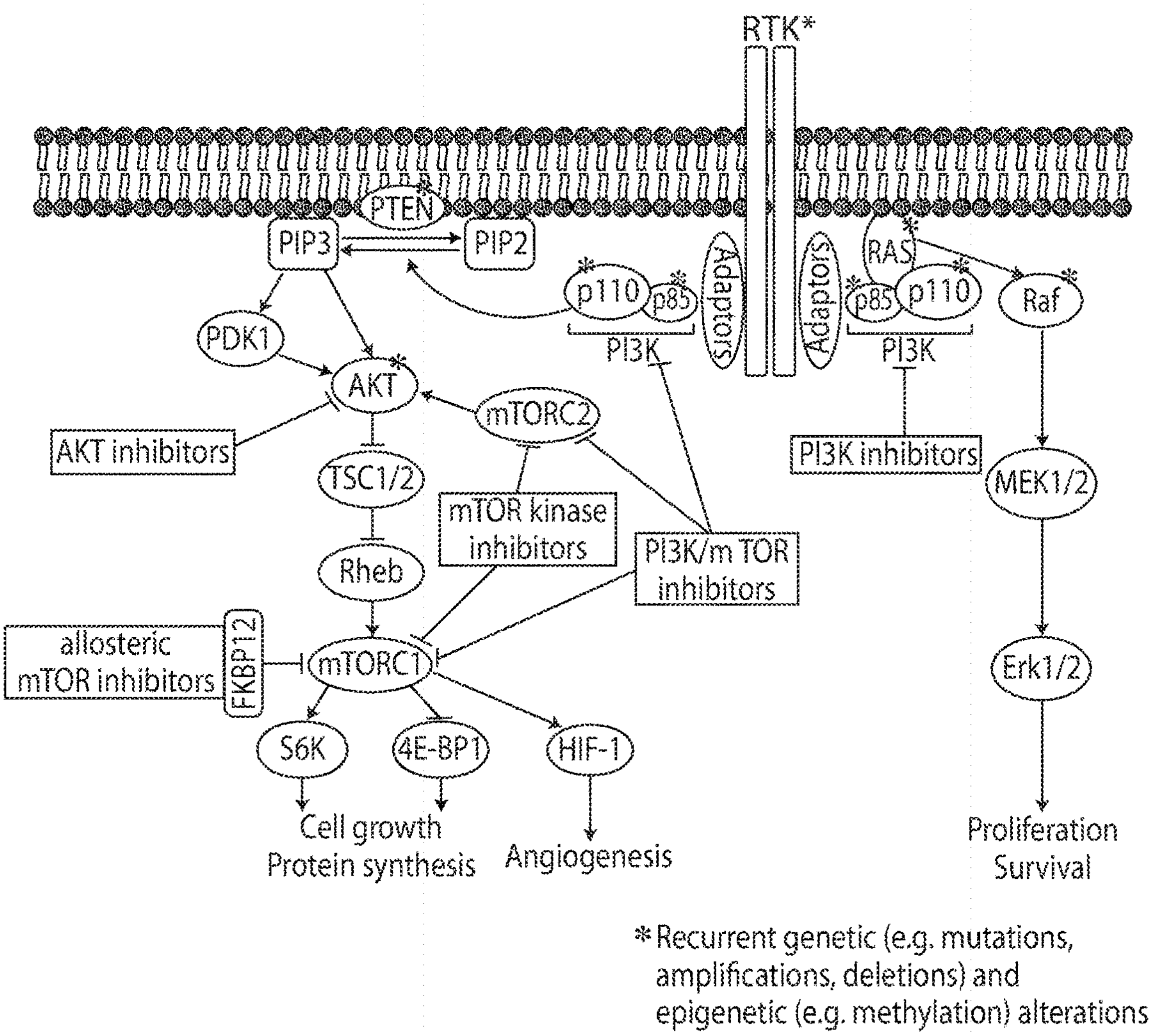
FIG. 1. Scheme of the PI3K Signal Transduction Pathway. Components of the class I PI3K signaling pathway (left) and of the mitogen-activated protein kinase (MAPK) pathway (right) recurrently targeted by genetic/epigenetic alterations in cancer are depicted with an asterisk. Several PI3K pathway inhibitors downstream of RTKs are being tested in clinical trials (gray boxes). mTOR, mechanistic target of rapamycin; mTORC, mTOR complex; PI3K, phosphoinositide 3-kinase; PIP2, phosphatidylinositol 4,5-bisphosphate; PIP3, phosphatidylinositol (3,4,5)-triphosphate; PTEN, phosphatase and tensin homolog; RTK, receptor tyrosine kinase; TSC, tuberous sclerosis protein.[54]

Provided herein are compounds of Formulae (I) and (II), and pharmaceutically acceptable salts, hydrates, solvates, polymorphs, co-crystals, tautomers, stereoisomers, isotopically labeled derivatives, and prodrugs thereof, and pharmaceutical compositions thereof. Also provided herein are nanoparticles and nanogels (e.g., P-selectin targeting nanoparticles and nanogels) comprising PI3K inhibitors, such as the compounds provided herein. The present disclosure also provides pharmaceutical compositions comprising the compounds, nanoparticles, and nanogels described herein. The compounds provided herein are PI3K inhibitors (e.g., PI3Kα inhibitors); therefore, the compounds, compositions, nanoparticles, and nanogels described herein can be used to treat and/or prevent diseases (e.g., inflammatory diseases and proliferative diseases such as cancer). In certain embodiments, the disease is a disease associated with a PI3K enzyme (e.g., PI3Kα) and/or P-selectin.

Compounds

Provided herein are compounds of Formula (I):

(I)

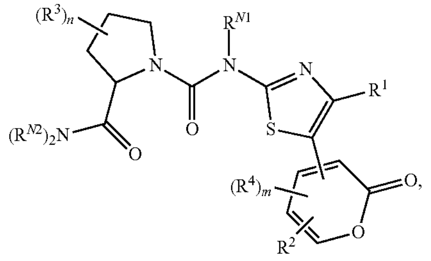

and pharmaceutically acceptable salts, hydrates, solvates, polymorphs, co-crystals, tautomers, stereoisomers, isotopically labeled derivatives, and prodrugs thereof, wherein:

$R^1$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

$R^2$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^3$ is independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^4$ is independently hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

$R^{N1}$ is hydrogen, optionally substituted alkyl, optionally substituted acyl, or a nitrogen protecting group;

each instance of $R^{N2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{N2}$ are joined together with the intervening atoms to form optionally substituted heterocyclyl or optionally substituted heteroaryl;

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are joined together with the intervening atoms to form optionally substituted heterocyclyl or optionally substituted heteroaryl;

each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group;

n is 0, 1, 2, 3, 4, 5, 6, or 7; and m is 0, 1, or 2.

In certain embodiments, a compound of Formula (I) is of one of the following formulae:

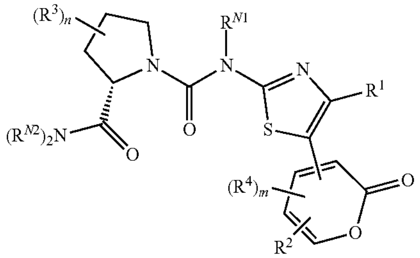

or

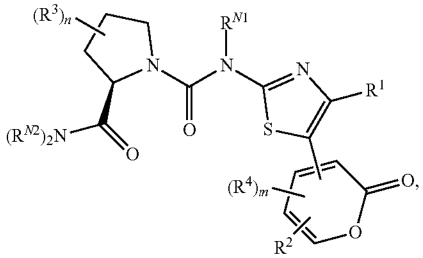

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

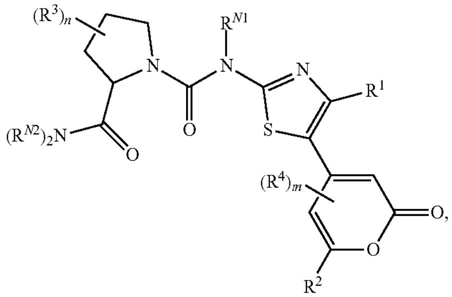

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of one of the following formulae:

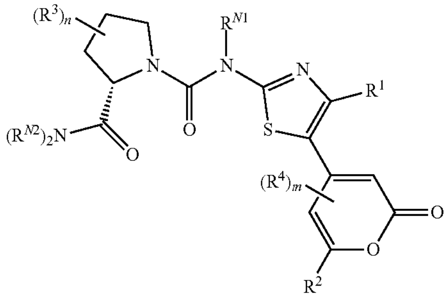

or

-continued

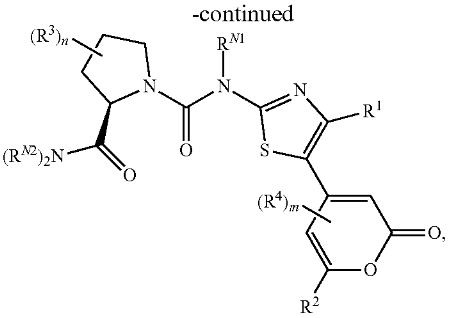

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

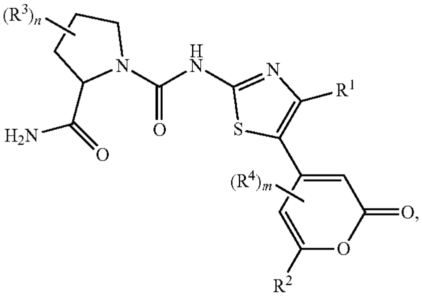

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of one of the following formulae:

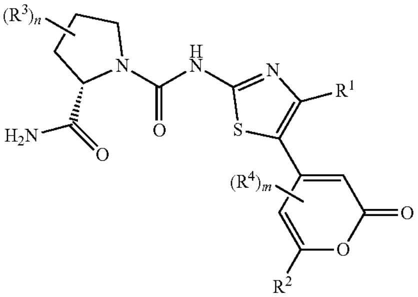

or

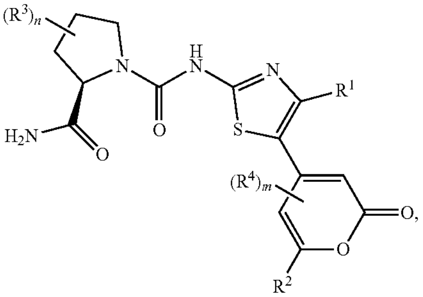

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

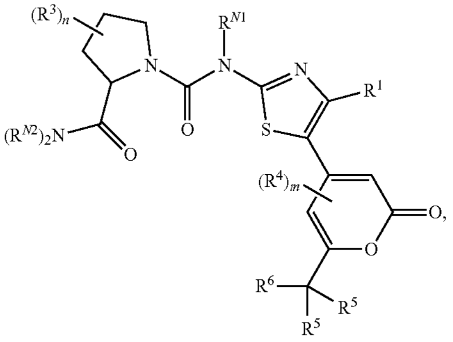

or a pharmaceutically acceptable salt, hydrate, solvate, polymorph, co-crystal, tautomer, stereoisomer, isotopically labeled derivative, or prodrug thereof, wherein:

each instance of $R^5$ is independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$; or two $R^5$ are joined together with the intervening atoms to form optionally substituted carbocyclyl or optionally substituted heterocyclyl; and $R^6$ is hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$.

In certain embodiments, a compound of Formula (I) is of one of the following formulae:

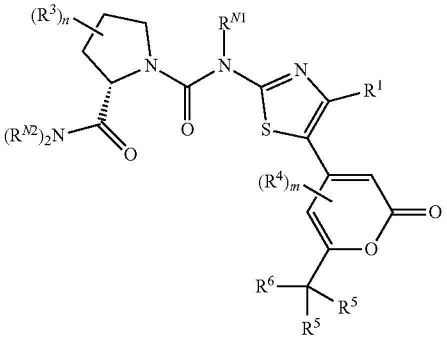

or

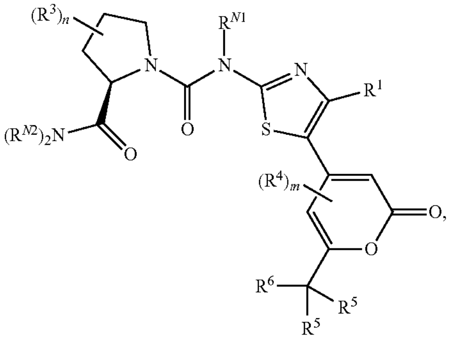

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

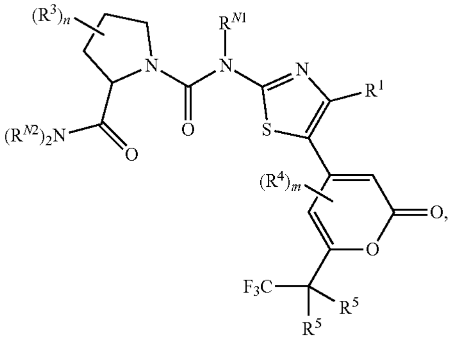

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of one of the following formulae:

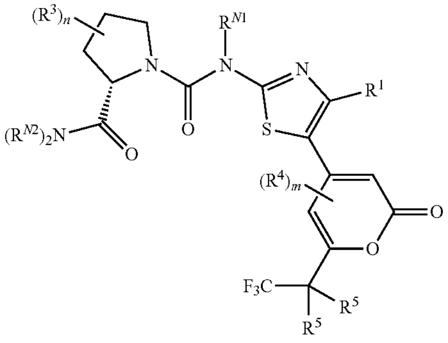

or

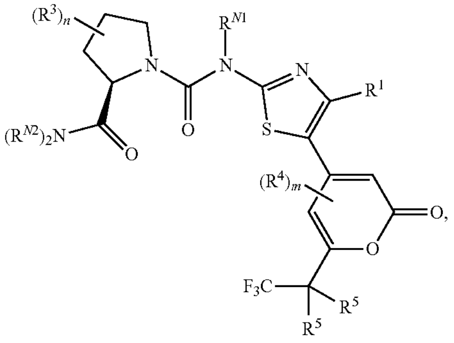

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

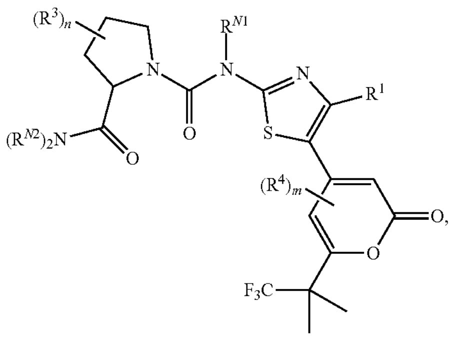

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of one of the following formulae:

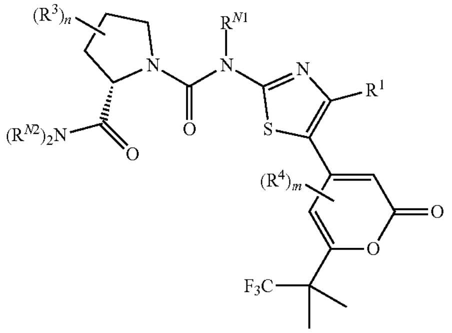

or

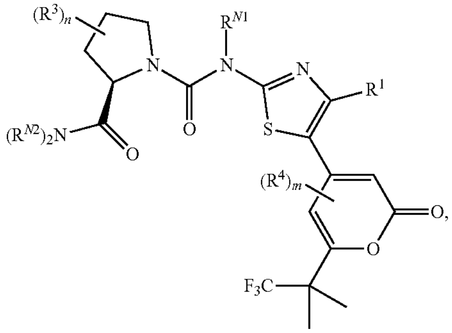

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

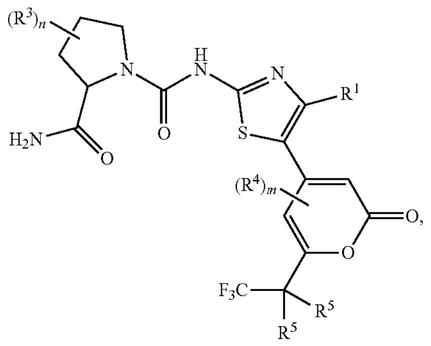

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of one of the following formulae:

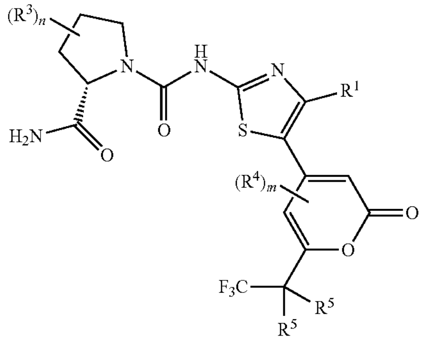

or

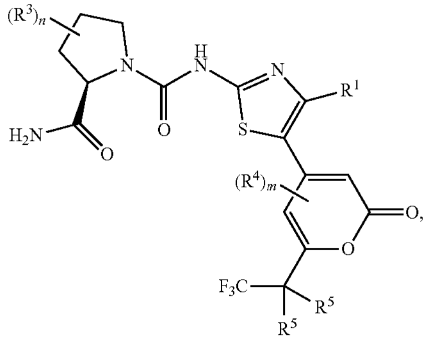

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

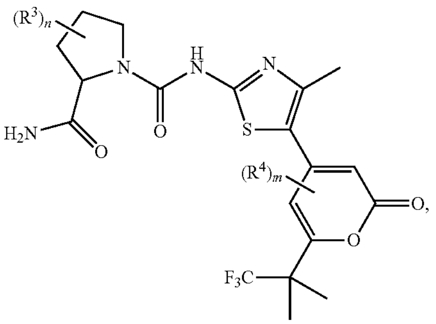

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of one of the following formulae:

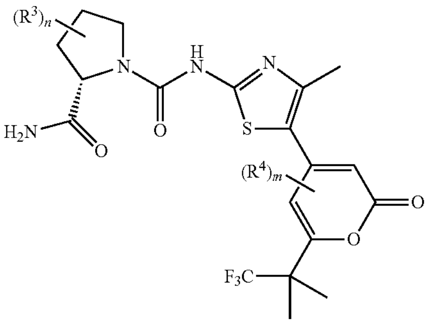

or

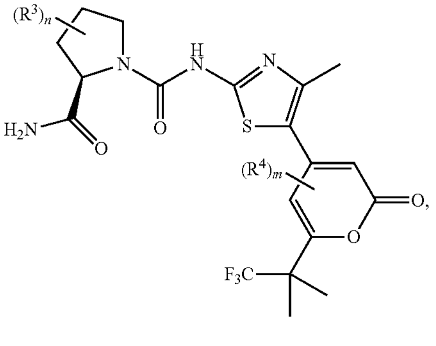

or a pharmaceutically acceptable salt, hydrate, solvate, polymorph, co-crystal, tautomer, stereoisomer, isotopically labeled derivative, or prodrug thereof.

In certain embodiments, for example, a compound of Formula (I) is selected from the group consisting of:

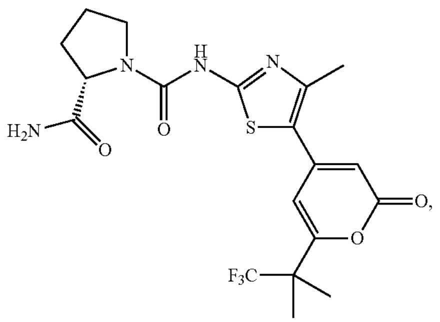

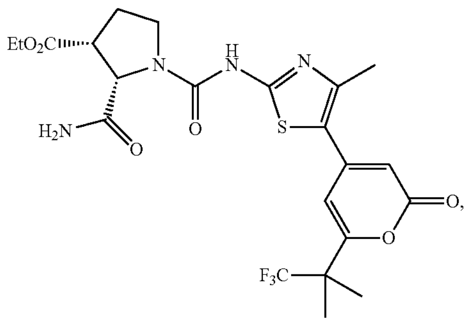

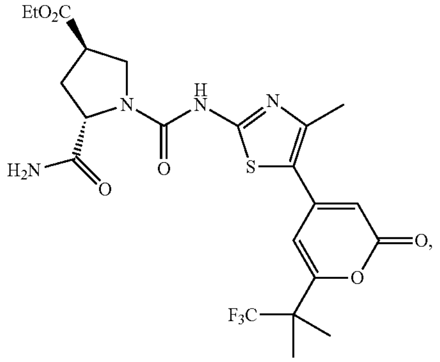

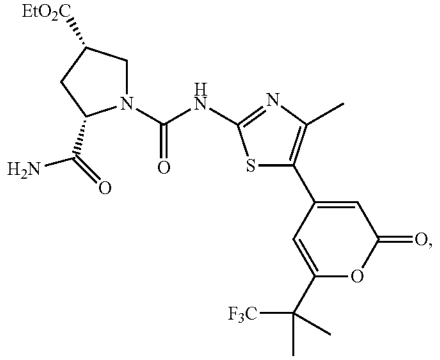

-continued

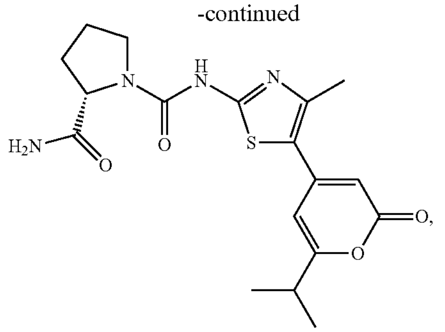

and

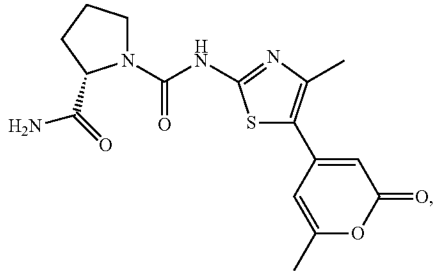 [SMILES: Cc1cc(-c2sc(NC(=O)N3CCC[C@H]3C(N)=O)nc2C)cc(=O)o1]

and pharmaceutically acceptable salts, hydrates, solvates, polymorphs, co-crystals, tautomers, stereoisomers, isotopically labeled derivatives, and prodrugs thereof.

Also provided herein are compounds of Formula (II):

(II)

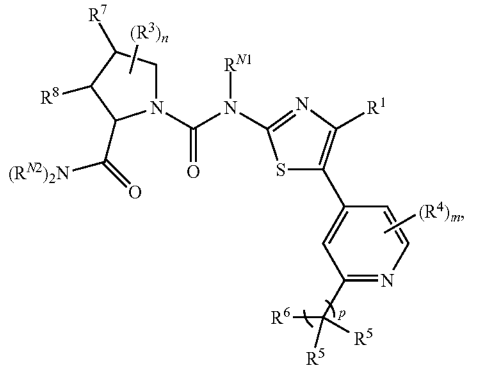

and pharmaceutically acceptable salts, hydrates, solvates, polymorphs, co-crystals, tautomers, stereoisomers, isotopically labeled derivatives, and prodrugs thereof, wherein:

$R^1$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^3$ is independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^4$ is independently hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^5$ is independently hydrogen, halogen, optionally substituted alkyl, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$; or two $R^5$ are joined together with the intervening atoms to form optionally substituted carbocyclyl or optionally substituted heterocyclyl;

$R^{N1}$ is hydrogen, optionally substituted alkyl, optionally substituted acyl, or a nitrogen protecting group;

each instance of $R^{N2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{N2}$ are joined together with the intervening atoms to form optionally substituted heterocyclyl or optionally substituted heteroaryl;

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are joined together with the intervening atoms to form optionally substituted heterocyclyl or optionally substituted heteroaryl;

each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group;

n is 0, 1, 2, 3, 4, or 5;

m is 0, 1, 2, or 3;

p is 0, 1, or 2;

$R^6$ is haloalkyl, —C(=O)$OR^{O2}$, —$(C(R^5)_2)_p$C(=O)$OR^{O2}$, —$OR^O$, —$N(R^N)_2$, or —$SR^S$;

$R^7$ and $R^8$ are each independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$; and each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

provided that when $R^6$ is $—CF_3$, $R^7$ and $R^8$ are independently hydrogen or optionally substituted acyl; and at least one of $R^7$ or $R^8$ is not hydrogen.

In certain embodiments, when $R^6$ is $—CF_3$, $R^7$ is hydrogen or optionally substituted acyl; and at least one of $R^7$ or $R^8$ is not hydrogen. In certain embodiments, when $R^6$ is $—CF_3$, $R^8$ is hydrogen or optionally substituted acyl; and at least one of $R^7$ or $R^8$ is not hydrogen. In certain embodiments, when $R^6$ is $—CF_3$, $R^7$ and $R^8$ are independently hydrogen or optionally substituted acyl; and at least one of $R^7$ or $R^8$ is not hydrogen. In certain embodiments, when $R^6$ is $—CF_3$, at least one instance of $R^7$ and $R^8$ is optionally substituted acyl. In certain embodiments, when $R^6$ is $—CF_3$, $R^7$ is not hydrogen. In certain embodiments, when $R^6$ is $—CF_3$, $R^7$ is optionally substituted acyl. In certain embodiments, when $R^6$ is $—CF_3$, $R^8$ is optionally substituted acyl. In certain embodiments, "optionally substituted acyl" is an ester group of the formula: $—C(═O)OR^{O2}$.

In certain embodiments, when $R^6$ is trihalomethyl, $R^7$ is hydrogen or optionally substituted acyl; and at least one of $R^7$ or $R^8$ is not hydrogen. In certain embodiments, when $R^6$ is trihalomethyl, $R^7$ and $R^8$ are independently hydrogen or optionally substituted acyl; and at least one of $R^7$ or $R^8$ is not hydrogen. In certain embodiments, when $R^6$ is trihalomethyl, at least one instance of $R^7$ and $R^8$ is optionally substituted acyl. In certain embodiments, when $R^6$ is trihalomethyl, $R^7$ is not hydrogen. In certain embodiments, when $R^6$ is trihalomethyl, $R^7$ is optionally substituted acyl. In certain embodiments, when $R^6$ is trihalomethyl, $R^8$ is optionally substituted acyl. In certain embodiments, "optionally substituted acyl" is an ester group of the formula: $—C(═O)OR^{O2}$.

In certain embodiments, when $R^6$ is haloalkyl, $R^7$ is hydrogen or optionally substituted acyl; and at least one of $R^7$ or $R^8$ is not hydrogen. In certain embodiments, when $R^6$ is haloalkyl, $R^7$ and $R^8$ are independently hydrogen or optionally substituted acyl; and at least one of $R^7$ or $R^8$ is not hydrogen. In certain embodiments, when $R^6$ is haloalkyl, at least one instance of $R^7$ and $R^8$ is optionally substituted acyl. In certain embodiments, when $R^6$ is haloalkyl, $R^7$ is not hydrogen. In certain embodiments, when $R^6$ is haloalkyl, $R^7$ is optionally substituted acyl. In certain embodiments, when $R^6$ is haloalkyl, $R^8$ is optionally substituted acyl. In certain embodiments, "optionally substituted acyl" is an ester group of the formula: $—C(═O)OR^{O2}$.

In certain embodiments, a compound of Formula (II) is of one of the following formulae:

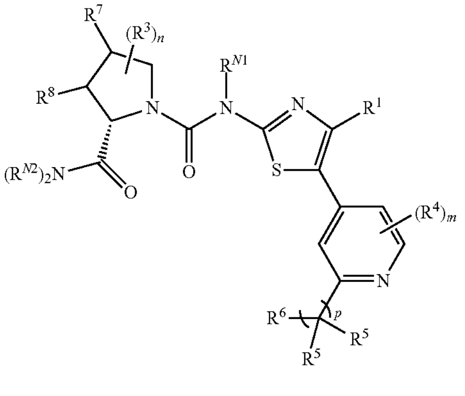

or

-continued

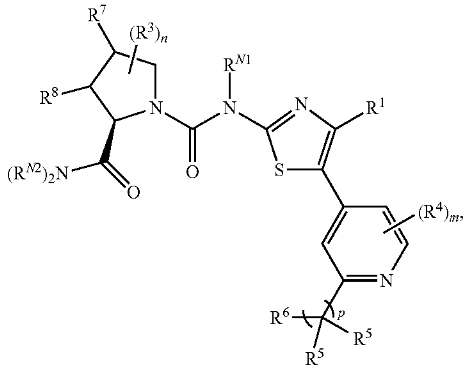

or a pharmaceutically acceptable salt, hydrate, solvate, polymorph, co-crystal, tautomer, stereoisomer, isotopically labeled derivative, or prodrug thereof.

In certain embodiments, a compound of Formula (II) is of the following formula:

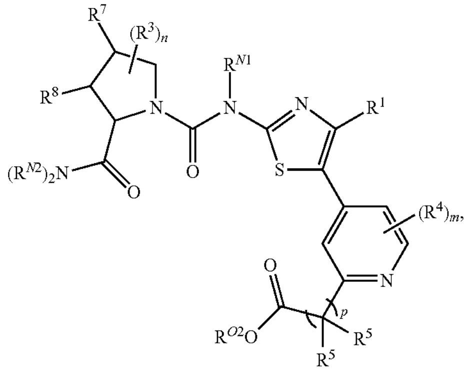

or a pharmaceutically acceptable salt, hydrate, solvate, polymorph, co-crystal, tautomer, stereoisomer, isotopically labeled derivative, or prodrug thereof.

In certain embodiments, a compound of Formula (II) is of one of the following formulae:

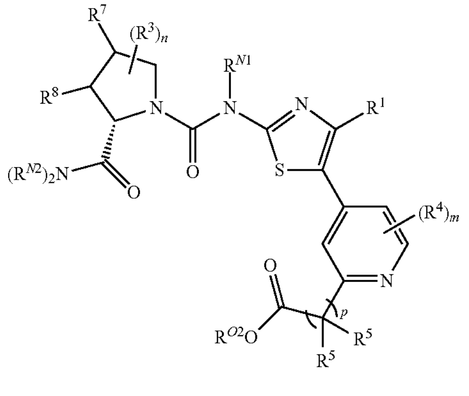

or

-continued

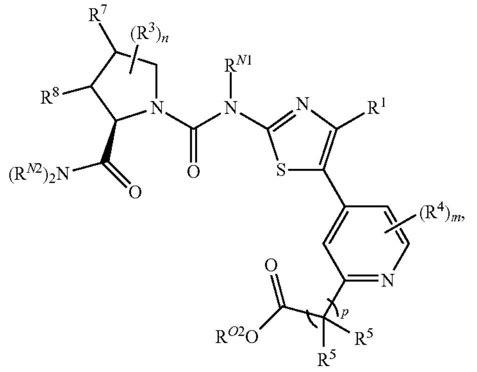

or a pharmaceutically acceptable salt, hydrate, solvate, polymorph, co-crystal, tautomer, stereoisomer, isotopically labeled derivative, or prodrug thereof.

In certain embodiments, a compound of Formula (II) is of one of the following formulae:

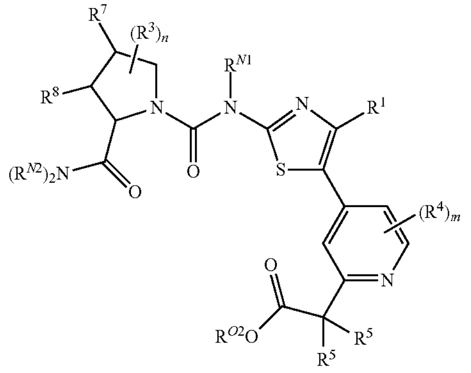

or

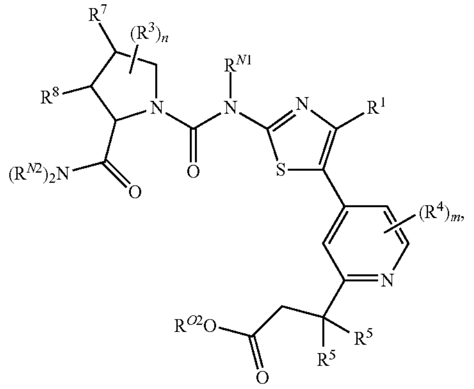

or a pharmaceutically acceptable salt, hydrate, solvate, polymorph, co-crystal, tautomer, stereoisomer, isotopically labeled derivative, or prodrug thereof.

In certain embodiments, a compound of Formula (II) is of one of the following formulae:

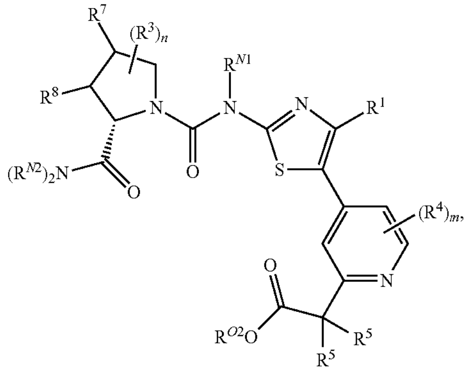

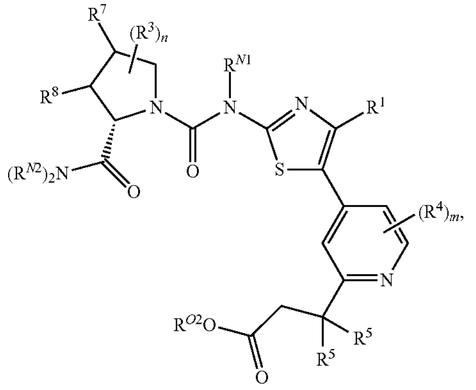

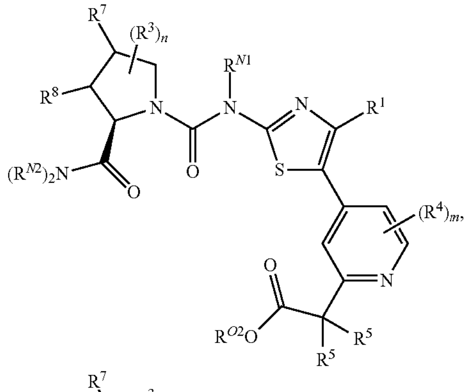

or

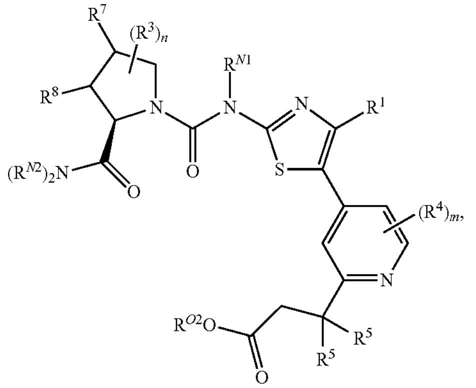

or a pharmaceutically acceptable salt, hydrate, solvate, polymorph, co-crystal, tautomer, stereoisomer, isotopically labeled derivative, or prodrug thereof.

In certain embodiments, a compound of Formula (II) is of the following formula:

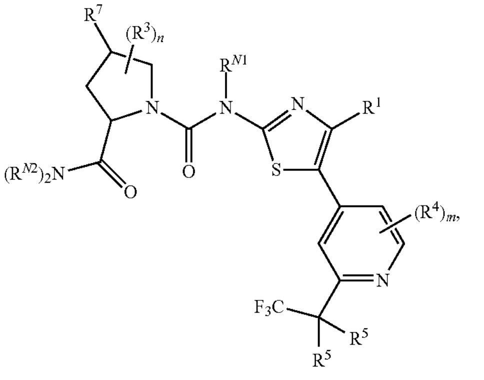

or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is —C(=O)OR$^{O2}$.

In certain embodiments, a compound of Formula (II) is of one of the following formulae:

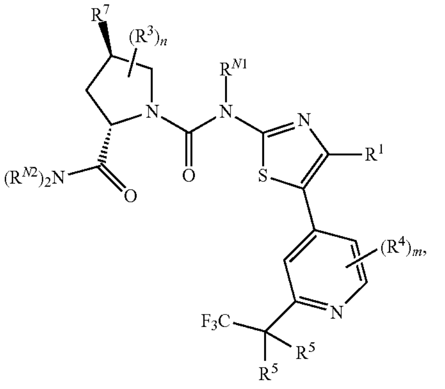

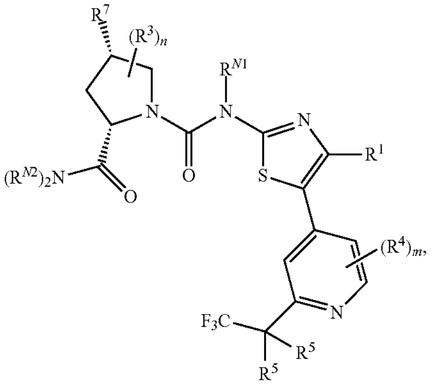

-continued

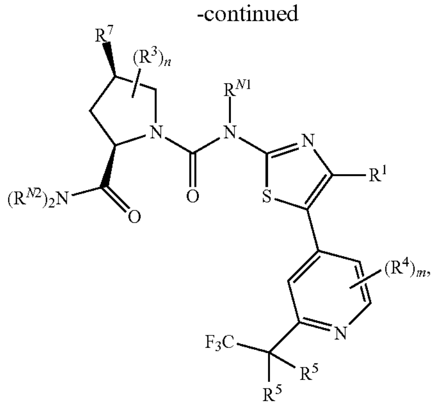

or

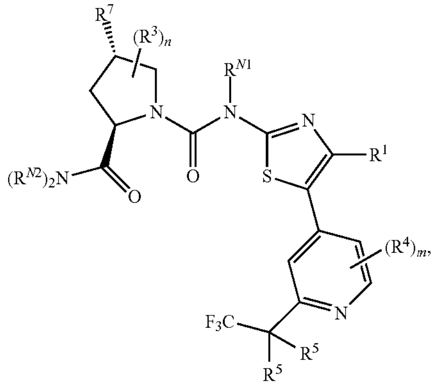

or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is —C(=O)OR$^{O2}$.

In certain embodiments, a compound of Formula (II) is of the following formula:

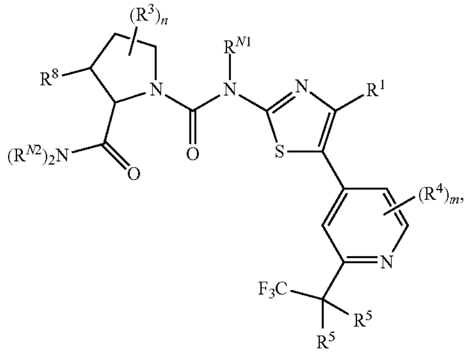

or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is —C(=O)OR$^{O2}$.

In certain embodiments, a compound of Formula (II) is of one of the following formulae:

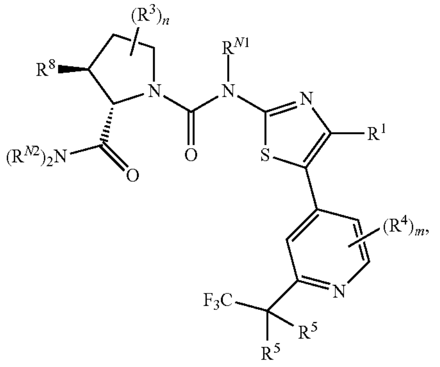

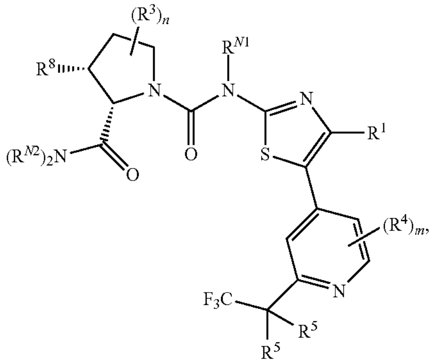

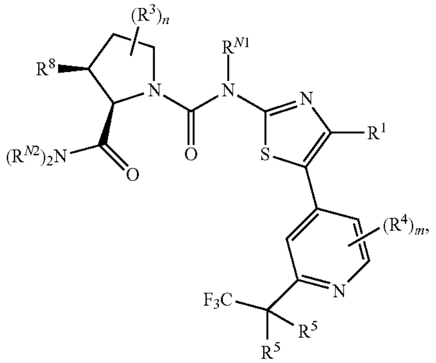

or

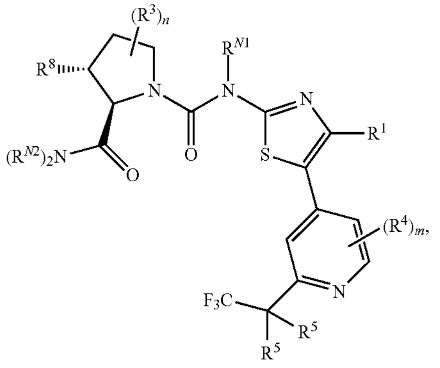

or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is —C(═O)OR$^{O2}$.

In certain embodiments, a compound of Formula (II) is of the following formula:

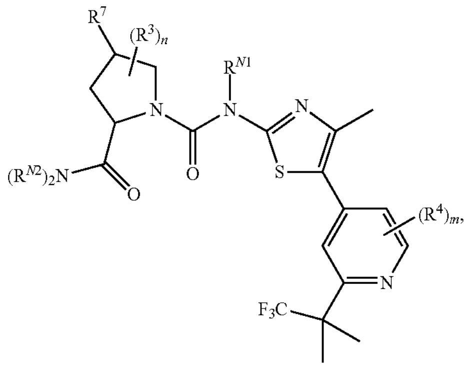

or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is —C(═O)OR$^{O2}$.

In certain embodiments, a compound of Formula (II) is of one of the following formulae:

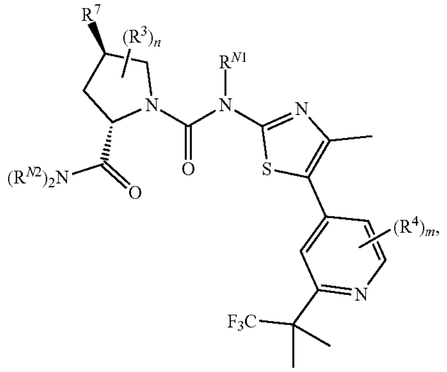

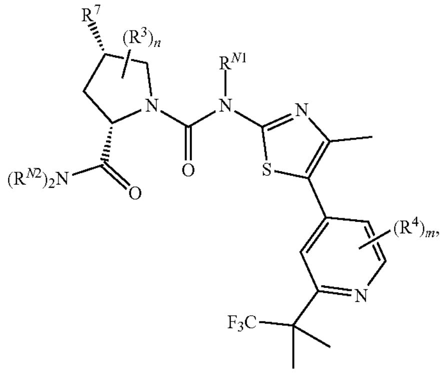

-continued

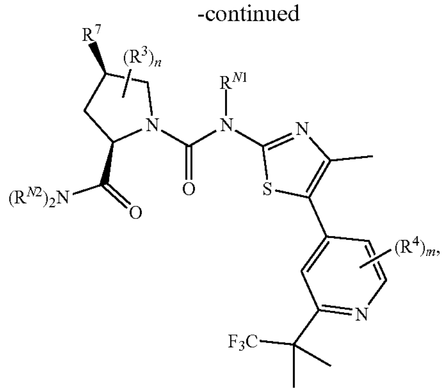

or

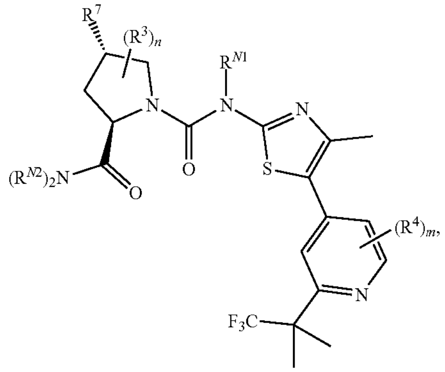

, or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is —C(═O)OR$^{O2}$.

In certain embodiments, a compound of Formula (II) is of the following formula:

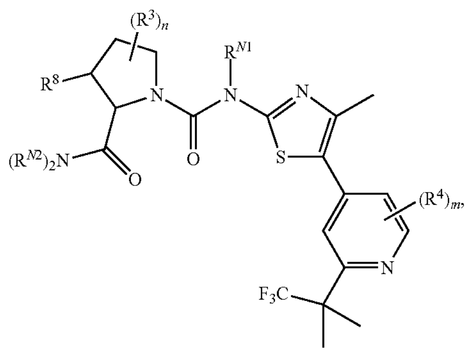

, or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is —C(═O)OR$^{O2}$.

In certain embodiments, a compound of Formula (II) is of one of the following formulae:

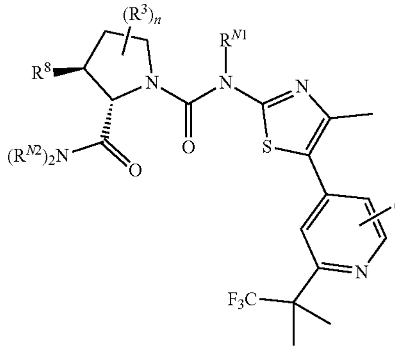

,

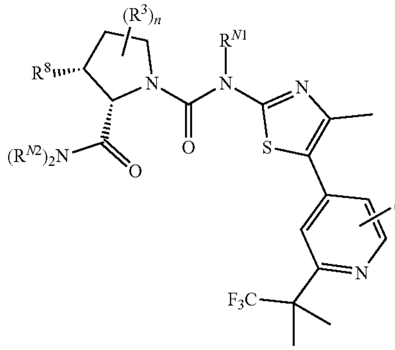

,

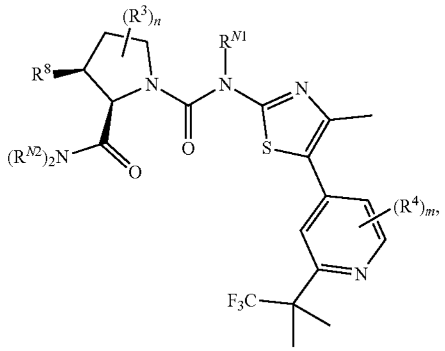

, or

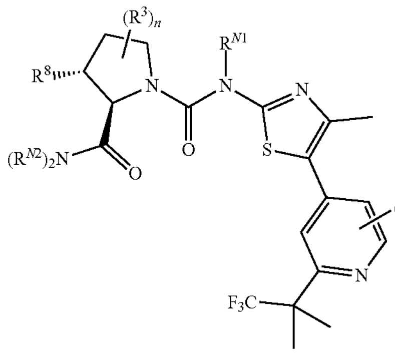

, or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is —C(═O)OR$^{O2}$.

In certain embodiments, a compound of Formula (II) is of the following formula:

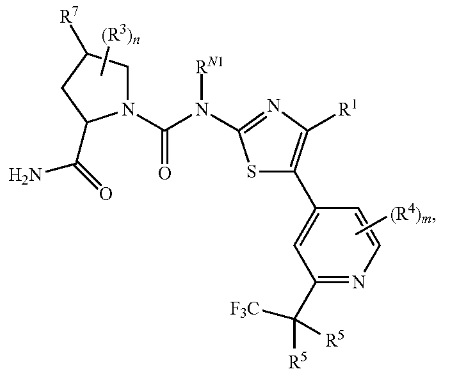

or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is $—C(═O)OR^{O2}$.

In certain embodiments, a compound of Formula (II) is of one of the following formulae:

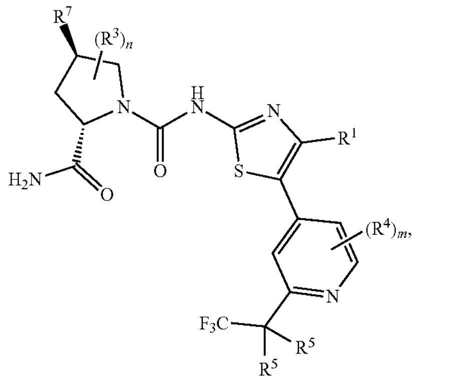

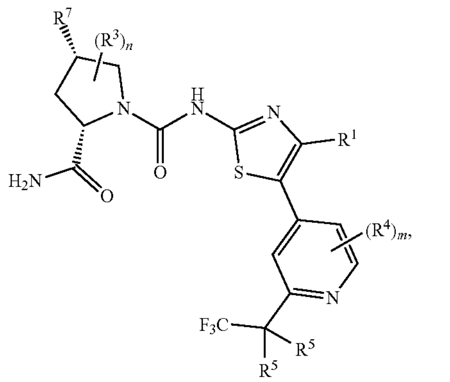

-continued

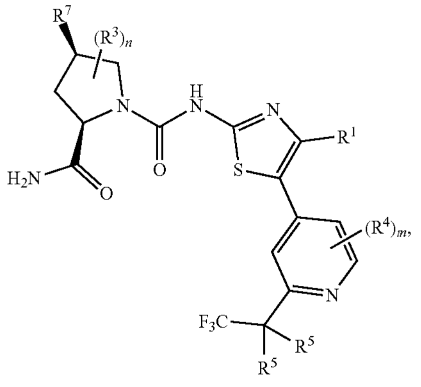

or

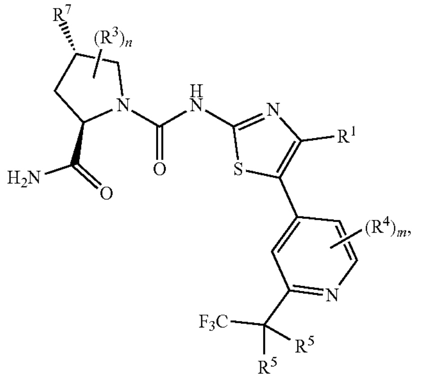

or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is $—C(═O)OR^{O2}$.

In certain embodiments, a compound of Formula (II) is of the following formula:

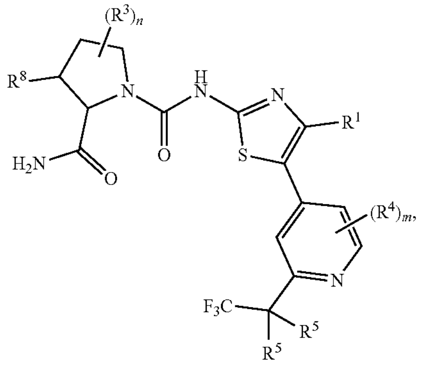

or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is $—C(═O)OR^{O2}$.

In certain embodiments, a compound of Formula (II) is of one of the following formulae:

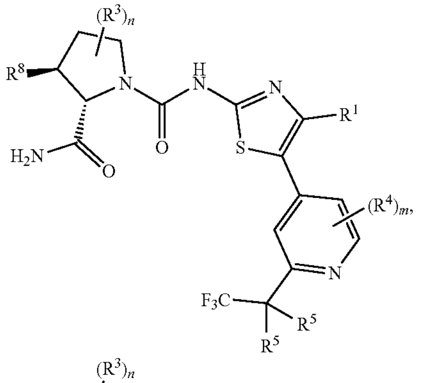

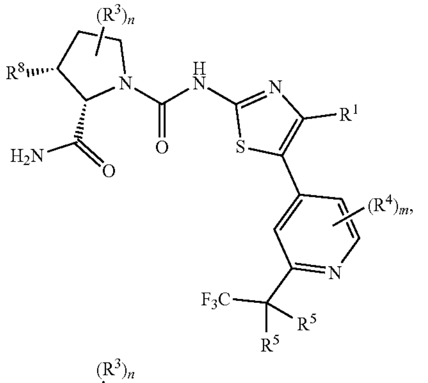

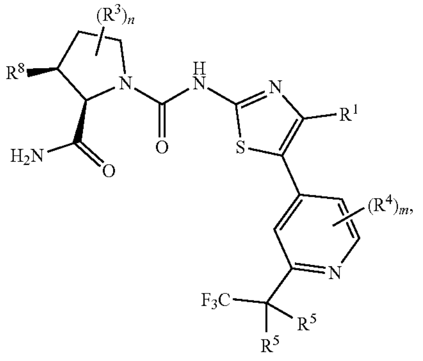

or

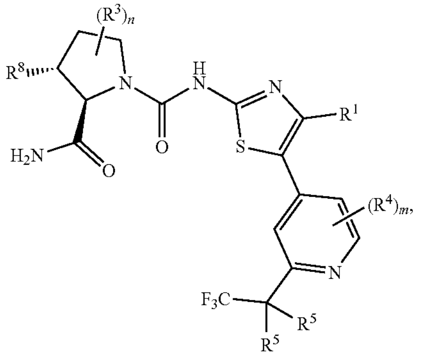

or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is —C(═O)OR$^{O2}$.

In certain embodiments, a compound of Formula (II) is of the following formula:

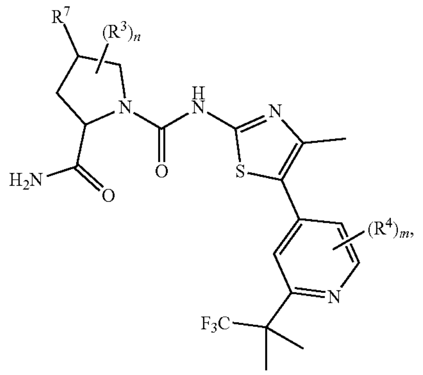

or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is —C(═O)OR$^{O2}$.

In certain embodiments, a compound of Formula (II) is of one of the following formulae:

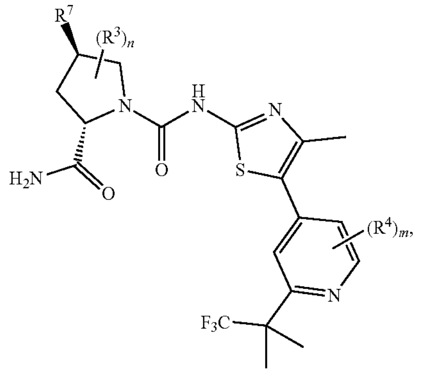

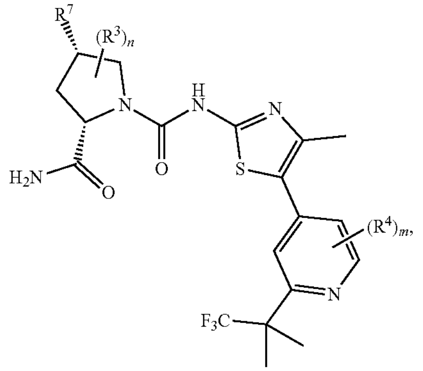

-continued

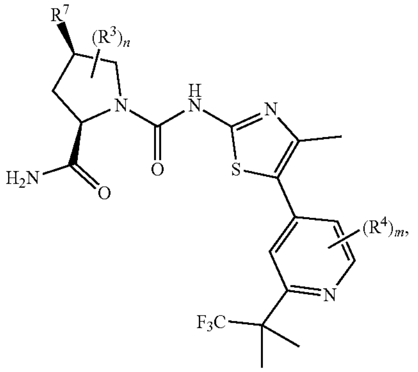

or

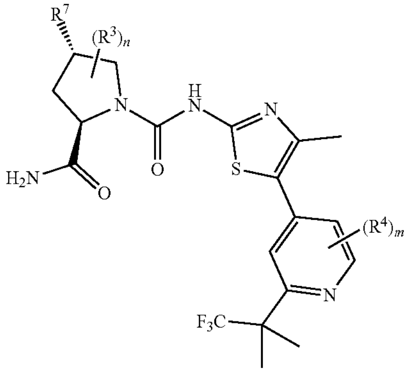

or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is —C(═O)OR$^{O2}$.

In certain embodiments, a compound of Formula (II) is of the following formula:

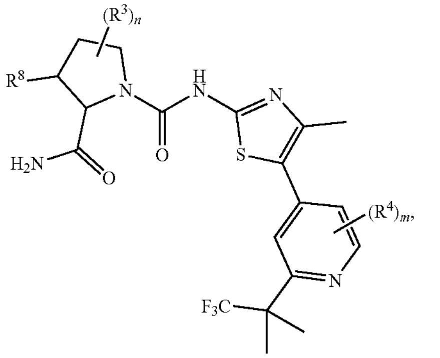

or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is —C(═O)OR$^{O2}$.

In certain embodiments, a compound of Formula (II) is of one of the following formulae:

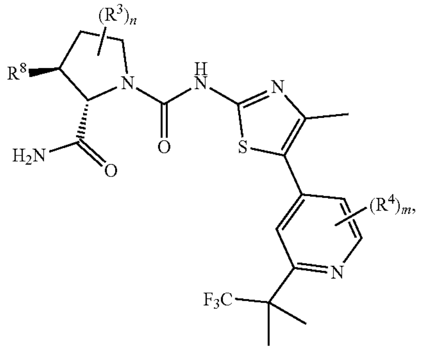

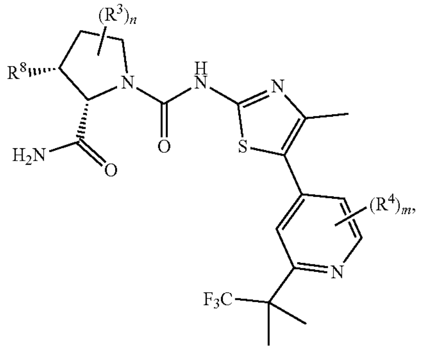

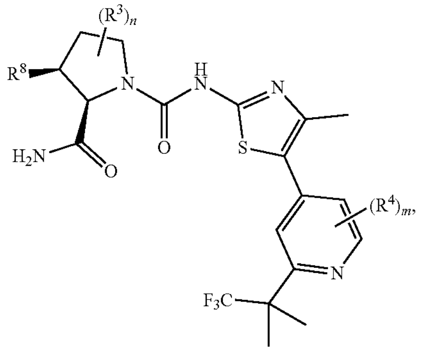

or

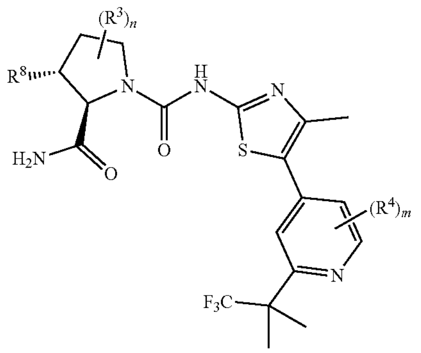

or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is —C(═O)OR$^{O2}$.

In certain embodiments, a compound of Formula (II) is of the following formula:

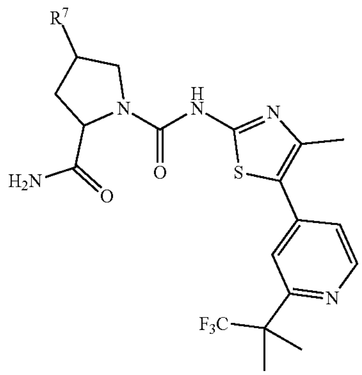

, or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is $-C(=O)OR^{O2}$.

In certain embodiments, a compound of Formula (II) is of one of the following formulae:

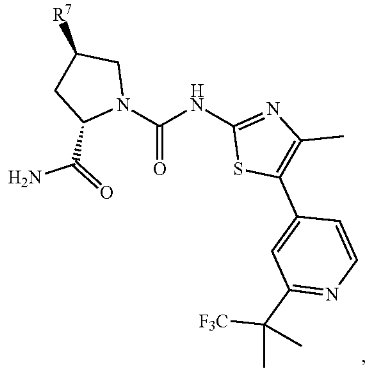

,

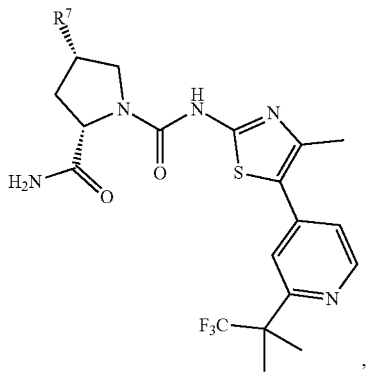

,

-continued

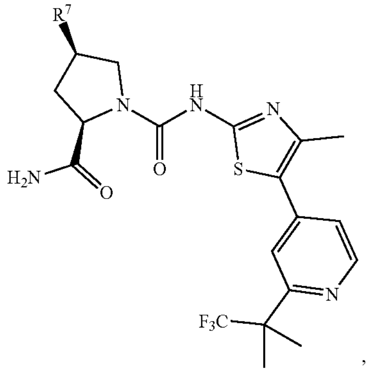

, or

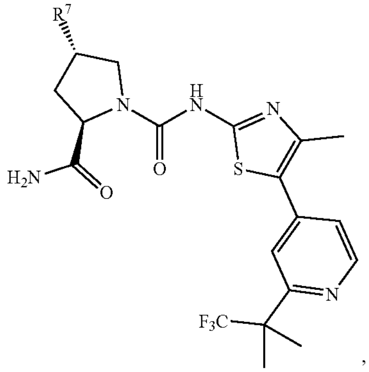

, or a pharmaceutically acceptable salt, hydrate, solvate, polymorph, co-crystal, tautomer, stereoisomer, isotopically labeled derivative, or prodrug thereof. In certain embodiments, $R^7$ is not hydrogen. In certain embodiments, $R^7$ is optionally substituted acyl. In certain embodiments, $R^7$ is $-C(=O)OR^{O2}$.

In certain embodiments, a compound of Formula (II) is of the following formula:

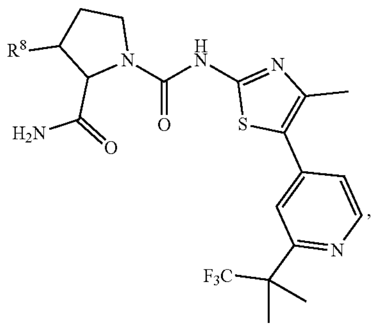

, or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is $-C(=O)OR^{O2}$.

In certain embodiments, a compound of Formula (II) is of one of the following formulae:

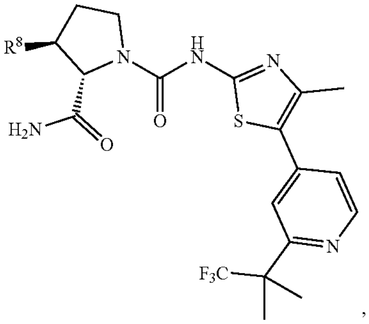

,

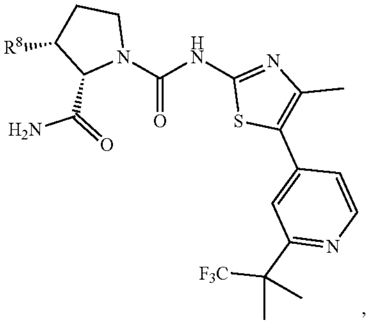

,

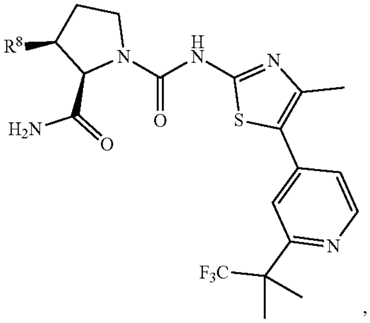

, or

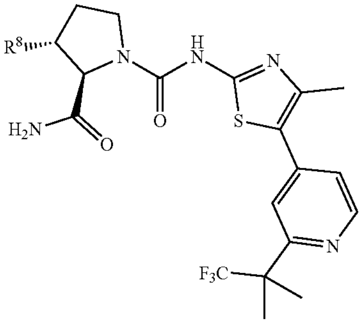

or a pharmaceutically acceptable salt, hydrate, solvate, polymorph, co-crystal, tautomer, stereoisomer, isotopically labeled derivative, or prodrug thereof. In certain embodiments, $R^8$ is not hydrogen. In certain embodiments, $R^8$ is optionally substituted acyl. In certain embodiments, $R^8$ is —C(═O)OR$^{O2}$.

In certain embodiments, for example, a compound of Formula (II) is selected from the group consisting of:

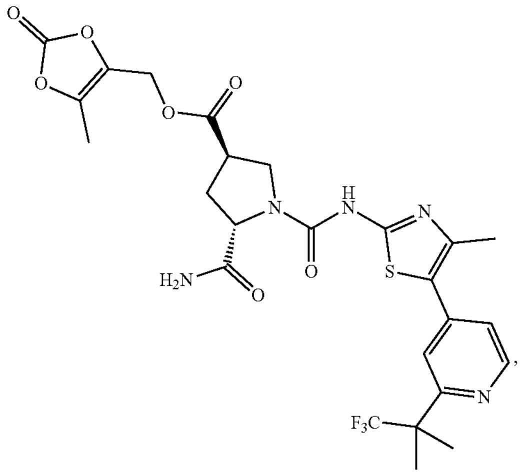

,

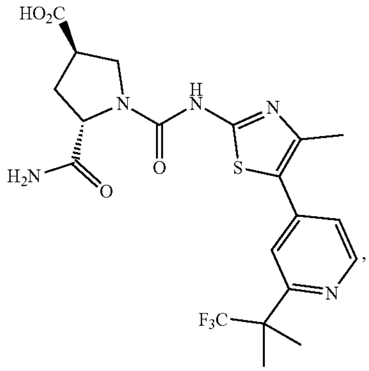

,

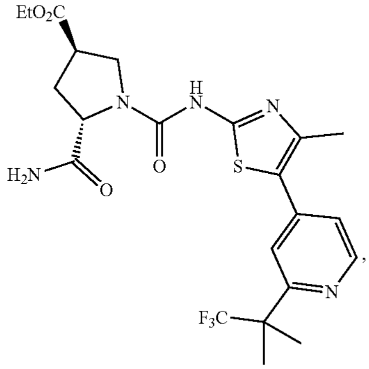

,

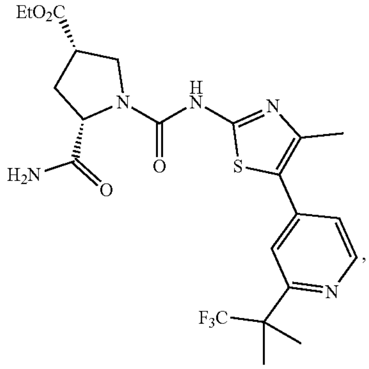

, and

-continued
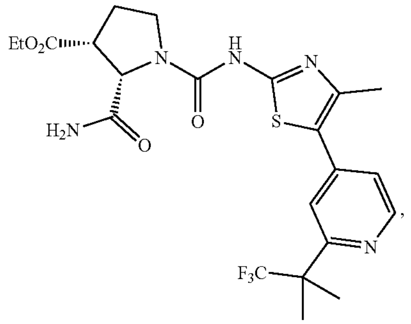 [SMILES: CCOC(=O)[C@@H]1CCN(C(=O)Nc2nc(C)c(-c3ccnc(C(C)(C)C(F)(F)F)c3)s2)[C@@H]1C(N)=O]
,
and pharmaceutically acceptable salts, hydrates, solvates, polymorphs, co-crystals, tautomers, stereoisomers, isotopically labeled derivatives, and prodrugs thereof.
In certain embodiments, for example, a compound of Formula (II) is selected from the group consisting of:
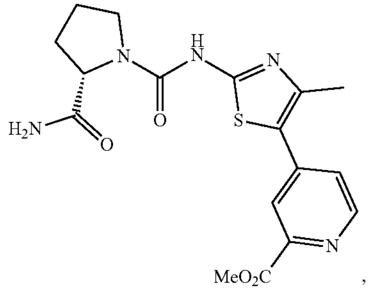
,
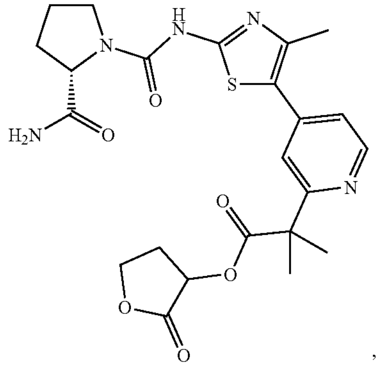
,
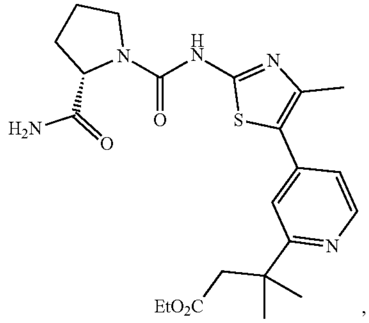
,
-continued
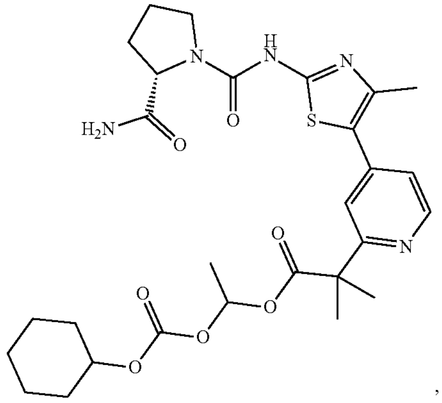
,
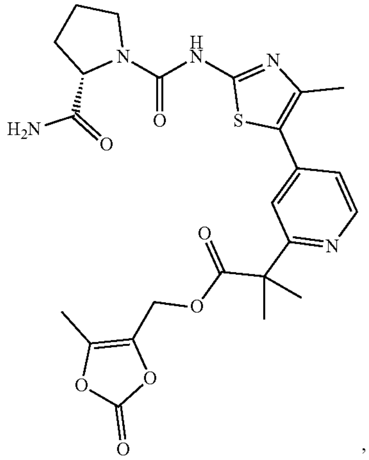
,
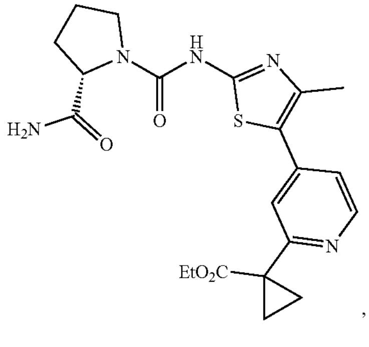
,
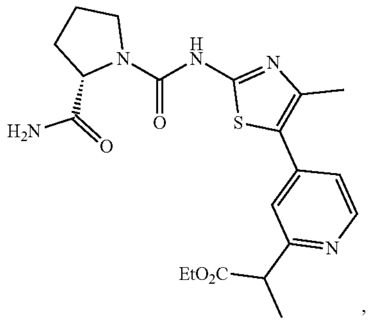
, -continued

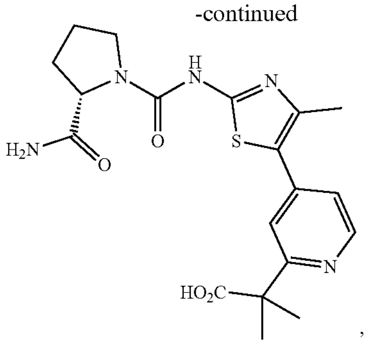

, and

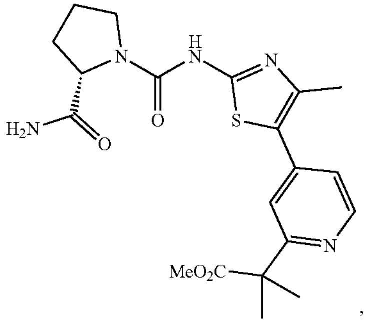 [SMILES: COC(=O)C(C)(C)c1cc(-c2sc(NC(=O)N3CCC[C@H]3C(N)=O)nc2C)ccn1]

, and pharmaceutically acceptable salts, hydrates, solvates, polymorphs, co-crystals, tautomers, stereoisomers, isotopically labeled derivatives, and prodrugs thereof.

Group $R^1$

As defined herein, $R^1$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$. In certain embodiments, $R^1$ is hydrogen. In certain embodiments, $R^1$ is halogen (e.g., —Cl, —Br, —F, —I). In certain embodiments, $R^1$ is —CN. In certain embodiments, $R^1$ is —$N_3$. In certain embodiments, $R^1$ is —$NO_2$. In certain embodiments, $R^1$ is optionally substituted alkenyl. In certain embodiments, $R^1$ is optionally substituted alkynyl. In certain embodiments, $R^1$ is optionally substituted carbocyclyl. In certain embodiments, $R^1$ is optionally substituted heterocyclyl. In certain embodiments, $R^1$ is optionally substituted aryl. In certain embodiments, $R^1$ is optionally substituted heteroaryl. In certain embodiments, $R^1$ is optionally substituted acyl. In certain embodiments, $R^1$ is —$OR^O$. In certain embodiments, $R^1$ is —$N(R^N)_2$. In certain embodiments, $R^1$ is —$SR^S$. In certain embodiments, $R^1$ is optionally substituted alkyl. In certain embodiments, $R^1$ is optionally substituted $C_{1-6}$ alkyl. In certain embodiments, $R^1$ is unsubstituted $C_{1-6}$ alkyl. In certain embodiments, $R^1$ is optionally substituted $C_{1-3}$ alkyl. In certain embodiments, $R^1$ is unsubstituted $C_{1-3}$ alkyl. In certain embodiments, $R^1$ is selected from the group consisting of methyl, ethyl, n-propyl, isopropyl, n-butyl, isobutyl, sec-butyl, and tert-butyl. In certain embodiments, $R^1$ is methyl. In certain embodiments, $R^1$ is ethyl.

Group $R^2$

As defined herein, $R^2$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$. In certain embodiments, $R^2$ is hydrogen. In certain embodiments, $R^2$ is halogen (e.g., —Cl, —Br, —F, —I). In certain embodiments, $R^2$ is —CN. In certain embodiments, $R^2$ is —$N_3$. In certain embodiments, $R^2$ is —$NO_2$. In certain embodiments, $R^2$ is optionally substituted alkenyl. In certain embodiments, $R^2$ is optionally substituted alkynyl. In certain embodiments, $R^2$ is optionally substituted carbocyclyl. In certain embodiments, $R^2$ is optionally substituted heterocyclyl. In certain embodiments, $R^2$ is optionally substituted aryl. In certain embodiments, $R^2$ is optionally substituted heteroaryl. In certain embodiments, $R^2$ is optionally substituted acyl. In certain embodiments, $R^2$ is —$OR^O$. In certain embodiments, $R^2$ is —$N(R^N)_2$. In certain embodiments, $R^2$ is —$SR^S$. In certain embodiments, $R^2$ is optionally substituted alkyl. In certain embodiments, $R^2$ is optionally substituted $C_{1-6}$ alkyl. In certain embodiments, $R^2$ is unsubstituted $C_{1-6}$ alkyl. In certain embodiments, $R^2$ is optionally substituted $C_{1-3}$ alkyl. In certain embodiments, $R^2$ is unsubstituted $C_{1-3}$ alkyl. In certain embodiments, $R^2$ is selected from the group consisting of methyl, ethyl, n-propyl, isopropyl, n-butyl, isobutyl, sec-butyl, and tert-butyl. In certain embodiments, $R^2$ is methyl. In certain embodiments, $R^2$ is isopropyl. In certain embodiments, $R^2$ is of the formula:

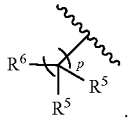

.

In certain embodiments, $R^2$ is of the formula:

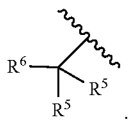

.

In certain embodiments, $R^2$ is of the formula:

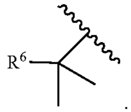

.

In certain embodiments, $R^2$ is of the formula:

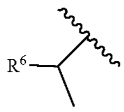

.

In certain embodiments, $R^2$ is of the formula:

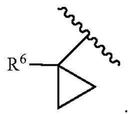

.

In certain embodiments, $R^2$ is of the formula:

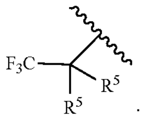

.

In certain embodiments, $R^2$ is of the formula:

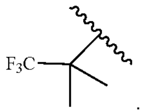 [SMILES: *C(C)(C)C(F)(F)F]

.

In certain embodiments, $R^2$ is of the formula:

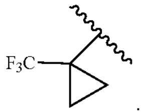 [SMILES: *C1(C(F)(F)F)CC1]

.

In certain embodiments, $R^2$ is of the formula:

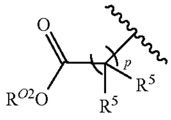

.

In certain embodiments, $R^2$ is of one of the following formulae:

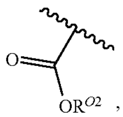

,

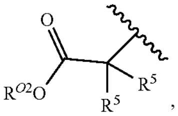

, or

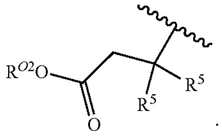

.

In certain embodiments, $R^2$ is of one of the following formulae:

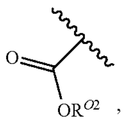

,

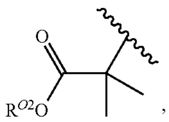

,

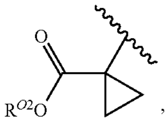

,

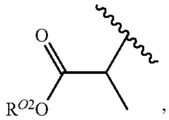

, or

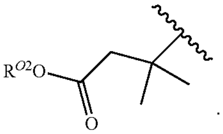

.

In certain embodiments $R^2$ is of one of the following formulae:

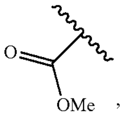

,

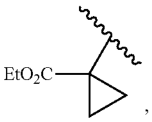

,

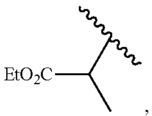

,

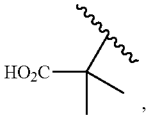

,

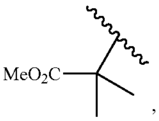

,

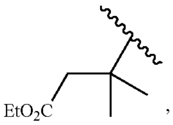

,

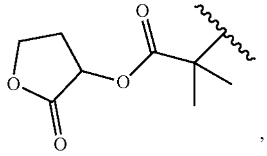

,

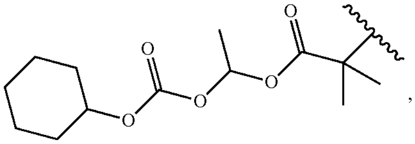

, or

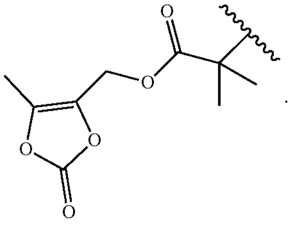

.

Group $R^3$ and n

As defined herein, each instance of $R^3$ is independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$. In certain embodiments, $R^3$ is hydrogen. In certain embodiments, $R^3$ is halogen (e.g., —Cl, —Br, —F, —I). In certain embodiments, $R^3$ is —CN. In certain embodiments, $R^3$ is optionally substituted alkenyl. In certain embodiments, $R^3$ is optionally substituted alkynyl. In certain embodiments, $R^3$ is optionally substituted carbocyclyl. In certain embodiments, $R^3$ is optionally substituted heterocyclyl. In certain embodiments, $R^3$ is optionally substituted aryl. In certain embodiments, $R^3$ is optionally substituted heteroaryl. In certain embodiments, $R^3$ is optionally substituted acyl. In certain embodiments, $R^3$ is —$OR^O$. In certain embodiments, $R^3$ is —$N(R^N)_2$. In certain embodiments, $R^3$ is —$SR^S$. In certain embodiments, $R^3$ is optionally substituted alkyl. In certain embodiments, $R^3$ is optionally substituted $C_{1-6}$ alkyl. In certain embodiments, $R^3$ is unsubstituted $C_{1-6}$ alkyl. In certain embodiments, $R^3$ is optionally substituted $C_{1-3}$ alkyl. In certain embodiments, $R^3$ is unsubstituted $C_{1-3}$ alkyl. In certain embodiments, $R^3$ is selected from the group consisting of methyl, ethyl, n-propyl, isopropyl, n-butyl, isobutyl, sec-butyl, and tert-butyl.

In certain embodiments, $R^3$ is of the formula:

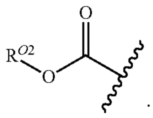
.

In certain embodiments, $R^3$ is selected from the group consisting of:

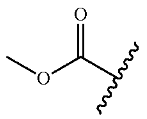
,
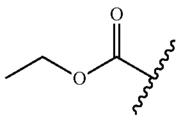
,
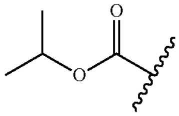
,
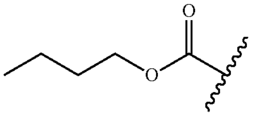
,
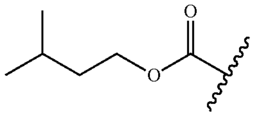
,
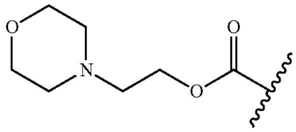
,
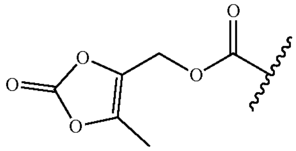
,
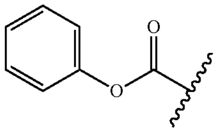
,
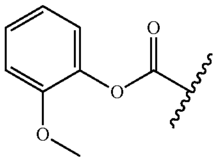
, and
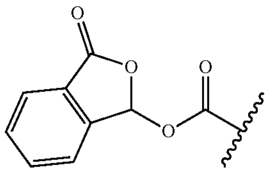
.

In certain embodiments, $R^3$ is $-CO_2H$. In certain embodiments, $R^3$ is $-CO_2Me$. In certain embodiments, $R^3$ is $-CO_2Et$. In certain embodiments, $R^3$ is $-CO_2$n-Pr. In certain embodiments, $R^3$ is $-CO_2$i-Pr. In certain embodiments, $R^3$ is $-CO_2$n-Bu. In certain embodiments, $R^3$ is $-CO_2$i-Bu. In certain embodiments, $R^3$ is $-CO_2$ sec-Bu. In certain embodiments, $R^3$ is $-CO_2$t-Bu. In certain embodiments, $R^3$ is of the formula:

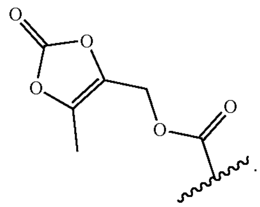 [SMILES: *C(=O)OCc1oc(=O)oc1C]
.

In certain embodiments, $R^3$ is of the formula:

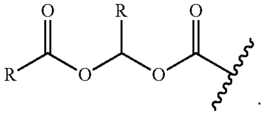
.

In certain embodiments, $R^3$ is selected from the group consisting of:

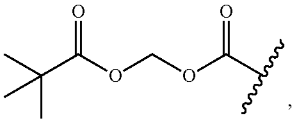
,
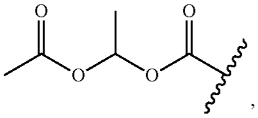
, and
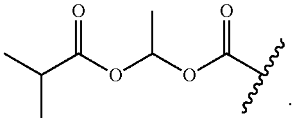
.

In certain embodiments, $R^3$ is of the formula:

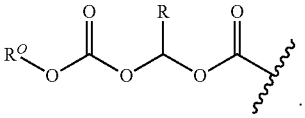
.

In certain embodiments, $R^3$ is of the formula:

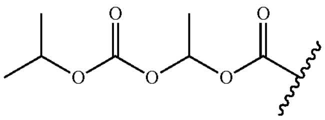
or
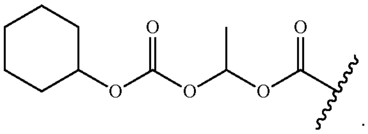
.

In certain embodiments, $R^3$ is of one of the following formulae:

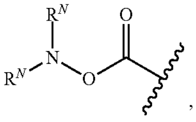, 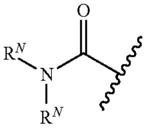, 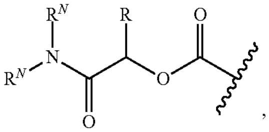, 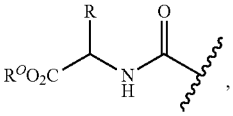, 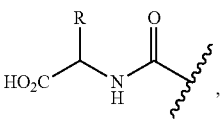, 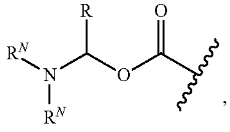, or 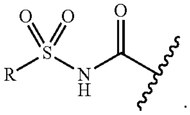.

As defined herein, n is 0, 1, 2, 3, 4, 5, 6, or 7. In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7.

Group $R^4$ and m

As defined herein, $R^4$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$. In certain embodiments, $R^4$ is hydrogen. In certain embodiments, $R^4$ is halogen (e.g., —Cl, —Br, —F, —I). In certain embodiments, $R^4$ is —CN. In certain embodiments, $R^4$ is —$N_3$. In certain embodiments, $R^4$ is —$NO_2$. In certain embodiments, $R^4$ is optionally substituted alkenyl. In certain embodiments, $R^4$ is optionally substituted alkynyl. In certain embodiments, $R^4$ is optionally substituted carbocyclyl. In certain embodiments, $R^4$ is optionally substituted heterocyclyl. In certain embodiments, $R^4$ is optionally substituted aryl. In certain embodiments, $R^4$ is optionally substituted heteroaryl. In certain embodiments, $R^4$ is optionally substituted acyl. In certain embodiments, $R^4$ is —$OR^O$. In certain embodiments, $R^4$ is —$N(R^N)_2$. In certain embodiments, $R^4$ is —$SR^S$. In certain embodiments, $R^4$ is optionally substituted alkyl. In certain embodiments, $R^4$ is optionally substituted $C_{1-6}$ alkyl. In certain embodiments, $R^4$ is unsubstituted $C_{1-6}$ alkyl. In certain embodiments, $R^4$ is optionally substituted $C_{1-3}$ alkyl. In certain embodiments, $R^4$ is unsubstituted $C_{1-3}$ alkyl. In certain embodiments, $R^4$ is selected from the group consisting of methyl, ethyl, n-propyl, isopropyl, n-butyl, isobutyl, sec-butyl, and tert-butyl. In certain embodiments, $R^4$ is methyl.

As defined herein, m is 0, 1, or 2. In certain embodiments, m is 0. In certain embodiments, m is 1. In certain embodiments, m is 2.

Group $R^5$ and p

As defined herein, each instance of $R^5$ is independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$; or two $R^5$ are joined together with the intervening atoms to form optionally substituted carbocyclyl or optionally substituted heterocyclyl. In certain embodiments, $R^5$ is hydrogen. In certain embodiments, $R^5$ is halogen (e.g., —Cl, —Br, —F, —I). In certain embodiments, $R^5$ is —CN. In certain embodiments, $R^5$ is optionally substituted alkenyl. In certain embodiments, $R^5$ is optionally substituted alkynyl. In certain embodiments, $R^5$ is optionally substituted carbocyclyl. In certain embodiments, $R^5$ is optionally substituted heterocyclyl. In certain embodiments, $R^5$ is optionally substituted aryl. In certain embodiments, $R^5$ is optionally substituted heteroaryl. In certain embodiments, $R^5$ is optionally substituted acyl. In certain embodiments, $R^5$ is —$OR^O$. In certain embodiments, $R^5$ is —$N(R^N)_2$. In certain embodiments, $R^5$ is —$SR^S$. In certain embodiments, $R^5$ is optionally substituted alkyl. In certain embodiments, $R^5$ is optionally substituted $C_{1-6}$ alkyl. In certain embodiments, $R^5$ is unsubstituted $C_{1-6}$ alkyl. In certain embodiments, $R^5$ is optionally substituted $C_{1-3}$ alkyl. In certain embodiments, $R^5$ is unsubstituted $C_{1-3}$ alkyl. In certain embodiments, $R^5$ is selected from the group consisting of methyl, ethyl, n-propyl, isopropyl, n-butyl, isobutyl, sec-butyl, and tert-butyl. In certain embodiments, both instances of $R^5$ are methyl. In certain embodiments, one instance of $R^5$ is methyl, and the other is hydrogen. In certain embodiments, two $R^5$ are joined together with the intervening atoms to form optionally substituted carbocyclyl. In certain embodiments, two $R^5$ are joined together with the intervening atoms to form optionally substituted optionally substituted heterocyclyl. In certain embodiments, two $R^S$ are joined together with the intervening atoms to form one of the following structures:

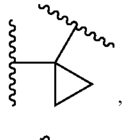, 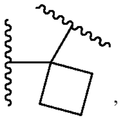, 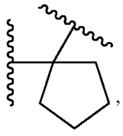, and 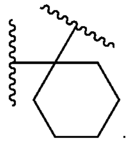.

As defined herein, p is 0, 1, or 2. In certain embodiments, p is 0. In certain embodiments, p is 1. In certain embodiments, p is 2.

Group $R^6$

As defined herein, $R^6$ is hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$. In certain embodiments, $R^6$ is hydrogen. In certain embodiments, $R^6$ is halogen (e.g., —Cl, —Br, —F, —I). In certain embodiments, $R^6$ is —CN. In certain embodiments, $R^6$ is optionally substituted alkenyl. In certain embodiments, $R^6$ is optionally substituted alkynyl. In certain embodiments, $R^6$ is optionally substituted carbocyclyl. In certain embodiments, $R^6$ is optionally substituted heterocyclyl. In certain embodiments, $R^6$ is optionally substituted aryl. In certain embodiments, $R^6$ is optionally substituted heteroaryl. In certain embodiments, $R^6$ is optionally substituted acyl. In certain embodiments, $R^6$ is —$OR^O$. In certain embodiments, $R^6$ is —$N(R^N)_2$. In certain embodiments, $R^6$ is —$SR^S$. In certain embodiments, $R^6$ is optionally substituted alkyl. In certain embodiments, $R^6$ is optionally substituted $C_{1-6}$ alkyl. In certain embodiments, $R^6$ is unsubstituted $C_{1-6}$ alkyl. In certain embodiments, $R^6$ is optionally substituted $C_{1-3}$ alkyl. In certain embodiments, $R^6$ is unsubstituted $C_{1-3}$ alkyl. In certain embodiments, $R^6$ is selected from the group consisting of methyl, ethyl, n-propyl, isopropyl, n-butyl, isobutyl, sec-butyl, and tert-butyl.

In certain embodiments, $R^6$ is haloalkyl, —$C(=O)OR^{O2}$, —$(C(R^S)_2)_pC(=O)OR^{O2}$, $OR^O$, —$N(R^N)_2$, or —$SR^S$. In certain embodiments, $R^6$ is haloalkyl. In certain embodiments, $R^6$ is perhaloalkyl. In certain embodiments, $R^6$ is perfluoroalkyl. In certain embodiments, $R^6$ is trihalomethyl. In certain embodiments, $R^6$ is trifluoromethyl (—$CF_3$). In certain embodiments, $R^6$ is —$CHF_2$ or —$CH_2F$. In certain embodiments, $R^6$ is —$C(=O)OR^{O2}$. In certain embodiments, $R^6$ is —$(C(R^S)_2)_pC(=O)OR^{O2}$. In certain embodiments, $R^6$ is —$CH_2C(=O)OR^{O2}$. In certain embodiments, $R^6$ is —$OR^O$. In certain embodiments, $R^6$ is —$N(R^N)_2$. In certain embodiments, $R^6$ is —$SR^S$. In certain embodiments, $R^6$ is of one of the following formulae: —$CO_2Et$, —$CO_2Me$, —$CO_2H$, —$CH_2CO_2Et$, —$CH_2CO_2Me$, —$CH_2CO_2H$,

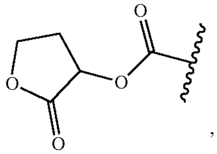
,
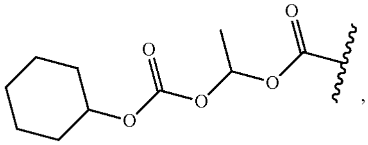
, or
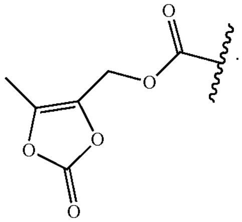

In certain embodiments, $R^6$ is of the formula:

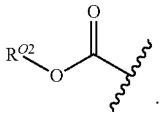

In certain embodiments, $R^6$ is selected from the group consisting of:

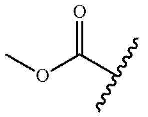
,
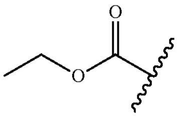
,

-continued

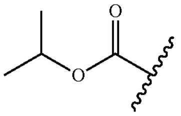
,
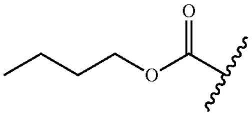
,
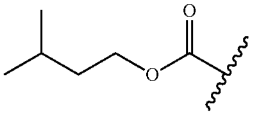
,
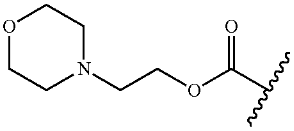
,
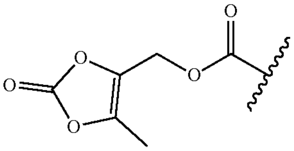
,
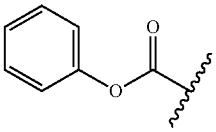
,
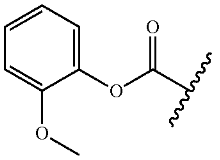
, and
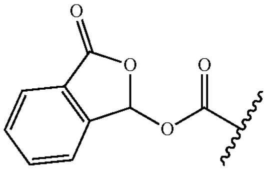

In certain embodiments, $R^6$ is of the formula:

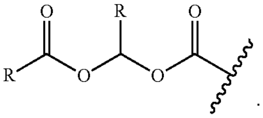

In certain embodiments, $R^6$ is selected from the group consisting of:

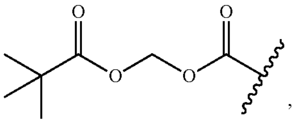
,
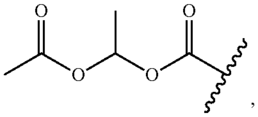
, and
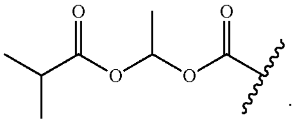

In certain embodiments, $R^6$ is of the formula:

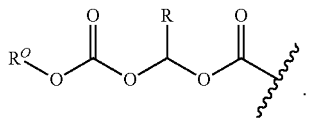

In certain embodiments, $R^6$ is of the formula:

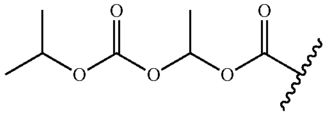

or

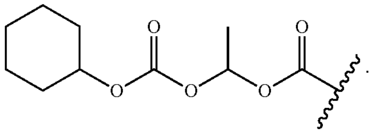

In certain embodiments, $R^6$ is of one of the following formulae:

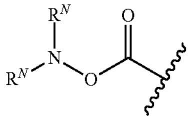

,

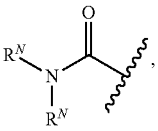

,

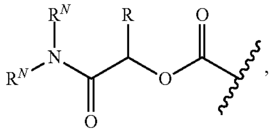

,

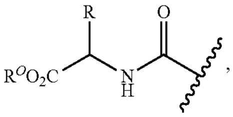

,

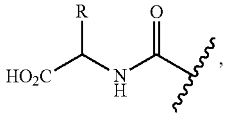

,

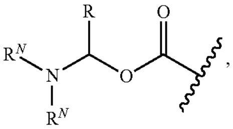

, or

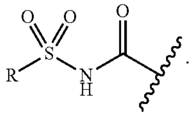

Groups $R^7$ and $R^8$

As defined herein, $R^7$ is hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $—OR^O$, $—N(R^N)_2$, or $—SR^S$. In certain embodiments, $R^7$ is hydrogen. In certain embodiments, $R^7$ is halogen (e.g., —Cl, —Br, —F, —I). In certain embodiments, $R^7$ is —CN. In certain embodiments, $R^7$ is optionally substituted alkenyl. In certain embodiments, $R^7$ is optionally substituted alkynyl. In certain embodiments, $R^7$ is optionally substituted carbocyclyl. In certain embodiments, $R^7$ is optionally substituted heterocyclyl. In certain embodiments, $R^7$ is optionally substituted aryl. In certain embodiments, $R^7$ is optionally substituted heteroaryl. In certain embodiments, $R^7$ is optionally substituted acyl. In certain embodiments, $R^7$ is $—OR^O$. In certain embodiments, $R^7$ is $—N(R^N)_2$. In certain embodiments, $R^7$ is $—SR^S$. In certain embodiments, $R^7$ is optionally substituted alkyl. In certain embodiments, $R^7$ is optionally substituted $C_{1-6}$ alkyl. In certain embodiments, $R^7$ is unsubstituted $C_{1-6}$ alkyl. In certain embodiments, $R^7$ is optionally substituted $C_{1-3}$ alkyl. In certain embodiments, $R^7$ is unsubstituted $C_{1-3}$ alkyl. In certain embodiments, $R^7$ is selected from the group consisting of methyl, ethyl, n-propyl, isopropyl, n-butyl, isobutyl, sec-butyl, and tert-butyl.

In certain embodiments, $R^7$ is of the formula:

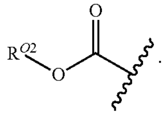

In certain embodiments, $R^7$ is selected from the group consisting of:

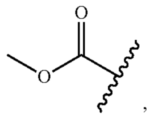

,

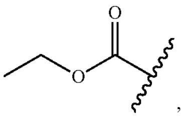

,

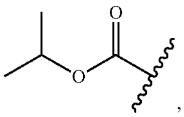

,

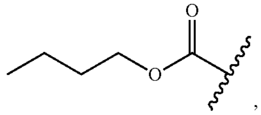

,

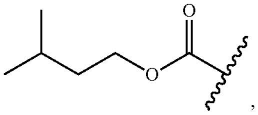

,

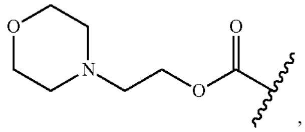

,

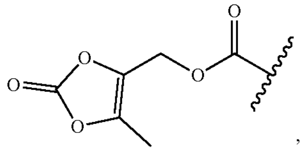

,

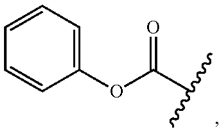

,

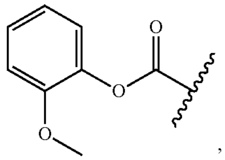

,

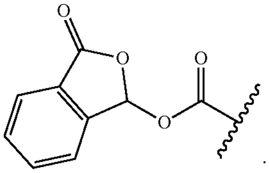

In certain embodiments, $R^7$ is $—CO_2H$. In certain embodiments, $R^7$ is $—CO_2Me$. In certain embodiments, $R^7$ is $—CO_2Et$. In certain embodiments, $R^7$ is $—CO_2n\text{-Pr}$. In certain embodiments, $R^7$ is $—CO_2i\text{-Pr}$. In certain embodiments, $R^7$ is $—CO_2n\text{-Bu}$. In certain embodiments, $R^7$ is $—CO_2i\text{-Bu}$. In certain embodiments, $R^7$ is $—CO_2$ sec-Bu. In certain embodiments, $R^7$ is $—CO_2t\text{-Bu}$. In certain embodiments, $R^7$ is of the formula:

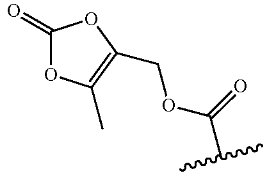

In certain embodiments, $R^7$ is of the formula:

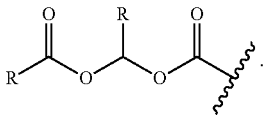

In certain embodiments, $R^7$ is selected from the group consisting of:

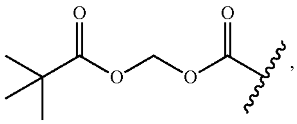,

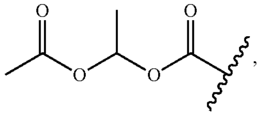, and

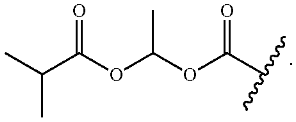.

In certain embodiments, $R^7$ is of the formula:

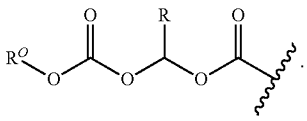

In certain embodiments, $R^7$ is of the formula: or

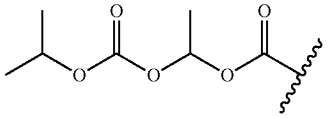 or

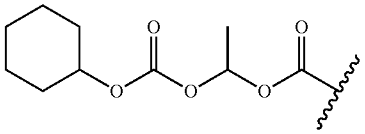.

In certain embodiments, $R^7$ is of one of the following formulae:

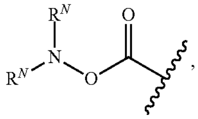, 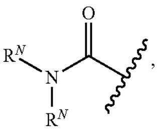,

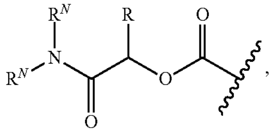, 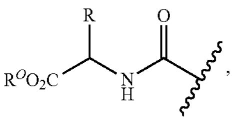,

-continued

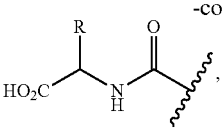, 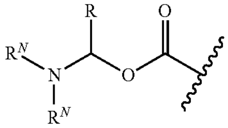, or

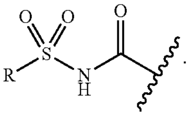.

As defined herein, $R^8$ is hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$. In certain embodiments, $R^8$ is hydrogen. In certain embodiments, $R^8$ is halogen (e.g., —Cl, —Br, —F, —I). In certain embodiments, $R^8$ is —CN. In certain embodiments, $R^8$ is optionally substituted alkenyl. In certain embodiments, $R^8$ is optionally substituted alkynyl. In certain embodiments, $R^8$ is optionally substituted carbocyclyl. In certain embodiments, $R^8$ is optionally substituted heterocyclyl. In certain embodiments, $R^8$ is optionally substituted aryl. In certain embodiments, $R^8$ is optionally substituted heteroaryl. In certain embodiments, $R^8$ is optionally substituted acyl. In certain embodiments, $R^8$ is —$OR^O$. In certain embodiments, $R^8$ is —$N(R^N)_2$. In certain embodiments, $R^8$ is —$SR^S$. In certain embodiments, $R^8$ is optionally substituted alkyl. In certain embodiments, $R^8$ is optionally substituted $C_{1-6}$ alkyl. In certain embodiments, $R^8$ is unsubstituted $C_{1-6}$ alkyl. In certain embodiments, $R^8$ is optionally substituted $C_{1-3}$ alkyl. In certain embodiments, $R^8$ is unsubstituted $C_{1-3}$ alkyl. In certain embodiments, $R^8$ is selected from the group consisting of methyl, ethyl, n-propyl, isopropyl, n-butyl, isobutyl, sec-butyl, and tert-butyl.

In certain embodiments, $R^8$ is of the formula:

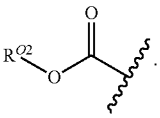.

In certain embodiments, $R^8$ is selected from the group consisting of:

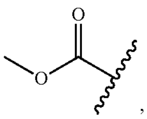, 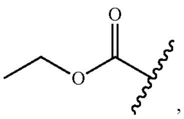, 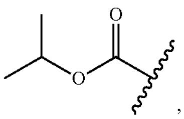,

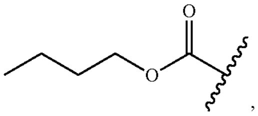, 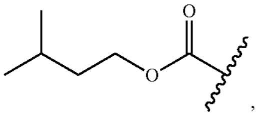,

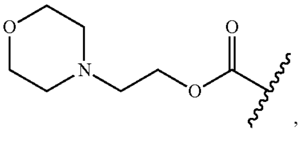,

-continued

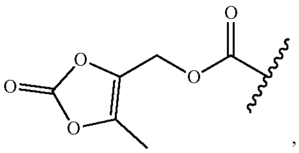,
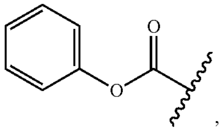,
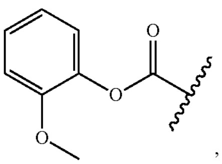,
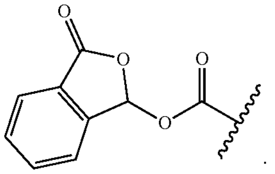.

In certain embodiments, $R^8$ is —$C_2H$. In certain embodiments, $R^8$ is —$CO_2Me$. In certain embodiments, $R^8$ is —$CO_2Et$. In certain embodiments, $R^8$ is —$CO_2$n-Pr. In certain embodiments, $R^8$ is —$CO_2$i-Pr. In certain embodiments, $R^8$ is —$CO_2$n-Bu. In certain embodiments, $R^8$ is —$CO_2$i-Bu. In certain embodiments, $R^8$ is —$CO_2$ sec-Bu. In certain embodiments, $R^8$ is —$CO_2$t-Bu. In certain embodiments, $R^8$ is of the formula:

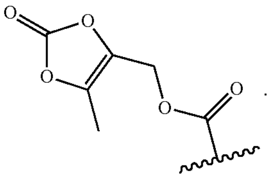 [SMILES: *C(=O)OCc1oc(=O)oc1C].

In certain embodiments, $R^8$ is of the formula:

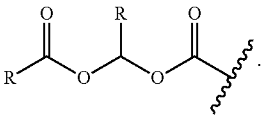.

In certain embodiments, $R^8$ is selected from the group consisting of:

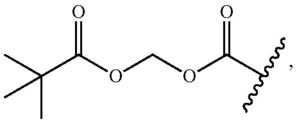,
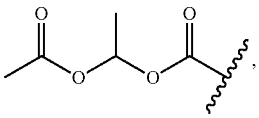, and
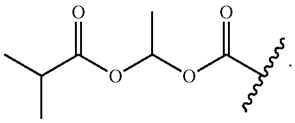.

In certain embodiments, $R^8$ is of the formula:

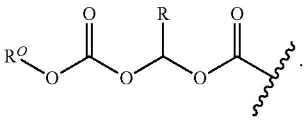.

In certain embodiments, $R^8$ is of the formula:

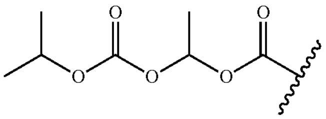 or
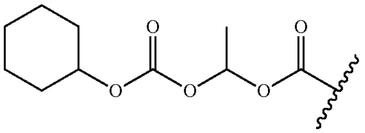.

In certain embodiments, $R^8$ is of one of the following formulae:

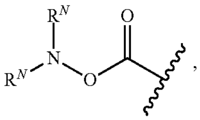,
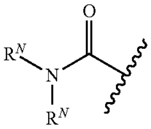,
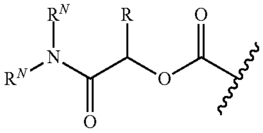,
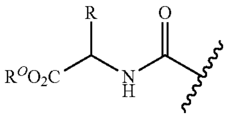,
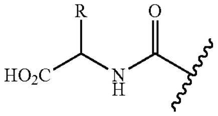,
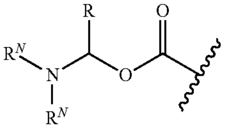, or
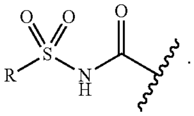.

In certain embodiments, $R^7$ is hydrogen and $R^8$ is optionally substituted acyl. In certain embodiments, $R^7$ is hydrogen and $R^8$ is of the formula:

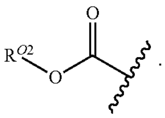.

In certain embodiments, $R^8$ is hydrogen and $R^7$ is optionally substituted acyl. In certain embodiments, $R^8$ is hydrogen and $R^7$ is of the formula:

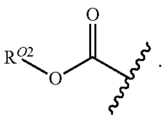.

Groups $R^N$, $R^{N1}$, $R^{N2}$, $R^O$, $R^{O2}$, $R^S$, and R

As defined herein, each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are joined together with the intervening atoms to form optionally substituted heterocyclyl or optionally substituted heteroaryl. In certain embodiments, $R^N$ is hydrogen. In certain embodiments, $R^N$ is optionally substituted alkyl. In certain embodiments, $R^N$ is optionally substituted alkenyl. In certain embodiments, $R^N$ is optionally substituted alkynyl. In certain embodiments, $R^N$ is optionally substituted carbocyclyl. In certain embodiments, $R^N$ is optionally substituted heterocyclyl. In certain embodiments, $R^N$ is optionally substituted aryl. In certain embodiments, $R^N$ is optionally substituted heteroaryl. In certain embodiments, $R^N$ is optionally substituted acyl. In certain embodiments, $R^N$ is a nitrogen protecting group. In certain embodiments, two $R^N$ on the same nitrogen atom are joined together with the intervening atoms to form optionally substituted heterocyclyl. In certain embodiments, two $R^N$ on the same nitrogen atom are joined together with the intervening atoms to form optionally substituted heteroaryl.

As defined herein, $R^{N1}$ is hydrogen, optionally substituted alkyl, optionally substituted acyl, or a nitrogen protecting group. In certain embodiments, $R^{N1}$ is hydrogen. In certain embodiments, $R^{N1}$ is optionally substituted alkyl. In certain embodiments, $R^{N1}$ is optionally substituted acyl. In certain embodiments, $R^{N1}$ is a nitrogen protecting group.

As defined herein, each instance of $R^{N2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{N2}$ are joined together with the intervening atoms to form optionally substituted heterocyclyl or optionally substituted heteroaryl. In certain embodiments, $R^{N2}$ is hydrogen. In certain embodiments, $R^{N2}$ is optionally substituted alkyl. In certain embodiments, $R^{N2}$ is optionally substituted alkenyl. In certain embodiments, $R^{N2}$ is optionally substituted alkynyl. In certain embodiments, $R^{N2}$ is optionally substituted carbocyclyl. In certain embodiments, $R^{N2}$ is optionally substituted heterocyclyl. In certain embodiments, $R^{N2}$ is optionally substituted aryl. In certain embodiments, $R^{N2}$ is optionally substituted heteroaryl. In certain embodiments, $R^{N2}$ is optionally substituted acyl. In certain embodiments, $R^{N2}$ is a nitrogen protecting group. In certain embodiments, two $R^{N2}$ on the same nitrogen atom are joined together with the intervening atoms to form optionally substituted heterocyclyl. In certain embodiments, two $R^{N2}$ on the same nitrogen atom are joined together with the intervening atoms to form optionally substituted heteroaryl. In certain embodiments, each $R^{N2}$ is hydrogen.

As defined herein, each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group. In certain embodiments, $R^O$ is hydrogen. In certain embodiments, $R^O$ is optionally substituted alkyl. In certain embodiments, $R^O$ is optionally substituted alkenyl. In certain embodiments, $R^O$ is optionally substituted alkynyl. In certain embodiments, $R^O$ is optionally substituted carbocyclyl. In certain embodiments, $R^O$ is optionally substituted heterocyclyl. In certain embodiments, $R^O$ is optionally substituted aryl. In certain embodiments, $R^O$ is optionally substituted heteroaryl. In certain embodiments, $R^O$ is optionally substituted acyl. In certain embodiments, $R^O$ is an oxygen protecting group.

As defined herein, each instance of $R^{O2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group. In certain embodiments, $R^{O2}$ is hydrogen. In certain embodiments, $R^{O2}$ is optionally substituted alkyl. In certain embodiments, $R^{O2}$ is optionally substituted alkenyl. In certain embodiments, $R^{O2}$ is optionally substituted alkynyl. In certain embodiments, $R^O$ is optionally substituted carbocyclyl. In certain embodiments, $R^{O2}$ is optionally substituted heterocyclyl. In certain embodiments, $R^{O2}$ is optionally substituted aryl. In certain embodiments, $R^{O2}$ is optionally substituted heteroaryl. In certain embodiments, $R^{O2}$ is optionally substituted acyl. In certain embodiments, $R^{O2}$ is an oxygen protecting group. In certain embodiments, $R^{O2}$ is optionally substituted $C_{1-6}$ alkyl. In certain embodiments, $R^{O2}$ is unsubstituted $C_{1-6}$ alkyl. In certain embodiments, $R^{O2}$ is optionally substituted $C_{1-3}$ alkyl. In certain embodiments, $R^{O2}$ is unsubstituted $C_{1-3}$ alkyl. In certain embodiments, $R^{O2}$ is selected from the group consisting of methyl, ethyl, n-propyl, isopropyl, n-butyl, isobutyl, sec-butyl, and tert-butyl. In certain embodiments, $R^{O2}$ is methyl. In certain embodiments, $R^{O2}$ is ethyl. In certain embodiments, $R^{O2}$ is of one of the following formulae:

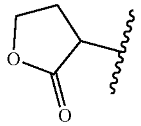,
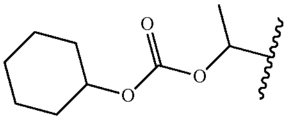, or
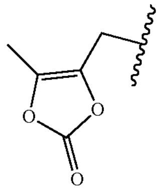.

In certain embodiments, $R^{O2}$ is selected from the group consisting of:

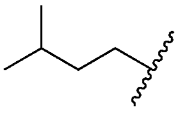,
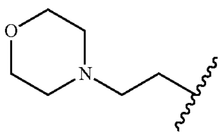,
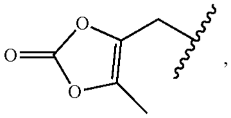,
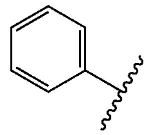,

-continued

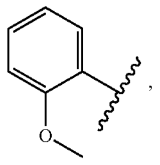

, and

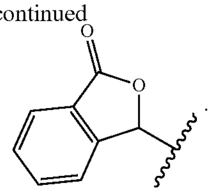

In certain embodiments, $R^{O2}$ is of the formula:

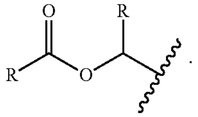

In certain embodiments, $R^{O2}$ is selected from the group consisting of:

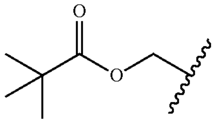

,

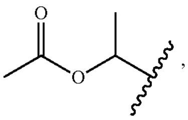

,

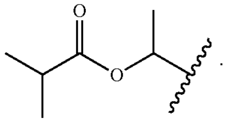

In certain embodiments, $R^{O2}$ is of the formula:

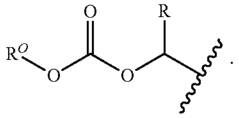

In certain embodiments, $R^{O2}$ is of the formula:

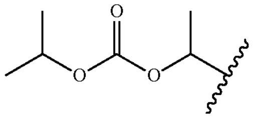

or

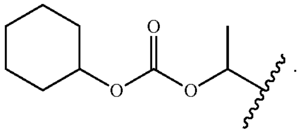

As defined herein, each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group. In certain embodiments, $R^S$ is hydrogen. In certain embodiments, $R^S$ is optionally substituted alkyl. In certain embodiments, $R^S$ is optionally substituted alkenyl. In certain embodiments, $R^S$ is optionally substituted alkynyl. In certain embodiments, $R^S$ is optionally substituted carbocyclyl. In certain embodiments, $R^S$ is optionally substituted heterocyclyl. In certain embodiments, $R^S$ is optionally substituted aryl. In certain embodiments, $R^S$ is optionally substituted heteroaryl. In certain embodiments, $R^S$ is optionally substituted acyl. In certain embodiments, $R^S$ is a sulfur protecting group.

As generally defined herein, each instance of R is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or optionally substituted acyl. In certain embodiments, R is hydrogen. In certain embodiments, R is optionally substituted alkyl. In certain embodiments, R is optionally substituted alkenyl. In certain embodiments, R is optionally substituted alkynyl. In certain embodiments, R is optionally substituted carbocyclyl. In certain embodiments, R is optionally substituted heterocyclyl. In certain embodiments, R is optionally substituted aryl. In certain embodiments, R is optionally substituted heteroaryl. In certain embodiments, R is or optionally substituted acyl. In certain embodiments, R is optionally substituted $C_{1-6}$ alkyl. In certain embodiments, R is unsubstituted $C_{1-6}$ alkyl. In certain embodiments, R is optionally substituted $C_{1-3}$ alkyl. In certain embodiments, R is unsubstituted $C_{1-3}$ alkyl. In certain embodiments, R is selected from the group consisting of methyl, ethyl, n-propyl, isopropyl, n-butyl, isobutyl, sec-butyl, and tert-butyl.

Nanoparticles and Nanogels

Provided herein are nanoparticles and nanogels comprising a PI3K inhibitor (e.g., PI3Kα inhibitor). In certain embodiments, the PI3K inhibitor is a small molecule. In certain embodiments, the PI3K inhibitor is a compound provided herein. Any PI3K inhibitor known in the art may be formulated in a nanoparticle or nanogel provided herein. In certain embodiments, the PI3K inhibitor is BYL719. In one aspect, provided herein are nanoparticles and nanogels comprising a compound of Formula (I) or (II), or a pharmaceutically acceptable salt, solvate, hydrate, polymorph, co-crystal, tautomer, stereoisomer, isotopically labeled derivative, or prodrug thereof. In one aspect, provided herein are polymeric nanoparticles and nanogels comprising a compound of Formula (I) or (II), or a pharmaceutically acceptable salt, solvate, hydrate, polymorph, co-crystal, tautomer, stereoisomer, isotopically labeled derivative, or prodrug thereof, that are capable of targeting to P-selectin and, therefore, are useful in the treatment of diseases and conditions associated with cells expressing P-selectin (e.g., cancer).

Examples of types of nanoparticles provided herein include, but are not limited to, polymeric particles, lipid nanoparticles, liposomes, micelles, dendrimers, amphiphilic particles, liquid-filled particles, solid particles, ceramic particles, carbon-based particles and nanotubes, metal particles, metal oxide particles, silica particles, quantum dots, layered particles, and composite or hybrid particles.

In certain embodiments, the nanoparticles and nanogels provided herein have an affinity for P-selectin and can therefore be used to treat diseases associated with cells expressing P-selectin (e.g., proliferative diseases, such as cancer). In certain embodiments, the nanoparticles and nanogels comprise a sulfated polymer comprising free hydroxyl moieties and sulfate moieties capable of targeting P-selectin. In certain embodiments, the sulfated polymer is a fucoidan polymer (e.g., a sulfated polysaccharide comprising sulfated ester moieties of fucose). In other aspects, provided herein are pharmaceutical compositions comprising a nanogel or a plurality of nanoparticles described herein.

Description of nanoparticles and nanogels useful in the present invention can be found in International Application Publication No. WO 2015/161192, published Oct. 22, 2015, the entire contents of which are incorporated herein by reference.

Without wishing to be bound to any particular theory, specific affinity to P-selectin requires both free hydroxyls and a proximate negative charge. Thus, presented herein are nanoparticles and nanogels comprising a PI3K inhibitor (e.g., a compound of Formula (I) or (II), or a pharmaceutically acceptable salt, solvate, hydrate, polymorph, co-crystal, tautomer, stereoisomer, isotopically labeled derivative, or prodrug thereof), having hydroxyls and sulfates that are free for targeting P-selectin. Furthermore, in certain embodiments, the nanoparticles and nanogels useful in the present invention offer a drug release mechanism based on acidic pH in the microenvironment of a tumor, thereby providing improved treatment targeting capability and allowing the use of lower drug doses, thereby reducing toxicity.

P-selectin is a new target for drug delivery in various cancers and contributes both at the tissue level and the cellular level. Since P-selectin is highly involved in inflammatory processes, the present invention is useful in the treatment of inflammatory diseases, such as arthritis and atherosclerosis, which involve P-selectin on endothelial cells. P-selectin is a cell adhesion molecule known to facilitate metastasis which is expressed in the vasculature of many human tumors. In certain embodiments, the nanoparticles target primary and metastatic tumors to impart a significant anti-tumor activity compared to untargeted nanoparticles encapsulating existing chemotherapies. In certain embodiments, ionizing radiation induced P-selectin expression guides the targeted nanoparticles to the tumor site, demonstrating a potential strategy to target disparate drug classes to almost any tumor.

In certain embodiments, the nanoparticles and nanogels described herein present fucoidan on their surface, specifically targeting P-selectin on cells (e.g., cancer or tumor cells). The fucoidan on the surface of the nanoparticles and nanogels have free hydroxyl moieties and free sulfate moieties. In certain embodiments, the nanoparticles and nanogels release the drug they contain (e.g., a PI3K inhibitor, a compound of Formula (I) or (II), or a pharmaceutically acceptable salt, solvate, hydrate, polymorph, co-crystal, tautomer, stereoisomer, isotopically labeled derivative, or prodrug thereof) in the acidic tumor microenvironment and lysosomes. In certain embodiments, the fucoidan also appears to act as an immunomodulator, inducing an immune response against the tumor. The particle size and charge can be modified according to the intended use.

In a certain embodiment, a fucoidan-based nanoparticle or nanogel is provided that delivers a PI3K inhibitor (e.g., compound of Formula (I) or (II), or a pharmaceutically acceptable salt, solvate, hydrate, polymorph, co-crystal, tautomer, stereoisomer, isotopically labeled derivative, or prodrug thereof). In certain embodiments, the compound is encapsulated by the nanoparticle. In certain embodiments, the compound is electrostatically associated with the nanoparticle. In certain embodiments, the compound is non-covalently associated with the nanoparticle or nanogel. In certain embodiments, the compound is covalently associated with the nanoparticle or nanogel.

In certain embodiments, a nanoparticle or nanogel is synthesized by non-covalent assembly of fucoidan with the compound to be delivered (e.g., a compound of Formula (I) or (II), or a pharmaceutically acceptable salt, solvate, hydrate, polymorph, co-crystal, tautomer, stereoisomer, isotopically labeled derivative, or prodrug thereof). In certain embodiments, the nanoparticle or nanogel encapsulates the compound.

In certain embodiments, provided herein is a polymeric nanoparticle with affinity to P-selectin, the nanoparticle comprising: (i) a sulfated polymer species comprising free hydroxyl moieties and sulfate moieties capable of targeting to P-selectin; and (ii) a PI3K inhibitor (e.g., PI3Kα inhibitor), or a pharmaceutically acceptable salt, solvate, hydrate, polymorph, co-crystal, tautomer, stereoisomer, isotopically labeled derivative, or prodrug thereof. In certain embodiments, provided herein is a polymeric nanoparticle with affinity to P-selectin, the nanoparticle comprising: (i) a sulfated polymer species comprising free hydroxyl moieties and sulfate moieties capable of targeting to P-selectin; and (ii) a compound of Formula (I) or (II), or a pharmaceutically acceptable salt, solvate, hydrate, polymorph, co-crystal, tautomer, stereoisomer, isotopically labeled derivative, or prodrug thereof. In certain embodiments, the sulfated polymer species is a sulfated polysaccharide and/or protein. In certain embodiments, the drug is a cationic drug. In certain embodiments, the sulfated polymer species is a fucoidan. In certain embodiments, the nanoparticle comprises fucoidan on the surface of nanoparticle. In certain embodiments, the fucoidan is a sulfated polysaccharide comprising sulfated ester moieties of fucose. In certain embodiments, the nanoparticle comprises nanoparticles that have a core comprising albumin, and a surface comprising fucoidan. In certain embodiments, the nanoparticle comprises polyethylene glycol (PEG), wherein the active compound is conjugated to the polyethylene glycol.

In certain embodiments, the nanoparticle comprises particles having an average particle diameter of from about 20 nm to about 400 nm (e.g., from about 100 nm to about 200 nm, or from about 150 nm to about 170 nm).

In certain embodiments, the nanoparticle or nanogel further comprises a fluorophore. In certain embodiments, the fluorophore is a near infra-red dye. In certain embodiments, the near infra-red dye is IR783 (2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide, inner salt sodium salt). Other examples of dyes include, but are not limited to, IR820, IR783, ICG, and Brilliant Blue G, the structures of which are provided herein.

Pharmaceutical Compositions, Kits, and Administration

The present disclosure provides pharmaceutical compositions comprising a compound of Formula (I) or (II), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical composition described herein comprises a compound of Formula (I) or (II), or a pharmaceutically acceptable salt, solvate, hydrate, polymorph, co-crystal, tautomer, stereoisomer, isotopically labeled derivative, or prodrug thereof, and a pharmaceutically acceptable excipient.

The present disclosure also provides pharmaceutical compositions comprising a plurality of nanoparticles provided herein, or a nanogel provided herein, and optionally a pharmaceutically acceptable excipient. In certain embodiments, the pharmaceutical composition described herein comprises a plurality of nanoparticles provided herein, and a pharmaceutically acceptable excipient.

In certain embodiments, the compound, nanoparticle, or nanogel described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating an inflammatory disease or proliferative disease (e.g., cancer) in a subject in need thereof. In certain embodiments, the effective amount is an amount effective for preventing an inflammatory disease or proliferative disease (e.g., cancer) in a subject in need thereof.

Pharmaceutical compositions described herein can be prepared by any method known in the art of pharmacology. In general, such preparatory methods include bringing the compound, nanoparticle, or nanogel described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and VEEGUM® (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (TWEEN® 20), polyoxyethylene sorbitan (TWEEN® 60), polyoxyethylene sorbitan monooleate (TWEEN® 80), sorbitan monopalmitate (SPAN® 40), sorbitan monostearate (SPAN® 60), sorbitan tristearate (SPAN® 65), glyceryl monooleate, sorbitan monooleate (SPAN® 80), polyoxyethylene esters (e.g., polyoxyethylene monostearate (MYRJ® 45), polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether (BRIJ® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT® PLUS, PHENONIP®, methylparaben, GERMALL® 115, GERMABEN® II, NEOLONE®, KATHON®, and EUXYL®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as CREMOPHOR®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents, such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds, compositions, nanoparticles, and nanogels provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds, compositions, nanoparticles, nanogels, and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound, compositions, nanoparticle, or nanogel required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound, nanoparticle, or nanogel described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound, composition, nanoparticle, nanogel, or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound, composition, nanoparticle, nanogel, or pharmaceutical composition thereof can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., inflammatory disease, proliferative disease such as cancer). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is an binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition, compound, nanoparticle, or nanogel described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound, nanoparticle, nanogel, or pharmaceutical composition described herein. In certain embodiments, the kits are useful for treating a disease (e.g., an inflammatory disease or proliferative disease such as cancer) in a subject in need thereof. In certain embodiments, the kits are useful for preventing a disease (e.g., an inflammatory disease or proliferative disease such as cancer) in a subject in need thereof. In certain embodiments, the kits are useful for reducing the risk of developing a disease (e.g., an inflammatory disease or proliferative disease such as cancer) in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. A kit described herein may include one or more additional pharmaceutical agents described herein as a separate composition.

Methods of Treatment and Uses

Provided herein are methods of using the compounds of Formulae (I) and (II), and pharmaceutically acceptable salts, solvates, hydrates, polymorphs, co-crystals, tautomers, stereoisomers, isotopically labeled derivatives, and prodrugs thereof, and pharmaceutical compositions thereof. Also provided herein are methods of using the nanoparticles and nanogels provided herein, and pharmaceutical compositions thereof.

Provided herein are methods of treating and/or preventing a disease or condition in a subject, the methods comprising administering to the subject a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof. Also provided herein are methods of treating and/or preventing a disease or condition in a subject, the methods comprising administering to the subject a nanoparticle or nanogel described herein, or a pharmaceutical composition thereof. In certain embodiments, the disease or conditions is a genetic disease, proliferative disease (e.g., cancer), a disease associated with angiogenesis, a neoplasm, inflammatory disease, autoimmune disease, liver disease, spleen disease, pulmonary disease, hematological disease, neurological disease, painful condition, psychiatric disorder, or metabolic disorder (e.g., a diabetic condition).

In certain embodiments, the disease is an inflammatory disease. In certain embodiments, the disease is a proliferative disease. In certain embodiments, the disease is cancer. Examples of cancers are provided herein. In certain embodiments, the cancer is head and neck cancer, brain cancer, breast cancer, ovarian cancer, cervical cancer, lung cancer, kidney cancer, bladder cancer, liver cancer, sarcoma, or hematological cancer. In certain embodiments, the cancer is head and neck cancer (e.g., head and neck squamous cell carcinoma (HNSCC)). In certain embodiments, the cancer is brain cancer (e.g., glioblastoma). In certain embodiments, the cancer is breast cancer. In certain embodiments, the cancer is ovarian cancer. In certain embodiments, the cancer is cervical cancer. In certain embodiments, the cancer is lung cancer. In certain embodiments, the cancer is kidney cancer. In certain embodiments, the cancer is bladder cancer. In certain embodiments, the cancer is liver cancer. In certain embodiments, the cancer is a sarcoma. In certain embodiments, the cancer is a hematological cancer.

In certain embodiments, the disease is a P-selectin associated disease. In certain embodiments, the disease is associated with cells expression P-selectin. In certain embodiments, the P-selectin associated disease is a proliferative disease (e.g., cancer). In certain embodiments, the P-selectin associated disease is an inflammatory disease (e.g., arthritis). In certain embodiments, the P-selectin associated disease is cancer. In certain embodiments, the P-selectin associated disease is a member selected from the group consisting of carcinoma, sarcoma, lymphoma, leukemia, sickle cell disease, arterial thrombosis, rheumatoid arthritis, ischemia, and reperfusion.

Also provided herein are compounds of Formulae (I) and (II), and pharmaceutically acceptable salts, solvates, hydrates, polymorphs, co-crystals, tautomers, stereoisomers, isotopically labeled derivatives, and prodrugs thereof, and pharmaceutical compositions thereof, for use in treating and/or preventing a disease in a subject. Also provided herein are nanoparticles and nanogels described herein, and pharmaceutical compositions thereof, for use in treating and/or preventing a disease in a subject.

Also provided herein are uses of compounds of Formulae (I) and (II), and pharmaceutically acceptable salts, solvates, hydrates, polymorphs, co-crystals, tautomers, stereoisomers, isotopically labeled derivatives, and prodrugs thereof, and pharmaceutical compositions thereof, for the manufacture of a medicament for treating and/or preventing a disease in a subject. Also provided herein are uses of nanoparticles and nanogels described herein, and pharmaceutical compositions thereof, for the manufacture of a medicament for treating and/or preventing a disease in a subject.

In another aspect, provided herein are methods of inhibiting a PI3K enzyme (e.g., PI3Kα) in a subject, cell, tissue, organ, or biological sample comprising administering to the subject, or contacting the cell, tissue, organ, or biological sample, with a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof.

In certain embodiments, the method is a method of inhibiting PI3K activity. In certain embodiments, the method is a method of inhibiting a PI3K pathway. In certain embodiments, the PI3K enzyme is PI3Kα.

Also provided herein are compounds of Formulae (I) and (II), and pharmaceutically acceptable salts, solvates, hydrates, polymorphs, co-crystals, tautomers, stereoisomers, isotopically labeled derivatives, and prodrugs thereof, and pharmaceutical compositions thereof, for use in inhibiting a PI3K enzyme (e.g., PI3Kα) in a subject, cell, tissue, organ, or biological sample.

Also provided herein are uses of compounds of Formulae (I) and (II), and pharmaceutically acceptable salts, solvates, hydrates, polymorphs, co-crystals, tautomers, stereoisomers, isotopically labeled derivatives, and prodrugs thereof, and pharmaceutical compositions thereof, for the manufacture of a medicament for inhibiting a PI3K enzyme (e.g., PI3Kα) in a subject, cell, tissue, organ, or biological sample.

In another aspect, provided herein are methods of inducing apoptosis in a cell of a subject or biological sample comprising contacting the cell with a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof. Also provided herein are methods of inducing apoptosis in a cell of a subject or biological sample comprising contacting the cell with a nanoparticle or nanogel described herein, or a pharmaceutical composition thereof.

Also provided herein are compounds of Formulae (I) and (II), and pharmaceutically acceptable salts, solvates, hydrates, polymorphs, co-crystals, tautomers, stereoisomers, isotopically labeled derivatives, and prodrugs thereof, and pharmaceutical compositions thereof, for use in inducing apoptosis in a cell of a subject or biological sample. Also provided herein are nanoparticles and nanogels described herein, and pharmaceutical compositions thereof, for use in inducing apoptosis in a cell of a subject or biological sample.

Also provided herein are uses of compounds of Formulae (I) and (II), and pharmaceutically acceptable salts, solvates, hydrates, polymorphs, co-crystals, tautomers, stereoisomers, isotopically labeled derivatives, and prodrugs thereof, and pharmaceutical compositions thereof, for the manufacture of a medicament for inducing apoptosis in a cell of a subject or biological sample. Also provided herein are uses of nanoparticles and nanogels described herein, and pharmaceutical compositions thereof, for the manufacture of a medicament for inducing apoptosis in a cell of a subject or biological sample.

In certain embodiments, the methods and uses described herein comprise administering to a subject a therapeutically effective amount of a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods and uses described herein comprise administering to a subject a therapeutically effective amount of a nanoparticle or nanogel described herein, or a pharmaceutical composition thereof. A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for treating a disease (e.g., a proliferative disease, such as cancer). In certain embodiments, a therapeutically effective amount is an amount sufficient for inhibiting a PI3K enzyme (e.g., PI3Kα) in a subject. In certain embodiments, a therapeutically effective amount is an amount sufficient for inducing apoptosis in a cell of a subject.

In certain embodiments, the methods described herein comprise administering to a subject a prophylactically effective amount of a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein comprise administering to a subject a prophylactically effective amount of a nanoparticle or nanogel described herein, or a pharmaceutical composition thereof. A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for preventing a proliferative disease (e.g., cancer) in a subject. In certain embodiments, a prophylactically effective amount is an amount sufficient for inhibiting a PI3K enzyme (e.g., PI3Kα) in a subject. In certain embodiments, a prophylactically effective amount is an amount sufficient for inducing apoptosis in a cell of a subject.

A compound, nanoparticle, nanogel, or composition provided herein may be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. In certain embodiments, the additional therapeutic agent is an anti-proliferative agent (e.g., anti-cancer agent).

In certain embodiments, the compounds, nanoparticles, nanogels, and compositions described herein can be administered in combination with an anti-cancer therapy, including, but not limited to, surgery, radiation therapy, transplantation (e.g., stem cell transplantation, bone marrow transplantation), immunotherapy, and chemotherapy.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal, such as a transgenic mouse or transgenic pig.

In certain embodiments, the provided methods comprise contacting a cell with an effective amount of a compound of Formula (I) or (II), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the provided methods comprise contacting a cell with an effective amount of a nanoparticle or nanogel described herein, or a pharmaceutical composition thereof. The cell may be contacted in vitro or in vivo. In certain embodiments, the contacting is performed in vivo. In certain embodiments, the contacting is performed in vitro.

EXAMPLES

Introduction: PI3Kα Inhibitors

New PI3Kα inhibitors have been developed that are efficacious in preclinical PDx models and, by virtue of their encapsulation in P-selectin targeting nanoparticles, exhibit a superior therapeutic index relative to advanced PI3K antagonists currently under clinical investigation for oncologic applications (e.g., cancers including head and neck squamous cell cancer (HNSCC)). PI3Kα inhibitors described herein are amenable to formulation in a fucosylated polysaccharide that targets P-selectin in the tumor microvasculature. Additional design criteria are also advantageous. An ideal PI3Kα inhibitor should be rapidly cleared systemically (i.e., Compound (14)), or be an antidrug (i.e., Compound (22), Compound (18)) that is directly converted by enzymes in the plasma and/or liver into an inactive metabolite, or be a cell impermeable compound (i.e., Compound (19)) that, when nanoparticle-formulated, is selectively delivered into the tumor vasculature. Examples provided herein show substantial anti-tumor efficacy while abrogating adverse systemic effects limiting current PI3Kα inhibitors.

Unmet Medical Need

Aberrant activation of the phosphoinositide-3-kinase (PI3K) pathway is frequent in estrogen receptor (ER)-positive breast tumors and occurs as a result of somatic activating mutations of PIK3CA, the gene encoding the alpha isoform of the PI3K catalytic subunit p110α (PI3Kα), activating mutations of AKT, or loss of function of phosphatase and tensin homolog (PTEN).[23] PIK3CA mutations are the most frequent somatic mutations in luminal (ER-positive) breast cancer, detected in over 40% of cases. Direct pharmacologic inhibition of PI3K in breast cancer is an attractive clinical strategy, and a number of PI3K pathway inhibitors are currently under clinical development, but the approach is limited by toxicities and therapeutic resistance. In addition to ER-positive breast cancer, HNSCC frequently harbors activating mutations or amplification in PIK3CA (34%-56%), rendering them susceptible to PI3Kα inhibitors. Treatment modalities for most HNSCC cases involve surgery and/or radiation therapy (RT). Chemotherapy is administered as a radiosensitizer and to decrease the odds of developing distant metastases in high-risk patients; however, the 5-year survival remains around 60% for all stages. Moreover, therapies commonly used for HNSCC (cisplatin and cetuximab) carry significant toxicities. Specific inhibitors of PI3Kα have entered the clinic, including BYL719[13] (alpelisib, Phase 3, metastatic breast cancer), GDC-0032 (taselisib, Phase 3, squamous cell lung cancer) and GDC-0084[39] (Phase 1, brain cancers). Their efficacy is constrained by a significant toxicity profile (including fatigue, skin rash, and intractable hyperglycemia) that limits their therapeutic window. In addition, the duration of clinical benefit is short in the majority of cases, likely due to compensatory pathways that result in drug resistance. Therapeutic combinations, such as with anti-ER therapies (anastrazole or fulvestrant) or the mTORC1 inhibitor everolimus, may prevent the emergence of resistance and are currently under investigation; however, these therapeutic interventions often result in significant dose-limiting toxicities.

Use of PI3K Inhibitors in Cancer Therapy

Antitumor kinase inhibitors have become a standard of care due to their specificity and selectivity to unique genomic aberrations present in certain malignancies. However, most of these compounds only lead to transient inhibition of their targets, necessitating daily or weekly administration in order to achieve clinically effective intratumoral drug concentrations. The amount of drug needed to efficaciously inhibit the target often yields off-target and on-target effects on healthy tissues and causes intolerable adverse effects due to systemic exposure. A narrow "therapeutic window" represents the main limitation for the antitumor activity of virtually any kinase inhibitor administered systemically. Activating mutations or amplification of PIK3CA, the gene encoding the class IA PI3K catalytic subunit p110a, is the most common genomic alteration in HNSCC, present in up to 40% of human papilloma virus-positive cases. Specific PI3Kα inhibitors are under current investigation in both pre-clinical and clinical settings of HNSCC.[24,25] The PI3Kα pathway is illustrated in FIG. 1.[54] The development of a PI3Kα inhibitors with substantially improved therapeutic window fulfills a key unmet medical need. To achieve this objective, the development of a serum- or liver-labile, high clearance inhibitor or a cell-impermeable inhibitor coupled with a nanoparticle encapsulation to protect the compound and target it specifically to the tumor cell and/or tumor vasculature is advantageous. This strategy prevents the active drug from reaching healthy (off-target) tissues responsible for toxicities.

The observation that P-selectin is expressed in HNSCC tumor milieu, and is further upregulated by irradiation, has been exploited to test the efficacy of P-selectin-mediated delivery of a specific PI3Kα inhibitor, BYL719, using fucoidan-based nanoparticles in models of HNSCC. The goal of this work was to investigate whether the specific accumulation of BYL719 in the tumor microenvironment is sufficient to exert the desired significant antitumor effects while sparing healthy tissues from systemic exposure and related toxicities. Nanoformulated BYL719 [Fi(BYL719)] administration led to prolonged and tumor-specific inhibition of the PI3K/AKT/mTOR pathway, which resulted in durable control of tumor growth.

These effects were enhanced by concomitant radiation therapy (RT) treatment, presumably due to both DNA damage induced and by PI3K inhibition, increased P-selectin mediated Fi(BYL719) tumor accumulation, and prolonged PI3K pathway inhibition. Healthy tissues were spared from systemic exposure and related toxicities. Indeed, this reverberating effect is particularly germane in HNSCC, where RT therapy is the standard of care.

P-Selectin Targeting Nanoparticles

Whereas P-selectin has been widely discussed as a clinical target, it has not been previously explored as a drug delivery target in cancer therapy.[22] P-selectin, an inflammatory cell adhesion molecule responsible for leukocyte recruitment and platelet binding, is produced in endothelial cells where it is stored in intracellular granules known as Weibel-Palade bodies.[22] Significantly elevated P-selectin expression has been found in the vasculature of human lung,[26] breast,[27] and kidney cancers.[28] Moreover, P-selectin has been shown to facilitate metastasis by coordinating the interaction between cancer cells, activated platelets, and activated endothelial cells. P-selectin was, therefore, investigated as a target in tumors in part to exploit the same mechanism by which tumors metastasize in order to deliver drugs to the tumor/metastatic niche. These associations with tumors and micrometastases, as well its induction with radiation, suggest P-selectin as a possible target for cancer drug delivery and radiation-guided drug delivery.[22]

Selectively targeting caner cells is of great clinical interest.[29,30,31,32,33] One solution involving nanoparticle targeting drug delivery was disclosed in 2016.[22] The report established that P-selectin functioned as an attractive target for localized drug delivery to tumor sites, including metastases. P-selectin expression is highly prevalent on multiple tumor cells (FIGS. 2A-2B) and in tumor vasculature, whereas normal tissues exhibit limited expression. Radiation therapy (RT) is a well-established common adjunct to chemotherapy, especially in HNSCC, and P-selectin is upregulated approximately four-fold upon exposure of cells to ionizing radiation (6 Gy), further increasing this divergence.

Figure 2A:
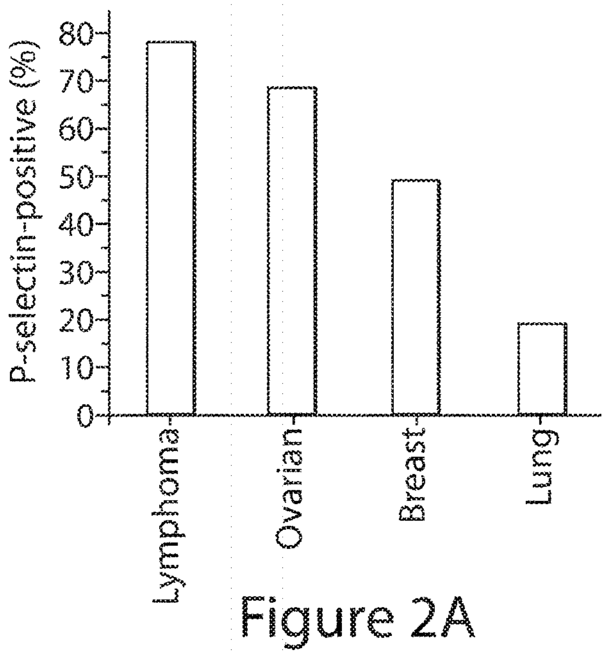
FIGS. 2A-2B. P-Selectin Expression in Human Cancers.
Figure 2B:
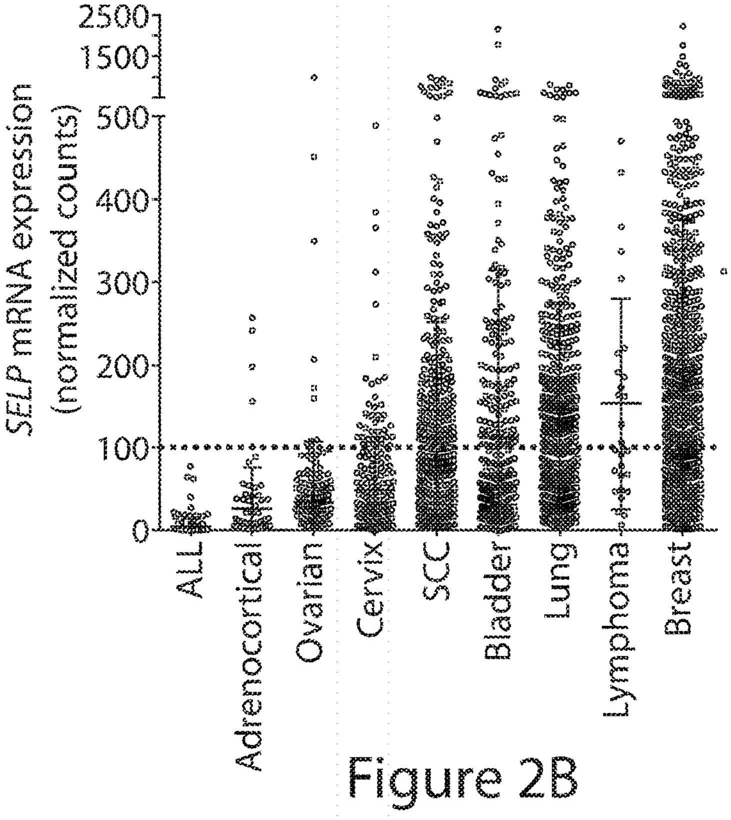

To exploit this differential, Heller et al. developed robust protocols to reproducibly synthesize nanoparticle carriers for chemotherapeutic drugs using the algae-derived polysaccharide fucoidan, which exhibits nanomolar affinity for P-selectin.[22] These drug-containing nanoparticles offer a high degree of selectivity over E-selectin, L-selectin, and bovine serum albumin (BSA) (FIGS. 2A-2B). The nanoparticles thus produced exhibited good serum stability over 5 days with pH-dependent drug release rates, and they could be reconstituted after lyophilization. In vitro experiments established that these fucoidan-based nanoparticles targeted activated endothelium and demonstrated penetration of endothelial barriers in vitro.

In Vivo Targeting and Antitumor Efficacy Mediated by P-Selectin

The high affinity of fucoidan for P-selectin was exploited to deliver locally therapeutically effective doses of these compounds, avoiding potentially toxic systemic drug exposure. To determine whether this approach was generalizable across a wide range of tumor types and pharmacophores, the penetration and antitumor activity of a series of nanoformulated anticancer agents in P-selectin-expressing tumors in vivo was tested. These studies investigated diverse anticancer agents: paclitaxel (FiPAX), doxorubicin (FiDOX), and MEK162 [Fi(MEK162)].[22] Consistent with the prior in vitro data, in each instance, high tumor accumulations of drug were noted for the polysaccharide encapsulated agents relative to non-formulated material. A greater modulation of target-mediated biomarkers relative to untargeted chemotherapeutic drugs or passively targeted nanoparticles in P-selectin-expressing tumors and metastases in vivo also was noted. In addition, in vivo studies of extended duration produced an unambiguous therapeutic advantage with no notable toxicity at greatly reduced dosages (one tenth to one seventh overall drug burden) in terms of mean survival rates for animals treated with the targeted agents relative to the maximum tolerated doses of free drug in these aggressive experimental metastasis models.

Similar results driven by P-selectin targeting were obtained following tumor irradiation in vivo in the Lewis lung carcinoma model, a mouse tumor model that does not spontaneously express P-selectin.[22] In this study, tumors on the irradiated (6 Gy) mouse flank absorbed more FiPAX (~3.8-fold levels relative to the non-irradiated flank); an uptake that directly corresponded with a commensurate increase in apoptosis. The use of nanoformulated NVP-BGJ398 [Fi(NVP-BGJ398)], a potent inhibitor of fibroblast growth factor receptor family of receptor tyrosine kinase (FGFR3), served as a valuable negative control for P-selectin targeting nanoparticles. In this orthotopic PDx model in which the tumors, which are sensitive to NVP-BGJ398, were devoid of P-selectin, treatment with Fi(NVP-BGJ398) had no meaningful effect, providing additional corroboration for targeted mediated uptake of drug through the P-selectin pathway.

P-Selectin Targeting Nanoparticles Containing PI3K Inhibitor BYL719

These P-selectin-focused investigations subsequently were extended to probe tumor-specific PI3K inhibition via nanoparticle-targeted delivery in HNSCC. Fucoidan-based nanoparticles containing BYL719 [Fi(BYL719)] were prepared by co-encapsulating both the drug and a near-infrared dye (IR820) to facilitate imaging.[23] As a negative control for these targeting studies, drug-loaded dextran sulfate-based nanoparticles [Dex(BYL719)] that lacked fucoidan were prepared using the same procedure. Dextran sulfate-based particles do not bind to P-selectin but could passively target tumors, likely via the enhanced permeability and retention effect (EPR).[22] Dex(BYL719) exhibited comparable physical properties to those of Fi(BYL719) and were assembled using the same procedures. The drug release profiles of BYL719 from Fi(BYL719) nanoparticles at pH 5.5 and pH 7.4 were then measured. Drug release accelerated substantially at low pH. Finally, the in vitro binding affinity of Fi(BYL719) and control Dex(BYL719) nanoparticles to bovine aortic endothelial cells stimulated to express P-selectin with either tumor necrosis factor α (TNFα) or RT were assessed. As expected, only Fi(BYL719) nanoparticles penetrated into the endothelial cells upon stimulation.

Figure 3A:
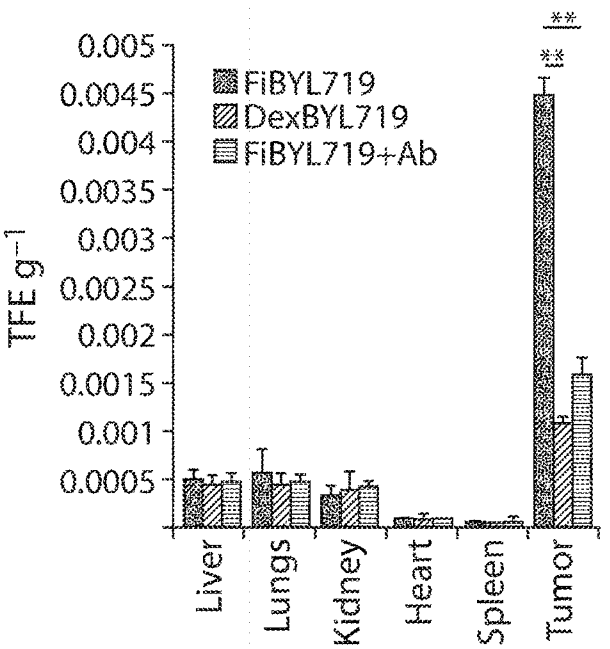
FIGS. 3A-3C. In Vivo Targeting of BYL719-Loaded Nanoparticles Prepared with Either Fucoidan (Fi) or Dextran Sulfate (Dex).
Figure 3B:
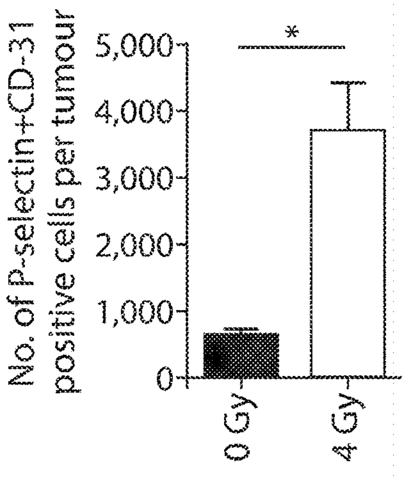
Figure 3C:
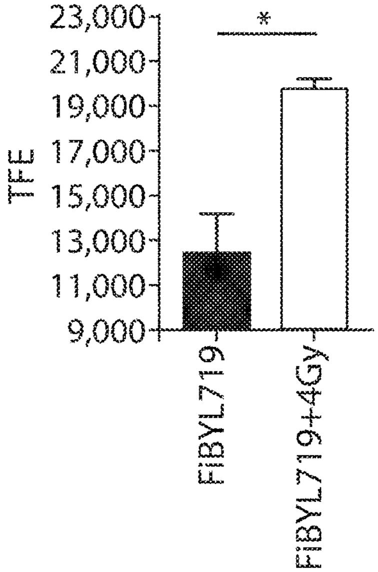

The nanoparticles were administered in nude mice bearing subcutaneous (SC) H22 PDX tumors. After 24 hours, a significantly higher tumor localization of Fi(BYL719) nanoparticles compared with Dex(BYL719) nanoparticles was observed (FIG. 3A). When the animals were pre-treated with a P-selectin blocking antibody, the localization of Fi(BYL719) nanoparticles in the tumor was abrogated. Upon irradiation of Cal-33 xenograft-bearing mice (4 Gy), an enhancement of P-selectin expression in the tumor vasculature occurred (FIG. 3B). Administration of Fi(BYL719) nanoparticles into the irradiated mice resulted in increased drug accumulation (FIG. 3C) and specific localization of the nanoparticles in the tumor microenvironment as evinced by fluorescence microscopy.

To determine whether tumor accumulation of Fi(BYL719) nanoparticles translated into PI3K/AKT/mTOR pathway inhibition in HNSCC tumors, Cal-33 tumor-bearing mice were treated with a single administration of BYL719: Free drug (50 mg/kg/day), the standard dose given PO in mice; Encapsulated into fucoidan nanoparticles (25 mg/kg, 2× weekly), the maximal dose amenable to encapsulation and IV infusion. This translates to $1/7^{th}$ the quantity of drug dosed orally.

Figure 4A:
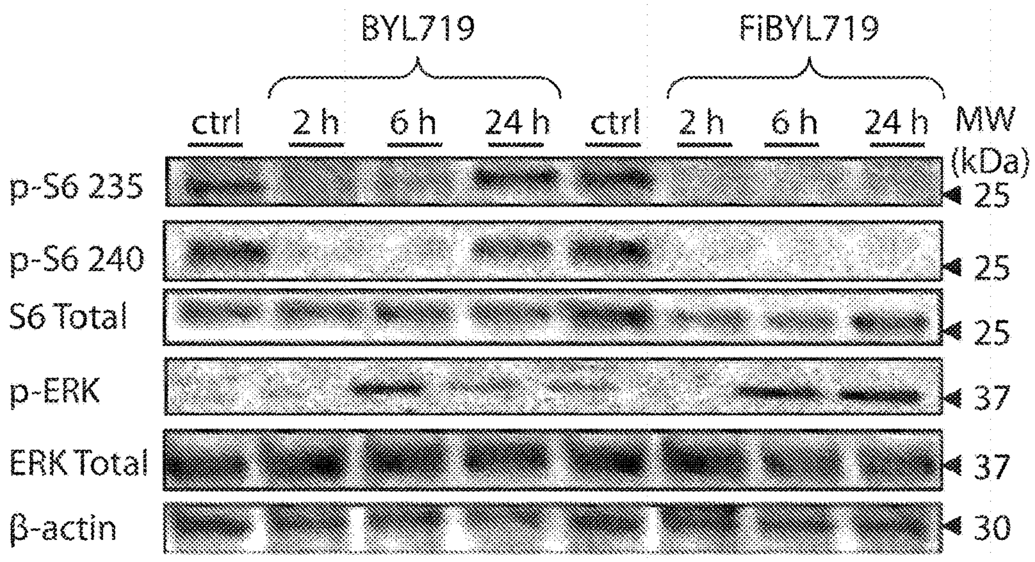
FIGS. 4A-4B. Antitumor Efficacy of Free BYL719 and Nanoparticle-Encapsulated FiBYL719 in Preclinical HNSCC Models.
Figure 4B:
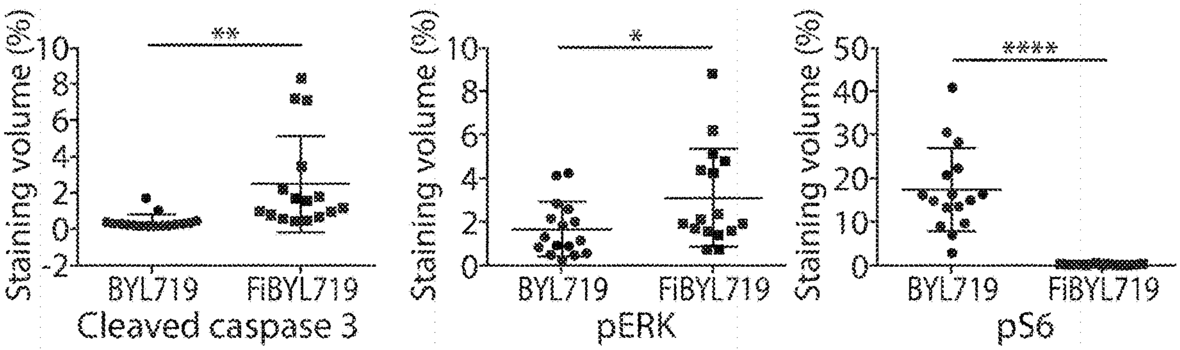

S6 ribosomal protein (S6) phosphorylation served as a readout of the pharmacodynamics of the inhibitor, as this marker integrates the effects of BYL719 on both PI3K/AKT and mTORC129. Treatment with free BYL719 elicited a strong albeit transient inhibition of the pathway, which was partially restored after 6 hours and fully restored by 24 hours, compatible with the relatively short half-life of BYL719 in plasma.[13] In contrast, treatment with Fi(BYL719) resulted in complete and durable suppression of S6 phosphorylation over 24 hours as shown by Western blot analysis of the same xenografts. This confirmed the lasting inhibition of S6 phosphorylation and showed concomitant activation of pERK (FIGS. 4A-4B), a well-known feedback mechanism triggered by suppression of the PI3K/AKT pathway.[3435] These findings were further confirmed in a 3-D reconstruction of an immunofluorescence analysis of two representative Cal-33 tumors collected at 24 hours post treatment. In tumor tissues treated with Fi(BYL719), diminished staining was observed for pS6. In addition, increased apoptosis, as denoted by caspase 3 cleavage, was measured compared with the tumor treated with oral BYL719 (FIGS. 4A-4B).

In vivo efficacy studies were conducted in both Cal-33 and H22 PDX models. Mice were randomized into 4 treatment arms: (1) Vehicle control; (2) Free BYL719 administered 7 mg/kg/day (total 50 mg/kg/week); (3) Free BYL719 administered 50 mg/kg/day (total 350 mg/kg/week); (4) Nanoparticle-encapsulated Fi(BYL719) administered 25 mg/kg twice a week (total 50 mg/kg/week)

Figure 5A:
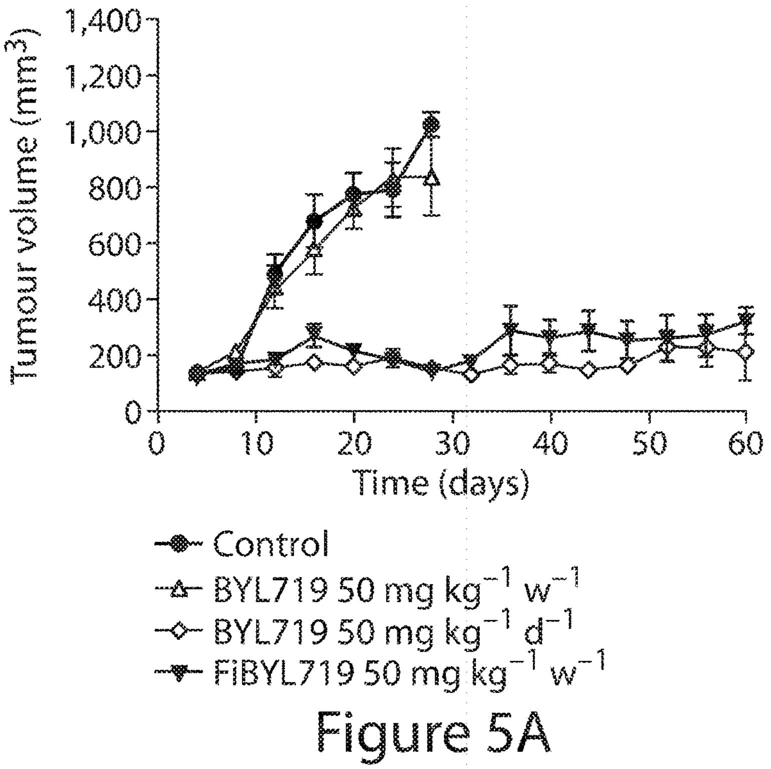
FIGS. 5A-5C. Antitumor Efficacy of Free BYL719 and Nanoparticle-Encapsulated FiBYL719 in Preclinical HNSCC Model.
Figure 5B:
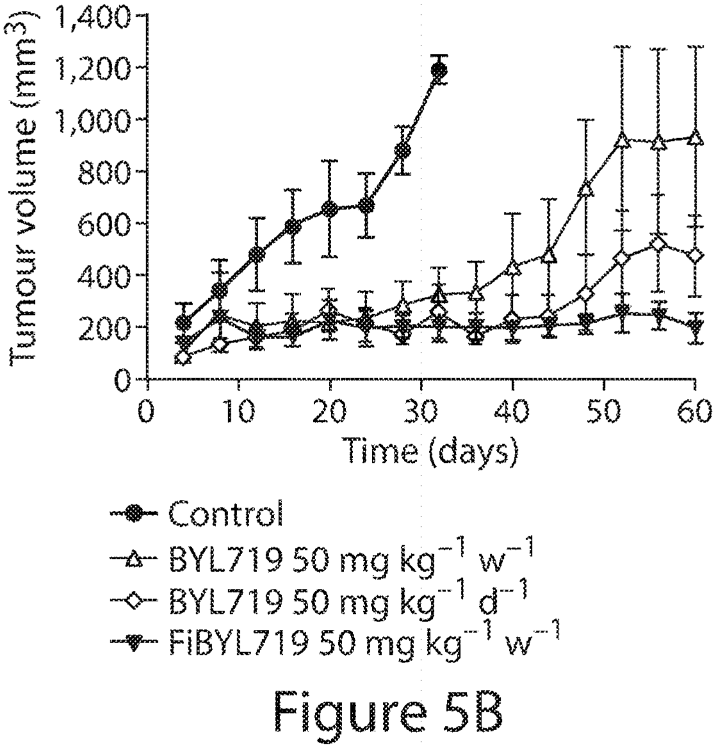
Figure 5C:
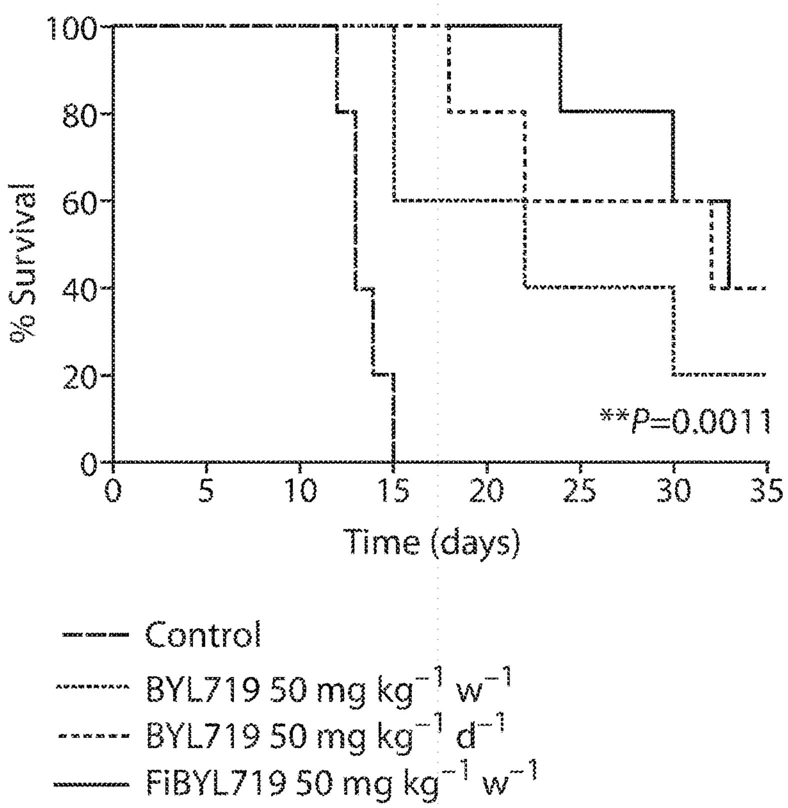

Significant tumor inhibition was observed in both Cal-33 and H22 models upon administration of Fi(BYL719) nanoparticles. The antitumor effects of a weekly dose of nanoparticles were comparable to those of a 7-fold higher dose of the free drug. The equivalent dose of free BYL719 administered at 7 mg/kg/day (50 mg/kg/week) elicited no appreciable antitumor activity in Cal-33 tumors (FIG. 5A), whereas in H22-bearing mice it resulted in transient delay of tumor growth followed by acquired insensitivity to the treatment (FIG. 5B).

The effects of RT on P-selectin-targeted PI3Kα inhibition were investigated. It was reasoned that increased efficacy may result from the combined effects of RT to increase nanoparticle localization to the tumor and of PI3Kα inhibition to sensitize HNSCC to RT. First, the effects of applying a single dose of 4 Gy RT to H22 tumor-bearing mice in combination with Fi(BYL719) (25 mg/kg) or free BYL719 (50 mg/kg) were measured. Approximately 24 hours after treatment, it was found that tumor γH2AX nuclear foci formation, an indicator of DNA damage, was significantly augmented upon treatment with the drug-loaded nanoparticles as compared with the free drug or RT alone. Apoptosis in the tumor tissue was also substantially increased by Fi(BYL719).

To establish whether the nanoparticle/RT combination could produce long-term inhibition of tumor growth in the H22 PDX model, a clinically relevant dose of fractionated RT (4 Gy, 5 doses) was administered alone or in combination with free BYL719 (7 mg/kg/day), free BYL719 (50 mg/kg/day) or Fi(BYL719) (25 mg/kg administered twice per week). Treatment without nanoparticle encapsulation was sufficient to delay tumor growth to some extent. However, only 5 days of treatment with Fi(BYL719) (two single administrations of 25 mg/kg) were sufficient to achieve durable stabilization of all tumors, as compared with free drug or RT alone (FIGS. 6A-6B).[23]

Figure 7A:
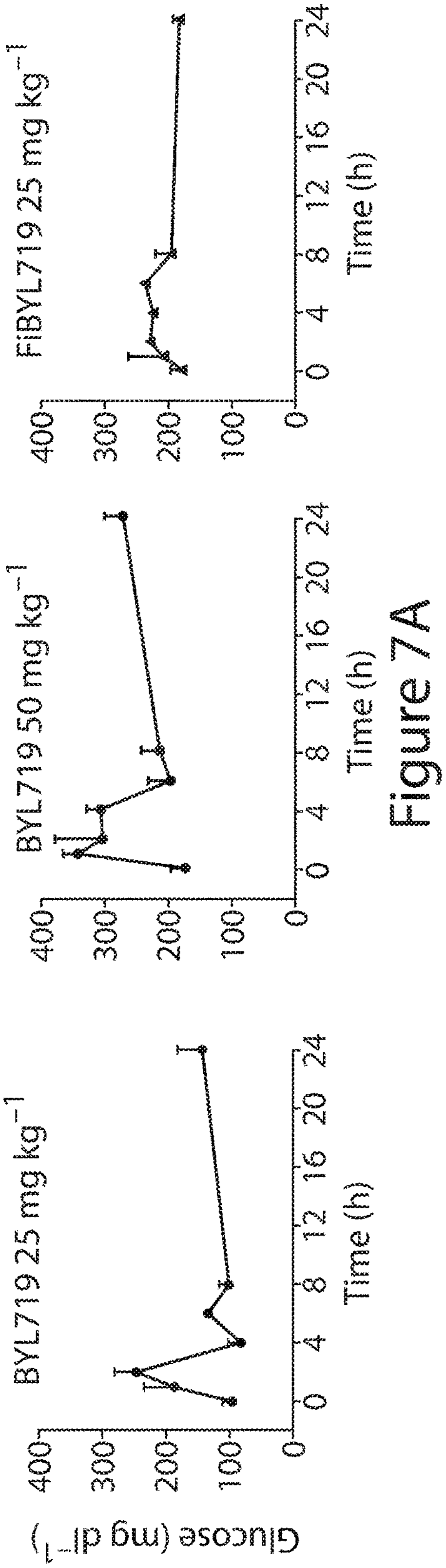
FIGS. 7A-7B. Amelioration of Systemic Metabolic Effects of PI3K Inhibition by P-Selectin-Targeted Delivery of BYL719. Serum glucose levels (FIG. 7A) and insulin levels (FIG. 7B) of mice treated with 25 and 50 mg/kg BYL719 or 25 mg/kg Fi(BYL719) (n=6).[23]
Figure 7B:
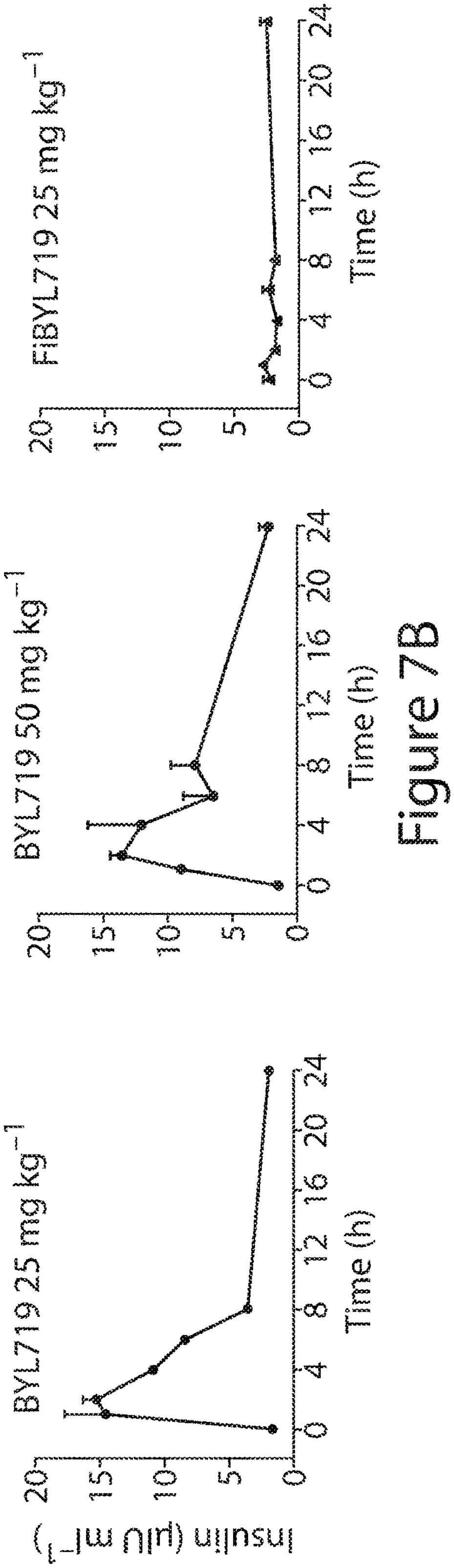

Upon systemic treatment with PI3K/AKT inhibitors, hyperglycemia is induced by phosphorylation of insulin receptor (IR) leading to loss of insulin signaling in peripheral tissue and pancreatic β cells.[9,10,11] To assess whether P-selectin-mediated-targeted delivery of BYL719 could prevent systemic drug exposure, serum glucose and insulin levels were measured in healthy mice treated with either BYL719 or Fi(BYL719). A single dose of free BYL719 (either 25 or 50 mg/kg) resulted in a spike in serum glucose and insulin levels 1-8 hours after treatment. Upon administration of nanoparticle-encapsulated 25 mg/kg Fi(BYL719), only a slight increase of glucose levels was observed, and no effect on insulin levels was detectable within 24 hours (FIGS. 7A-7B).

Figure 8A:
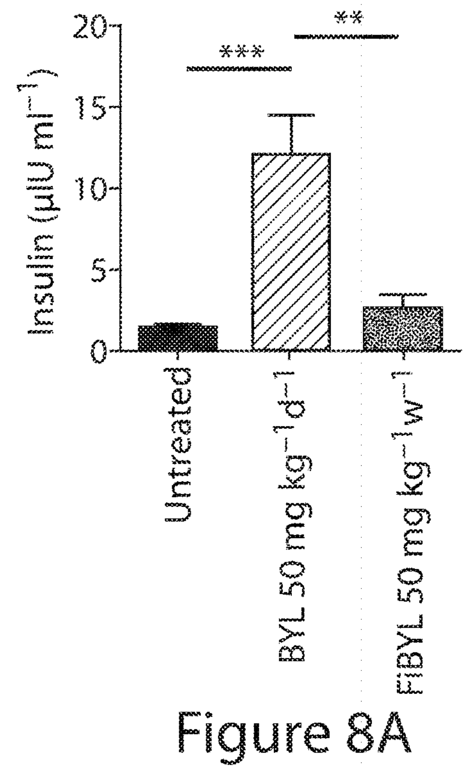
FIGS. 8A-8B. Amelioration of Systemic Metabolic Effects of PI3K Inhibition by P-Selectin-Targeted Delivery of BYL719. Serum insulin (FIG. 8A) and glucose (FIG. 8B) levels of mice following 60 days of treatment with 50 mg/kg BYL719 daily or 25 mg/kg Fi(BYL719) bi-weekly (n=6).[23]
Figure 8B:
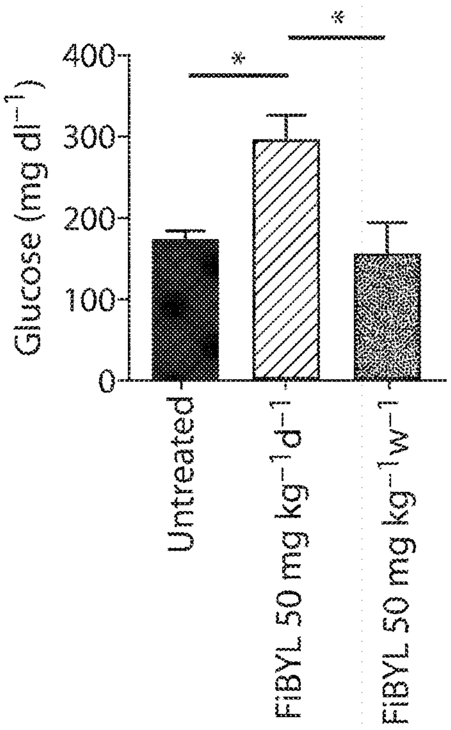
Figure 9:
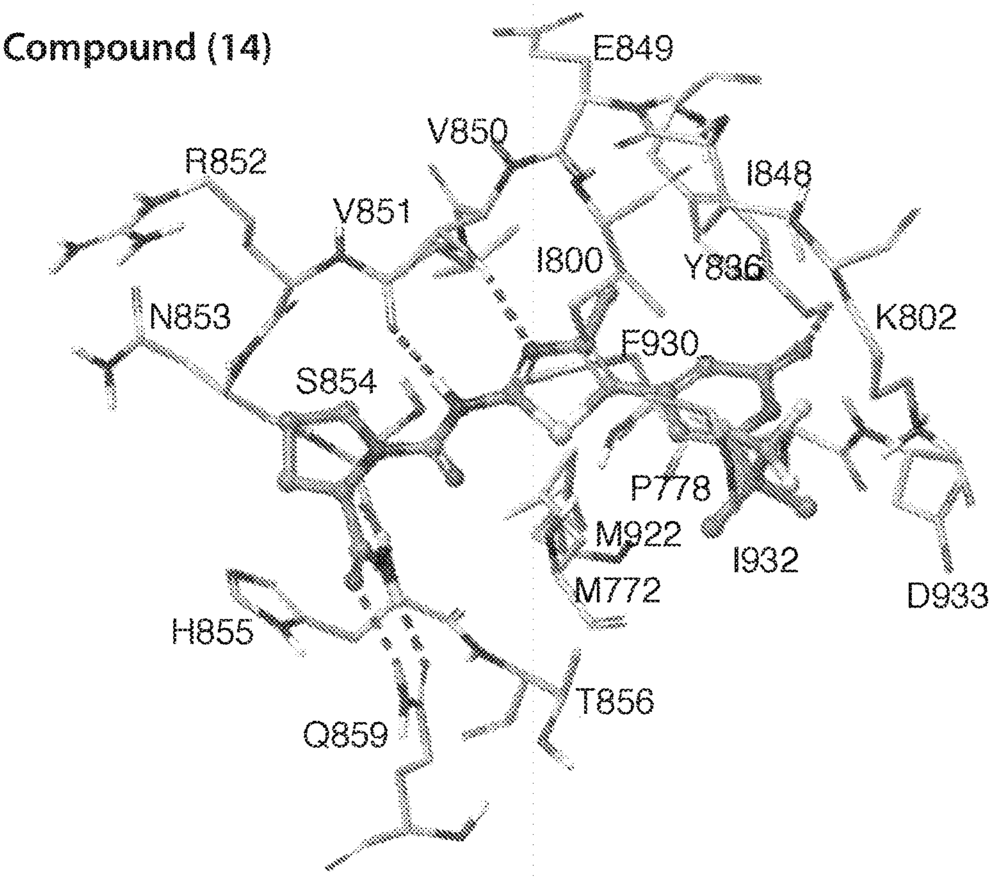
FIG. 9. Proposed Binding Mode of Compound (14) in the ATP Pocket of PI3Kα. Compound (14) was docked to the crystal structure of PI3Kα using Glide in the Schrodinger suite.[13] Hydrogen bonds are represented as dashed lines. Also shown is the structure of Compound (14).
Figure 9:
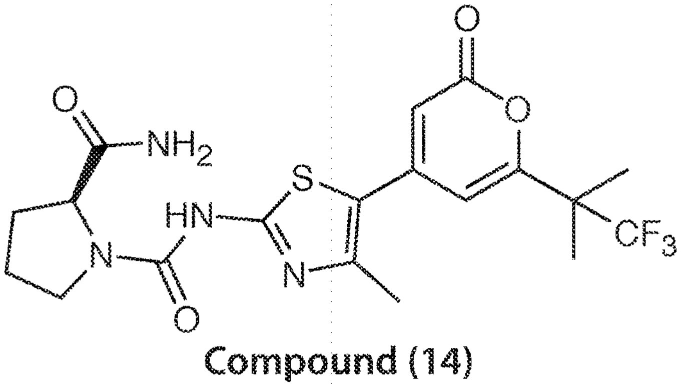
Figure 10:
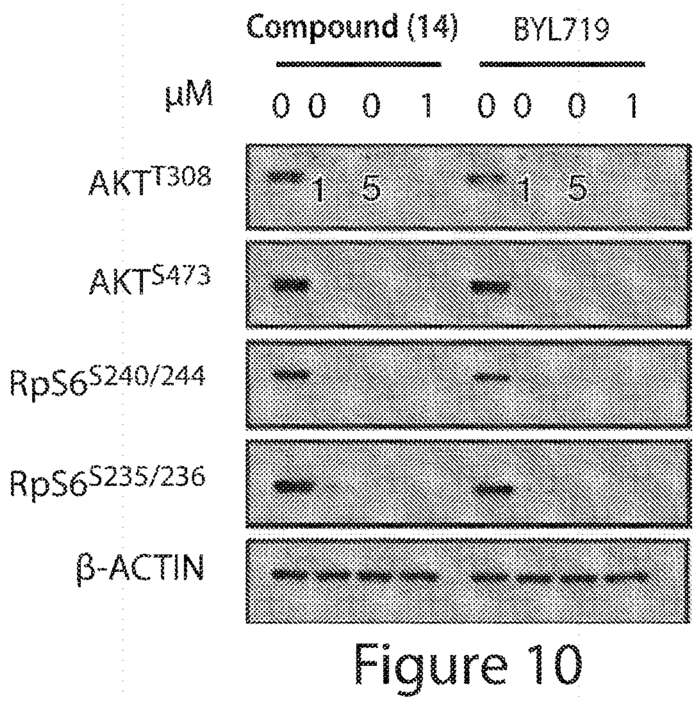
FIG. 10. Impact of Compound (14) or BYL719 on Expression of Different Isoforms of the Indicated Proteins in T47D Cells. Western blot showing the changes in expression of the indicated proteins upon treatment (2 hours) of T47D cells with increasing concentrations (0.1, 0.5, and 1 M) of Compound (14) or BYL719.

To evaluate whether continuous treatment with Fi(BYL719) nanoparticles could also obviate the chronic effects of prolonged PI3K inhibition on glucose metabolism.[11] Mice were treated for 60 consecutive days with either BYL719 (50 mg/kg/day) or Fi(BYL719) nanoparticles (50 mg/kg/week). Despite the dramatic difference in total drug load between the two treatment paradigms, these are efficacy-matched regimens. Treatments were then halted for 72 hour before blood and pancreas samples were collected for analysis. Significantly elevated serum glucose and insulin levels were found in the mice treated with free BYL719 but not in the Fi(BYL719)-treated group (FIGS. 8A-8B). Moreover, a lower number of insulin-producing R cells per islet and a higher number of glucagon-producing a cells per islet were detected in the free BYL719-treated versus Fi(BYL719)-treated animals. These findings suggest that Fi(BYL719) treatment can produce durable tumor-specific inhibition of the PI3K pathway without the emergence of chronic hyperglycemia and hyperinsulinemia that results in exhaustion of the insulin-producing R cells and compensatory augmentation of glucagon-producing a cells.

New PI3Kα Inhibitors In Vitro

The results detailed above served to identify P-selectin as a target for tumor selective drug delivery and that the high affinity of fucoidan for P-selectin can be exploited to deliver locally therapeutically effective doses of the PI3K inhibitor BYL719, avoiding potentially toxic systemic drug exposure. Next, attention was turned to novel PI3K inhibitors with superior in vivo characteristics with respect to antitumor efficacy and known, mechanism-based PI3K liabilities. This effort led to the discovery of new PI3Kα inhibitors, whose properties are detailed below.

Compound (14) was evaluated in classical PI3Kα kinase assays and found to be a potent inhibitor with excellent efficacy (+++) in PI3K cellular assays (Table 1). Compound (14) displayed a similar magnitude of pathway inhibition relative to BYL719 in biochemical and cellular PI3K assays. PI3Kα $IC_{50}$ Activity Scale: <100 nM: (+++); <500 nM: (++); <1000 nM: (+).

TABLE 1

PI3K Inhibitors

| | Compound (14) | BYL719 |
|---|---|---|
| | 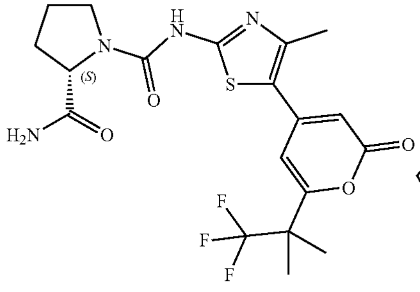 | 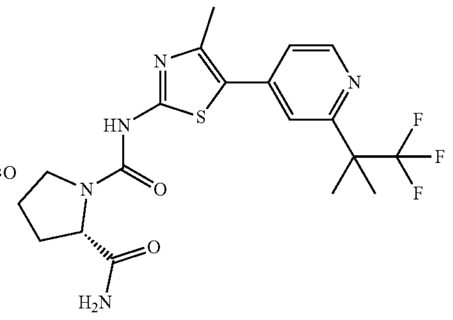 |
| PI3Kα ($IC_{50}$, nM) | (+++)** | (+++)** |
| PI3K cellular activity | (+++)*** | (+++)*** |
| Nanoparticle formulation | Yes | Yes |
| Nanoparticle drug load, % | 22 | 22 |

**$IC_{50}$ Activity Scale: <100 nM: (+++); <500 nM: (++); <1000 nM: (+)

***Activity scale: Inactive (−); Low (+); Intermediate (++); High (+++)

New PI3Kα Inhibitors In Vivo

Figure 11:
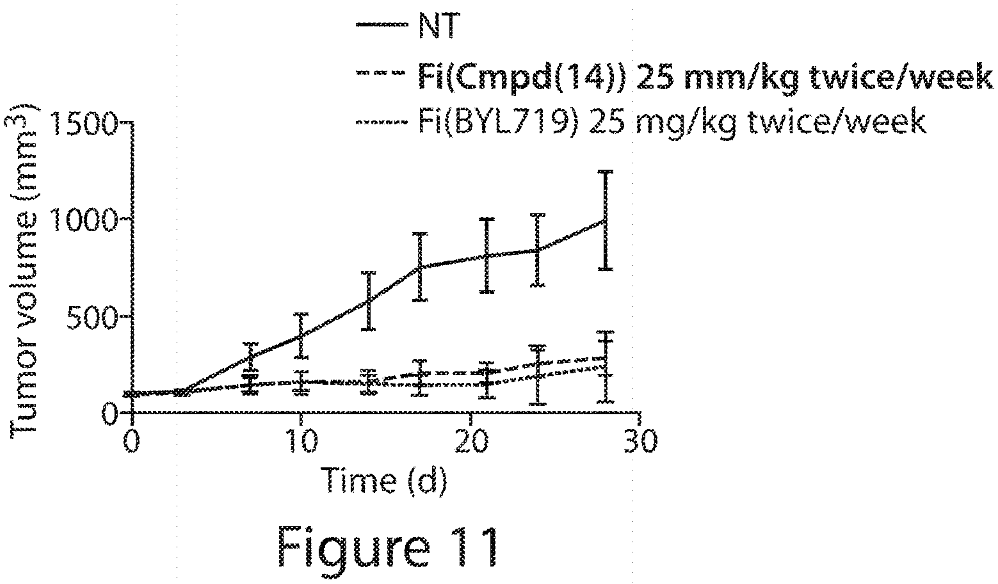
FIG. 11. Tumor Growth Inhibition of Fi(Compound (14)) and Fi(BYL719) in Cal-33 Xenografts. Tumor growth inhibition induced by encapsulated Compound (14) [Fi(Compound (14))] compared to encapsulated BYL719 [Fi (BYL719)]. Both nanoformulated compounds were administered at doses of 25 mg/kg IV twice weekly for 4 weeks (n=6).

Compound (14) was evaluated for effectiveness in Cal-33 xenografts. In this 28-day study, encapsulated Compound (14) [Fi(Compound (14))] and encapsulated BYL719 [Fi (BYL719)] were administered at doses of 25 mg/kg IV twice weekly for 4 weeks. No toxicity, as manifested by weight loss, was noted for either analog in this study. Systemic plasma drug concentrations were not determined in this study. As illustrated in FIG. 11, tumor growth inhibition induced by Fi(Compound (14)) compared favorably to encapsulated Fi(BYL719). On a dosage basis, both Fi(Compound (14)) and Fi(BYL719), therefore, are fully efficacious in this murine PDx models at one seventh the dose requirement for equivalent efficacy using orally dosed BYL719.

Figure 6A:
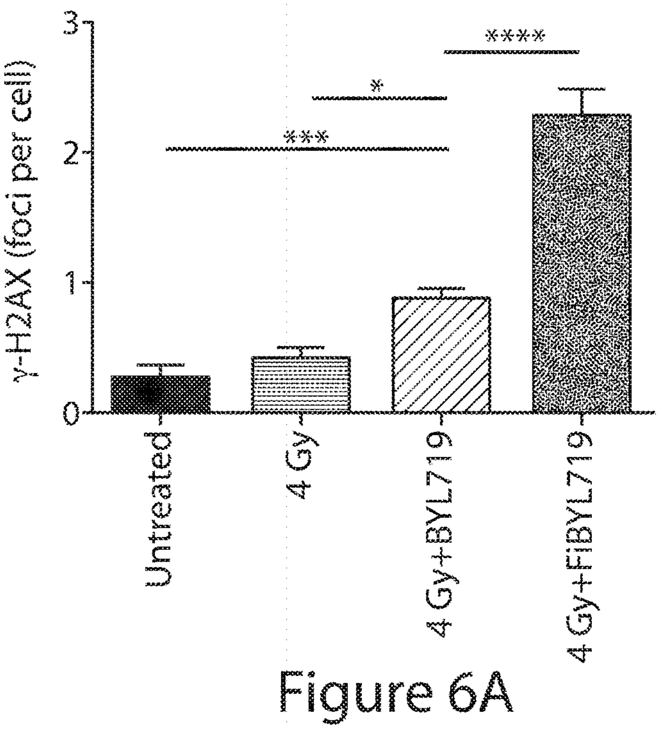
FIGS. 6A-6B. Radiosensitization Effects of Preclinical HNSCC Models by Free and Nanoparticle-Encapsulated BYL719.
Figure 6B:
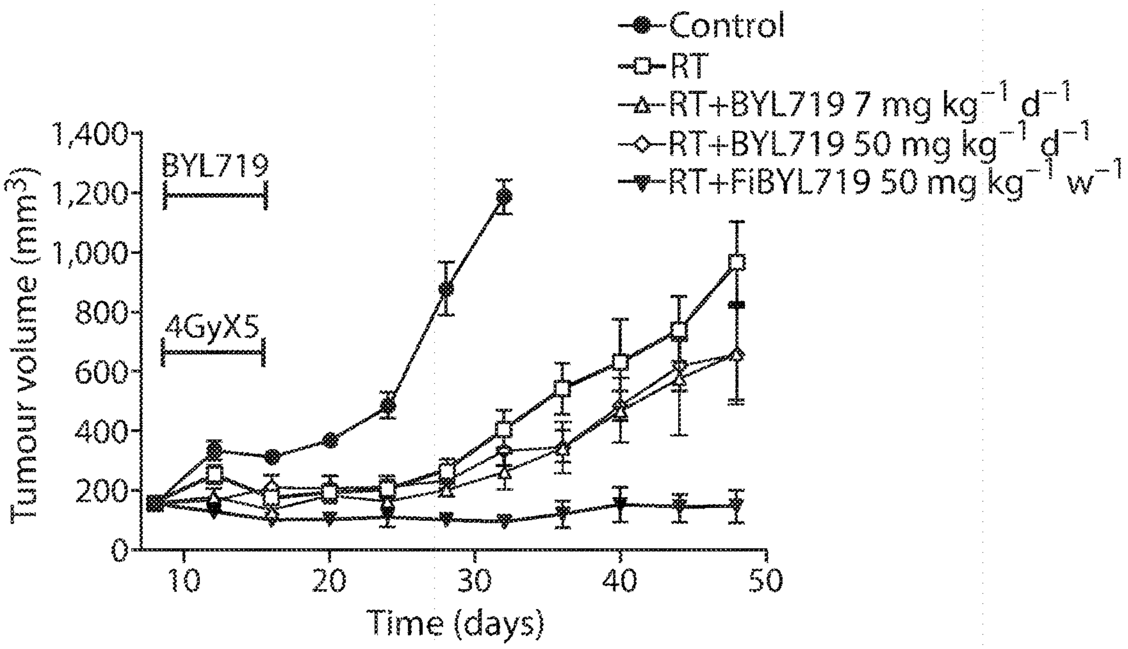
Figure 12:
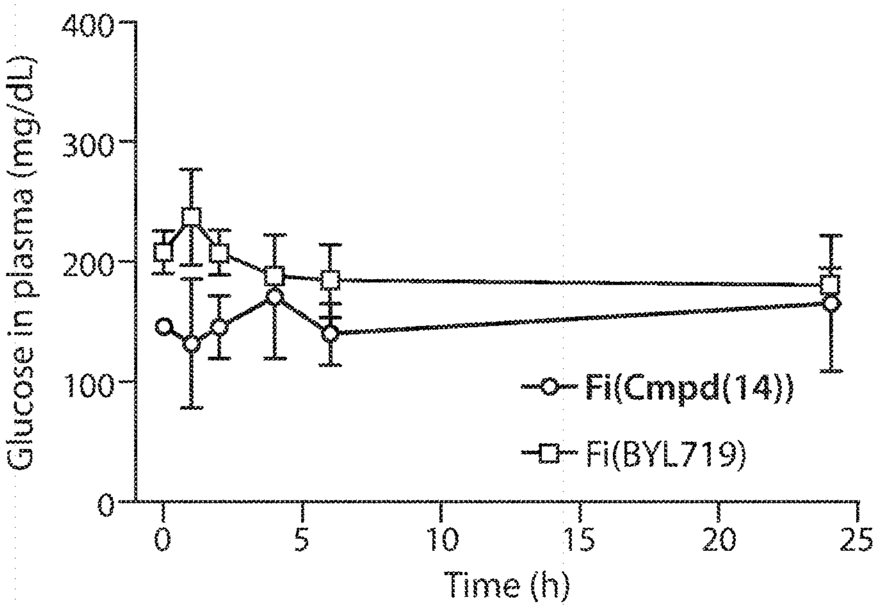
FIG. 12. Glycemic Response of Compound (14) in Cal-33 xenografts. Changes in glucose levels of animals (n=6) treated with one dose of encapsulated Compound (14) [Fi(Compound (14))] compared to one dose of encapsulated BYL719 [Fi(BYL719)]. Both nanoformulated compounds were administered at a dose of 25 mg/kg IV.

Importantly, in a direct comparison to Fi(BYL719), Fi(Compound (14)) effected essentially negligible changes to glucose and insulin levels in the serum of treated mice (FIG. 12). This result confirms the lack of appreciable systemic exposure of the PI3K inhibitor Compound (14) in this study. These data establish that Fi(Compound (14)) has a superior TI with respect to mechanism-based systemic liabilities relative to Fi(BYL719) and exhibits an improved profile with respect to glycemic parameters evinced by orally dosed BYL719 in this same model (FIGS. 6A-6B). This is the first evidence that new PI3Kα inhibitors, such as Compound (14), that are high clearance compounds, once encapsulated in fucoidan polysaccharides retain efficacy comparable to existing, systemically administered PI3Kα inhibitors while possessing a significantly improved TI.

Biomarkers

Activation of the PI3K pathway is commonly observed in human cancer and is critical for tumor progression and resistance to antineoplastic drugs, including cytotoxic chemotherapy and targeted agents. As a result, this pathway has been the focus of intense interest with drug discovery efforts culminating in the invention of over 50 new drugs inhibiting the PI3K/AKT/mTOR pathway advancing to different stages of development in this highly validated pathway.[17] An additional beneficial outcome of this sustained scrutiny is that biomarkers (BMx), preclinically or clinically, relevant to PI3K inhibition are thoroughly vetted at this juncture and include blood- and skin-based samples.[4,17] Many of these BMx are readily quantified by immuno-histochemistry. Key efficacy related BMx for PI3K inhibition include: Phosphorylated S6 (S235/236 and S240/244); Phosphorylated mTOR; Phosphorylated AKT (S473 and T308); Phosphorylated ERK; Cleaved caspase 3; Inhibition of phosphorylation of GSK3β.

Figure 13:
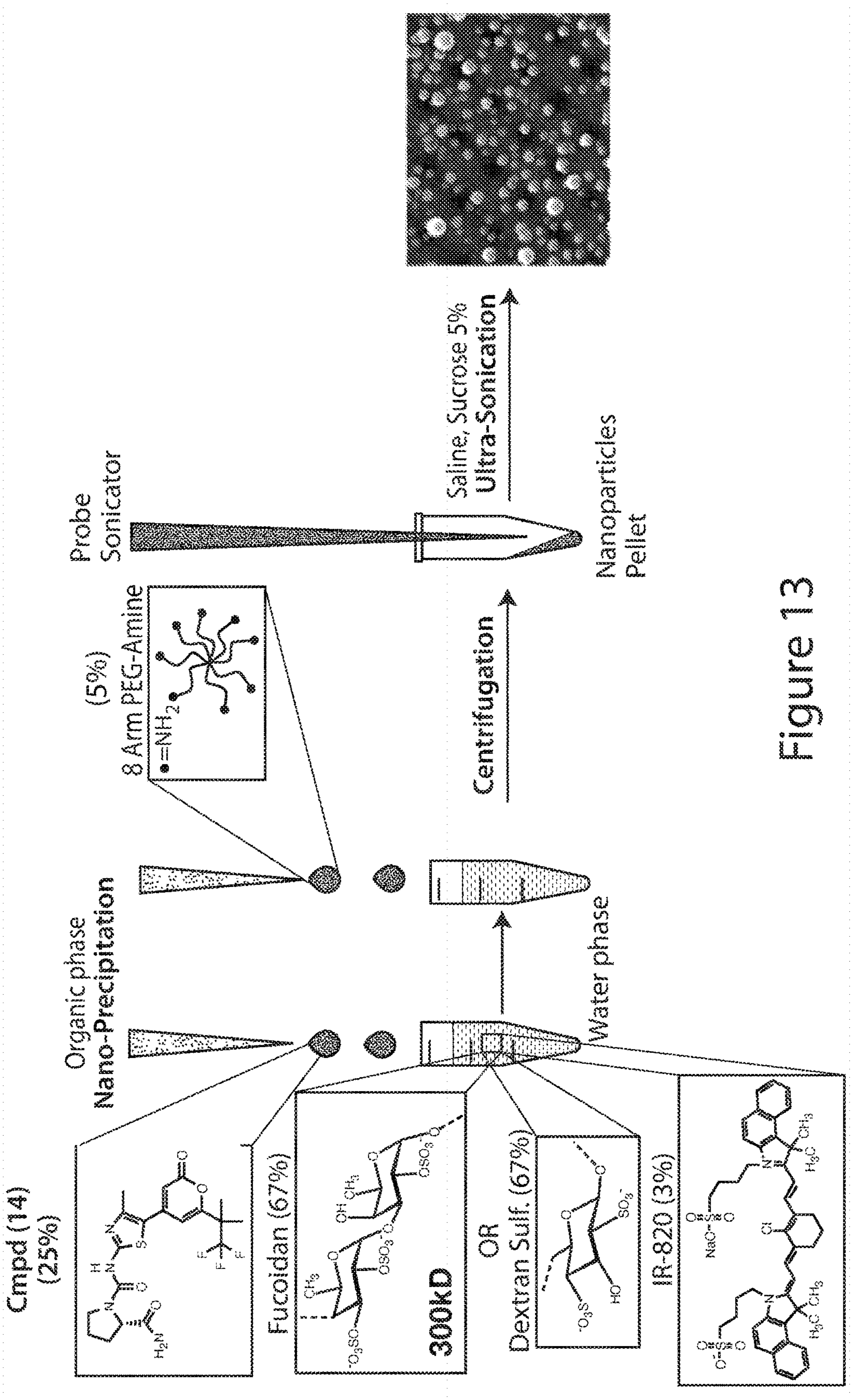
FIG. 13. Generation of Compound (14) Nanoparticles [Fi(Compound (14))]. An aliquot of 0.1 mL of Compound (14) dissolved in dimethyl sulfoxide (25 mg/mL) was added drop-wise (20 ml per 15 s) to a 0.6 mL aqueous polysaccharide solution (15 mg/mL) containing IR820 (2.5 mg/mL) and 0.05 mM sodium bicarbonate. An aliquot of 0.1 mL of 8-arm PEG-amine dissolved in water (Creative Peg Works, 20 kD, 5 mg/mL) was added drop-wise to the mixture followed by centrifugation (20,000 g, 30 min). The nanoparticle pellet was re-suspended in 1 mL of sterile PBS. The suspension was sonicated for 10 s with a probe tip ultrasonicator at 40% intensity (Sonics inc). The nanoparticles were lyophilized in a 5% saline/sucrose solution.
Figure 14:
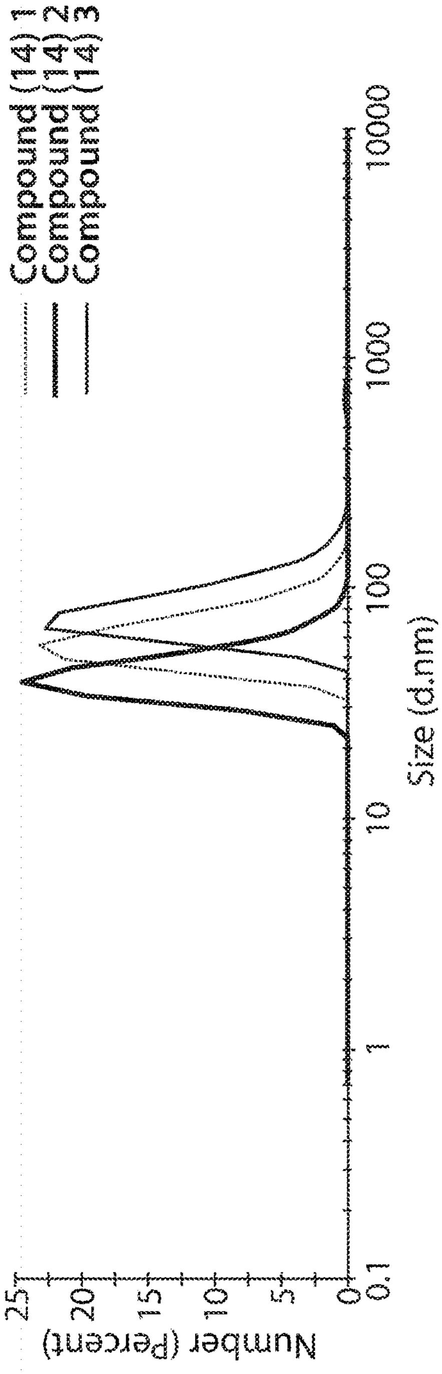
FIG. 14. Batch-to-Batch Variability of Fi(Compound (14)) Nanoparticles. Three independently generated batches of Fi(Compound (14)) were analyzed for particle size. Measurements were performed in duplicate.

Upon systemic treatment with PI3K/AKT inhibitors, hyperglycemia is invariably induced by loss of insulin signalling.[9,10] Thus, an acute increase of glucose and decrease of insulin in the bloodstream can be used as a BMx readout of systemic drug exposure and engagement of PI3K in healthy tissues. Accordingly, a rapid spike in both glycemia and drop in insulinemia was observed in mice following oral administration of BYL719, whereas these effects were largely attenuated by targeted delivery of BYL719 using fucoidan nanoparticles. Based on this data, the following BMx can serve to help define the TI for nanoformulated PI3K inhibitors: Phosphorylated IRS-1; Rapid and dramatic hyperglycemia; Rapid and dramatically decreased insulin levels; Increased C-peptide Structural/Physicochemical Properties Nanoformulated Compound (14) [Fi(Compound (14))] was typically prepared as illustrated in FIG. 13 by adding a DMSO solution dropwise to an aqueous polysaccharide solution containing the near-IR dye IR820. This was followed by the addition of an aqueous solution containing 20 kD, 8-arm PEG-amine, centrifugation and ultra-sonication yielding nanoparticles (<200 nm) with good batch consistency (FIG. 14). The actual composition in terms of percentage by weight is also provided in Table 1. Dextran sulfate could be substituted for fucoidan to yield control nanoparticles that will not target P-selectin.

Drug Metabolism Pharmacokinetic Characteristics

Mouse PK data for Compound (14) (cassette dosing) for free drug (i.e., not nanoformulated) is tabulated in Table 2 using amorphous material. Compound (14) showed modest oral bioavailability and high total clearance coupled to a short mean residence time in this cassette dosing experiment. The corresponding rat PK data is tabulated in Table 3, where the results are consistent with mouse PK data. Compound (14), based on this data and as intended, would not persist systemically for significant lengths of time were it to leach from the nanoparticles or diffuse from tumor cells to which it had been specifically delivered, thereby minimizing systemic mechanism-based PI3K liabilities. In contrast, the PK characteristics for BYL719[13] are presented in Table 2. BYL719 is drug optimized for a once-a-day (QD) oral dosing regimen and, as such, it was designed to be a metabolically stable molecule exhibiting a superior half-life and clearance properties (both values are approximately 4 times greater in mice and rats, relative to Compound (14)). Indeed, these BYL719 design attributes translated into an observed half-life in humans of 11.5 hour, a very attractive profile for a QD drug.

TABLE 2

Mouse Pharmacokinetic Properties of Cassette Dosed Free Compound (14) and BYL719

| $C5_{min}$ (ng/mL) | $AUC_{iv}$ (ng*h/mL) | $MRT_{iv}$ (h) | $VD_{ss}$ (mL/kg) | $Cl_{total}$ (mL/h/kg) | $C_{max}$ (ng/mL) | $T_{max}$ (h) | $AUC_{po}$ (ng*h/mL) | $MRT_{po}$ (h) | BA (%) |
|---|---|---|---|---|---|---|---|---|---|
| Compound (14)** | | | | | | | | | |
| 66.4 | 17.8 | 0.31 | 1783 | 5787 | 17.1 | 0.42 | 24 | 1.07 | 13.5 |
| BYL719** | | | | | | | | | |
| 56.4 | 73.9 | 1.12 | 1543 | 1375 | 183.6 | 1 | 526 | 2.12 | 71.2 |

**Dose: IV 0.1 mg/kg, 1 mL/kg (10-in-One); PO 1 mg/kg, 5 mL/kg (5-in-One)

TABLE 3

Rat Pharmakokinetic Properties of Cassette Dosed Free Compound (14) and BYL719

| $C5_{min}$ (ng/mL) | $AUC_{iv}$ (ng*h/mL) | $MRT_{iv}$ (h) | $VD_{ss}$ (mL/kg) | $Cl_{total}$ (mL/h/kg) | $C_{max}$ (ng/mL) | $T_{max}$ (h) | $AUC_{po}$ (ng*h/mL) | $MRT_{po}$ (h) | BA (%) |
|---|---|---|---|---|---|---|---|---|---|
| Compound (14)** | | | | | | | | | |
| 113.6 | 45.1 | 0.42 | 932 | 2221 | 11.8 | 0.5 | 26.9 | 2.1 | 5.9 |
| BYL719*** | | | | | | | | | |
| ND* | ND* | 2.9 | 1900 | 600 | ND* | ND* | ND* | ND* | 58 |

*ND: no data

**Dose: IV 0.1 mg/kg, 1 mL/kg (10-in-One); PO 1 mg/kg, 5 mL/kg (5-in-One)

***BYL719 dose: 3.4 mg/kg IV, 15 mg/kg PO[13]

Synthetic Preparation of Compounds (1), (3), and (4)

A synthetic route to Compounds (1), (3), and (4) is shown in the scheme below

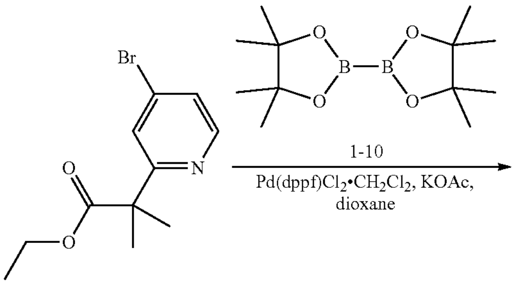

1-21

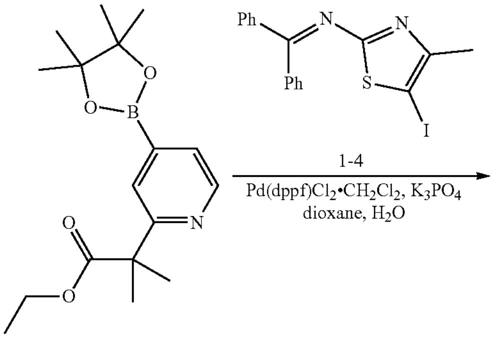

1-28

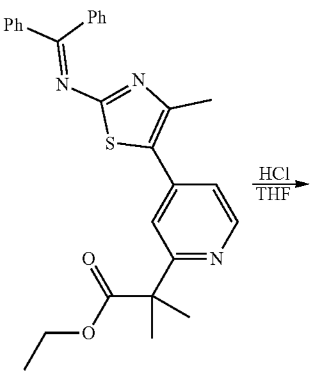

1-29

-continued

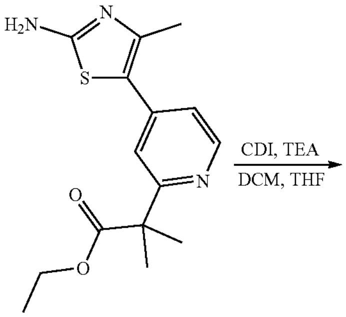

1-30

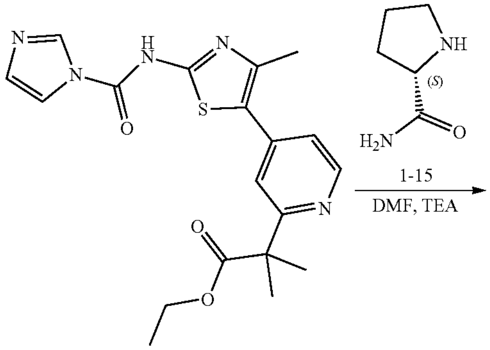

1-31

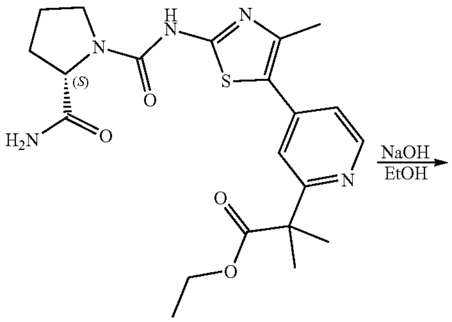

1-32

-continued
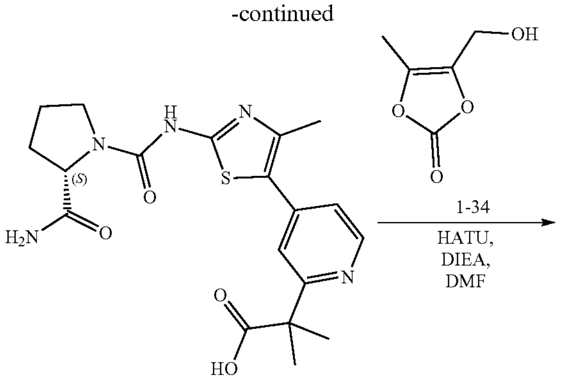
1-33
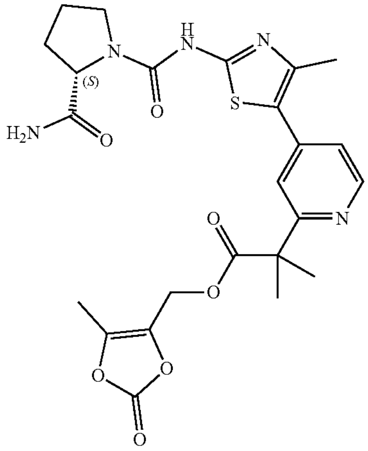
Compound (4)
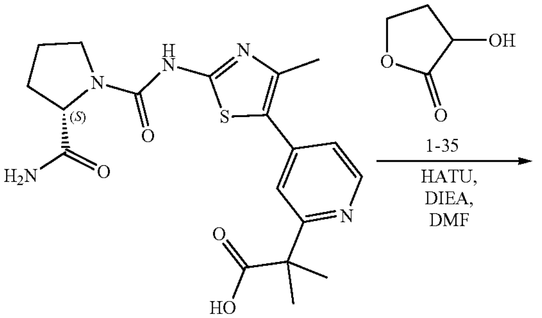
1-33
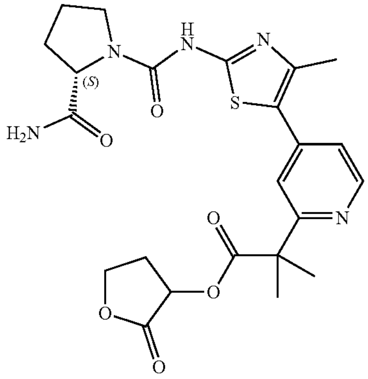
Compound (1)
-continued
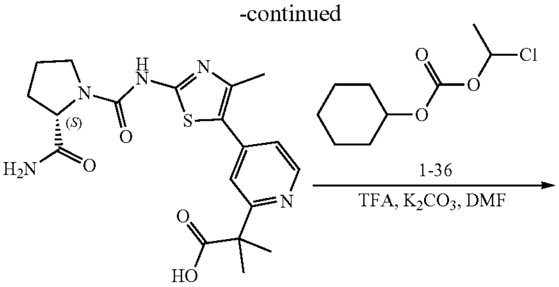
1-33
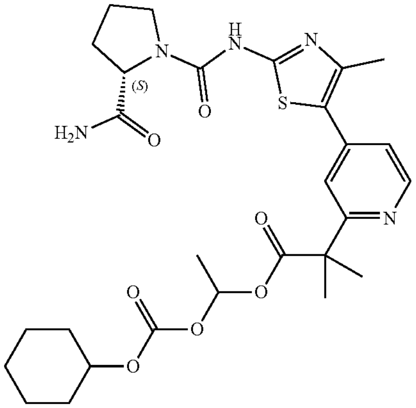
Compound (3)
Experimental Procedures for Compounds (1), (3), and (4)
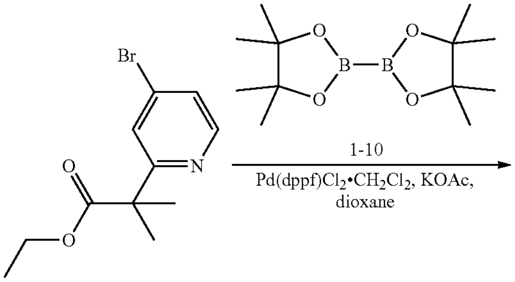
1-21
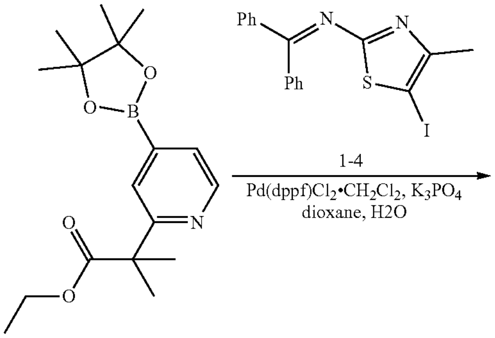
1-28

-continued

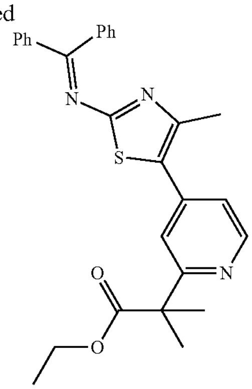

1-29

To a solution of compound 1-21 (5.00 g, 18.37 mmol, 1 eq) and compound 1-10 (5.13 g, 20.21 mmol, 1.1 eq) in dioxane (50 mL) was added potassium acetate (5.41 g, 55.12 mmol, 3 eq) and $Pd(dppf)Cl_2 \cdot CH_2Cl_2$ (750 mg, 918.65 umol, 0.05 eq). The mixture was degassed and purged with nitrogen for 3 times. Then the mixture was stirred at 95° C. for 3 hours under nitrogen atmosphere. TLC (petroleum ether:ethyl acetate=5:1) indicated the starting material was consumed completely and a new spot formed. To the reaction mixture was added compound 1-4 (7.42 g, 18.36 mmol, 1 eq) in water (15 mL), potassium phosphate (11.69 g, 55.07 mmol, 3 eq) and $Pd(dppf)Cl_2 \cdot CH_2Cl_2$ (750 mg, 917.91 umol, 0.05 eq). The mixture was degassed under vacuum and purged with nitrogen for 3 times, and stirred at 110° C. for 16 hours under nitrogen atmosphere. LCMS showed the starting material was consumed completely and desired mass was detected. The mixture was poured into water (40 mL), extracted with ethyl acetate (100 mL×3). The combined organic phase was washed with brine (50 mL), dried over anhydrous sodium sulfate, filtered and concentrated under reduced pressure to give a residue. The residue was purified by column chromatography ($SiO_2$, petroleum ether: ethyl acetate=40:1~20:1, monitored by TLC, petroleum ether:ethyl acetate=2:1) to afford compound 1-29 (4.5 g, crude) as yellow oil. LCMS: RT=0.926 min, purity: 83.14%, m/z 470.2 $[M+H]^+$. $^1H$ NMR ($CDCl_3$, 400 MHz): δ 8.50 (d, J=5.2 Hz, 1H), 7.88 (J=7.6 Hz, 2H), 7.52-7.50 (m, 4H), 7.45-7.41 (m, 2H), 7.33-7.31 (m, 2H), 7.17 (s, 1H), 7.04 (d, J=5.2 Hz, 1H), 4.16 (q, J=7.2 Hz, 2H), 2.50 (s, 3H), 1.59 (s, 6H), 1.19 (t, J=6.8 Hz, 3H).

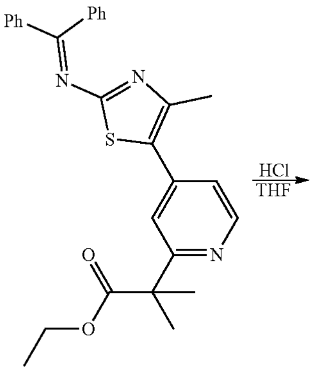

1-29

-continued

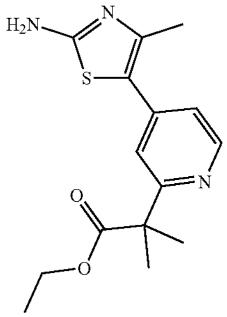

1-30

To a solution of compound 1-29 (3 g, 6.39 mmol, 1 eq) in tetrahydrofuran (30 mL) was added hydrochloric acid (2 M, 15.97 mL, 5 eq). The mixture was stirred at 20° C. for 30 minutes. LCMS showed the starting material was consumed completely and desired mass was detected. The mixture was poured into water (20 mL), extracted with ethyl acetate (20 mL×3). The organic phases were discarded. The aqueous phase was adjusted to pH=8 with sodium bicarbonate solid, extracted with a mixture of ethyl acetate:methanol=10:1 (v/v, 20 mL×3). The combined organic phase was washed with brine (20 mL), dried over anhydrous sodium sulfate, filtered and concentrated under reduced pressure to give a residue. The residue was purified by reverse phase flash (hydrochloric acid condition) to afford compound 1-30 (670 mg, 2.19 mmol, 34.34% yield) as yellow oil. LCMS: RT=0.562 min, purity: 35.80%, m/z 306.1 $[M+H]^+$. $^1H$ NMR ($CDCl_3$, 400 MHz): δ 8.52 (dd, $J_1$=5.2 Hz, $J_2$=0.8 Hz, 1H), 7.24 (d, J=0.8 Hz, 1H), 7.13 (dd, $J_1$=5.2 HZ, $J_2$=1.6 Hz, 1H), 5.16 (br. s, 2H), 4.19 (q, J=7.2 Hz, 2H), 2.40 (s, 3H), 1.64 (s, 6H), 1.23 (t, J=7.2 Hz, 3H).

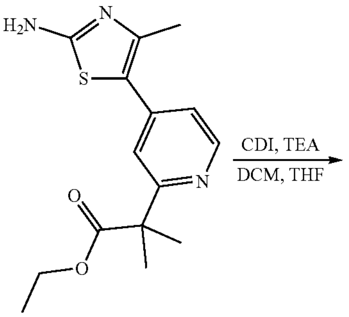

1-30

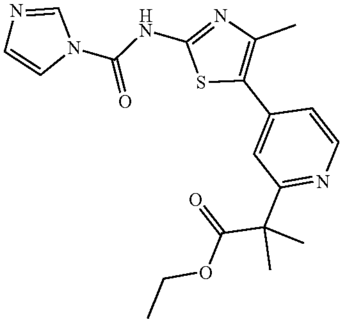

1-31

To a solution of compound 1-30 (880 mg, 2.88 mmol, 1 eq) in dichloromethane (8 mL) and tetrahydrofuran (4 mL)

was added triethylamine (437 mg, 4.32 mmol, 601.61 uL, 1.5 eq) and CDI (701 mg, 4.32 mmol, 1.5 eq). The mixture was stirred at 50° C. for 16 hours. TLC (petroleum ether: ethyl acetate=0:1) indicated the starting material was consumed completely and a new spot was formed. The mixture was concentrated to afford compound 1-31 (1.1 g, crude) as a yellow solid.

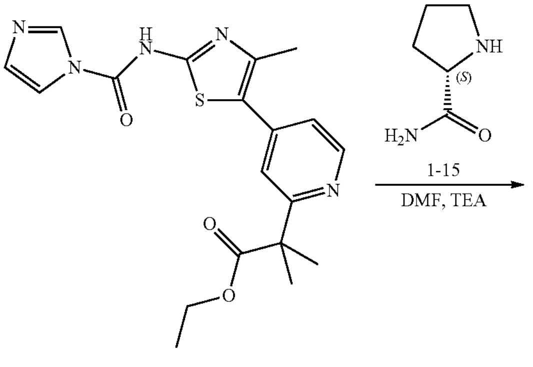

1-31

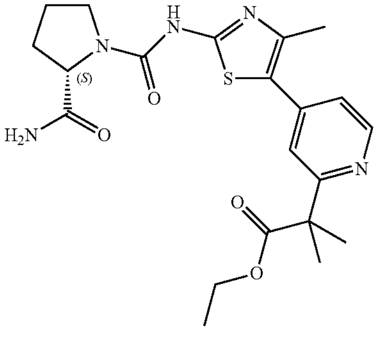

1-32

To a solution of compound 1-31 (1.1 g, 2.75 mmol, 1 eq) in dimethylformamide (5 mL) was added triethylamine (557 mg, 5.51 mmol, 766.56 uL, 2 eq) and compound 1-15 (629 mg, 5.51 mmol, 2 eq). The mixture was stirred at 25° C. for 1 hour. LCMS showed the starting material was consumed completely and one main peak with desired mass was detected. The mixture was concentrated in vacuo. The residue was purified by column chromatography ($SiO_2$, petroleum ether:ethyl acetate=5:1~0:1, monitored by TLC, petroleum ether:ethyl acetate=0:1), further purified by prep-HPLC (column: PHENOMENEX® Gemini 150*25 mm*10 um; mobile phase: [water (0.05% ammonia hydroxide v/v)-ACN]; B %: 20%-50%, 12 min). The fraction was extracted with ethyl acetate (50 mL×3). The combined organic phase was washed with brine (20 mL), dried over anhydrous sodium sulfate, filtered and concentrated under reduced pressure to afford compound 1-32 (550 mg, 1.23 mmol, 44.83% yield). LCMS: RT=0.672 min, purity: 58.55%, m/z 446.2 $[M+H]^+$. $^1H$ NMR ($CD_3OD$, 400 MHz): δ 8.28 (d, J=5.2 Hz, 1H), 7.28 (s, 1H), 7.21-7.20 (m, 1H), 4.38 (br. s, 1H), 4.04 (q, J=6.8 Hz, 2H), 3.55-3.44 (m, 2H), 2.31 (s, 3H), 2.14-1.86 (m, 4H), 1.50 (s, 6H), 1.09 (t, J=7.2 Hz, 3H).

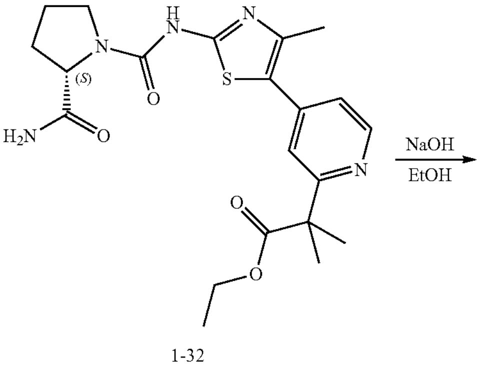

1-32

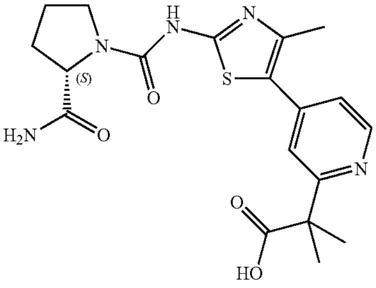

1-33

A solution of sodium hydroxide mg, 4.94 mmol, eq) and compound 1-32 (550 mg, 1.23 mmol, 1 eq) in ethanol (4 mL) was stirred at 85° C. for 40 minutes. TLC (petroleum ether:ethyl acetate=0:1) indicated the starting material was consumed completely and a new spot was formed. The mixture was concentrated to afford compound 1-33 (540 mg, 1.23 mmol, 99.31% yield, Na salt) as a yellow solid. LCMS: RT=0.592 min, purity: 88.54%, m/z 418.0$[M+H]^+$. $^1H$ NMR ($CD_3OD$, 400 MHz): δ 8.28 (d, J=5.2 Hz, 1H), 7.49 (d, J=1.2 Hz, 1H), 7.18 (dd, $J_1$=5.6 Hz, $J_2$=2.0 Hz, 1H), 7.05 (d, J=1.2 Hz, 1H), 4.61-5.51 (m, 1H), 3.58-3.50 (m, 2H), 2.39 (s, 3H), 2.09-1.94 (m, 2H), 1.95-1.87 (m, 2H), 1.55 (s, 6H).

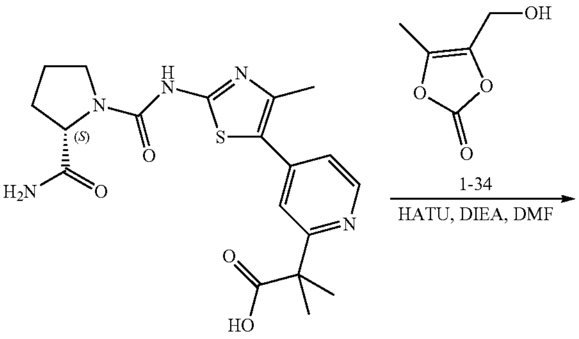

1-33

-continued

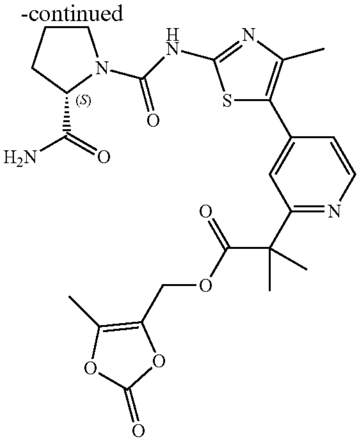

Compound (4)

To a solution of compound 1-33 (180 mg, 408.65 umol, 1 eq, Na salt) in dimethylformamide (3 mL) was added diisopropylethylamine (158 mg, 1.23 mmol, 213.54 uL, 3 eq) and HATU (311 mg, 817.31 umol, 2 eq) at 0° C. under nitrogen atmosphere, then compound 1-34 (160 mg, 1.23 mmol, 3 eq) was added. The mixture was stirred at 20° C. for 16 hours. LCMS showed the starting material was consumed completely and one main peak with desired mass was detected. The mixture was poured into water (10 mL) and extracted with dichloromethane (20 mL×3). The combined organic phase was washed with brine (20 mL), dried over anhydrous sodium sulfate, filtered and concentrated under reduced pressure to give a residue. The residue was purified by prep-HPLC (column: PHENOMENEX® Synergi C18 150*25*10 um; mobile phase: [water (0.1% TFA)-ACN]; B %: 15%-45%, 10 min). The fraction was adjusted to pH=8 with sodium bicarbonate solid and extracted with dichloromethane (20 mL×3). The combined organic phase was washed with brine (20 mL), dried over anhydrous sodium sulfate, filtered and concentrated under reduced pressure to afford Compound (4) (23.58 mg, 41.80 umol, 10.23% yield) as a white solid. LCMS: RT=1.910 min, purity: 93.87%, m/z 530.1 $[M+H]^+$. $^1H$ NMR ($CD_3OD$, 400 MHz): δ 8.44 (d, J=4.8 Hz, 1H), 7.39 (s, 1H), 7.33 (dd, $J_1$=5.2 Hz, $J_2$=1.6 Hz, 1H), 4.94 (s, 2H), 4.47-4.45 (m, 1H), 3.73-3.69 (m, 1H), 3.61-3.53 (m, 1H), 2.42 (s, 3H), 2.30-2.24 (m, 1H), 2.14 (s, 3H), 2.07-2.04 (m, 3H), 1.62 (s, 6H).

-continued

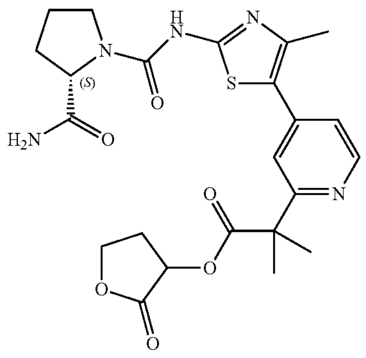

Compound (1)

To a solution of compound 1-33 (300 mg, 681.09 umol, 1 eq, Na salt) in dimethylformamide (4 mL) was added trifluoroacetic acid (87 mg, 762.41 umol, 56.45 uL, 1.12 eq), diisopropylethylamine (279 mg, 2.16 mmol, 375.49 uL, 3.17 eq) and HATU (546 mg, 1.44 mmol, 2.11 eq) at 0° C. under nitrogen atmosphere, the mixture was stirred at 0° C. for 15 minutes, then compound 1-35 (220 mg, 2.16 mmol, 168.00 uL, 3.17 eq) was added. The mixture was stirred at 25° C. for 16 hours. LCMS showed the starting material was consumed completely and desired mass was detected. The mixture was concentrated to give crude product. The crude product was purified by prep-HPLC (column: PHENOMENEX® Synergi C18 150*25*10 um; mobile phase: [water (0.1% TFA)-ACN]; B %: 5%-35%, 10 min). The fraction was adjusted to pH=8 with sodium bicarbonate solid. The mixture was extracted with dichloromethane (20 mL×3). The combined organic phase was washed with brine (20 mL), dried over anhydrous sodium sulfate, filtered and concentrated under reduced pressure to afford Compound (1) (34.2 mg, 68.19 umol, 10.01% yield, 100.00% purity) as a white solid. LCMS: RT=0.821 min, purity 100.00%, m/z 502.1 $[M+H]^+$. $^1H$ NMR ($CD_3OD$, 400 MHz): δ 8.48 (d, J=5.2 Hz, 1H), 7.46 (s, 1H), 7.34 (dd, $J_1$=4.8 Hz, $J_2$=1.2 Hz, 1H), 5.52 (t, J=9.2 Hz, 1H), 4.48-4.44 (m, 1H), 4.43-4.40 (m, 1H), 4.34-4.30 (m, 1H), 3.75-3.68 (m, 1H), 3.62-3.58 (m, 1H), 2.66-2.64 (m, 1H), 2.43 (s, 3H), 2.32-2.21 (m, 2H), 2.12-2.04 (m, 3H), 1.67-1.65 (m, 6H).

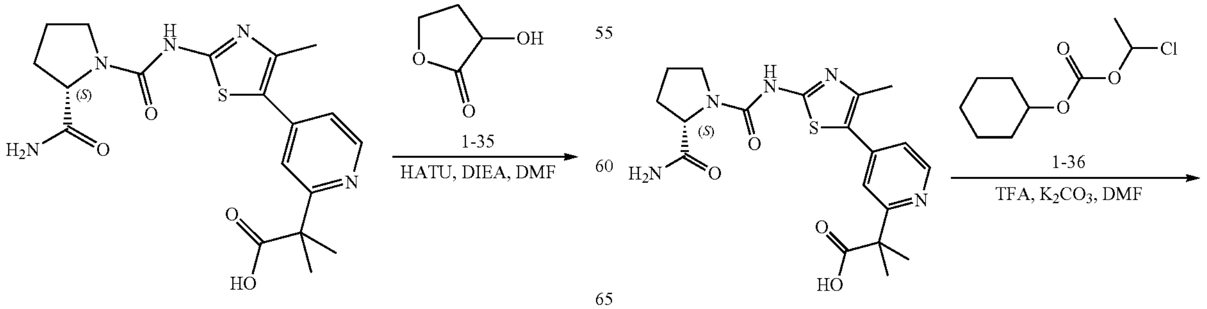

1-33

1-33

-continued

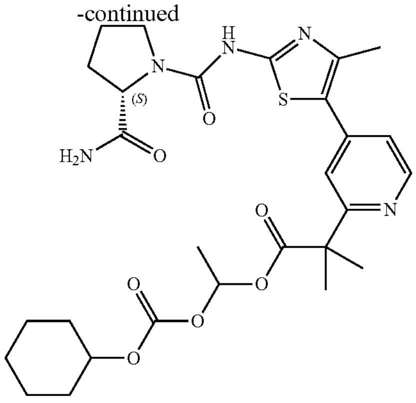

Compound (3)

To a solution of compound 1-33 (180 mg, 408.65 umol, 1 eq, Na salt) in dimethylformamide (3 mL) was added trifluoroacetic acid (47 mg, 408.65 umol, 30.26 uL, 1 eq), potassium carbonate (124 mg, 899.04 umol, 2.2 eq) and compound 1-36 (310 mg, 531.25 umol, 3.6 eq). The mixture was stirred at 20° C. for 32 hours. LCMS showed the starting material was consumed completely and desired mass was detected. The mixture was poured into water (10 mL) and then extracted with dichloromethane (20 mL×3). The combined organic phase was washed with brine (20 mL), dried over anhydrous sodium sulfate, filtered and concentrated under reduced pressure to give a residue. The residue was purified by prep-HPLC (column: PHENOMENEX® Synergi C18 150*25*10 um; mobile phase: [water (0.1% TFA)-ACN]; B %: 25%-55%, 13 min). The fraction was adjusted to pH=8 with sodium bicarbonate solid, extracted with dichloromethane (20 mL×3). The combined organic phase was washed with brine (20 mL), dried over anhydrous sodium sulfate, filtered and concentrated under reduced pressure to afford Compound (3) (23.45 mg, 39.90 umol, 9.76% yield, 100.00% purity) as a white solid. LCMS: RT=2.631 min, purity: 100.00%, m/z 588.1[M+H]$^+$. $^1$H NMR ($CD_3OD$, 400 MHz): δ 8.46 (d, J=5.2 Hz, 1H), 7.40 (s, 1H), 7.33 (dd, $J_1$=5.2 Hz, $J_2$=1.2 Hz, 1H), 6.73 (dd, $J_1$=10.8 Hz, $J_2$=5.6 Hz, 1H), 4.50-4.44 (m, 2H), 3.73-3.69 (m, 1H), 3.60-3.54 (m, 1H), 2.44 (s, 3H), 2.29-2.24 (m, 1H), 2.07-2.01 (m, 3H), 1.81-1.67 (m, 4H), 1.61 (d, J=5.2 Hz, 6H), 1.53-1.51 (m, 1H), 1.42-1.40 (m, 4H), 1.38-1.30 (m, 4H).

Synthetic Preparation of Compound (2)

A synthetic route to Compound (2) is shown in the scheme below.

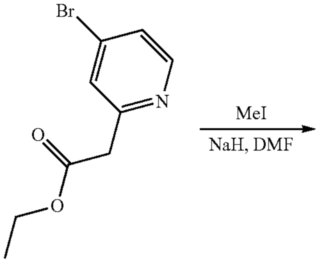

2-7

-continued

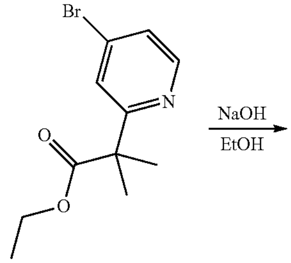

2-21

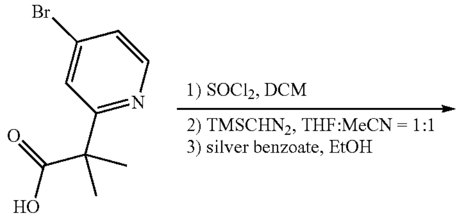

2-22

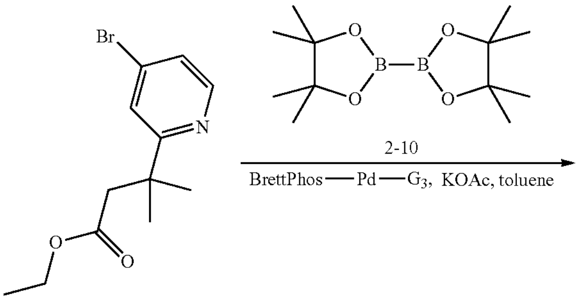

2-23

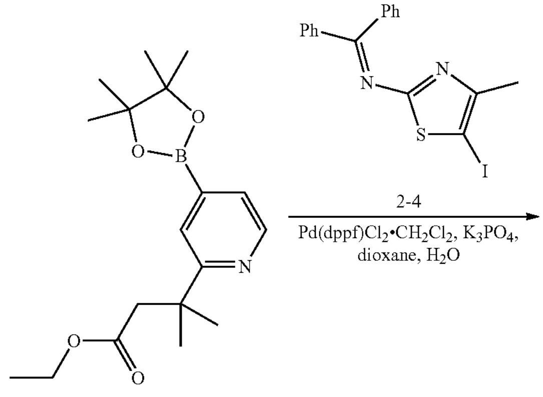

2-24

-continued

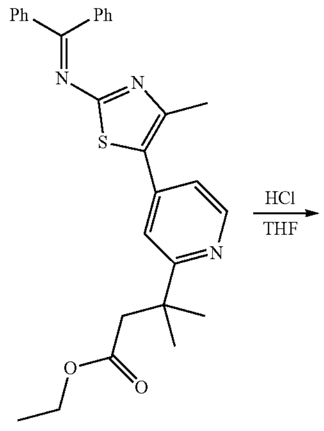

2-25

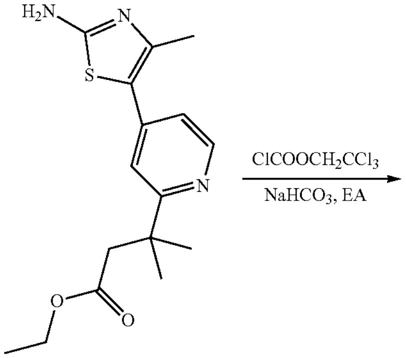

2-26

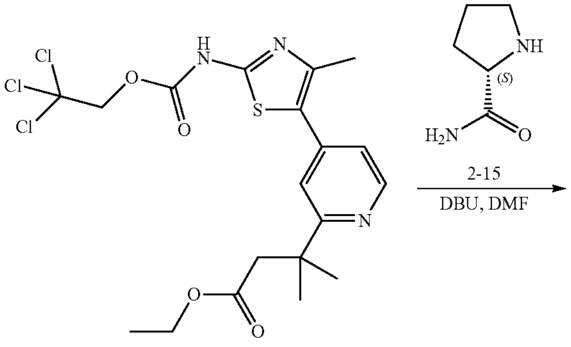

2-27

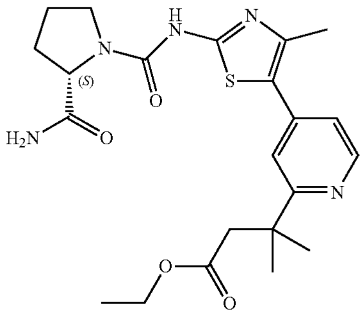

Compound (2)

Experimental Procedures for Compound (2)

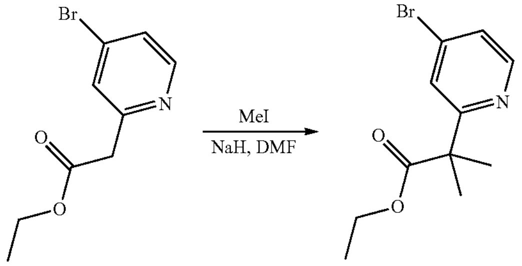

2-7 2-21

To a solution of compound 2-7 (1.3 g, 5.33 mmol, 1 eq) in dimethylformamide (2 mL) was added sodium hydride (533 mg, 13.32 mmol, 60% purity in mineral oil, 2.5 eq) at 0° C. under nitrogen atmosphere. The mixture was stirred at 0° C. for 20 minutes and methyl iodide (3.78 g, 26.63 mmol, 1.66 mL, 5 eq) was added. The mixture was stirred at 20° C. for 10 minutes. TLC (petroleum ether:ethyl acetate=5:1) indicated the starting material was consumed completely and a new spot was formed. The mixture was poured into water (10 mL) and 1N hydrochloric acid (4 mL). The mixture was adjusted to pH=8 with sodium bicarbonate solid and extracted with ethyl acetate (20 mL×3). The combined organic phase was washed with brine (20 mL), dried over anhydrous sodium sulfate, filtered and concentrated under reduced pressure to afford compound 2-21 (1.44 g, 4.90 mmol, 91.92% yield) as yellow oil. LCMS: RT=1.408 min, purity: 92.52%, m/z 271.9, 273.9 $[M+H]^+$. $^1H$ NMR ($CDCl_3$, 400 MHz): δ 8.38 (d, J=7.2 Hz, 1H), 7.48 (d, J=2.0 Hz, 1H), 7.34 (dd, $J_1$=7.2 Hz, $J_2$=2.4 Hz, 1H), 4.17 (q, J=9.6 Hz, 2H), 1.61 (s, 6H), 1.21 (t, J=9.2 Hz, 3H).

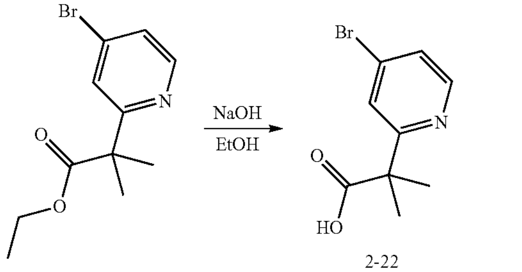

2-21 2-22

A solution of compound 2-21 (1 g, 3.67 mmol, 1 eq) and sodium hydroxide (176 mg, 4.41 mmol, 1.2 eq) in ethanol (50 mL) was stirred at 80° C. for 16 hours. TLC (petroleum ether:ethyl acetate=2:1) indicated the starting material was consumed completely and a new spot was formed. The mixture was concentrated to afford compound 2-22 (980 mg, 3.67 mmol, 99.86% yield, Na salt) as a yellow solid. $^1H$ NMR ($D_2O$, 400 MHz): δ 8.22 (d, J=5.6 Hz, 1H), 7.62 (d, J=1.6 Hz, 1H), 7.48 (dd, $J_1$=5.2 Hz, $J_2$=1.6 Hz, 1H), 1.45 (s, 6H).

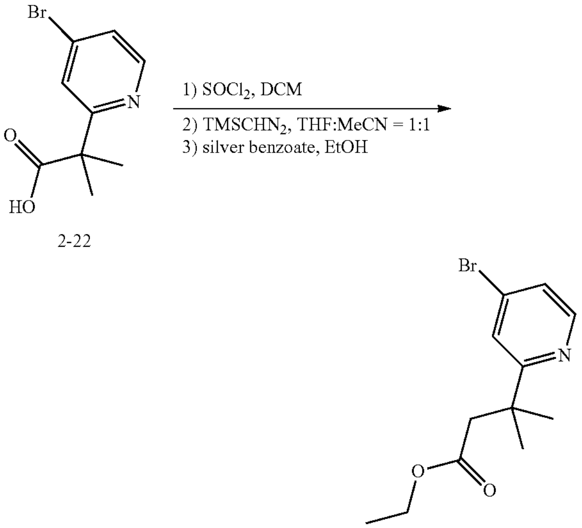

2-22

2-23

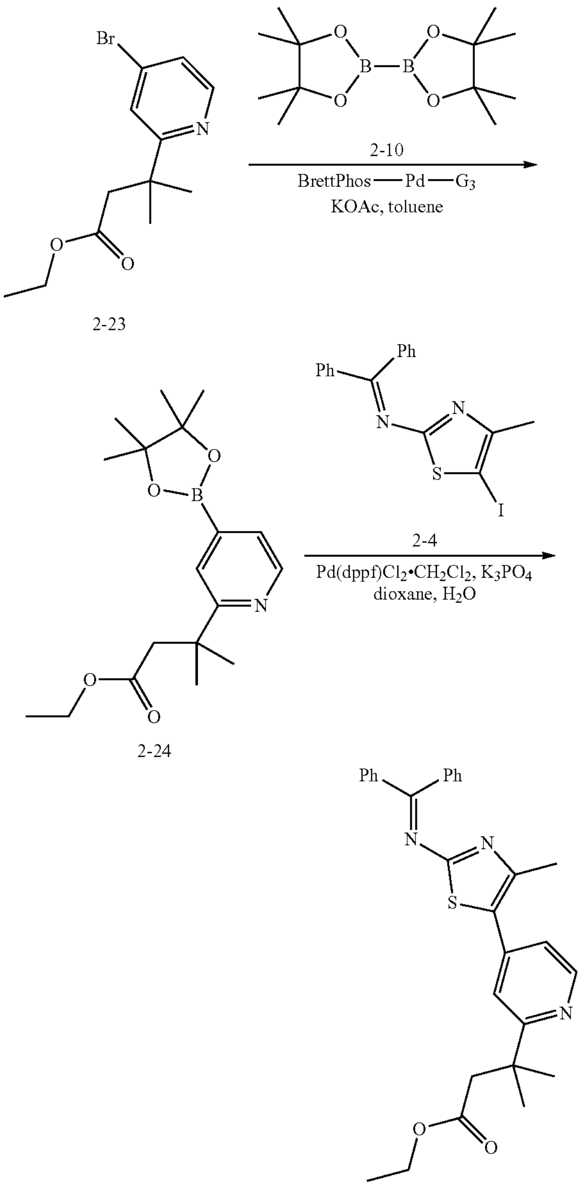

2-23

2-24

2-25

To a solution of compound 2-22 (980 mg, 3.67 mmol, 1 eq, Na salt) in dichloromethane (10 mL) was added dimethylformamide (27 mg, 366.94 umol, 28.23 uL, 0.1 eq) and oxalyl dichloride (1.45 g, 11.42 mmol, 1 mL, 3.11 eq) at 0° C. under nitrogen atmosphere and the mixture was stirred at 20° C. for 0.5 hour. LCMS showed the starting material was consumed completely. The mixture was concentrated in vacuum. The crude product dissolved in tetrahydrofuran (10 mL) and acetonitrile (10 mL) was added to a solution of trimethylsilyldiazomethane (2 M, 15.00 mL, 2.5 eq) and triethylamine (4.25 g, 42.00 mmol, 5.85 mL, 3.5 eq) in tetrahydrofuran (10 mL) and acetonitrile (10 mL) dropwise at 0° C. under nitrogen atmosphere. After addition, the mixture was warmed to 20° C. and stirred for 16 hours. TLC (petroleum ether:ethyl acetate=5:1) indicated a new spot formed. The mixture was poured into water (40 mL) and extracted with ethyl acetate (100 mL×3). The combined organic phase was washed with saturated sodium bicarbonate (50 mL×3), brine (50 mL), dried over anhydrous sodium sulfate. After filtration and concentration, the residue was purified by column chromatography ($SiO_2$, petroleum ether: ethyl acetate=50:1~20:1) to afford the intermediate (2.4 g, 8.95 mmol, 74.61% yield) as black oil.

The intermediate (2.4 g, 8.95 mmol, 1 eq) in ethanol (16 mL) was added to a solution of benzoyloxysilver (410 mg, 1.79 mmol, 0.2 eq) and triethylamine (3.62 g, 35.81 mmol, 4.98 mL, 4 eq) in ethanol (4 mL). The mixture was stirred at 20° C. for 16 hours. TLC (petroleum ether:ethyl acetate=5:1) indicated the starting material was consumed completely and a new spot was formed. The mixture was poured into water (40 mL) and extracted with ethyl acetate (40 mL×3). The combined organic phase was washed with brine (20 mL), dried over anhydrous sodium sulfate, filtered and concentrated under reduced pressure to give a residue. The residue was purified by column chromatography ($SiO_2$, petroleum ether:ethyl acetate=50:1~40:1), then by reverse phase flash (TFA condition) to afford compound 2-23 (760 mg, 2.66 mmol, 29.67% yield) as yellow oil. LCMS: RT=0.722 min, purity: 73.52%, m/z 286.0, 288.0 $[M+H]^+$. $^1H$ NMR ($CDCl_3$, 400 MHz): δ 8.36 (d, J=5.2 Hz, 1H), 7.50 (d, J=1.6 Hz, 1H), 7.28 (dd, $J_1$=5.6 Hz, $J_2$=2.0 Hz, 1H), 4.00 (q, J=7.2 Hz, 2H), 2.81 (s, 2H), 1.44 (s, 6H), 1.13 (t, J=7.2 Hz, 3H).

To a solution of compound 2-23 (340 mg, 1.19 mmol, 1 eq) and compound 2-10 (362 mg, 1.43 mmol, 1.2 eq) in toluene (3 mL) was added potassium acetate (233 mg, 2.38 mmol, 2 eq) and BrettPhos-Pd-$G_3$ (54 mg, 59.41 umol, 0.05 eq). The mixture was degassed and purged with nitrogen for 3 times, and then the mixture was stirred at 90° C. for 16 hours under nitrogen atmosphere. LCMS showed the starting material was consumed completely and desired mass was detected. The mixture was concentrated to afford compound 2-24 (390 mg, crude) as black oil.

To a solution of compound 2-24 (390 mg, 1.17 mmol, 1 eq) and compound 2-4 (473 mg, 1.17 mmol, 1 eq) in dioxane (5 mL) and water (1.5 mL) was added potassium phosphate (745 mg, 3.51 mmol, 3 eq) and $Pd(dppf)Cl_2 \cdot CH_2Cl_2$ (96 mg, 117.04 umol, 0.1 eq). The mixture was degassed and purged with nitrogen for 3 times, and stirred at 110° C. for 2 hours under nitrogen atmosphere. LCMS showed the starting material was consumed completely and desired mass was detected. The mixture was poured into water (40 mL) and extracted with ethyl acetate (40 mL×3). The combined organic phase was washed with brine (20 mL), dried over anhydrous sodium sulfate, filtered and concentrated under reduced pressure to give a residue. The residue was purified by column chromatography ($SiO_2$, petroleum ether:ethyl acetate=20:1~10:1, monitored by TLC, petroleum ether: ethyl acetate=3:1) to afford compound 2-25 (520 mg, 1.08 mmol, 91.87% yield) as yellow oil. LCMS: RT=0.776 min, purity: 39.58%, m/z 484.2 $[M+H]^+$ $^1H$ NMR ($CD_3OD$, 400 MHz): δ 8.44 (dd, $J_1$=5.2 Hz, $J_2$=0.4 Hz, 1H), 7.84 (d, J=7.6 Hz, 2H), 7.59-7.46 (m, 6H), 7.34-7.30 (m, 3H), 7.13 (dd, $J_1$=5.2 Hz, $J_2$=1.6 Hz, 1H), 4.10 (q, J=7.6 Hz, 2H), 2.79 (s, 2H), 2.45 (s, 3H), 1.43 (s, 6H), 1.03 (t, J=6.8 Hz, 3H).

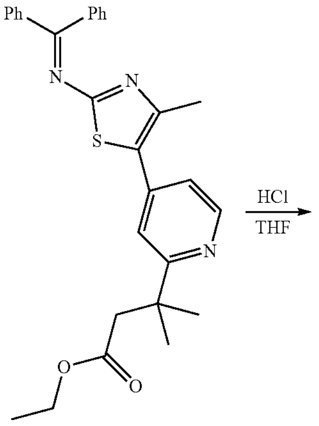

2-25

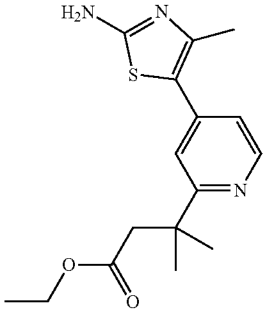

2-26

To a solution of compound 2-25 (520 mg, 1.08 mmol, 1 eq) in tetrahydrofuran (8 mL) was added hydrochloric acid (2 M, 2.69 mL, 5 eq, in water). The mixture was stirred at 25° C. for 30 minutes. TLC (petroleum ether:ethyl acetate=3:1) indicated the starting material was consumed completely and a new spot was formed. The mixture was poured into water (10 mL), extracted with ethyl acetate (20 mL×3). The combined organic phase was discarded. The aqueous phase was adjusted to pH=10 with sodium carbonate solid, extracted with ethyl acetate (20 mL×3). The combined organic phase was washed with brine (20 mL), dried over anhydrous sodium sulfate, filtered and concentrated under reduced pressure to afford compound 2-26 (290 mg, 885.31 umol, 82.34% yield) as colorless oil. LCMS: RT=0.564 min, purity: 44.54%, m/z 320.1 $[M+H]^+$. $^1H$ NMR ($CD_3OD$, 400 MHz): δ 8.30 (d, J=5.2 Hz, 1H), 7.24 (d, J=1.2 Hz, 1H), 7.08 (dd, $J_1$=5.2 Hz, $J_2$=1.6 Hz, 1H), 3.84 (q, J=7.2 Hz, 2H), 2.71 (s, 2H), 2.24 (s, 3H), 1.36 (s, 6H), 0.96 (t, J=7.2 Hz, 3H).

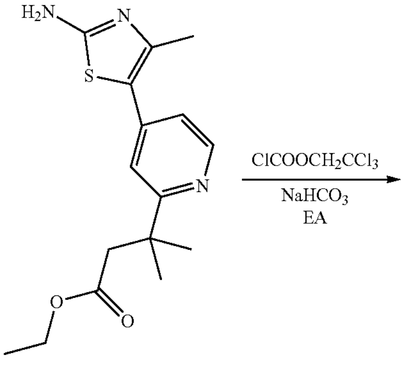

2-26

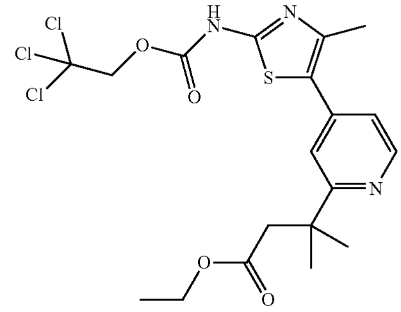

2-27

To a solution of compound 2-26 (50 mg, 156.53 umol, 1 eq) in ethyl acetate (0.8 mL) was added sodium bicarbonate (26 mg, 313.07 umol, 12.18 uL, 2 eq) and 2,2,2-trichloroethyl carbonochloridate (33 mg, 156.53 umol, 20.99 uL, 1 eq) at 0° C. under nitrogen atmosphere. The mixture was stirred at 25° C. for 30 minutes. TLC (petroleum ether:ethyl acetate=3:1) showed most of the starting material was consumed and a new spot was detected. The mixture was poured into water (10 mL), extracted with dichloromethane (10 mL×3). The combined organic phase was washed with brine (20 mL), dried over anhydrous sodium sulfate, filtered and concentrated under reduced pressure to give a residue. The crude product was purified by prep-TLC (petroleum ether:ethyl acetate=3:1) to afford compound 2-27 (23 mg, 44.77 umol, 28.60% yield, 96.313% purity) as a white solid. LCMS: RT=1.373 min, purity: 96.31%, m/z 493.8, 495.8, 497.8 $[M+H]^+$. $^1H$ NMR ($CDCl_3$, 400 MHz): δ 8.57 (d, J=5.2 Hz, 1H), 7.36 (d, J=1.2 Hz, 1H), 7.16 (dd, $J_1$=5.2 Hz, $J_2$=1.6 Hz, 1H), 4.92 (s, 2H), 4.00 (q, J=7.6 Hz, 2H), 2.85 (s, 2H), 2.49 (s, 3H), 1.49 (s, 6H), 1.12 (t, J=7.2 Hz, 3H).

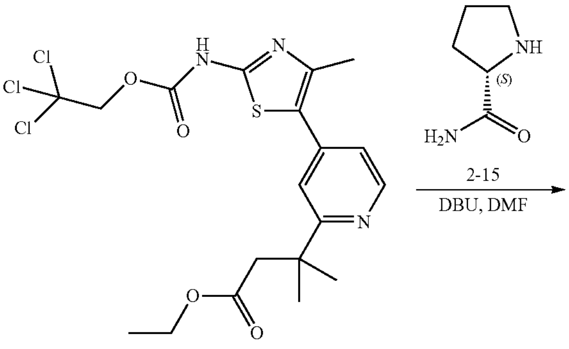

2-27

-continued

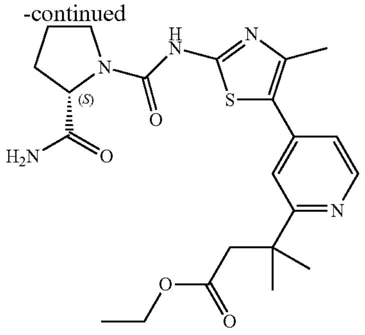

Compound (2)

To a solution of compound 2-27 (90 mg, 181.88 umol, 1 eq) and compound 2-15 (166 mg, 1.46 mmol, 8 eq) in dimethylformamide (2 mL) was added DBU (28 mg, 181.88 umol, 27.42 uL, 1 eq). The mixture was stirred at 60° C. for 16 hours. LCMS showed the starting material was consumed completely and desired mass was detected. The mixture was poured into water (10 mL), extracted with ethyl acetate (20 mL×3). The combined organic phase was dried over anhydrous sodium sulfate, filtered and concentrated under reduced pressure to give a residue. The residue was purified by column chromatography ($SiO_2$, petroleum ether:ethyl acetate=1:1~1:3) to afford compound (2) (52.2 mg, 109.55 umol, 60.23% yield) as a yellow solid. LCMS: RT=2.033 min, purity: 96.45%, m/z 460.1[M+H]$^+$. $^1$H NMR ($CD_3OD$, 400 MHz): δ 8.47 (d, J=5.2 Hz, 1H), 7.44 (d, J=1.2 Hz, 1H), 7.28 (dd, $J_1$=5.2 Hz, $J_2$=1.6 Hz, 1H), 4.60-4.44 (m, 1H), 3.94 (q, J=7.6 Hz, 2H), 3.71-3.70 (m, 1H), 3.59-3.58 (m, 1H), 2.83 (s, 2H), 2.43 (s, 3H), 2.28-2.25 (m, 1H), 2.07-2.01 (m, 3H), 1.47 (s, 6H), 1.06 (t, J=7.2 Hz, 3H).

Synthetic Preparation of Compound (5)

A synthetic route to Compound (5) is shown in the scheme below

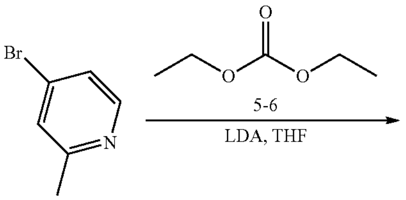

5-5

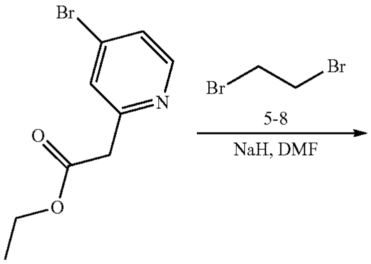

5-7

-continued

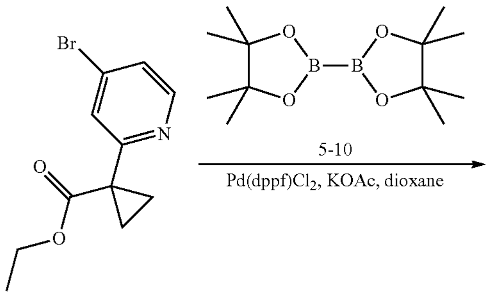

5-9

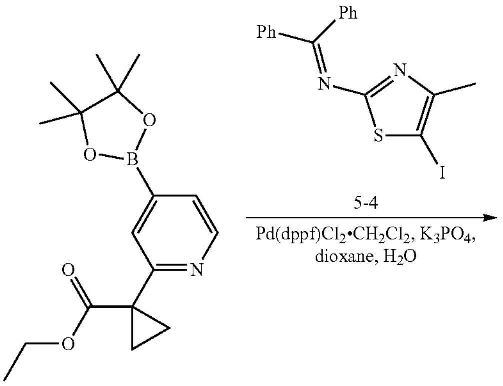

5-11

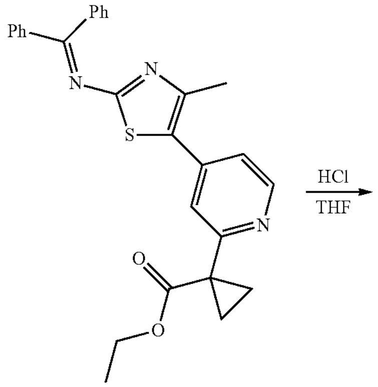

5-12

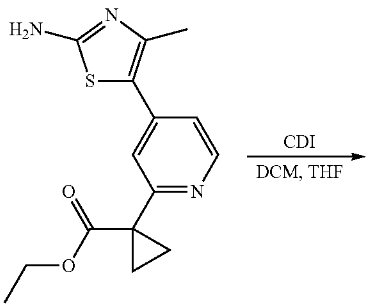

5-13

-continued

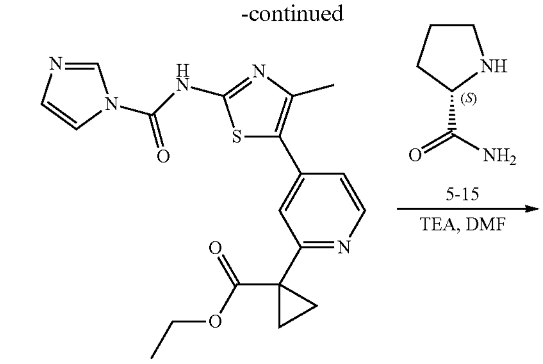

5-14

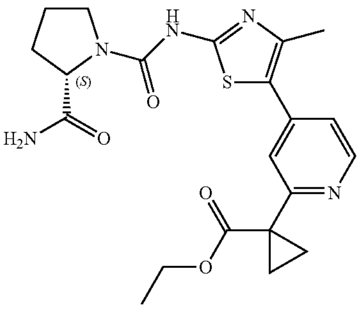

Compound (5)

Experimental Procedures for Compound (5)

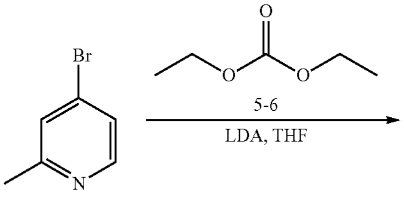

5-5

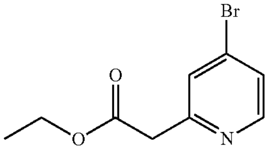

5-7

To a solution of compound 5-5 (26 g, 151.14 mmol, 1 eq) and compound 5-6 (23.40 g, 198.09 mmol, 24 mL, 1.31 eq) in tetrahydrofuran (300 mL) was added LDA (2 M, 39 mL) at −70° C. under nitrogen atmosphere. The mixture was stirred at −70° C. for 1 hour prior to the addition of LDA (2 M, 39.00 mL). The reaction was stirred at −70° C. for another 1 hour. LCMS showed 25% of starting material remained and 54% of desired compound mass was detected. The reaction mixture was quenched with water (50 mL), and extracted with ethyl acetate (100 mL×3). The combined organic layers was dried over anhydrous sodium sulfate, filtered and concentrated in vacuum. The residue was purified by reverse phase flash (trifluoroacetic acid condition). Then basified with saturated sodium bicarbonate (10 mL), extracted with ethyl acetate (100 mL×3). The combined organic layers was dried over anhydrous sodium sulfate, filtered and concentrated in vacuum to give compound 5-7 (22 g, 59.63% yield) as yellow oil.

$^1$H NMR ($CDCl_3$, 400 MHz): δ 8.45 (d, J=5.6 Hz, 1H), 7.61 (d, J=2.0 Hz, 1H), 7.50 (dd, $J_1$=5.6 Hz, $J_2$=2.0 Hz, 1H), 4.20 (q, J=7.2 Hz, 2H), 3.89 (s, 2H), 1.27 (t, J=7.2 Hz, 3H).

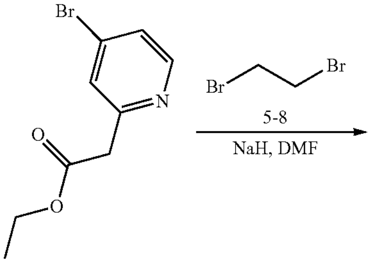

5-7

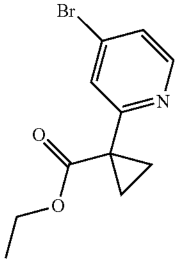

5-9

To a solution of compound 5-7 (2 g, 8.19 mmol, 1 eq) in dimethylformamide (20 mL) was added sodium hydride (819 mg, 20.48 mmol, 60% purity in mineral oil, 2.5 eq) at 0° C. and the mixture was stirred at 20° C. for 30 minutes. The mixture was cooled to 0° C. and then compound 5-8 (1.69 g, 9.01 mmol, 680.02 uL, 1.1 eq) was added. The mixture was stirred at 20° C. for 1 hour. TLC indicated the starting material was consumed completely and a new spot formed. The mixture was poured into water (20 mL) and extracted with ethyl acetate (20 mL×3). The combined organic phase was washed with brine (20 mL), dried over anhydrous sodium sulfate, filtered and concentrated under reduced pressure to afford compound 5-9 (1 g, 3.11 mmol, 37.90% yield, 83.88% purity) as yellow oil. LCMS: RT=0.722 min, purity: 83.88%, m/z 269.9, 271.9 $[M+H]^+$.

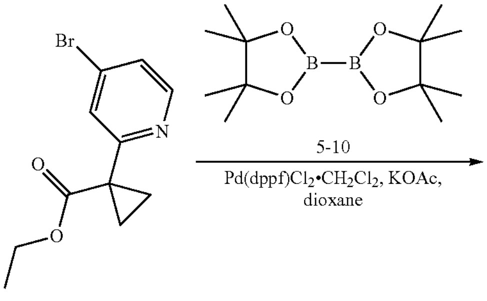

5-9

-continued

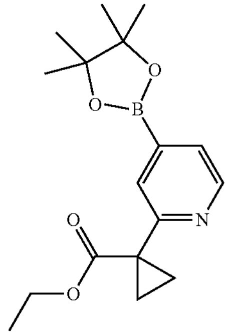

5-11

To a solution of compound 5-9 (1 g, 3.11 mmol, 1 eq) and compound 5-10 (867 mg, 3.42 mmol, 1.1 eq) in dioxane (10 mL) was added $Pd(dppf)Cl_2 \cdot CH_2Cl_2$ (254 mg, 310.53 umol, 0.1 eq) and potassium acetate (914 mg, 9.32 mmol, 3 eq). The mixture was degassed under vacuum and purged with nitrogen for 3 times. The resulting mixture was stirred at 90° C. for 3 hours under nitrogen atmosphere. TLC (petroleum ether:ethyl acetate=5:1) indicated the starting material was consumed completely and new spot formed. The mixture was used for next reaction directly without purification (0.98 g, crude, in 10 mL dioxane).

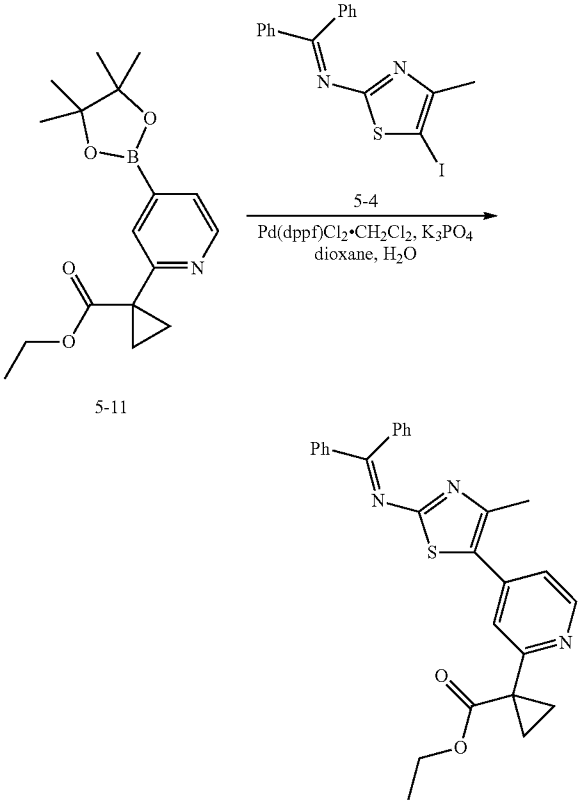

5-11

5-12

To a solution of compound 5-11 (980 mg, 3.09 mmol, 1 eq) (in 10 mL dioxane) and compound 5-4 (1.25 g, 3.09 mmol, 1 eq) in water (3 mL) was added $Pd(dppf)Cl_2 \cdot CH_2Cl_2$ (126 mg, 154.48 umol, 0.05 eq) and potassium phosphate (1.97 g, 9.27 mmol, 3 eq). The mixture was degassed and purged with nitrogen for 3 times and then stirred at 110° C. for 16 hours under nitrogen atmosphere. LCMS showed the starting material was consumed completely and desired mass was detected. The mixture was poured into water (40 mL) and extracted with ethyl acetate (20 mL×3). The combined organic phase was washed with brine (20 mL), dried over anhydrous sodium sulfate, filtered and concentrated under reduced pressure to give a residue. The residue was purified by column chromatography ($SiO_2$, petroleum ether:ethyl acetate=40:1~20:1, monitored by TLC. petroleum ether:ethyl acetate=2:1) to afford compound 5-12 (1.2 g, 2.34 mmol, 75.84% yield) as yellow oil. LCMS: RT=0.863 min, purity: 91.31%, m/z 468.0[M+H]$^+$. $^1$H NMR ($CDCl_3$, 400 MHz): δ 8.45 (d, J=5.2 Hz, 1H), 7.88 (d, J=7.6 Hz, 2H), 7.51-7.49 (m, 4H), 7.44-7.43 (m, 3H), 7.41-7.33 (m, 2H), 7.04 (dd, $J_1$=5.2 Hz, $J_2$=1.6 Hz, 1H), 4.18-4.14 (m, 2H), 2.52 (s, 3H), 1.67-1.65 (m, 2H), 1.47-1.45 (m, 2H), 1.22-1.18 (m, 3H).

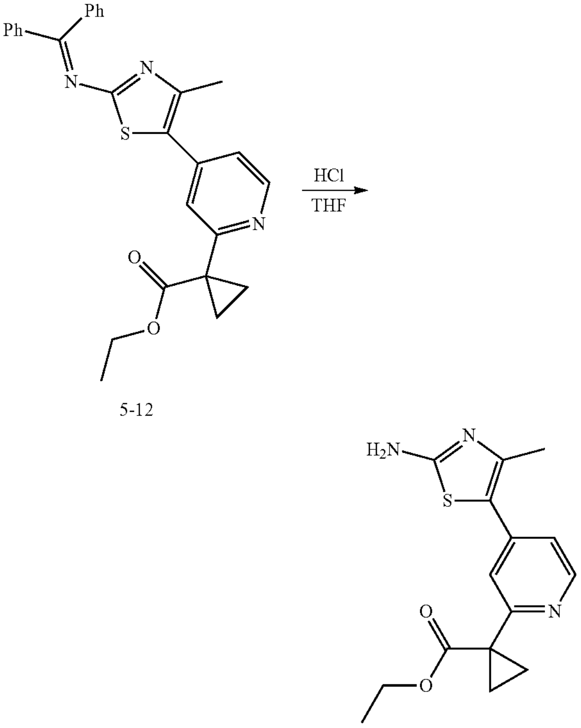

5-12

5-13

To a solution of compound 5-12 (600 mg, 1.28 mmol, 1 eq) in tetrahydrofuran (10 mL) was added hydrochloric acid (2 M, 5.13 mL, 8 eq). The mixture was stirred at 20° C. for 0.5 hour. TLC (petroleum ether:ethyl acetate=2:1) indicated the starting material was consumed completely and a new spot formed. The mixture was poured into water (20 mL) and extracted with ethyl acetate (20 mL×3). The organic phase was discarded. The aqueous phase was adjusted to pH=8 with sodium bicarbonate, extracted with a mixture of ethyl acetate:methanol=10:1 (20 mL×3, v/v). The combined organic phase was washed with brine (20 mL), dried over anhydrous sodium sulfate, filtered and concentrated under reduced pressure to afford compound 5-13 (260 mg, 789.05 umol, 61.49% yield, 92.07% purity) as a white solid. LCMS: RT=1.053 min, purity: 92.07%, m/z 304.0[M+H]$^+$. $^1$H NMR ($CDCl_3$, 400 MHz): δ 8.46-8.45 (m, 1H), 7.48-7.46 (m, 1H), 7.13-7.11 (m, 1H), 4.19-4.14 (m, 2H), 2.42-2.34 (m, 3H), 1.69-1.67 (m, 2H), 1.49-1.48 (m, 2H), 1.24-1.22 (m, 3H).

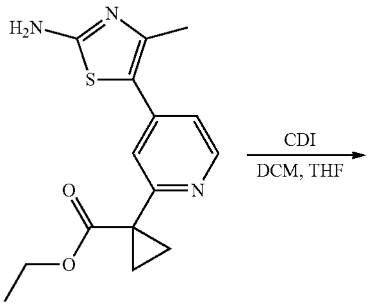

5-13

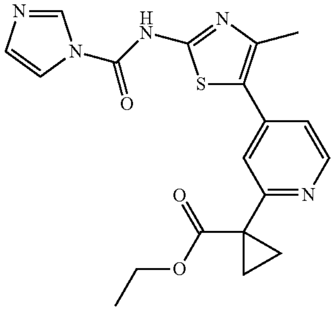

5-14

To a solution of compound 5-13 (255 mg, 840.53 umol, 1 eq) in dichloromethane (5 mL) and tetrahydrofuran (2.5 mL) was added CDI (409 mg, 2.52 mmol, 3 eq). The mixture was stirred at 50° C. for 16 hours. TLC (petroleum ether: ethyl acetate=0:1) showed the starting material was consumed completely. The mixture was concentrated in vacuo to afford compound 5-14 (350 mg, crude) as a yellow solid. $^1H$ NMR ($CDCl_3$, 400 MHz): δ 9.03 (s, 1H), 8.70 (d, J=5.2 Hz, 1H), 7.77 (d, J=0.8 Hz, 1H), 7.50 (s, 1H), 7.38 (dd, $J_1$=5.2 Hz, $J_2$=1.6 Hz, 1H), 7.22 (s, 1H), 4.31 (q, J=7.2 Hz, 2H), 2.75 (s, 3H), 1.87-1.84 (m, 2H), 1.68-1.65 (m, 2H), 1.39-1.35 (m, 3H).

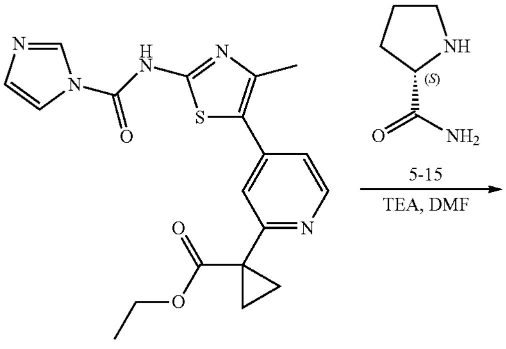

5-14

-continued

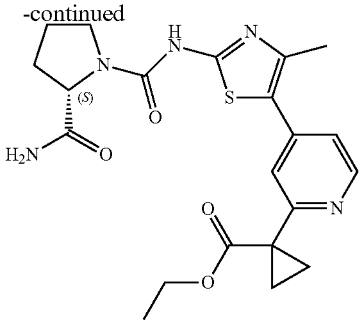

Compound (5)

To a solution of compound 5-14 (350 mg, 880.61 umol, 1 eq) in dimethylformamide (5 mL) was added triethylamine (178 mg, 1.76 mmol, 245.14 uL, 2 eq) and compound 5-15 (121 mg, 1.06 mmol, 1.2 eq). The mixture was stirred at 25° C. for 1 hour. LCMS showed the starting material was consumed completely and desired mass was detected. The mixture was concentrated to give the residue. The residue was purified by prep-HPLC (column: PHENOMENEX® Gemini 150*25 mm*10 um; mobile phase: [water (0.05% ammonia hydroxide v/v)-ACN]; B %:16%-46%, 12 min) to afford Compound (5) (76.40 mg, 169.55 umol, 19.25% yield, 98.43% purity) as a white solid. LCMS: RT=2.156 min, purity: 98.43%, m/z 444.1[M+H]$^+$. $^1H$ NMR ($CD_3OD$, 400 MHz): δ 8.44 (dd, $J_1$=5.2 Hz, $J_2$=0.4 Hz, 1H), 7.56 (d, J=1.2 Hz, 1H), 7.36 (dd, $J_1$=5.2 Hz, $J_2$=1.6 Hz, 1H), 4.46-4.44 (m, 1H), 4.13 (q, J=7.2 Hz, 2H), 3.73-3.67 (m, 1H), 3.60-3.54 (m, 1H), 2.43 (s, 3H), 2.30-2.22 (m, 1H), 2.08-2.01 (m, 3H), 1.66-1.63 (m, 2H), 1.43-1.40 (m, 2H), 1.19 (t, J=6.8 Hz, 3H).

Synthetic Preparation of Compound (6)

A synthetic route to Compound (6) is shown in the scheme below

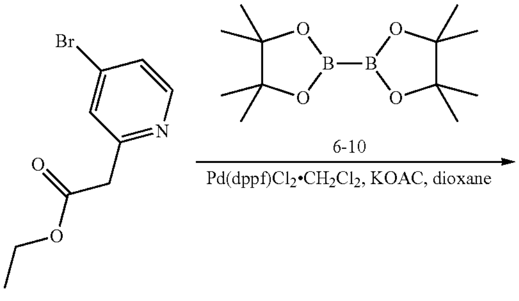

6-7

-continued
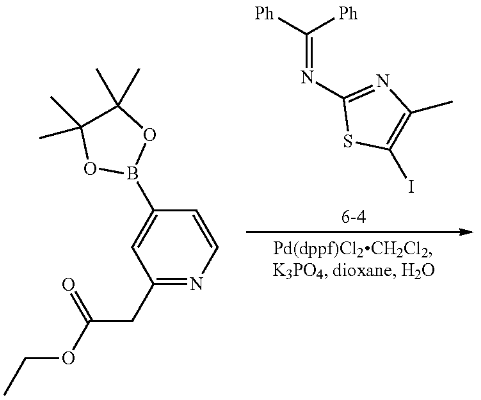
6-16
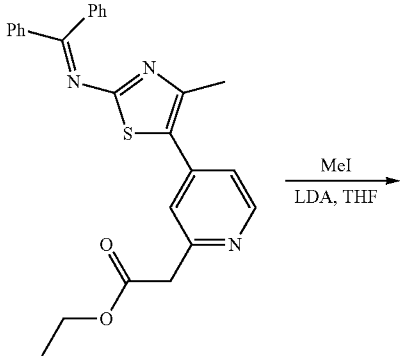
6-17
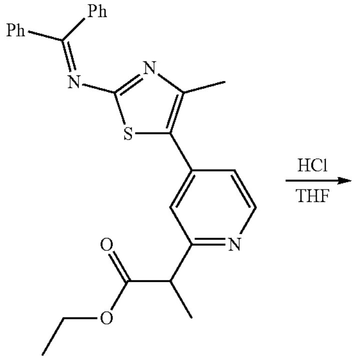
6-18
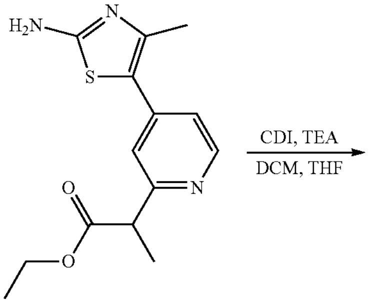
6-19
-continued
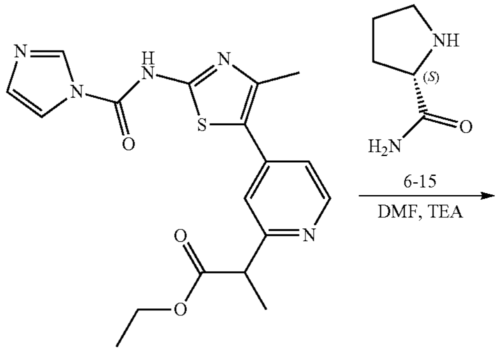
6-20
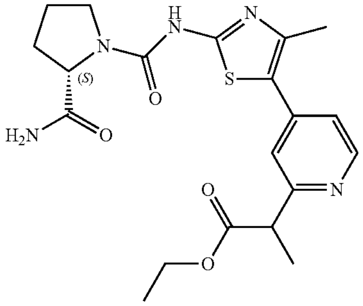
Compound (6)
Experimental Procedures for Compound (6)
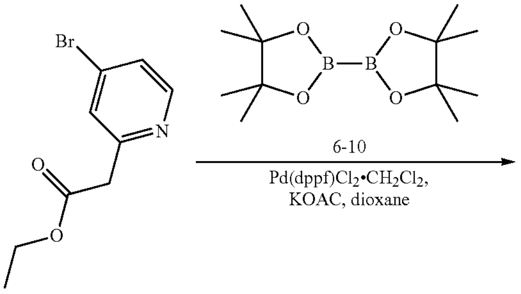
6-7
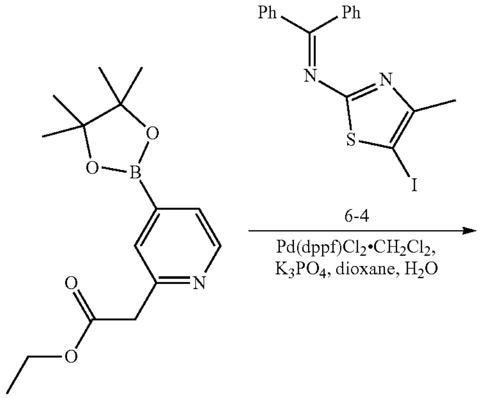
6-16

-continued

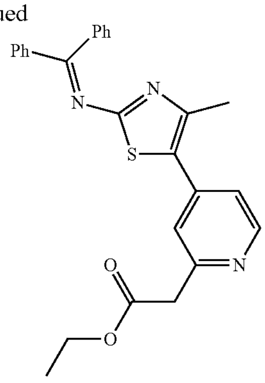

6-17

-continued

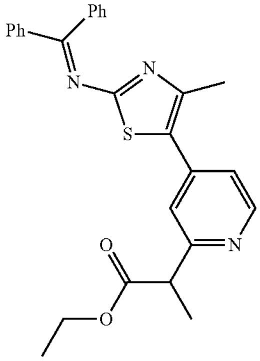

6-18

To a solution of compound 6-7 (2.5 g, 10.24 mmol, 1 eq) and compound 6-10 (2.6 g, 10.24 mmol, 1 eq) in dioxane (40 mL) was added potassium acetate (3.02 g, 30.73 mmol, 3 eq) and Pd(dppf)$Cl_2$·$CH_2Cl_2$ (418 mg, 512.12 umol, 0.05 eq). The mixture was degassed under vacuum and purged with nitrogen for three times. The mixture was stirred at 85° C. for 2 hours under nitrogen atmosphere. TLC (petroleum ether:ether:ethyl acetate=2:1) showed the starting material was consumed completely and a new spot was formed. The mixture was used directly without work up.

To the previous mixture solution and compound 6-4 (3.89 g, 9.62 mmol, 1 eq) in water (10 mL) was added Pd(dppf) $Cl_2$·$CH_2Cl_2$ (393 mg, 480.85 umol, 0.05 eq) and potassium phosphate (6.12 g, 28.85 mmol, 3 eq). The mixture was degassed and purged with nitrogen for 3 times, and stirred at 110° C. for 12 hours under nitrogen atmosphere. TLC (petroleum ether:ethyl acetate=2:1) showed the starting material was consumed completely and one main new spot was formed. The reaction mixture was quenched with water (20 mL), and extracted with ethyl acetate (30 mL×3). The combined organic layers were washed with brine (30 mL×3), dried over anhydrous sodium sulfate, filtered and concentrated in vacuum. The residue was purified by column chromatography ($SiO_2$, petroleum ether:ethyl acetate=30:1~8:1) to give compound 6-17 (2.6 g, 61.23% yield) as yellow oil. $^1H$ NMR ($CDCl_3$, 400 MHz): δ 8.50 (d, J=5.6 Hz, 1H), 7.88 (d, J=7.2 Hz, 2H), 7.51-7.49 (m, 4H), 7.44-7.40 (m, 2H), 7.31 (d, J=6.4 Hz, 2H), 7.19 (s, 1H), 7.10 (dd, $J_1$=5.2 Hz, $J_2$=1.6 Hz, 1H), 4.19 (q, J=7.2 Hz, 2H), 3.83 (s, 2H), 2.50 (s, 3H), 1.28 (t, J=7.2 Hz, 3H).

To a solution of compound 6-17 (1 g, 2.26 mmol, 1 eq) in tetrahydrofuran (10 mL) was dropwise added LDA (2 M, 1.47 mL, 1.3 eq) at −70° C. under nitrogen atmosphere. The mixture was stirred at −70° C. for 30 minutes. Then iodomethane (1.61 g, 11.32 mmol, 704.96 uL, 5 eq) was added and the mixture was stirred at 20° C. for 1 hour. LCMS showed the starting material was consumed completely and desired compound mass was detected. The reaction mixture was quenched with water (15 mL), and extracted with ethyl acetate (30 mL×3). The combined organic layers was dried over anhydrous sodium sulfate, filtered and concentrated in vacuum. The residue was purified by column chromatography ($SiO_2$, petroleum ether: ethyl acetate=20:1~6:1) to give compound 6-18 (285 mg, 88.86% purity) as yellow oil. LCMS: RT=0.899 min, purity: 88.86%, m/z 456.0 $[MS+H]^+$. $^1H$ NMR ($CDCl_3$, 400 MHz): δ 8.58 (d, J=5.2 Hz, 1H), 7.96 (d, J=7.6 Hz, 2H), 7.60-7.57 (m, 4H), 7.53-7.49 (m, 2H), 7.40 (d, J=6.8 Hz, 2H), 7.36 (d, J=1.2 Hz, 1H), 7.16 (d, J=5.2 Hz, 1H), 4.26-4.20 (m, 2H), 4.02 (q, J=7.2 Hz, 1H), 2.59 (s, 3H), 1.65 (d, J=7.2 Hz, 3H), 1.30 (t, J=7.2 Hz, 3H).

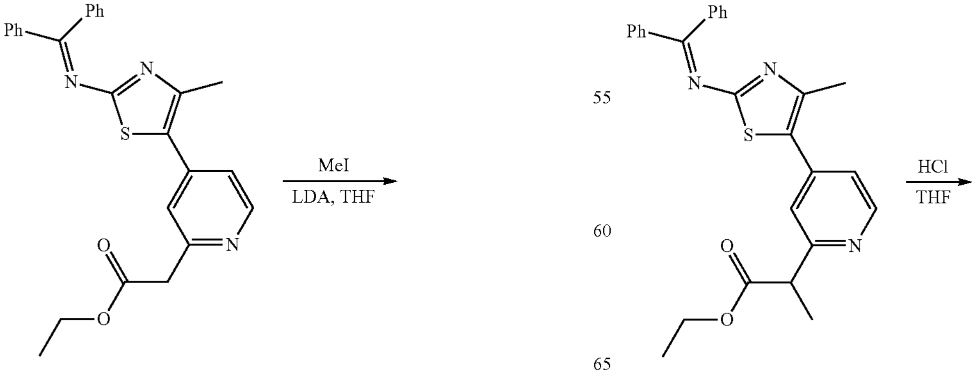

6-17 6-18

-continued

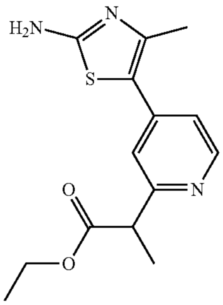

6-19

-continued

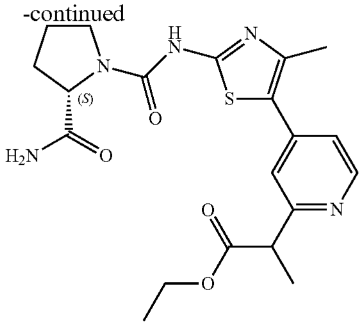

Compound (6)

A mixture of compound 6-18 (280 mg, 614.61 umol, 1 eq) in tetrahydrofuran (3 mL) was added hydrochloric acid (2 M, in water, 5 mL, 16.27 eq). The reaction mixture was stirred at 26° C. for 0.5 hour. LCMS showed the starting material was consumed completely and desired compound mass was detected. The mixture was diluted with water (8 mL), extracted with ethyl acetate (20 mL×3). The organic layers were discarded. The aqueous phase was basified to pH=9 with saturated sodium bicarbonate aqueous, extracted with ethyl acetate (20 mL×3), the organic layers was dried over anhydrous sodium sulfate, filtered and concentrated in vacuum to give compound 6-19 (105 mg, 53.09% yield) as yellow oil. LCMS: RT=0.823 min, purity: 90.54%, m/z 292.0 $[MS+H]^+$. $^1H$ NMR ($CDCl_3$, 400 MHz): δ 8.51 (d, J=5.6 Hz, 1H), 7.23 (s, 1H), 7.14 (dd, $J_1$=5.6 Hz, $J_2$=2.0 Hz, 1H), 5.33 (br. s, 2H), 4.20-4.13 (m, 2H), 3.76-3.73 (m, 1H), 2.39 (s, 3H), 1.57 (d, J=7.2 Hz, 3H), 1.25-1.23 (m, 3H).

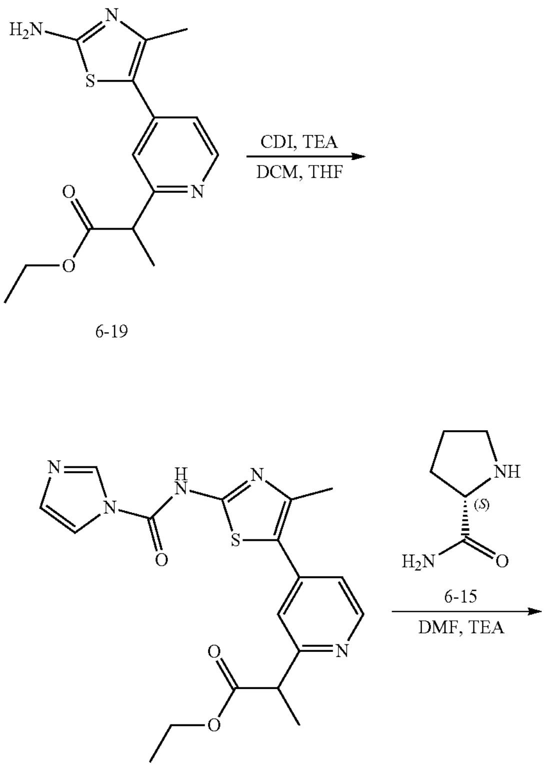

6-19

6-20

To a solution of compound 6-19 (100 mg, 343.21 umol, 1 eq) in tetrahydrofuran (1 mL) and dichloromethane (2 mL) was added CDI (111 mg, 686.42 umol, 2 eq) and triethylamine (52 mg, 514.81 umol, 71.66 uL, 1.5 eq). The mixture was stirred at 50° C. for 3 hours. LCMS showed the starting material was consumed completely and desired mass was detected. The residue was concentrated in vacuum to give the crude 6-20 (130 mg, crude) as a yellow solid.

To a solution of compound 6-20 (130 mg, 337.28 umol, 1 eq, crude) in dimethylformamide (2 mL) was added triethylamine (102 mg, 1.01 mmol, 140.84 uL, 3 eq) and compound 6-15 (154 mg, 1.35 mmol, 4 eq). The reaction was stirred at 26° C. for 2 hours. LCMS showed the starting material was consumed completely and desired mass was detected. The residue was quenched with water (0.5 mL) and concentrated in vacuum. The mixture was purified by prep-HPLC (column: Boston pH-lex 150*25 10 um; mobile phase: [water (0.1% TFA)-ACN]; B %: 16%-40%, 8 min). After lyophilization, the solid was dissolved in a mixture of methanol:water=10:1 (5 mL, v/v), the mixture was adjusted to pH=8 with trifluoroacetic acid exchange resin. The mixture was stirred at 20° C. for 30 minutes, filtered and the filtrate was concentrated in vacuum. The residue was purified by column chromatography ($SiO_2$, petroleum ether petroleum ether:ethyl acetate=3:1~1:8) to give Compound (6) (50 mg, 109.27 umol, 32.40% yield, 94.30% purity) as a yellow solid. LCMS: RT=2.146 min, purity: 94.30%, m/z 432.1 $[MS+H]^+$. $^1H$ NMR ($CD_3OD$, 400 MHz): δ 8.44 (d, J=5.2 Hz, 1H), 7.42 (s, 1H), 7.36 (dd, $J_1$=5.2 Hz, $J_2$=1.6 Hz, 1H), 4.47 (d, J=6.8 Hz, 1H), 4.19-4.11 (m, 2H), 4.00 (q, J=7.2 Hz, 1H), 3.73-3.69 (m, 1H), 3.58-3.56 (m, 1H), 2.42 (s, 3H), 2.30-2.22 (m, 1H), 2.06-2.04 (m, 3H), 1.53 (d, J=7.2 Hz, 3H), 1.20 (t, J=7.2 Hz, 3H).

Synthetic Preparation of Compounds (7) and (8)

A synthetic route to Compounds (7) and (8) is shown in the scheme below.

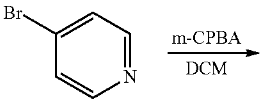

7-21

-continued

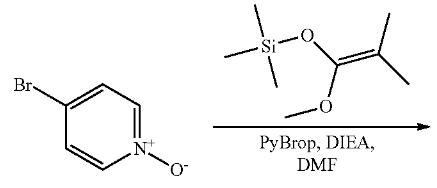

7-22

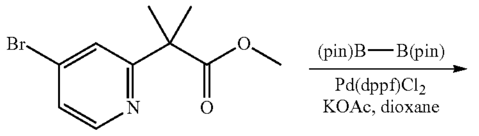

7-23

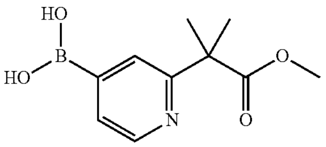

7-24

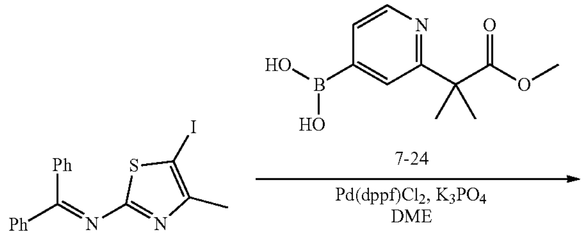

7-24

7-7

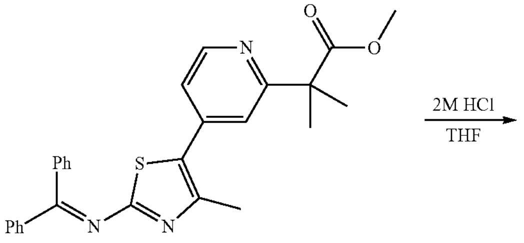

7-25

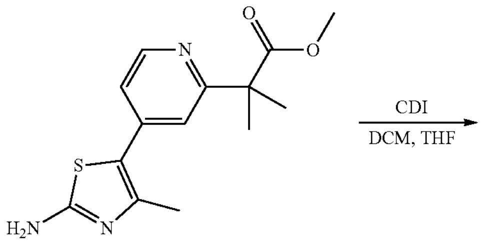

7-26

-continued

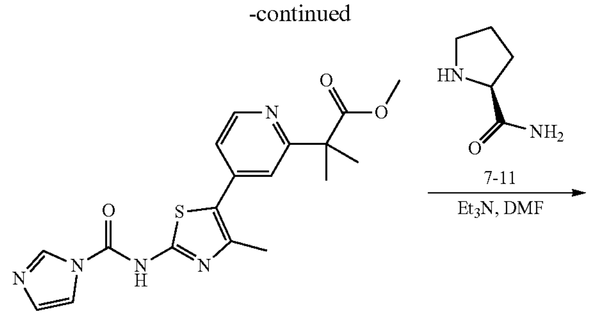

7-27

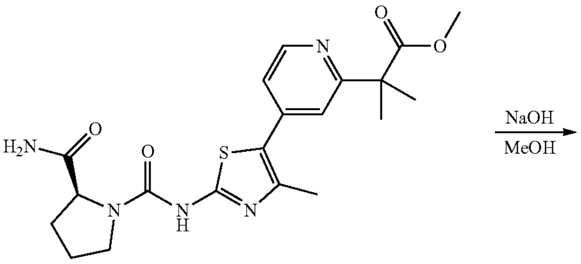

Compound (8)

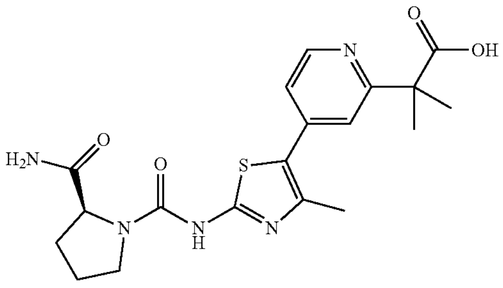

Compound (7)

Experimental Procedures for Compounds (7) and (8)

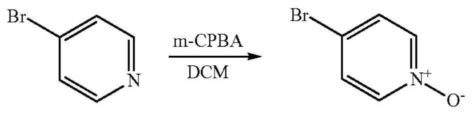

7-21 7-22

A solution of compound 7-21 (10 g, 51.42 mmol, hydrochloric acid salt) in dichloromethane (200 mL) was treated with potassium carbonate (8.53 g, 61.71 mmol) in portions. The reaction was stirred for 1 hour at 20° C., then m-CPBA (20.88 g, 102.85 mmol, 85% purity) was added in portions. The mixture was stirred at 20° C. for 16 hours. TLC (ethyl acetate) showed the starting material was consumed. The reaction mixture was quenched by addition of a solution of sodium sulfite (8.8 g) in water (100 mL). The mixture was stirred for 20 min at 20° C. and then filtered. The organic phase was washed with brine (10 mL×2), dried over sodium sulfate and concentrated in vacuo to afford compound 7-22 (10 g, crude) as a yellow solid. LCMS: RT=0.142 min, m/z 174.0, 176.0 $[M+H]^+$ $^1H$ NMR ($CDCl_3$, 400 MHz)

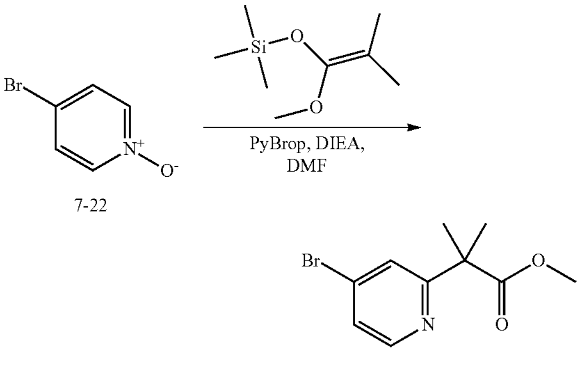

7-22

7-23

To a mixture of compound 7-22 (10 g, 57.47 mmol), (1-methoxy-2-methyl-prop-1-enoxy)-trimethyl-silane (17 g, 97.70 mmol) in tetrahydrofuran (100 mL) was added N,N-diisopropylethylamine (22.28 g, 172.41 mmol, 30.11 mL) and PYBROP® (29.47 g, 63.22 mmol). The mixture was stirred at 20° C. for 1 hour. TLC (petroleum ether:ethyl acetate=10:1) showed the starting material was consumed. The residue was poured into water (100 mL), extracted with ethyl acetate (200 mL×2). The combined organic phase was washed with brine (100 mL×2), dried over sodium sulfate and concentrated in vacuo. The residue was purified by flash column ($SiO_2$, petroleum ether:ethyl acetate=100:1~10:1) to afford compound 7-23 (2.5 g, 9.69 mmol, 16.85% yield) as yellow oil. $^1$H NMR ($CDCl_3$, 400 MHz) δ 8.37 (d, J=5.2 Hz, 1H), 7.47 (d, J=1.6 Hz, 1H), 7.34(dd, J=1.6 Hz, 5.2 Hz, 1H), 3.69 (s, 3H), 1.60 (s, 6H).

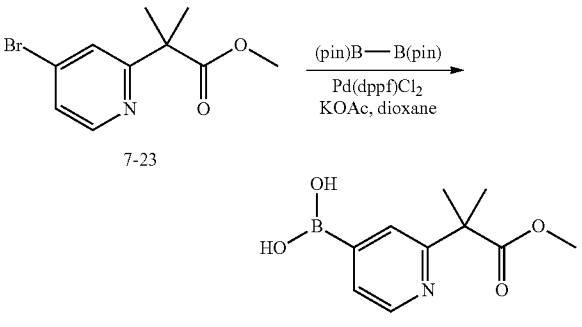

7-23

7-24

To a solution of compound 7-23 (2.5 g, 9.69 mmol), 4,4,5,5-tetramethyl-2-(4,4,5,5-tetramethyl-1,3,2-dioxaborolan-2-yl)-1,3,2-dioxaborolane (2.95 g, 11.63 mmol) and potassium acetate (1.43 g, 14.54 mmol) was added Pd(dppf)$Cl_2$ (791 mg, 969.00 umol). The reaction mixture was degassed with nitrogen three times. The reaction mixture was stirred at 90° C. for 12 hours under nitrogen atmosphere. TLC (petroleum ether:ethyl acetate=1:1) showed the starting material was consumed. The reaction mixture was diluted with ethyl acetate (50 mL) and filtered. The filtrate was concentrated in vacuo. The residue was purified by column ($SiO_2$, petroleum ether:ethyl acetate=10:1-1:1) to give compound 7-24 (2 g, 5.20 mmol, 53.67% yield, 58% purity) as a yellow oil. LCMS: RT=0.195 min, m/z 224.2 [M+H]$^+$. $^1$H NMR ($CDCl_3$, 400 MHz) δ 8.57 (d, J=4.8 Hz, 1H), 7.63 (s, 1H), 7.50 (t, J=4.8 Hz, 1H), 3.67 (s, 3H), 1.35 (s, 6H).

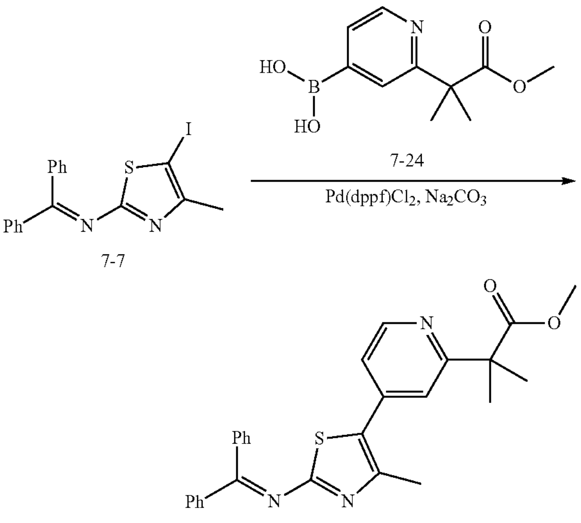

7-24

7-7

7-25

To a solution of compound 7-7 (500 mg, 1.24 mmol), compound 7-24 (692 mg, 3.10 mmol), sodium carbonate (394 mg, 3.72 mmol) in methanol (5 mL) and DME (25 mL) was added Pd(dppf)$Cl_2$ (102 mg, 124.00 umol) under nitrogen. The mixture was stirred at 80° C. for 13 hours under nitrogen. TLC (petroleum ether:ethyl acetate=5:1) showed most of the starting material remained and desired product was detected on LCMS. The mixture was filtered and the filtrate was concentrated in vacuo. The crude was purified by column eluted with petroleum ether:ethyl acetate=10:1-4:1 to afford the compound 7-25 (400 mg, 667.30 umol, 53.81% yield, 76% purity) as yellow oil. LCMS: RT=0.908 min, m/z 456.1 [M+H]$^+$. $^1$H NMR ($CDCl_3$, 400 MHz) δ 8.49 (t, J=6.0 Hz, 1H), 7.88 (d, J=8.0 Hz, 2H), 7.52-7.42 (m, 8H), 7.17 (s, 1H), 7.04 (d, J=5.2 Hz, 1H), 3.69 (s, 3H), 2.50 (s, 3H), 1.60 (s, 6H).

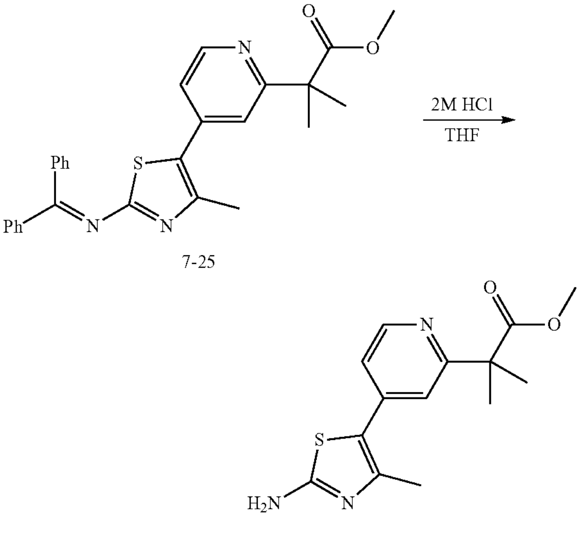

7-25

7-26

To a solution of compound 7-25 (700 mg, 952.65 umol) in tetrahydrofuran (10 mL) was added hydrochloric acid (2 M, 3.81 mL). The reaction mixture was stirred at 25° C. for 1 hour. TLC (petroleum ether:ethyl acetate=2:1) showed the reaction was completed. The reaction mixture was diluted with hydrochloric acid (20 mL, 1 M). The mixture was extracted with ethyl acetate (15 mL×2). The pH of the aqueous layer was adjusted to 8 with sodium bicarbonate, then extracted with dichloromethane(50 mL×2). The organic layer was washed with brine (10 mL×2), dried over anhydrous sodium sulfate, concentrated in vacuo. The crude product was purified by column eluted with petroleum ether:ethyl acetate=10:1~0:1 to give compound 7-26 (180 mg, 617.77 umol, 64.85% yield) as yellow oil. LCMS: RT=0.505 min, m/z 292.1 $[M+H]^+$. $^1H$ NMR ($CDCl_3$, 400 MHz) δ 8.52 (dd, J=0.8 Hz, 5.2 Hz, 1H), 7.23 (s, 1H), 7.12 (d, J=5.2 Hz, 1H), 4.98 (br. s, 2H), 3.71 (s, 3H), 2.39 (s, 3H), 1.62 (s, 6H).

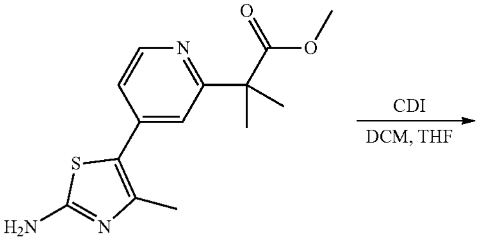

7-26

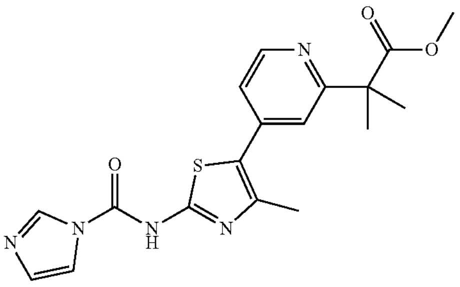

7-27

A solution of compound 7-26 (180 mg, 617.77 umol) in dichloromethane (4 mL) and tetrahydrofuran (2 mL) was warmed to 50° C., then CDI (160 mg, 988.43 umol) was added. The reaction mixture was stirred at 50° C. for 12 hours. TLC (petroleum ether:ethyl acetate=0:1, quenched with methanol) showed the reaction was completed. The mixture was concentrated in vacuo to give compound 7-27 (238 mg, crude) as a white solid, which was used for the next step directly. LCMS: RT=0.664 min, m/z 350.2 (quenched with methanol, detected as methyl ester) $^1H$ NMR ($CDCl_3$, 400 MHz) δ 9.29 (s, 1H), 8.62 (d, J=5.2 Hz, 1H), 7.74-7.73 (m, 1H), 7.36 (s, 1H), 7.23 (d, J=5.2 Hz, 1H), 7.14 (s, 1H), 7.09 (s, 1H), 3.72 (s, 3H), 2.62 (s, 3H), 1.67 (s, 6H).

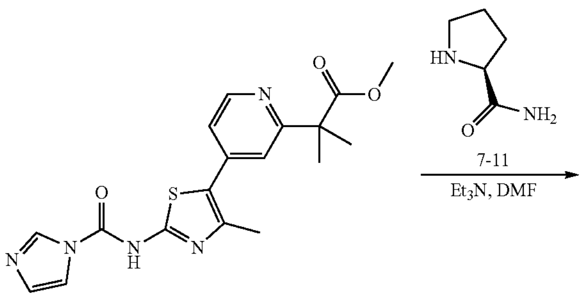

7-27

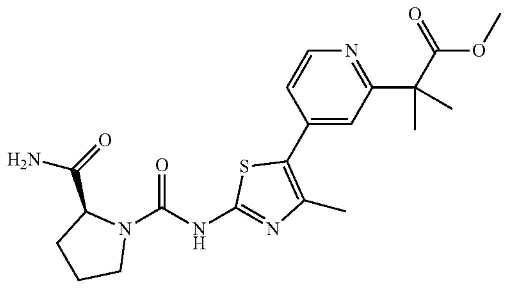

Compound (8)

To a solution of compound 7-11 (78 mg, 679.23 umol) and triethylamine (125 mg, 1.23 mmol, 171.19 uL) in DMF (3 mL) was added compound 7-27 (238 mg, 617.48 umol). The reaction mixture was stirred at 25° C. for 1 hour. TLC (petroleum ether:ethyl acetate=0:1) showed the reaction was completed. The mixture was quenched with water (10 mL), and then extracted with ethyl acetate (20 mL×2). The organic layer was washed with brine (10 mL×2), dried over anhydrous sodium sulfate, concentrated in vacuo. The crude was trituration with water (10 mL) and methanol (2 mL), then purified by prep-HPLC (column: PHENOMENEX® Gemini C18 250 mm*21.2 mm*5 um; mobile phase: [water (0.05% ammonia hydroxide v/v)-ACN]; B %: 15%-45%, 2 min) to give Compound (8) (53.00 mg, 117.31 umol, 56.24% yield, 95.51% purity) as a white solid. LCMS: RT=1.803 min, m/z 432.1 $[M+H]^+$. $^1H$ NMR ($CDCl_3$, 400 MHz) δ 8.55 (d, J=5.2 Hz, 1H), 7.32 (s, 1H), 7.20 (dd, J=1.6 Hz, 4.8 Hz, 1H), 4.63-4.62 (m, 1H), 3.71 (s, 3H), 3.52-3.50 (m, 2H), 2.44 (s, 4H), 2.17-2.08 (m, 3H), 1.64 (s, 6H).

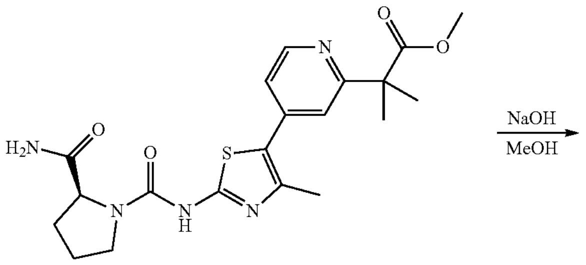

Compound (8)

-continued

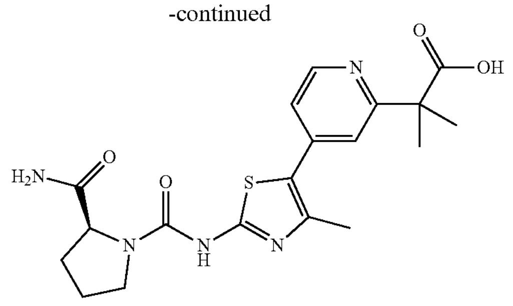

Compound (7)

To a solution of Compound (8) (100 mg, 231.74 umol) in methanol (1 mL) was added sodium hydroxide (56 mg, 1.39 mmol). The mixture was stirred at 25° C. for 3 hours. LCMS showed the desired product was detected. The pH of the mixture was adjusted to ~7 with 1N hydrogen chloride under an ice bath. The crude was purified by prep-HPLC (column: WATERS™ XBRIDGE® 150 mm*25 mm*5 um; mobile phase: [water (10 mM $NH_4HCO_3$)-ACN]; B %: 1%-30%, 11 min) to give Compound (7) (60.00 mg, 120.49 umol, 52.00% yield, 83.84% purity) as a yellow solid. LCMS: RT=9.65 min, m/z 418.2 $[M+H]^+$. $^1H$ NMR ($CD_3OD$, 400 MHz) δ 8.41 (d, J=5.2 Hz, 1H), 7.51 (s, 1H), 7.23 (dd, J=2.0 Hz, 5.2 Hz, 1H), 4.46-4.43 (m, 1H), 3.69-3.68 (m, 1H), 3.58-3.56 (m, 1H), 2.42 (s, 3H), 2.25-2.23 (m, 1H), 2.07-2.04 (m, 3H), 1.33 (s, 6H).

Synthetic Preparation of Compound (9)

A synthetic route to Compound (9) is shown in the scheme below.

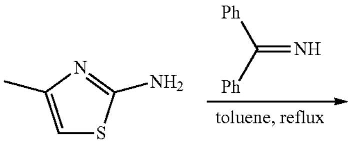

9-1

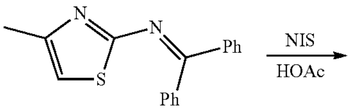

9-2

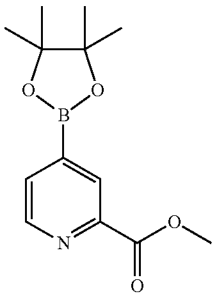

9-4

Pd(dppf)$Cl_2$•$CH_2Cl_2$, $Na_2CO_3$,
DME/MeOH

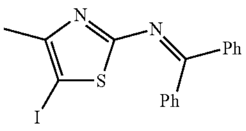

9-3

-continued

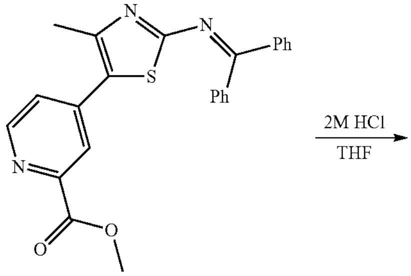

9-5

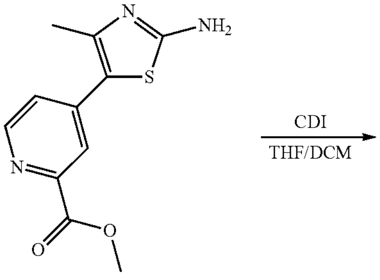

9-6

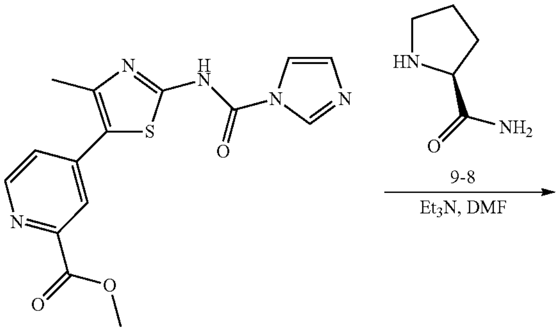

9-7

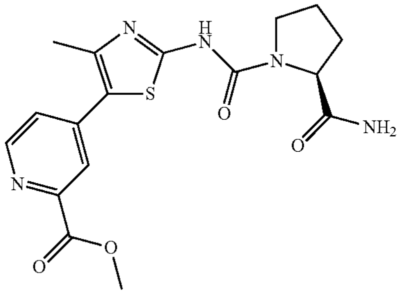

Compound (9)

Experimental Procedures for the Preparation of Compound (9)

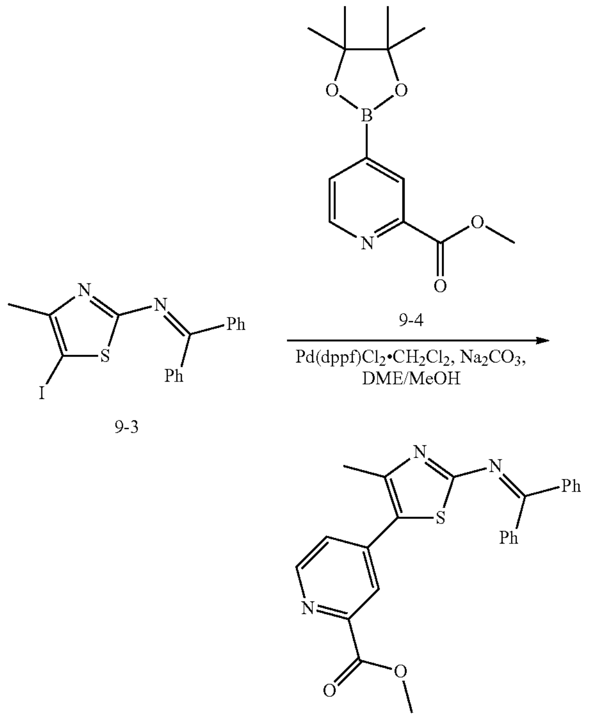

9-4

9-3

9-5

To a solution of compound 9-3 (1.50 g, 3.71 mmol, 1.00 eq), compound 9-4 (2.30 g, 4.45 mmol, 1.20 eq), sodium carbonate (1.18 g, 11.13 mmol, 3.00 eq) in methanol (15 mL) and 1,2-dimethoxyethane (75 mL) was added Pd(dppf) $Cl_2 \cdot CH_2Cl_2$ (303 mg, 371.00 umol, 0.10 eq) under nitrogen atmosphere. The mixture was stirred at 80° C. for 72 hours. LCMS showed the starting material was consumed completely. The mixture was diluted with dichloromethane (150 mL) and then filtered. The filtrate was concentered in vacuum and purified by column chromatography ($SiO_2$, Petroleum ether/Ethyl acetate=5/1 to 1/1) to give compound 9-5 (840 mg, 1.69 mmol, 40.22% yield, 83.01% purity) as a red solid. LCMS: RT=0.995 min, m/z 413.9 $[M+H]^+$. $^1H$ NMR ($CDCl_3$, 400 MHz) δ 8.68 (d, J=4.8 Hz, 1H), 8.04 (d, J=1.2 Hz, 1H), 7.87 (d, J=6.4 Hz, 2H), 7.55-7.32 (m, 9H), 4.04 (s, 3H), 2.53 (s, 3H).

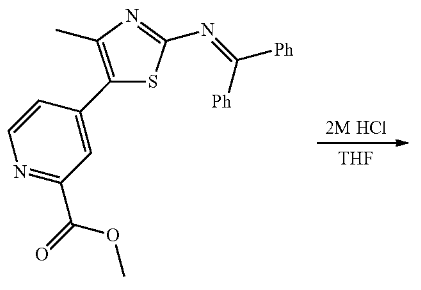

9-5

-continued

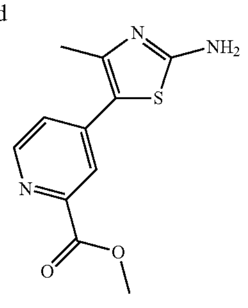

9-6

To a solution of compound 9-5 (840 mg, 2.03 mmol, 1.00 eq) in tetrahydrofuran (16 mL) was added hydrochloric acid solution (2 M, 8 mL). The mixture was stirred at 25° C. for 1 hour. TLC (petroleum ether:ethyl acetate=2:1) showed the starting material was consumed completely. The mixture was diluted with hydrochloric acid aqueous (20 mL, 1 M) and then extracted with ethyl acetate (15 mL×2). The aqueous layer was adjust to pH=8 by sodium bicarbonate. The precipitate was formed and precipitated out. The mixture was filtered, washed with water (5 mL×3) and dried under vacuum to afford the desired product 9-6 (280 mg, 957.86 umol, 47.19% yield, 85.28% purity) as a light yellow solid. LCMS: RT=0.758 min, m/z 250.0 $[M+H]^+$. $^1H$ NMR (DMSO-$d_6$, 400 MHz) δ 8.59 (d, J=5.2 Hz, 1H), 7.87 (s, 1H), 7.52 (dd, $J_1$=5.2 Hz, $J_2$=2.0 Hz, 1H), 7.44 (s, 2H), 3.89 (s, 3H), 2.34 (s, 3H).

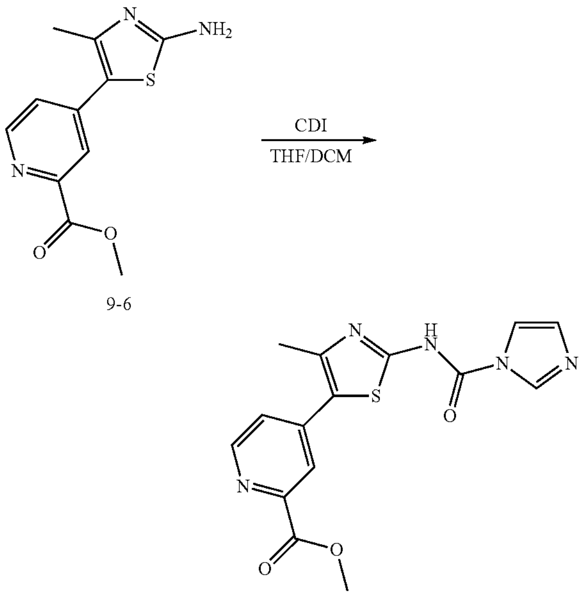

9-6

9-7

To a solution of compound 9-6 (280.00 mg, 1.12 mmol, 1.00 eq) in dichloromethane (10 mL) and tetrahydrofuran (5 mL) at 50° C. was added 1,1'-Thiocarbonyldiimidazole (291 mg, 1.80 mmol, 1.60 eq) with portion wise. The reaction mixture was stirred at 50° C. for 18 hours. LCMS showed the starting material was consumed completely. The mixture was concentrated in vacuum to give compound 9-7 (560 mg, crude) as a light yellow solid, which was used into the next step without further purification. LCMS: RT=0.725 min, m/z 308.0 [M+H]+ (quenched with methanol, detected as carbamate)

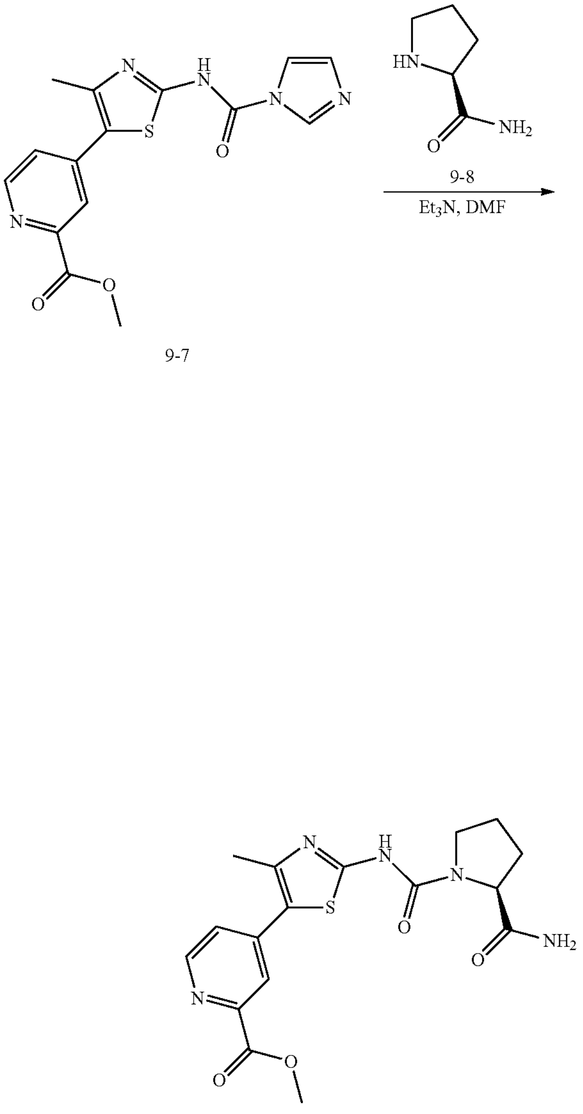

9-7

Compound (9)

To a solution of compound 9-8 (70 mg, 615.35 umol, 1.10 eq) and triethylamine (113 mg, 1.12 mmol, 155.09 uL, 2.00 eq) in dimethyl formamide (4 mL) was added compound 9-7 (280 mg, 559.41 umol, 1.00 eq). The mixture was stirred at 25° C. for 1 hour. LCMS showed the most of starting material was consumed. The mixture was quenched with water (0.1 mL) and then concentrated in vacuum. The residue was diluted with water (10 mL), methanol (2 mL), DMSO (2 mL) and the solid was filtered. The filter cake was washed with water (2 mL×3) and dried under vacuum to give the Compound (9) (105.00 mg, 254.82 umol, 45.55% yield, 94.51% purity) as a yellow solid. LCMS: RT=1.830 min, m/z 390.1 $[M+H]^+$. $^1H$ NMR (DMSO-d6, 400 MHz) δ 11.02 (br. s, 1H), 8.69 (d, J=4.8 Hz, 1H), 8.00 (s, 1H), 7.68 (d, J=3.6 Hz, 1H), 7.40 (s, 1H), 6.97 (s, 1H), 4.30-4.25 (m, 1H), 3.90 (s, 3H), 3.60-3.40 (m, 2H), 2.45 (s, 3H), 2.09-2.07 (m, 1H), 1.87-1.86 (m, 3H).

Synthetic Preparation of Compound (10)

A synthetic route to Compound (10) is shown in the scheme below.

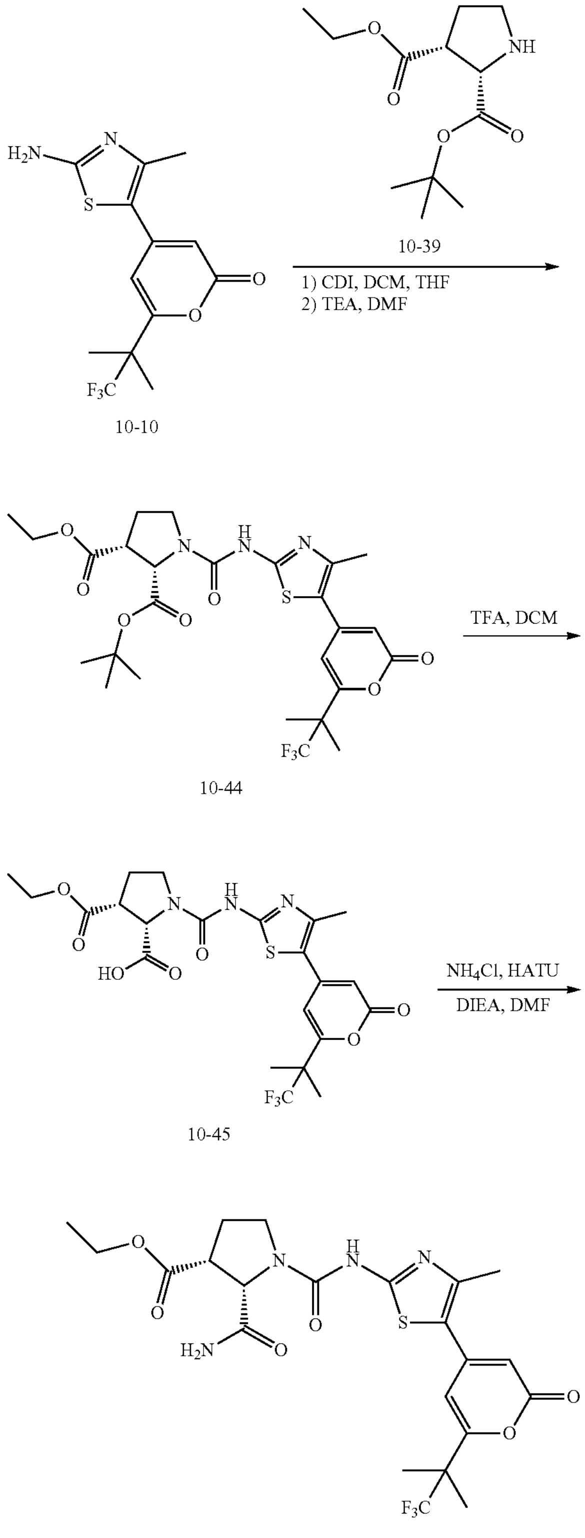

10-10

10-44

10-45

Compound (10)

Experimental Procedures for Compound (10)

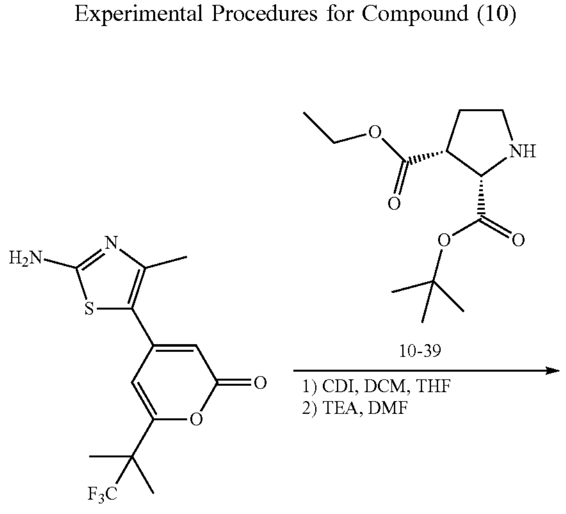

10-10 10-39

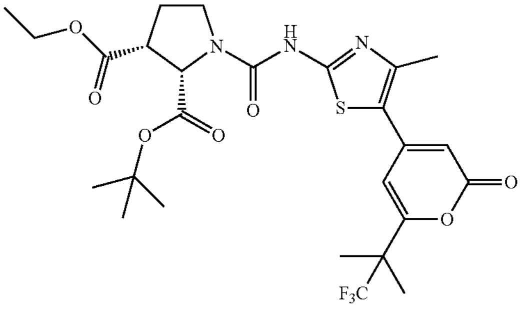

10-44

A mixture of compound 10-10 (209 mg, 0.657 mmol) and 1,1'-carbonyldiimidazole (104 mg, 0.657 mmol) in tetrahydrofuran (0.2 mL) and dichloromethane (0.4 mL) was stirred at 50° C. for 20 hours. LCMS showed little of the starting material remained. The mixture was concentrated in vacuum to give a residue which was dissolved in N,N-dimethylformamide (0.4 mL), then triethylamine (208 mg, 2.06 mmol) and compound 10-39 (200 mg, 0.822 mmol) was added. The mixture was stirred at 25° C. for 6 hours. LCMS showed the starting material was consumed completely and the desired mass was detected. The mixture was poured into ice-water (10 mL) and extracted with ethyl acetate (20 mL×2). The combined organic phase was washed with brine (5 mL×2) and dried over anhydrous sodium sulfate. After filtration and concentration, the crude product was purified by column chromatography ($SiO_2$, petroleum ether:ethyl acetate=100:1~1:1) to give compound 10-44 (330 mg, 0.561 mmol, 65% yield) as yellow gum. LCMS: RT=0.900 min, purity: 99.81%, m/z 588.1 $[M+H]^+$. $^1H$ NMR ($CDCl_3$, 400 MHz): δ 6.30 (d, J=1.2 Hz, 1H), 6.29 (d, J=1.6 Hz, 1H), 4.70-4.55 (m, 1H), 4.28-4.14 (m, 2H), 3.82-3.74 (m, 1H), 3.66-3.55 (m, 1H), 3.35-3.25 (m, 1H), 2.60-2.55 (m, 1H), 2.51 (s, 3H), 2.35-2.28 (m, 1H), 1.55 (s, 6H), 1.50 (s, 9H), 1.32 (t, J=7.2 Hz, 3H). SFC: $RT_1$=1.330 min, $RT_2$=1.405 min, de %=95.7%

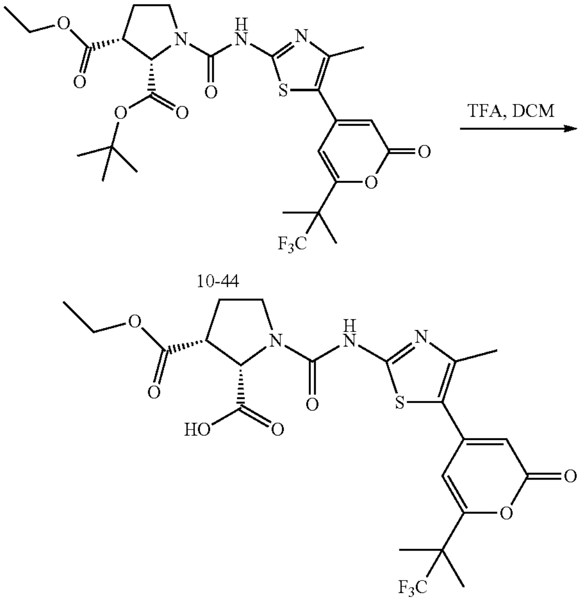

10-44

10-45

To a mixture of compound 10-44 (330 mg, 0.561 mmol, 1 eq) in dichloromethane (2 mL) was added trifluoroacetic acid (3.08 g, 27.0 mmol) and the mixture was stirred at 25° C. for 4 hours. LCMS showed the starting material was consumed completely and the desired mass was detected. The mixture was concentrated to give compound 10-45 (296 mg, 0.556 mmol, 99% yield) as yellow gum, which was used directly for next step without purification. LCMS: RT=0.873 min, purity: 73.92%, m/z 532.2 $[M+H]^+$.

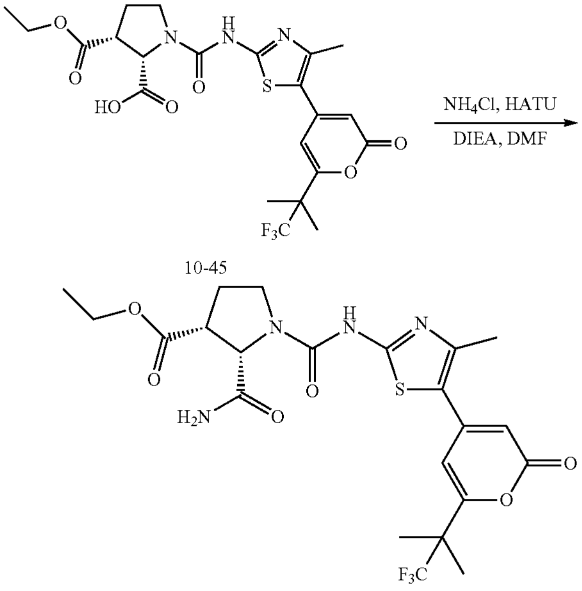

10-45

Compound (10)

To a mixture of compound 10-45 (186 mg, 0.349 mmol), ammonium chloride (199 mg, 3.72 mmol) and HATU (184 mg, 0.485 mmol) in N,N-dimethylformamide (0.2 mL) was added N,N-diisopropylethylamine (155 mg, 1.20 mmol).

The mixture was stirred at 25° C. for 16 hours. TLC (petroleum ether:ethyl acetate=0:1) showed the starting material was consumed. The mixture was poured into ice-water (10 mL) and extracted with ethyl acetate (20 mL×2). The combined organic phase was washed with brine (10 mL×2) and dried over anhydrous sodium sulfate. After filtration and concentration, the crude product was purified by prep-TLC ($SiO_2$, petroleum ether:ethyl acetate=0:1) followed by prep-HPLC (column: UniSil 120*30*10 um; mobile phase: [water(0.1% TFA)-ACN]; B %: 30%-60%, 10 min) to give Compound (10) (7 mg, 0.011 mol, 3.43% yield) as a white solid. LCMS: RT=2.483 min, purity: 80.08%, m/z 531.1 $[M+H]^+$. $^1H$ NMR ($CDCl_3$, 400 MHz): δ 6.59 (br. s, 1H), 6.35 (s, 1H), 6.27 (s, 1H), 5.53 (br. s, 1H), 4.87 (d, J=7.6 Hz, 1H), 4.25-4.15 (m, 2H), 3.78-3.75 (m, 1H), 3.65-3.55 (m, 1H), 3.31-3.10 (m, 1H), 2.80-2.66 (m, 1H), 2.49 (s, 3H), 2.41-2.32 (m, 1H), 1.53 (s, 6H), 1.27 (t, J=7.2 Hz, 3H).

Synthetic Preparation of Compound (11)

A synthetic route to Compound (11) is shown in the scheme below.

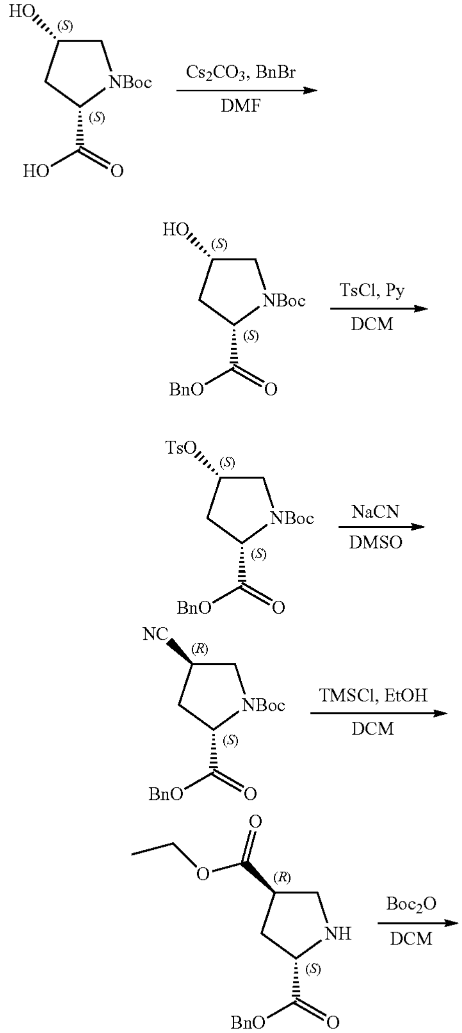

-continued

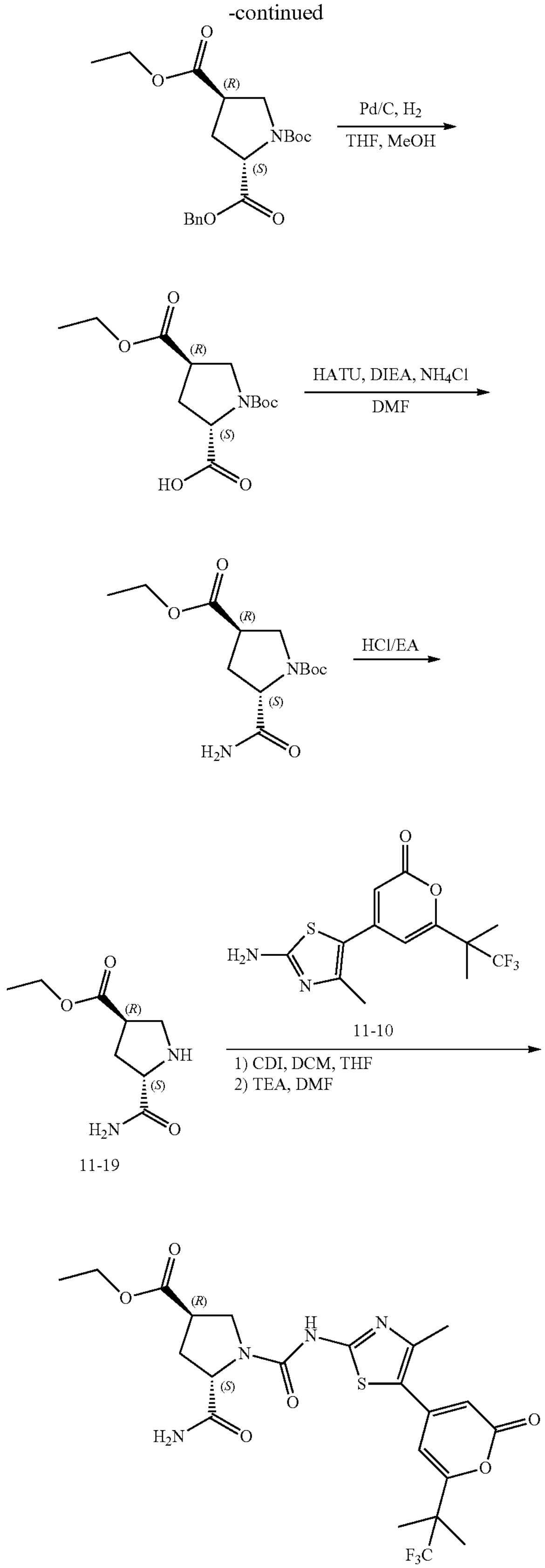

11-10

11-19

Compound (11)

Experimental Procedures for Compound (11)

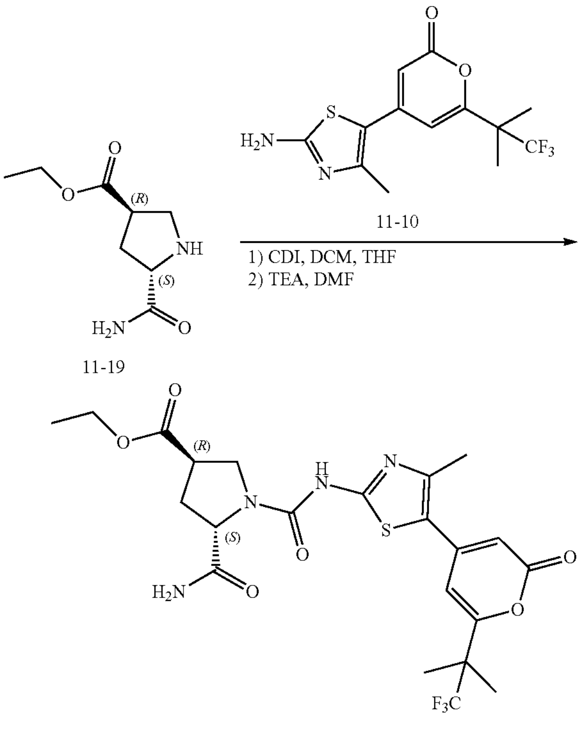

11-10

11-19

Compound (11)

To a solution of compound 11-10 (0.06 g, 188.49 umol, 1 eq) in dichloromethane (2 mL) and tetrahydrofuran (1 mL) was added CDI (46 mg, 282.74 umol, 1.5 eq) at 25° C. under nitrogen atmosphere. The mixture was stirred for 18 hours at 50° C. under nitrogen atmosphere. TLC (petroleum ether: ethyl acetate=0:1, quenched with methanol) showed the reaction was completed. The mixture was concentrated in vacuo to give a residue, which was added to a solution of compound 11-19 (46 mg, 205.39 umol, 1.1 eq, HCl salt) and triethylamine (38 mg, 373.44 umol, 51.98 uL, 2 eq) in N,N-dimethylformamide (1 mL) at 0° C. The mixture was stirred at 25° C. for 3 hours under nitrogen atmosphere. TLC showed the reaction was completed. The mixture was quenched with water (10 mL) and extracted with ethyl acetate (30 mL×3). The organic layer was washed with brine (10 mL×3), dried over anhydrous sodium sulfate, filtered and concentrated in vacuo. The residue was purified by triturated with ethyl acetate (3 mL), filtered to give the desired product. The filtrate was further purified by column chromatography ($SiO_2$, petroleum ether:ethyl acetate=3:1-0:1). So totally 41.55 mg of Compound (11) (41.95% yield, 100% purity) was obtained as a yellow solid. LCMS: RT=1.886 min, purity: 100%, m/z 531.1 $[M+H]^+$. $^1H$ NMR ($CD_3OD$, 400 MHz): δ 6.61 (d, J=1.6 Hz, 1H), 6.28 (s, 1H), 4.60-4.59 (m, 1H), 4.18 (q, J=7.2 Hz, 2H), 3.90-3.84 (m, 2H), 3.40-3.39 (m, 1H), 2.52-2.47 (m, 1H), 2.48 (s, 3H), 2.28-2.27 (m, 1H), 1.56 (s, 6H), 1.27 (t, J=7.2 Hz, 3H). SFC: RT=1.583 min, de %=100%

Synthetic Preparation of Compound (12)

A synthetic route to Compound (12) is shown in the scheme below.

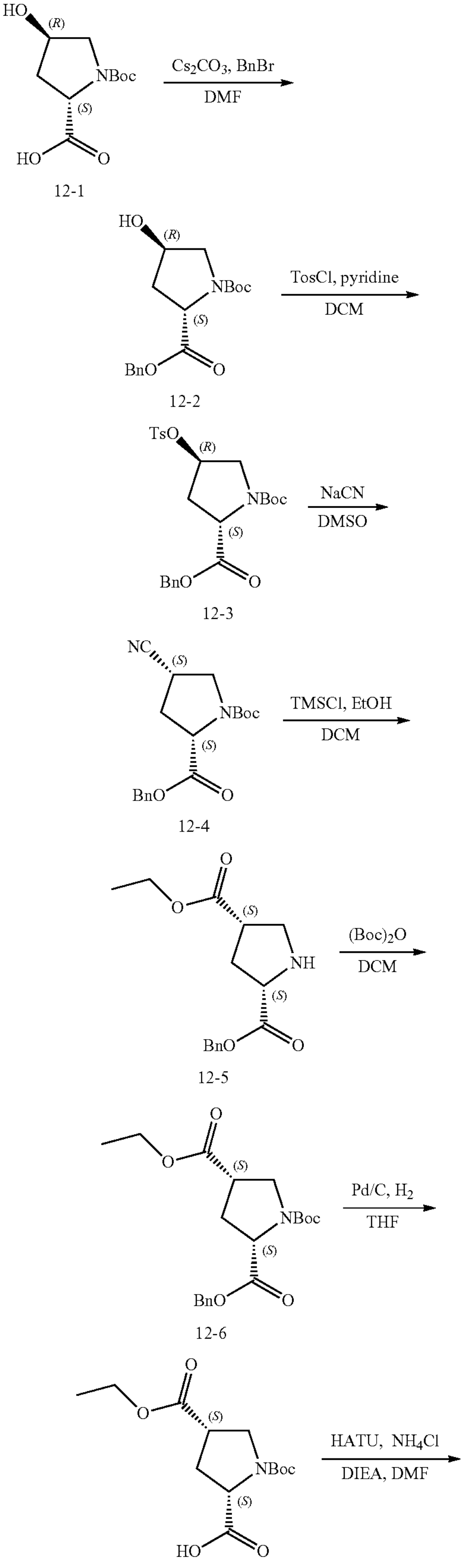

12-1

12-2

12-3

12-4

12-5

12-6

12-7

-continued

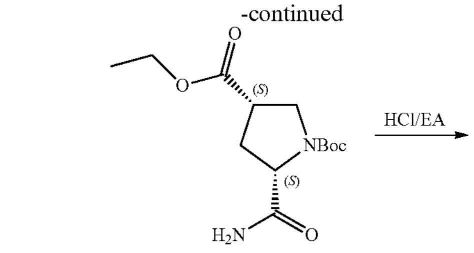

12-8

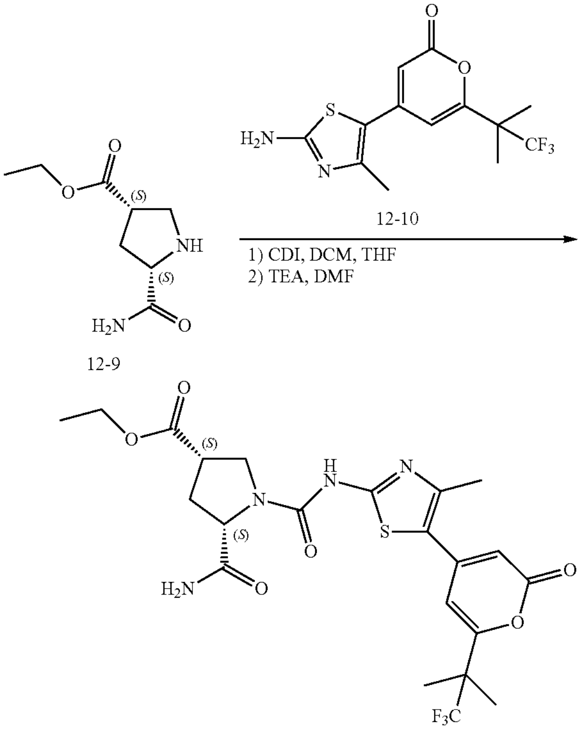

12-10

12-9

Compound (12)

Experimental Procedures for Compound (12)

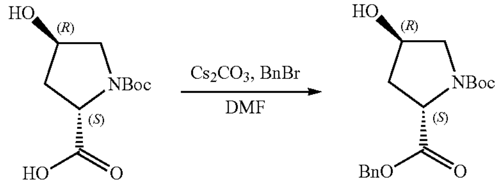

12-1 12-2

To a mixture of compound 12-1 (10 g, 43.24 mmol, 1 eq) in N,N-dimethylformamide (100 mL) was added cesium carbonate (14.09 g, 43.24 mmol, 1 eq), then benzyl bromide (8.14 g, 47.57 mmol, 5.65 mL, 1.1 eq) was added dropwise. The mixture was stirred at 50° C. for 12 hours. LCMS showed the starting material was consumed and desired mass was detected. The mixture was quenched with water (250 mL) and extracted with ethyl acetate (100 mL×3). The combined organic layers were washed with brine (50 mL×2), dried over anhydrous sodium sulfate, filtered and concentrated in vacuum to give compound 12-2 (14 g, crude) as colorless oil. LCMS: RT=0.798 min, purity: 17.99%, m/z 222.1 $[M-Boc+H]^+$. $^1$H NMR ($CDCl_3$, 400 MHz): δ 7.38-7.36 (m, 5H), 5.26-5.14 (m, 2H), 4.47-4.44 (m, 2H), 3.65-3.58 (m, 2H), 2.28-2.26 (m, 1H), 2.10-2.05 (m, 1H), 1.35 (s, 9H).

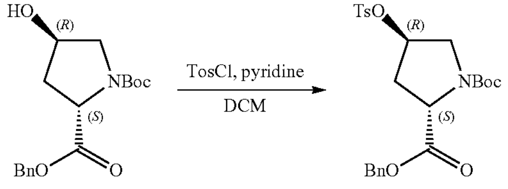

12-2 12-3

To a mixture of compound 12-2 (14 g, 43.56 mmol, 1 eq) in dichloromethane (140 mL) was added toluenesulfonyl chloride (16.61 g, 87.13 mmol, 2 eq) and pyridine (13.78 g, 174.26 mmol, 14.06 mL, 4 eq) at 25° C. The mixture was stirred at 25° C. for 30 hours. TLC (petroleum ether:ethyl acetate=3:1) showed the starting material was consumed and a major new spot with lower polarity was observed. The mixture was diluted with dichloromethane (100 mL) and washed with hydrochloric acid (1 M, 100 mL×2). The organic layer was dried over anhydrous sodium sulfate, filtered and concentrated in vacuum to give a residue, which was purified by flash column chromatography ($SiO_2$, petroleum ether:ethyl acetate=10:1~0:1) to give compound 12-3 (6 g, 12.62 mmol, 28.96% yield) as colorless oil. $^1$H NMR ($CDCl_3$, 400 MHz): δ 7.77 (d, J=8.4 Hz, 2H), 7.37-7.33 (m, 7H), 5.25-5.00 (m, 3H), 4.48-4.38 (m, 1H), 3.65-3.55 (m, 2H), 2.56-2.44 (m, 1H), 2.46 (s, 3H), 2.19-2.05 (m, 1H), 1.43-1.33 (m, 9H).

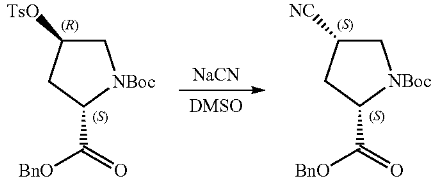

12-3 12-4

To a mixture of compound 12-3 (5 g, 10.51 mmol, 1 eq) in dimethylsulfoxide (60 mL) was added sodium cyanide (0.93 g, 18.98 mmol, 1.80 eq), the mixture was stirred at 80° C. for 4 hours. LCMS showed the desired mass was detected. The mixture was quenched water (200 mL), extracted with ethyl acetate (100 mL×3). The combined organic layers were washed with brine (100 mL×2), dried over anhydrous sodium sulfate, filtered and concentrated in vacuum to give a residue, which was purified by column chromatography ($SiO_2$, petroleum ether:ethyl acetate=30:1~5:1) to give compound 12-4 (1.8 g, 5.45 mmol, 51.82% yield, 100% purity) as a white solid. LCMS: RT=0.841 min, purity: 100.00%, m/z 353.0 $[M+Na]^+$. $^1$H NMR ($CDCl_3$, 400 MHz): δ 7.38-7.37 (m, 5H), 5.27-5.19 (m, 2H), 4.46-4.33 (m, 1H), 4.02-3.89 (m, 1H), 3.71-3.66 (m, 1H), 3.12-3.08 (m, 1H), 2.73-2.68 (m, 1H), 2.35-2.28 (m, 1H), 1.45-1.33 (m, 9H). SFC: RT=0.539 min, de %=100%.

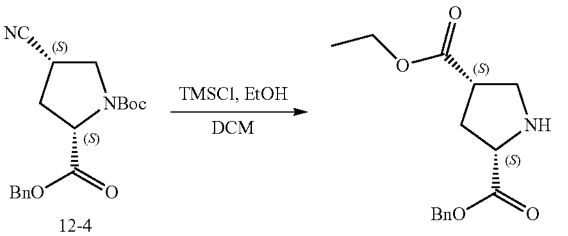

12-4 12-5

Trimethylchlorosilane (8.88 g, 81.72 mmol, 10.37 mL, 15 eq) was added drop-wise to ethanol (20 mL) at 0° C., then a solution of compound 12-4 (1.8 g, 5.45 mmol, 1 eq) in dichloromethane (20 mL) was added to the above mixture. The result mixture was stirred at 25° C. for 20 hours. LCMS showed the starting material was consumed and desired mass was detected. The mixture was cooled to 0° C., quenched with water (50 mL), adjusted to pH=7 with saturate sodium dicarbonate solution and extracted with dichloromethane (30 mL×3). The combined organic layer was washed with brine (20 mL×3), dried over anhydrous sodium sulfate, filtered and concentrated in vacuum to give compound 12-5 (1.5 g, crude) as colorless oil, which was used directly without purification. LCMS: RT=0.614 min, purity: 47.76%, m/z 278.1 $[M+H]^+$.

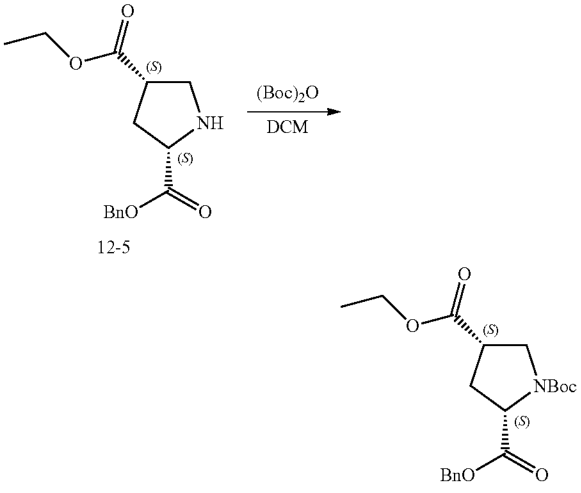

12-5

12-6

To a mixture of compound 12-5 (1.5 g, 5.41 mmol, 1 eq) in dichloromethane (20 mL) was added di-tert-butyl dicarbonate (1.18 g, 5.41 mmol, 1.24 mL, 1 eq). The mixture was stirred at 25° C. for 1 hour. LCMS showed the starting material was consumed and the desired mass was detected. The mixture was concentrated in vacuum to give a residue, which was purified by column chromatography (petroleum ether:ethyl acetate=30:1~5:1) to afford compound 12-6 (1.8 g, crude) as colorless oil. LCMS: RT=0.897 min, purity: 51.44%, m/z 278.1 $[M-Boc+H]^+$. $^1H$ NMR ($CDCl_3$, 400 MHz): δ 7.37-7.28 (m, 5H), 5.27-5.05 (m, 1H), 4.43-4.23 (m, 1H), 4.18-4.10 (m, 3H), 3.89-3.77 (m, 1H), 3.70-3.65 (m, 1H), 3.10-2.99 (m, 1H), 2.55-2.46 (m, 1H), 2.39-2.25 (m, 1H), 1.46-1.33 (m, 9H), 1.26-1.21 (m, 3H).

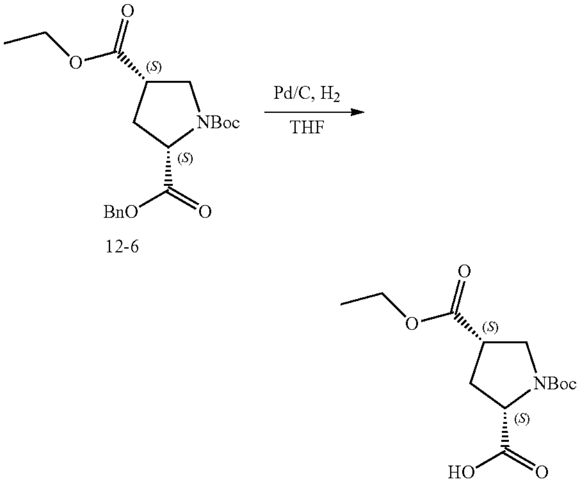

12-6

12-7

To a mixture of compound 12-6 (1.4 g, 3.71 mmol, 1 eq) in tetrahydrofuran (20 mL) was added Pd/C (10 mg, 10% purity on carbon) under nitrogen atmosphere. The result mixture was degassed with hydrogen atmosphere for three times and stirred at 25° C. for 2 hours under hydrogen atmosphere (15 psi). LCMS showed the starting material was consumed and the desired mass was detected. The mixture was filtered through a celite pad. The filtrate was diluted with ethyl acetate (60 mL) and washed with saturated sodium dicarbonate solution (30 mL×3). The organic layer was discarded, the aqueous phase was adjusted to pH=6-7 with hydrochloric acid (2 M) and extracted with ethyl acetate (50 mL×3). The combined organic layer was dried over anhydrous sodium sulfate, filtered and concentrated in vacuum to give compound 12-7 (500 mg, crude) as colorless oil. $^1H$ NMR ($CDCl_3$, 400 MHz): δ 4.35-4.28 (m, 1H), 4.16 (q, J=7.2 Hz, 2H), 3.88-3.63 (m, 2H), 3.07-3.04 (m, 1H), 2.57-2.39 (m, 2H), 1.48-1.43 (m, 9H), 1.29-1.26 (m, 3H).

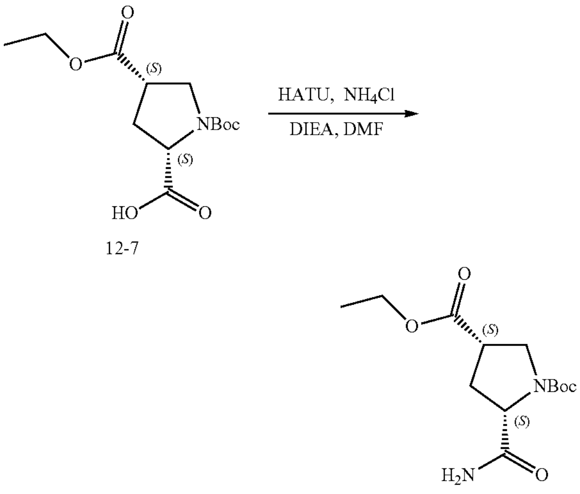

12-7

12-8

To a mixture of compound 12-7 (500 mg, 1.74 mmol, 1 eq) in N,N-dimethylformamide (6 mL) was added N,N-diisopropylethylamine (675 mg, 5.22 mmol, 909.38 uL, 3 eq), then HATU (993 mg, 2.61 mmol, 1.5 eq) was added at 0° C. After stirring at 0° C. for 15 minutes, ammonium chloride (186 mg, 3.48 mmol, 121.69 uL, 2 eq) was added. The mixture was stirred at 25° C. for 6 hours. The mixture was poured into water (30 mL) and extracted with ethyl acetate (15 mL×3). The combined organic layer was dried over anhydrous sodium sulfate, filtered and concentrated in vacuum to give compound 12-8 (500 mg, crude), which was used in next step directly without purification.

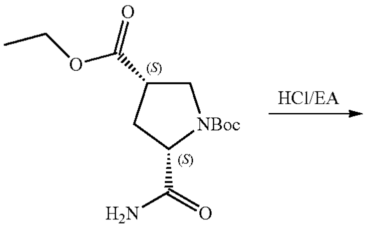

12-8

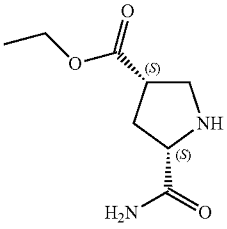

12-9

To a solution of compound 12-8 (400 mg, 1.4 mmol, 1 eq) in ethyl acetate (4 mL) was added hydrochloric acid/ethyl acetate (4 M, 2.0 mL, 5.73 eq) dropwise at 0° C. The mixture was stirred at 25° C. for 1 hour. TLC showed the starting material was consumed. The mixture was concentrated in vacuum to give a residue, which was triturated with ethyl acetate (5 mL), filtered and the solid was collected to afford compound 12-9 (250 mg, crude, HCl salt) as a white solid. $^1$H NMR ($CD_3OD$, 400 MHz): δ 4.39-4.37 (m, 1H), 4.18 (t, J=7.2 Hz, 2H), 3.71-3.70 (m, 1H), 3.68-3.59 (m, 1H), 3.44-3.42 (m, 1H), 2.82-2.76 (m, 1H), 2.35-2.30 (m, 1H), 1.27 (t, J=7.2 Hz, 3H).

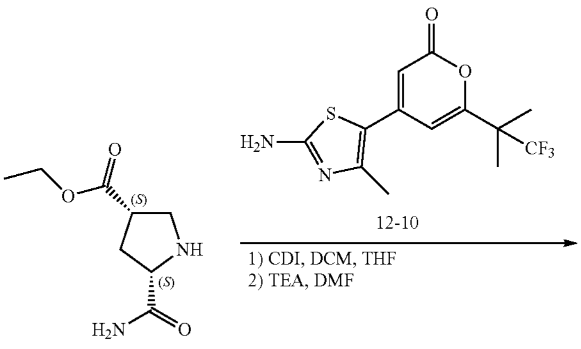

12-10

12-9

-continued

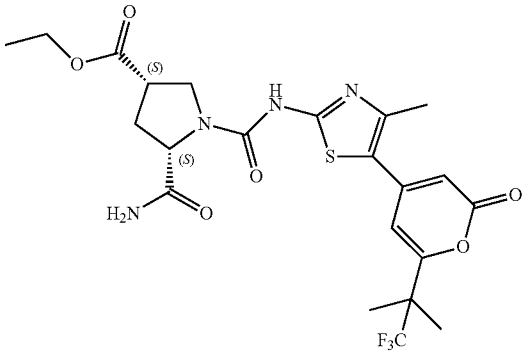

Compound (12)

To a solution of compound 12-10 (60 mg, 188.49 umol, 1 eq) in tetrahydrofuran (1 mL) and dichloromethane (2 mL) was added 1,1'-carbonyldiimidazole (46 mg, 282.74 umol, 1.5 eq). The mixture was stirred at 50° C. for 20 hours. LCMS showed trace of the starting material remained. The mixture was concentrated in vacuum to give a residue. To a solution of the above residue in N,N-dimethylformamide (2 mL) was added triethylamine (57 mg, 565.48 umol, 78.71 uL, 3 eq) and compound 12-9 (63 mg, 282.74 umol, 1.5 eq, HCl salt). The mixture was stirred at 25° C. for 6 hours. LCMS showed the desired mass was detected. The mixture was poured into water (20 mL), extracted with ethyl acetate (10 mL×3). The combined organic layers were combined and washed with brine (10 mL×3), dried over anhydrous sodium sulfate, filtered and concentrated in vacuum to give a residue. The residue was purified by prep-TLC (ethyl acetate) to afford Compound (12) (34.2 mg, 63.80 umol, 33.85% yield, 98.97% purity) as a yellow solid. LCMS: RT=1.919 min, purity: 98.97%, m/z 531.2 $[M+H]^+$. $^1$H NMR ($CD_3OD$, 400 MHz): δ 6.61 (s, 1H), 6.27 (s, 1H), 4.48 (t, J=7.2 Hz, 1H), 4.18 (q, J=7.2 Hz, 2H), 3.97-3.89 (m, 2H), 3.30-3.25 (m, 1H), 2.64-2.56 (m, 1H), 2.48 (s, 3H), 2.37-2.30 (m, 1H), 1.56 (s, 6H), 1.28 (t, J=7.2 Hz, 3H). SFC: RT=1.733 min, de %=100%.

Synthetic Preparation of Compound (13)

A synthetic route to Compound (13) is shown in the scheme below.

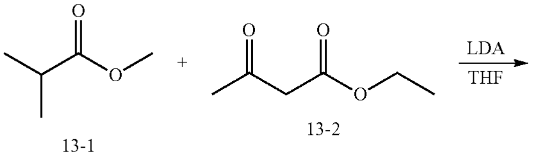

13-1

13-2

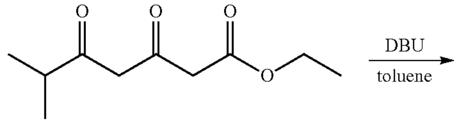

13-3

-continued

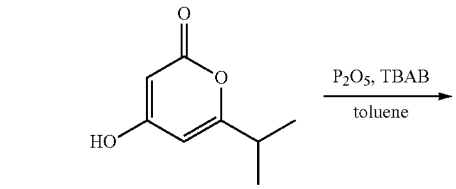

13-4

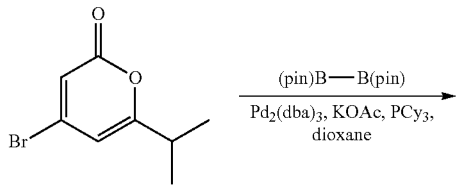

13-5

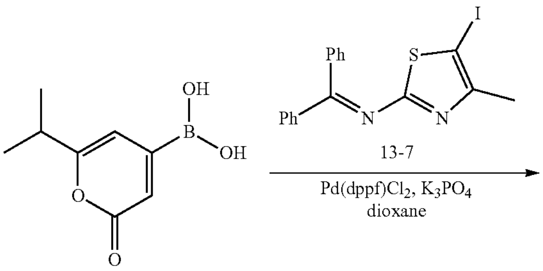

13-7

13-6

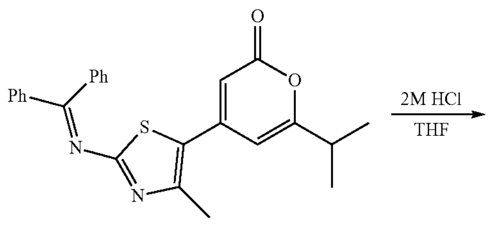

13-8

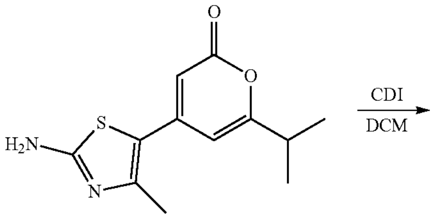

13-9

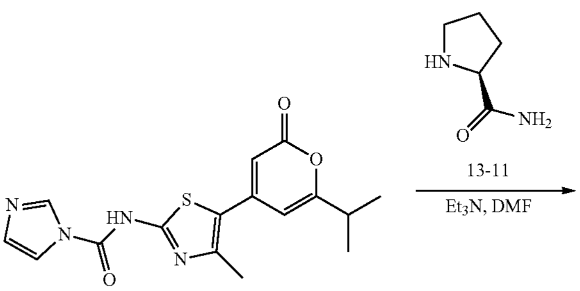

13-11

13-10

-continued

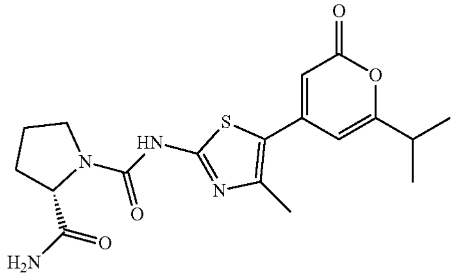

Compound (13)

Experimental Procedures for the Preparation of Compound (13)

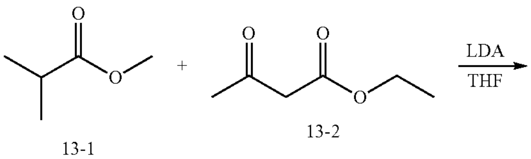

13-1

13-2

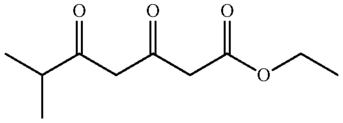

13-3

To a solution of lithium diisopropylamide (2 M, 159 mL) in tetrahydrofuran (50 mL) was added a solution of compound 13-2 (16.6 g, 127.29 mmol, 16.09 mL) in tetrahydrofuran (50 mL) at −78° C. under nitrogen atmosphere. The reaction mixture was stirred at −78° C. for 30 min, then compound 13-1 (13 g, 127.29 mmol, 14.61 mL) was added. The reaction mixture was stirred for at −78° C. 12 hours. TLC (petroleum ether:ethyl acetate=5:1) showed compound 13-2 still remained and a new spot was detected. The reaction mixture was quenched with saturated ammonium chloride solution (50 mL) and 1N hydrogen chloride (60 mL), extracted with ethyl acetate (100 mL×3). The combined organic layer was washed with brine(50 mL×2), dried over anhydrous sodium sulfate, concentrated in vacuo. The crude product was purified by flash silica gel chromatography (petroleum ether:ethyl acetate=20:1~5:1) to give the compound 13-3 (1 g, 24.47 mmol, 21.58% yield, 55% purity) as a yellow oil. $^1$H NMR ($CDCl_3$, 400 MHz) δ 15.21 (br. s, 1H), 5.61 (s, 1H), 4.12 (q, J=7.2 Hz, 2H), 3.33 (s, 2H), 2.50-2.45 (m, 1H), 1.28 (t, J=7.2 Hz, 3H), 1.14 (d, J=6.8 Hz, 6H).

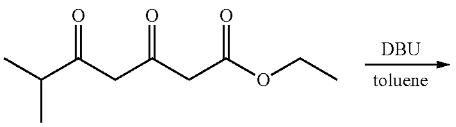

13-3

-continued

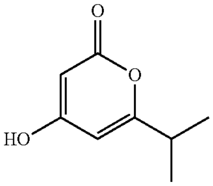

13-4

To a solution of compound 13-3 (11.5 g, 57.23 mmol) in toluene (15 mL) was added DBU (10.5 g, 68.68 mmol, 10.36 mL). The reaction mixture was stirred at 90° C. for 12 hours. LCMS showed the starting material was consumed and desired product was detected. The reaction mixture was adjusted to pH~7 with 1N hydrochloric acid, extracted with ethyl acetate (50 mL×3). The combined organic layer was washed with brine (20 mL×2), dried over sodium sulfate, concentrated in vacuo. The residue was purified by reverse flash to give compound 13-4 (1.23 g, 7.50 mmol, 13.11% yield, 94% purity) as brown oil. LCMS: RT=0.568 min, m/z 155.0 $[M+H]^+$. $^1H$ NMR ($CDCl_3$, 400 MHz) δ 5.98 (d, J=1.6 Hz, 1H), 5.58 (d, J=2.0 Hz, 1H), 2.78-2.71 (m, 1H), 1.24 (d, J=6.8 Hz, 6H).

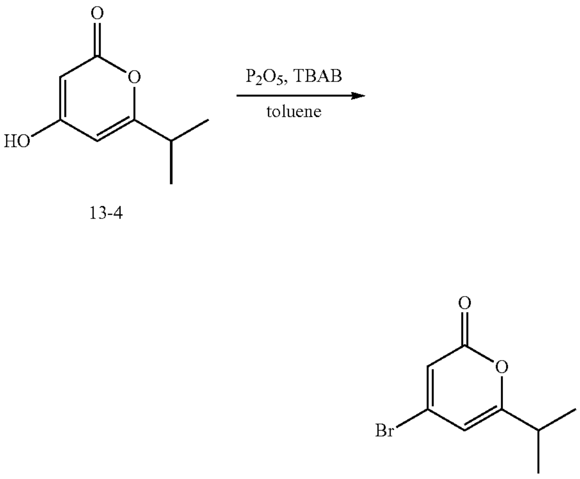

13-4

13-5

To a mixture of compound 13-4 (1.23 g, 7.98 mmol) and phosphorus pentoxide (2.83 g, 19.95 mmol, 1.23 mL) in toluene (13 mL) was added tetrabutylammonium bromide (3.86 g, 11.97 mmol). The reaction mixture was stirred at 90° C. for 1 hour. TLC (petroleum ether ethyl acetate=8:1) showed the starting material was consumed and one new spot was formed. The reaction mixture was poured into 10 mL of saturated sodium bicarbonate, extracted with ethyl acetate (20 mL×2). The combined organic layer was washed with brine (10 mL×2), dried over sodium sulfate, concentrated in vacuo. The residue was purified by column chromatography ($SiO_2$, petroleum ether:ethyl acetate=20:1~5:1) to give compound 13-5 (847 mg, 3.58 mmol, 44.84% yield, 91.7% purity) as yellow oil. LCMS: RT=0.773 min, m/z 216.9, 218.9 $[M+H]^+$ $^1H$ NMR ($CDCl_3$, 400 MHz) δ 6.46 (d, J=1.6 Hz, 1H), 6.17 (d, J=1.6 Hz, 1H), 2.78-2.71 (m, 1H), 1.26 (d, J=6.8 Hz, 6H).

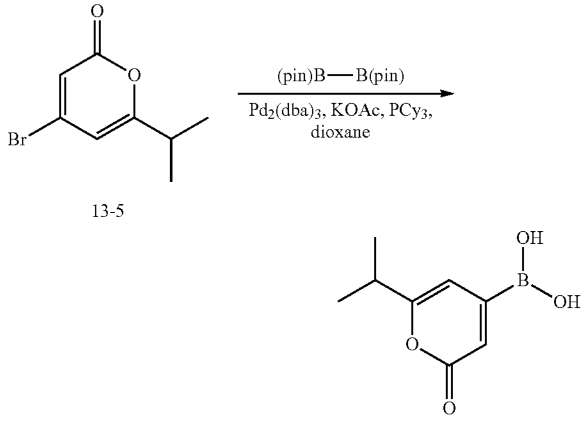

13-5

13-6

To a solution of compound 13-5 (400 mg, 1.84 mmol) in dioxane (4 mL) was added potassium acetate (542 mg, 5.52 mmol), 4,4,5,5-tetramethyl-2-(4,4,5,5-tetramethyl-1,3,2-dioxaborolan-2-yl)-1,3,2-dioxaborolane (1.17 g, 4.60 mmol), tricyclohexyl phosphine (62 mg, 220.80 umol, 71.17 uL) and $Pd_2(dba)_3$ (168 mg, 184.00 umol). The reaction mixture was stirred at 80° C. for 2 hours under nitrogen atmosphere. LCMS showed the starting material was consumed and desired product was detected. The reaction mixture was filtered and concentrated under reduced pressure to give compound 13-6 (1.56 g, 1.68 mmol, 91.31% yield, 19.6% purity) as a yellow solid. LCMS: RT=0.633 min, m/z 183.1 $[M+H]^+$.

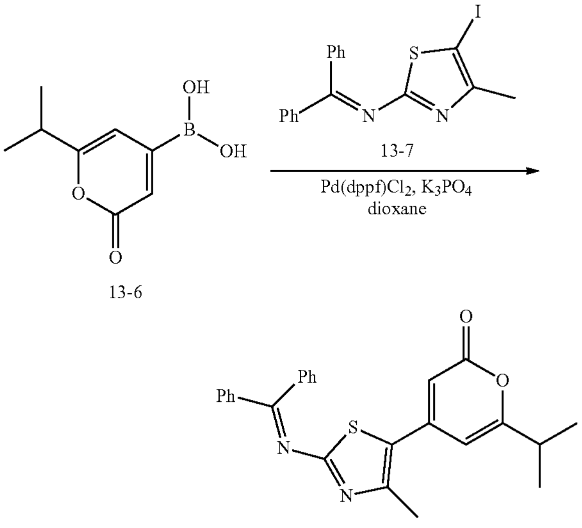

13-7

13-6

13-8

To a solution of compound 13-6 (1.56 g, 1.80 mmol) and compound 13-7 (728 mg, 1.80 mmol) in dioxane (10 mL) was added a solution of potassium phosphate (573 mg, 2.70 mmol) in water (1 mL). The reaction mixture was degassed with nitrogen for three times, $Pd(dppf)Cl_2$ (147 mg, 180.00 umol) was added under nitrogen atmosphere. The mixture was stirred at 90° C. for 15 hours and LCMS showed partial of starting material was still remained and desired product was detected. The reaction mixture was filtered through a celite pad and the filtrate was concentrated in vacuo. The residue was purified by column chromatography (petroleum ether:ethyl acetate=30:1~5:1) to give compound 13-8 (1 g) as a yellow solid. LCMS: RT=0.989 min, m/z 415.0 $[M+H]^+$. $^1H$ NMR ($CDCl_3$, 400 MHz) δ 7.86 (s, 2H), 7.54-7.33 (m, 8H), 6.03 (s, 1H), 5.96 (s, 1H), 2.74-2.71 (m, 1H), 2.52 (s, 3H), 1.32-1.26 (m, 6H).

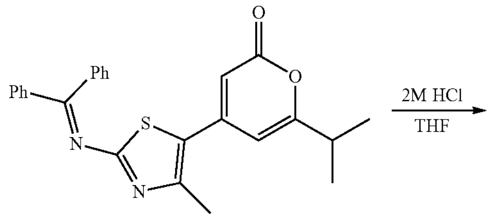

13-8

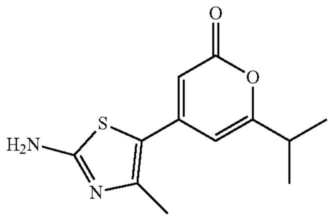

13-9

To a solution of compound 13-8 (1 g, 2.41 mmol) in tetrahydrofuran (15 mL) was added hydrochloric acid (2 M, 6.03 mL). The reaction mixture was stirred at 25° C. for 1 hour under nitrogen atmosphere. TLC (petroleum ether: ethyl acetate=0:1) showed the starting material was consumed and a new spot was formed. The reaction mixture was adjusted to pH 8 with sodium bicarbonate, extracted with ethyl acetate (20 mL×3). The combined organic layer was washed with brine (10 mL×2), dried over sodium sulfate, concentrated under reduced pressure. The residue was purified by column chromatography (petroleum ether:ethyl acetate=5:1~0:1) to give compound 13-9 (183 mg, 694.51 umol, 28.82% yield, 95% purity) as a yellow solid. LCMS: RT=0.584 min, m/z 251.0 $[M+H]^+$. $^1H$ NMR ($CDCl_3$, 400 MHz) δ 6.06 (d, J=3.6 Hz, 2H), 5.25 (br. s, 2H), 3.50 (s, 1H), 2.78-2.74 (m, 1H), 2.43 (s, 3H), 1.28 (d, J=7.2 Hz, 6H).

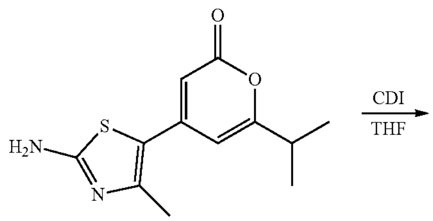

13-9

-continued

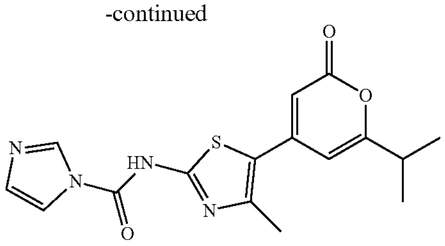

13-10

To a solution of compound 13-9 (183 mg, 731.06 umol) in tetrahydrofuran (4 mL) and dichloromethane (8 mL) was added 1,1'-carbonyldiimidazole (190 mg, 1.17 mmol). The reaction mixture was stirred at 50° C. for 12 hours under nitrogen atmosphere. TLC (petroleum ether:ethyl acetate=0:1) showed the starting material was consumed and a new spot was formed. The reaction mixture was concentrated in vacuo to give compound 13-10 (251 mg, crude) as a yellow solid, which was used for the next step directly. $^1H$ NMR ($CDCl_3$, 400 MHz) δ 7.71 (s, 1H), 7.10 (s, 2H), 6.21 (d, J=1.6 Hz, 1H), 6.15 (d, J=0.8 Hz, 1H), 2.84-2.78 (m, 1H), 2.65 (s, 3H), 1.31 (d, J=6.8 Hz, 6H).

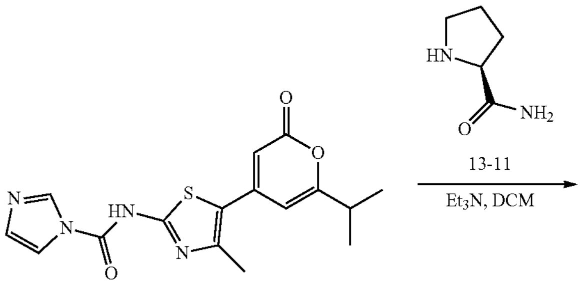

13-10

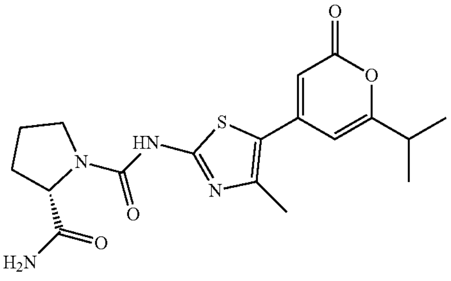

Compound (13)

To a solution of compound 13-10 (251 mg, 728.82 umol) in dimethyl formamide (2.5 mL) was added triethylamine (148 mg, 1.46 mmol, 0.2 mL) and compound 13-11 (92 mg, 801.70 umol). The reaction mixture was stirred at 25° C. for 1 hour under nitrogen atmosphere. TLC (petroleum ether: ethyl acetate=0:1) showed the starting was consumed and a new spot was formed. The reaction mixture was poured into water (10 mL), extracted with ethyl acetate (30 mL×3). The combined organic layer was washed with brine (15 mL×5), dried over sodium sulfate, concentrated in vacuo. The mixture was diluted with a mixture of ethyl acetate and petroleum ether (10 mL), and then filtered to give Compound (13) (99.50 mg, 254.83 umol, 34.96% yield, and 100% purity) as a yellow solid. LCMS: RT=1.441 min, m/z 391.1 $[M+H]^+$. $^1H$ NMR ($CD_3OD$, 400 MHz) δ 6.35 (d, J=1.6 Hz, 1H), 6.15

(d, J=1.6 Hz, 1H), 4.46-4.43 (m, 1H), 3.72-3.68 (m, 1H), 3.61-3.56 (m, 1H), 2.88-2.81 (m, 1H), 2.47 (s, 3H), 2.30-2.26 (m, 1H), 2.07-2.05 (m, 3H), 1.29 (d, J=6.8 Hz, 6H).

Synthetic Preparation of Compound (14)

Figure 15:
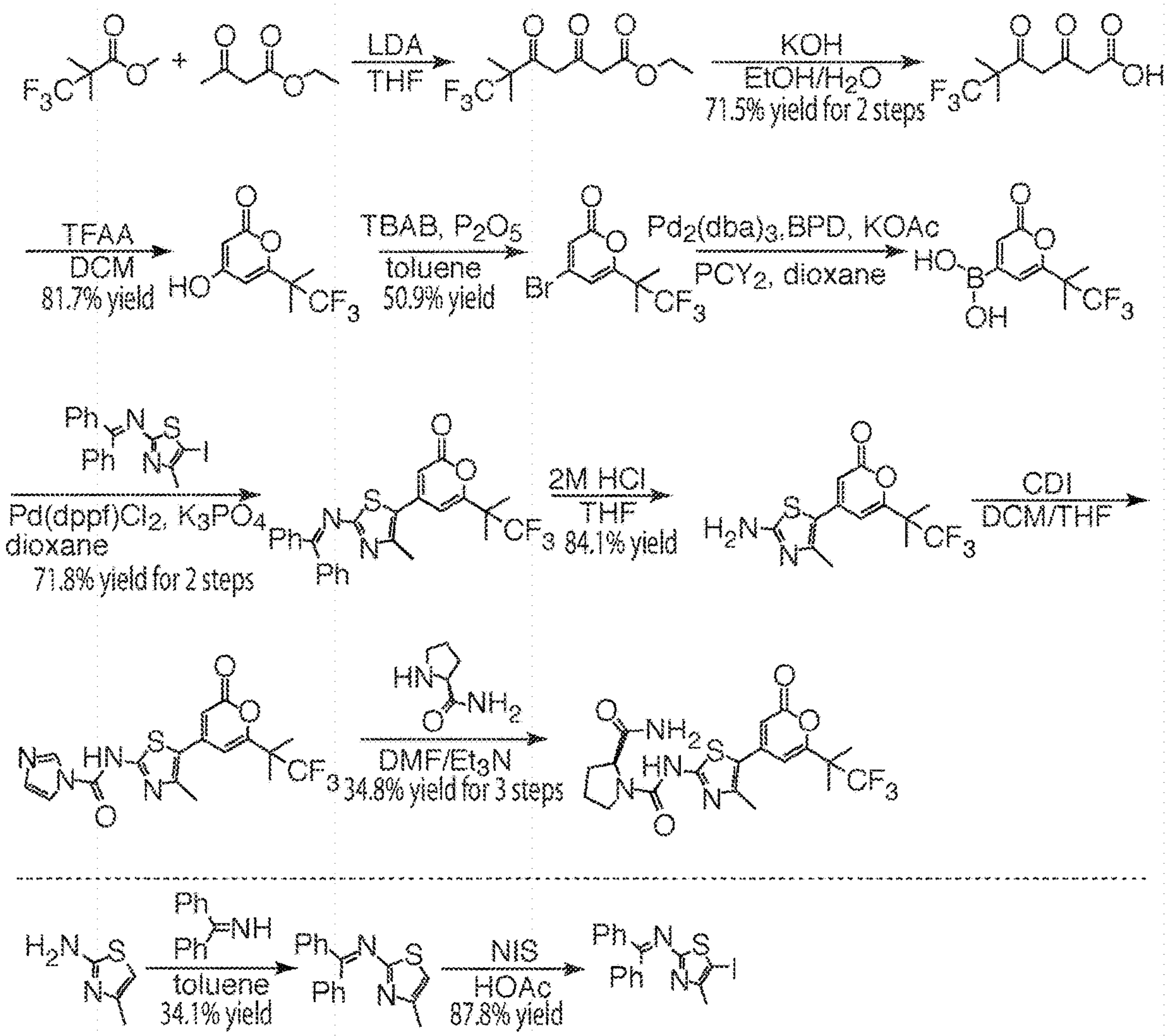
FIG. 15. Exemplary synthesis of Compound (14).
Figure 16:
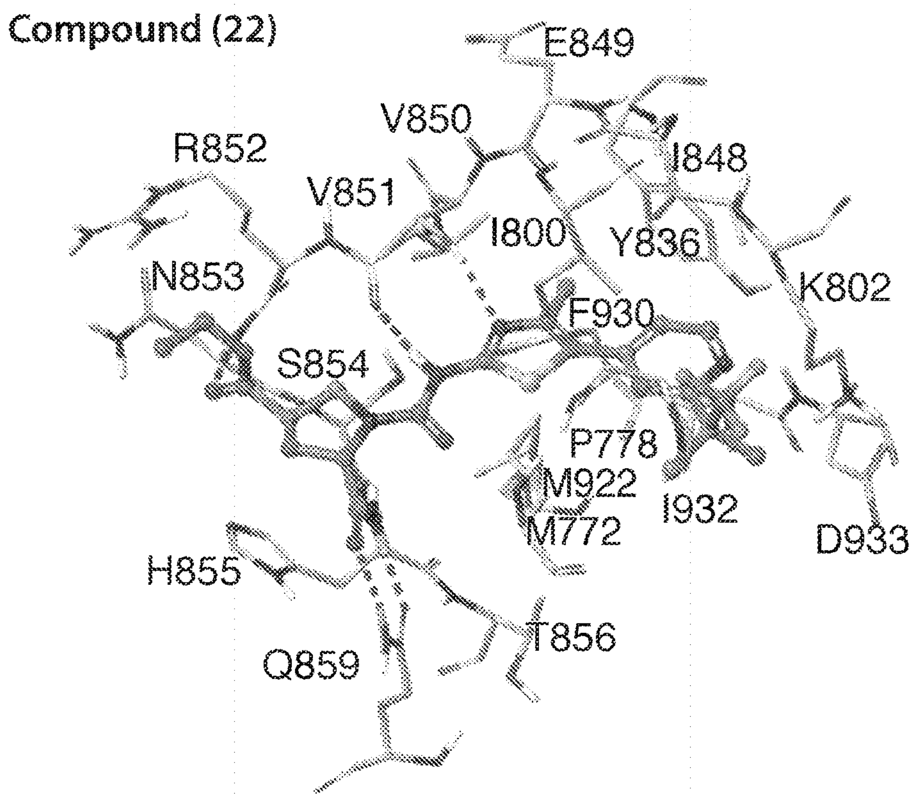
FIG. 16. Proposed Binding Mode of Compound (22) in the ATP Pocket of PI3Kα. Compound (22) was docked to the crystal structure of PI3Kα using Glide in the Schrodinger suite.[13] Hydrogen bonds are represented as dashed lines.
Figure 17:
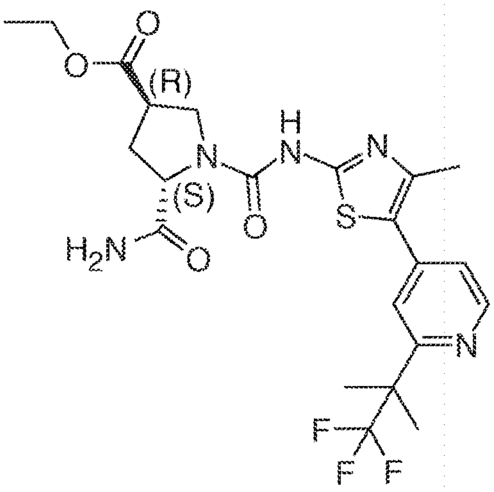
FIG. 17. Structure of Compound (22).

An exemplary synthesis of Compound (14) is carried out in eight chemical steps in its longest linear sequence to yield amorphous product (FIG. 15). Also see the scheme below. A separate 2-step process can be carried out to prepare intermediate 14-7.

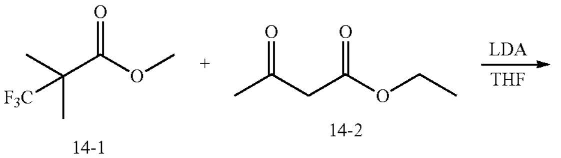

14-1 14-2

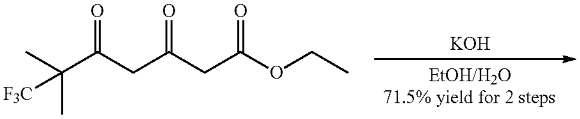

14-3

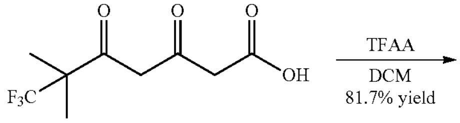

14-3A

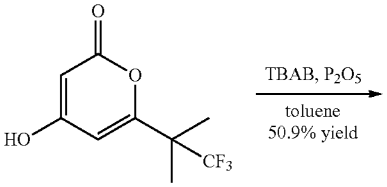

14-4

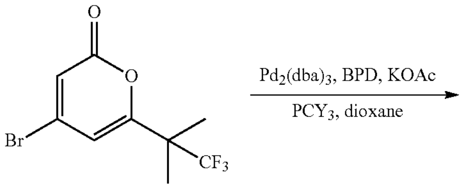

14-5

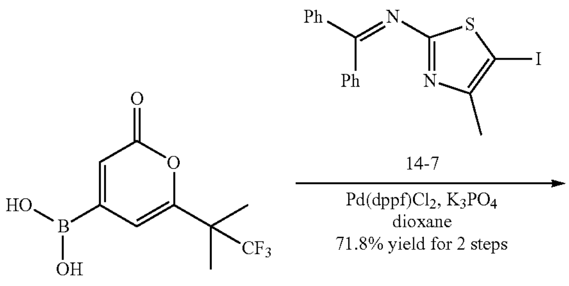

14-7

14-6

-continued

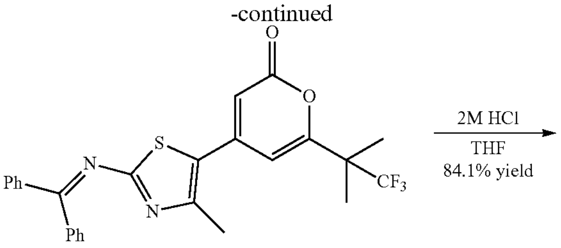

14-8

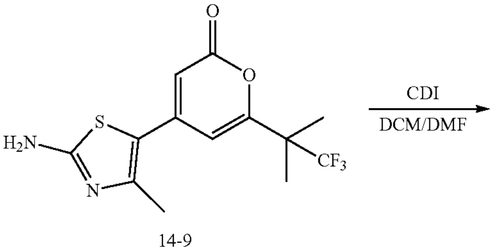

14-9

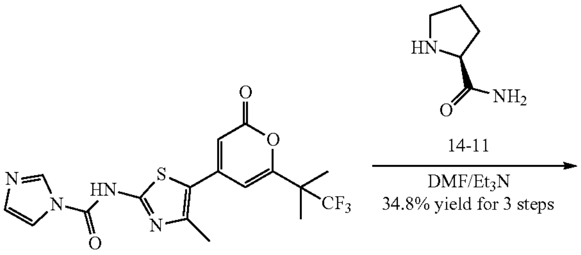

14-11

14-10

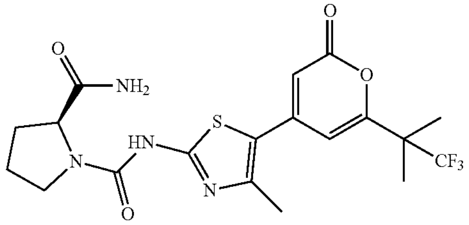

Compound (14)

Experimental Procedures for the Preparation of Compound (14)

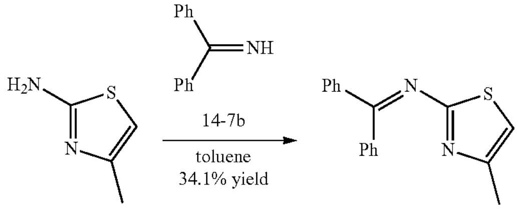

14-7b 14-7a 14-7c

To a solution of compound 14-7a (20.0 g, 0.175 mol, 1.00 eq) in toluene (100 mL) was added compound 14-7b (30.2 g, 0.167 mol, 27.9 mL, 0.950 eq). The mixture was stirred at 110° C. for 16 h under $N_2$. TLC (Petroleum ether:Ethyl acetate=3:1) showed a few of compound 14-7a ($R_f$=0.24) remained and a yellow new spot ($R_f$=0.5) was detected. The reaction was cooled to room temperature and washed with brine (50.0 mL*2). The combined organic layer was dried over $Na_2SO_4$, filtered and concentrated. The residue was purified by column chromatography ($SiO_2$, Petroleum ether/Ethyl acetate=1/0 to 30:1, $R_f$=0.5) to afford compound 14-7c (16.7 g, 59.7 mmol, 34.1% yield, 99.5% purity) as a yellow solid. LCMS: $R_t$=0.902 min, m/z=279.2 $(M+H)^+$. $^1H$ NMR: 400 MHz $CDCl_3$ δ 7.87 (br d, J=7.70 Hz, 2H), 7.53-7.44 (m, 4H), 7.43-7.37 (m, 2H), 7.32-7.25 (m, 2H), 6.55 (d, J=0.90 Hz, 1H), 2.36 (d, J=0.90 Hz, 3H).

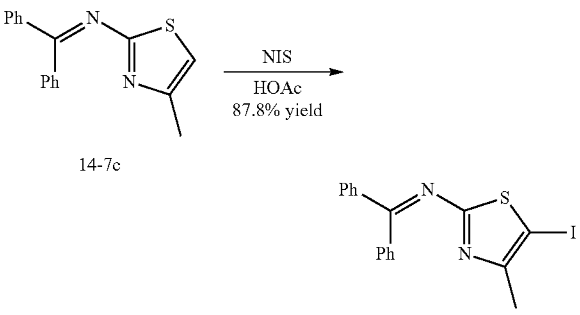

14-7c 14-7

To a solution of compound 14-7c (16.7 g, 59.7 mmol, 1.00 eq) in HOAc (170 mL) was added NIS (13.4 g, 59.7 mmol, 1.00 eq). The mixture was stirred at 25° C. for 1 h. TLC (Petroleum ether:Ethyl acetate=3:1) showed the compound 7c ($R_f$=0.7) was consumed and a new main spot ($R_f$=0.8) was detected. The reaction was poured into water (400 mL). The precipitate was collected by filtration and washed with Petroleum ether (150 mL), dried in vacuum to give compound 14-7 (21.4 g, 52.4 mmol, 87.8% yield, 99.0% purity) as a yellow solid. LCMS: $R_t$=1.064 min, m/z=405.1 $(M+H)^+$. $^1H$ NMR: 400 MHz $CDCl_3$ δ 7.98-7.71 (m, 2H), 7.63-7.34 (m, 6H), 7.27 (s, 2H), 2.40 (s, 3H).

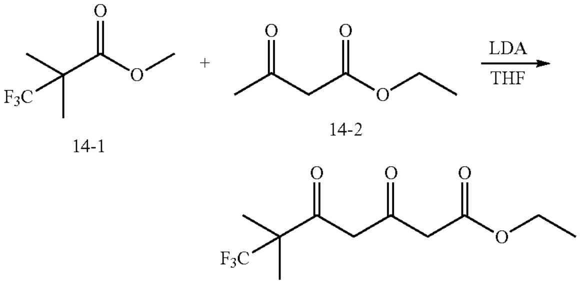

14-1

14-2

14-3

To a solution of LDA (2 M, 331 mL, 2.50 eq) in THF (250 mL) was added a solution of compound 14-2 (34.4 g, 265 mmol, 33.4 mL, 1.00 eq) in THF (250 mL) at −78° C. under $N_2$. The mixture was stirred at −78° C. for 0.5 h, then compound 14-1 (45.0 g, 0.265 mol, 1.00 eq) was added to the mixture. The reaction was stirred at −78° C. for 2 h. LCMS showed compound 14-1 was consumed. Solution of saturated $NH_4Cl$ (250 mL) was added to the reaction and extracted with ethyl acetate (250 mL×3). The combined organic layer was washed with 1N HCl (250 mL×2) and brine (500 mL), dried over $Na_2SO_4$, filtered and concentrated to give the compound 14-3 (70.0 g, crude) as a yellow oil. It was used for next step without further purification. LCMS: $R_t$=0.950 min. $^1H$ NMR: 400 MHz $CDCl_3$ δ 15.21 (br s, 1H), 5.81 (s, 1H), 4.17-4.08 (m, 3H), 3.30 (s, 2H), 1.32 (s, 6H), 1.21-1.19 (m, 3H).

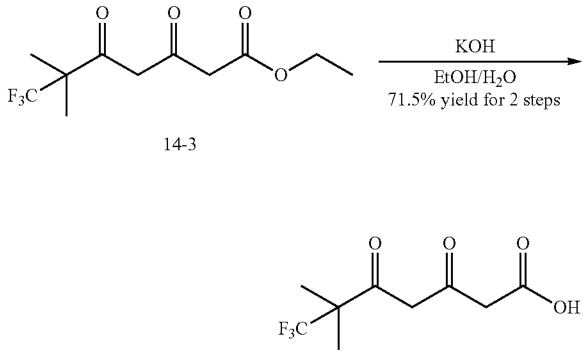

14-3

14-3A

To a solution of KOH (147 g, 2.61 mol, 5.00 eq) in EtOH (1.40 L) and $H_2O$ (140 mL) was added compound 14-3 (140 g, 522 mmol, 1.00 eq) at 20° C. The mixture was stirred at 20° C. for 3 h. LCMS showed the desired MS (0.767 min, 254 nm) was detected. The reaction was concentrated to remove most of solvents. The residue was diluted with ethyl acetate (1.50 L) and quenched with 2N HCl (1.50 L). The aqueous layer was extracted with ethyl acetate (500 mL×3). Combined organic layer was washed with brine (500 mL), dried over $Na_2SO_4$, filtered and concentrated to give compound 14-3A (94.9 g, 374 mmol, 71.5% yield, 94.5% purity) as a yellow oil. LCMS: $R_t$=0.823 min, m/z=241.2 $(M+H)^+$.

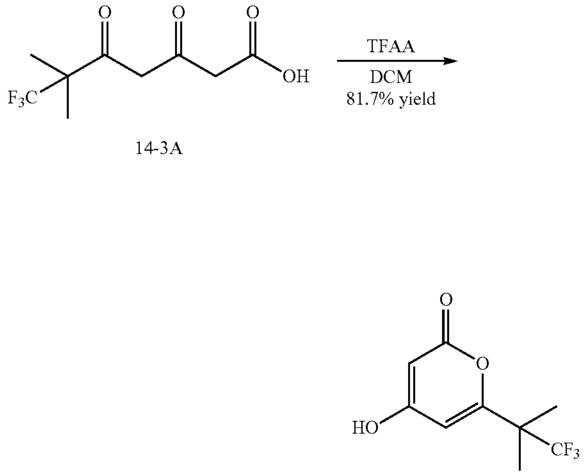

14-3A 14-4

To a solution of compound 14-3A (94.9 g, 374 mmol, 1.00 eq) in dichloromethane (1.00 L) was added TFAA (78.4 g, 374 mmol, 51.9 mL, 1.00 eq) at 0° C. The mixture was stirred at 20° C. for 2 h. TLC (ethyl acetate) showed compound 3A ($R_f$=0) was consumed completely and a new spot ($R_f$=0.24) was detected. The reaction was concentrated to remove the solvents. The residue was diluted with ethyl acetate (500 mL) and water (200 mL). The organic layer was washed with brine (200 mL), dried over $Na_2SO_4$ and concentrated to give compound 14-4 (73.2 g, 305 mmol, 81.7% yield, 92.6% purity) as a yellow solid. LCMS: $R_t$=0.775 min, m/z=223.2 $(M+H)^+$. $^1H$ NMR: 400 MHz $CDCl_3$ δ 10.43 (br s, 1H), 6.30 (s, 1H), 5.71 (s, 1H), 1.49 (s, 6H).

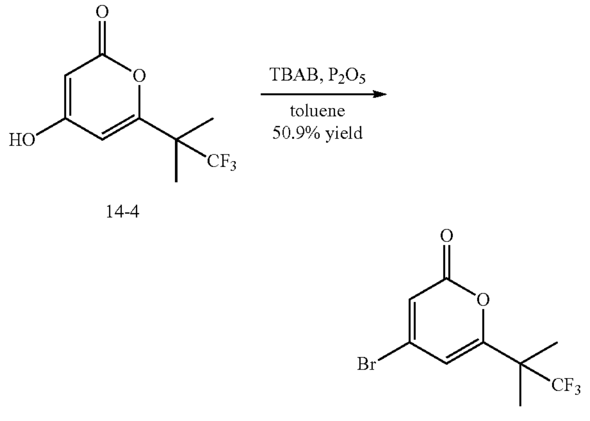

14-4

14-5

To a mixture of compound 14-4 (35.0 g, 146 mmol, 1.00 eq) and $P_2O_5$ (51.8 g, 365 mmol, 22.5 mL, 2.50 eq) in toluene (350 mL) was added TBAB (70.7 g, 219 mmol, 1.50 eq). The mixture was stirred at 90° C. for 1 h. TLC (Petroleum ether:Ethyl acetate=5:1) showed the compound 14-4 ($R_f$=0.0) was consumed and a new main spot ($R_f$=0.6) was detected. After being cooled to 25° C., the reaction mixture was adjusted to pH=7 with saturated $NaHCO_3$ solution, extracted with ethyl acetate (500 mL×3). The combined organic layer was washed with brine (500 mL), dried over $Na_2SO_4$, filtered and concentrated. The residue was purified by column chromatography ($SiO_2$, Petroleum ether/Ethyl acetate=1/0 to 50:1, $R_f$=0.6) to give compound 14-5 (42.7 g, 149 mmol, 50.9% yield, 99.2% purity) as a yellow solid. LCMS: Rt=0.885 min, m/z=285.1 $(M+H)^+$. $^1$H NMR: 400 MHz $CDCl_3$ δ 6.58 (d, J=1.6 Hz, 1H), 6.43 (d, J=1.6 Hz, 1H), 1.51 (s, 6H).

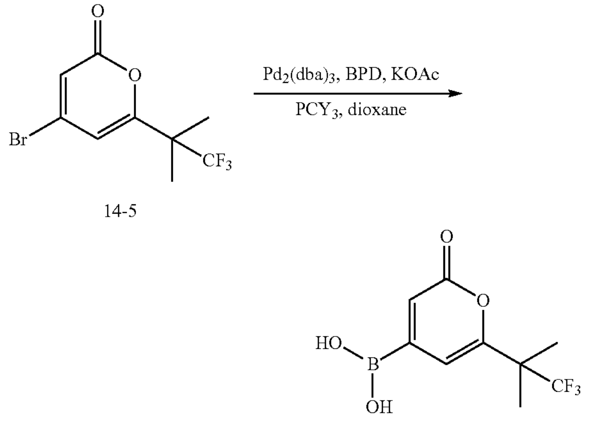

14-5

14-6

To a mixture of compound 14-5 (21.0 g, 73.1 mmol, 1.00 eq) and BPD (22.3 g, 87.7 mmol, 1.20 eq) in toluene (210 mL) was added KOAc (10.8 g, 110 mmol, 1.50 eq) under $N_2$. Then $PCy_3$ (2.46 g, 8.77 mmol, 2.84 mL, 0.12 eq) and $Pd_2(dba)_3$ (3.35 g, 3.65 mmol, 0.05 eq) was added to the mixture under $N_2$. The mixture was stirred at 50° C. for 1 h. LCMS (EW10071-23-P1A2) showed the desired MS (0.773 min, 0.880 min) was detected. The reaction mixture was filtered and the filtrate was concentrated to give compound 14-6 (44.0 g, crude) as a brown solid. LCMS: Rt=0.773 min, m/z=223.2 $(M+H)^+$.

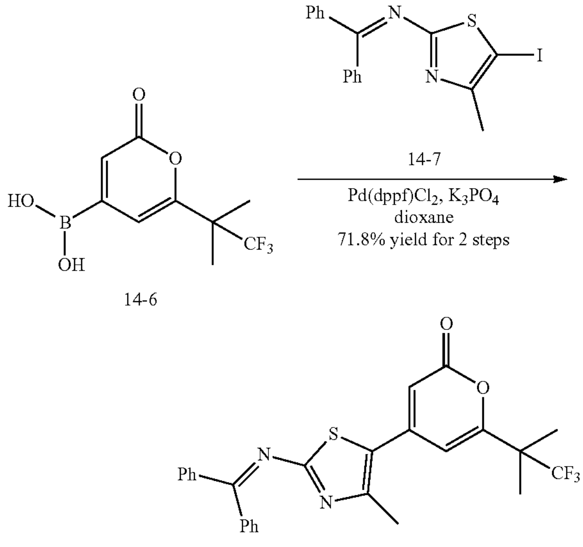

14-7

14-6

14-8

To a solution of compound 14-6 (44.0 g, 176 mmol, 1.00 eq) and compound 14-7 (37.6 g, 93.0 mmol, 5.28 e−1 eq) in dioxane (440 mL) was added a solution of $K_3PO_4$ (44.8 g, 212 mmol, 1.20 eq) in $H_2O$ (44.0 mL). The mixture was added Pd(dppf)$Cl_2$·$CH_2Cl_2$ (14.4 g, 17.6 mmol, 0.10 eq) under $N_2$. Then the mixture was stirred at 90° C. for 12 h. TLC (Petroleum ether:Ethyl acetate=5:1) showed compound 14-6 ($R_f$=0.0) was consumed and a new main yellow spot ($R_f$=0.3) was detected. The reaction was filtered and the filtrate was concentrated. The residue was purified by column chromatography ($SiO_2$, Petroleum ether/Ethyl acetate=20/1 to 5:1, $R_f$=0.3) to give compound 14-8 (28.9 g, 52.9 mmol, 30.1% yield, 88.3% purity) as an orange solid. LCMS: Rt=1.089 min, m/z=483.4 $(M+H)^+$. $^1$H NMR: 400 MHz $CDCl_3$ δ 7.87 (br s, 2H), 7.58-7.29 (m, 8H), 6.28 (s, 1H), 6.12 (d, J=1.20 Hz, 1H), 2.53 (s, 3H), 1.51 (s, 6H).

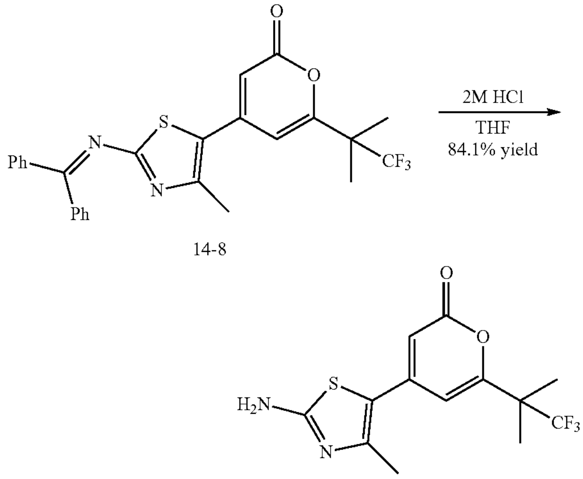

14-8

14-9

To a solution compound 14-8 (28.9 g, 52.89 mmol, 1 eq) in THF (290 mL) was added HCl (2 M, 249 mL, 9.41 eq) drop-wise. The mixture was stirred at 25° C. for 0.5 h. TLC (Petroleum ether:Ethyl acetate=2:1) showed compound 14-8

($R_f$=0.6) was consumed and a new spot ($R_f$=0.0) was detected. The reaction was poured into water (600 mL) and extracted with petroleum ether (500 mL×2). The organic layer was discarded. The aqueous layer was basified to pH=7 with aq.$NaHCO_3$, then the precipitate was collected and washed with petroleum ether (100 mL). The filter cake was dried in vacuum. The residue was triturated with Petroleum ether:Ethyl acetate=10:1(100 mL×2) and filtered, the filter cake was dried under vacuum to give compound 14-9 (14.6 g, 44.5 mmol, 84.1% yield, 97.0% purity) as a yellow solid. LCMS: Rt=1.089 min, m/z=483.4 $(M+H)^+$. $^1H$ NMR 400 MHz $CDCl_3$ δ 6.40-6.34 (m, 1H), 6.14 (d, J=1.20 Hz, 1H), 5.38 (br s, 2H), 2.43 (s, 3H), 1.54 (s, 6H)

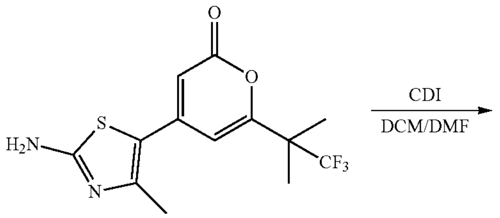

14-9

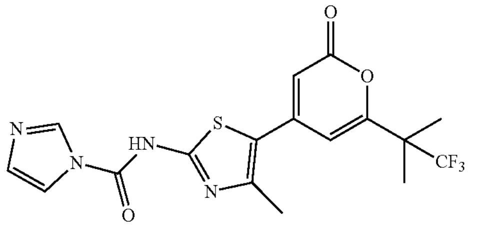

14-10

To a solution of compound 14-9 (12.0 g, 36.6 mmol, 1.00 eq) in THF (96.0 mL) and DCM (190 mL) was added CDI (8.89 g, 54.9 mmol, 1.50 eq) under $N_2$. The mixture was warmed to 50° C. and stirred at 50° C. for 16 h. TLC (Ethyl acetate) showed compound 14-9 ($R_f$=0.6) was consumed and a new spot ($R_f$=0.0) was detected. The reaction was concentrated to give compound 14-10 (15.1 g, crude) as a yellow solid. The residue was used next step without further purification.

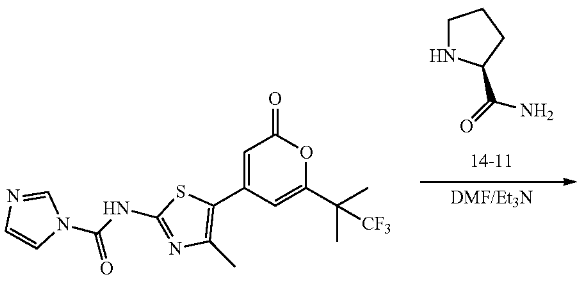

14-10

-continued

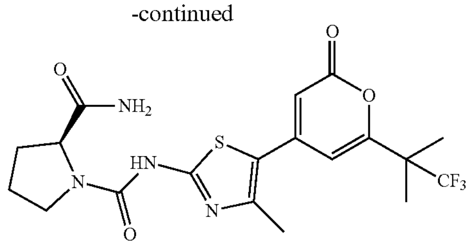

Compound (14)

To a mixture of compound 14-10 (15.1 g, 36.6 mmol, 1.00 eq) in DMF (96.0 mL) was added compound 14-11 (8.35 g, 73.2 mmol, 2.00 eq) and $Et_3N$ (11.1 g, 110 mmol, 15.3 mL, 3.00 eq). The mixture was stirred at 20° C. for 20 h. LCMS showed compound 14-10 was consumed and the desired MS (0.829 min) was detected. The reaction was poured into brine (1.00 L), extracted with dichloromethane/methanol=10:1 (500 mL×3). The combined organic layer was dried over $Na_2SO_4$, filtered and concentrated to give Compound (14) (50.0 g, crude) as a brown solid. LCMS: Rt=0.831 min, m/z=459.2 $(M+H)^+$. HPLC: Rt=1.841 min.

To a solution of Compound (14) (50.0 g, 109 mmol, 1.00 eq) in DMF (400 mL) was added ammonia; pyrrolidine-1-carbodithioic acid (8.96 g, 54.5 mmol, 0.50 eq) and $H_2O$ (2.00 mL). The mixture was stirred at 25° C. for 12 h. The solution was filtered (<1 um filter). The filtrate was added ammonia; pyrrolidine-1-carbodithioic acid (3.23 g, 19.6 mmol, 0.18 eq) and stirred at 25° C. for 1 h. The solution was filtered (<1 um filter) and the filtrate was concentrated to remove most of solvents. The residue was poured into brine (3.00 L) and extracted with dichloromethane/methanol=10:1 (500 mL×6). Combined the organic layer was washed with brine (1.00 LX2). The organic layer was dried over $Na_2SO_4$, filtered and concentrated. The residue was triturated with Petroleum ether:Ethyl acetate=2:1 (1.50 L) at 25° C. for 12 h, filtered and the filter cake was dissolved with dichloromethane (400 mL) and added petroleum ether (800 mL) drop-wise. The slurry solution was heated to 50° C. for 0.5 h, then the precipitated solution was filtered (twice), then the cake dried under vacuum to give Compound (14) (6.05 g, 13.1 mmol, 99.5% purity, Pd residue: 398 ppm) as a yellow solid. LCMS: Rt=0.851 min, m/z=459.3 $(M+H)^+$. HPLC: Rt=1.850 min. SFC: Rt=1.010 min. $^1H$ NMR: 400 MHz MeOD-d4 δ 6.61 (s, 1H), 6.27 (s, 1H), 5.49 (s, 1H), 4.45 (br d, J=9.90 Hz, 1H), 3.75-3.65 (m, 1H), 3.62-3.52 (m, 1H), 2.48 (s, 3H), 2.33-2.21 (m, 1H), 2.06 (br d, J=7.90 Hz, 3H), 1.56 (s, 6H).

To a solution of Compound (14) (6.05 g, 13.1 mmol, 1.00 eq, Pd residue: 398 ppm) in DMF (110 mL) was added ammonia; pyrrolidine-1-carbodithioic acid (1.08 g, 6.57 mmol, 0.500 eq) and $H_2O$ (4.00 mL). The mixture was stirred at 25° C. for 12 h. The mixture was filtered (<1 um filter). The filtrate was added ammonia; pyrrolidine-1-carbodithioic acid (1.08 g, 6.57 mmol, 0.500 eq) and $H_2O$ (4.00 mL). The reaction was stirred at 25° C. for 2 h. The mixture was filtered (<1 um filter) and the filtrate was concentrated to remove most of solvents. The residue was poured into brine (1.10 L) and extracted with DCM/MeOH=10:1(500 mL×6). Combined the organic layer was washed with brine (500 mL×2), dried over $Na_2SO_4$, filtered and concentrated. The residue was triturated with PE/EA=2:1 (600 mL) at 25° C. for 12 h, filtered and the filter cake was purified by re-crystallization from MeOH (600 mL) at 55° C., then cooled to 15° C. slowly. The slurry was filtered and the filter cake was dried under vacuum to afford Compound (14) (5.20 g, 100% purity, Pd residue: 13 ppm).

Compound (14) (5.20 g, 11.4 mmol, 1.00 eq, Pd residue: 13 ppm) was dissolved in 107 mL mixture of $H_2O$ (2.80 mL), DMAC (52.0 mL), ACN (52.0 mL). Isopropylxanthic acid potassium salt (98.9 mg, 567 umol, 0.05 eq) was added in one portion and the mixture was stirred at 20° C. for 30 min. A second portion of Isopropylxanthic acid potassium salt (98.9 mg, 567 umol, 0.05 eq) was added and the mixture was stirred at 20° C. for 30 min. 12 (72.0 mg, 284 umol, 57.2 uL, 0.025 eq) was then added and the mixture was stirred at 20° C. for 16 h. The mixture was filtered (<1 um filter) and the filtrate was concentrated to remove most of solvents. The residue was poured into water (300 mL) and extracted with dichloromethane:MeOH=10:1 (50.0 mL×8). The combined the organic layer was washed with brine (50.0 mL×3). The organic layer was dried over $Na_2SO_4$, filtered and concentrated. The residue was triturated with Petroleum ether:Ethyl acetate=2:1 (300 mL) at 25° C. for 4 h, filtered and the filter cake was purified by re-crystallization from MeOH (54.0 mL) at 60° C., then cooled to 15° C. slowly. The slurry solution was filtered and the cake was dried under vacuum to give Compound (14) (4.70 g, 10.2 mmol, 99.4% purity, Pd residue: 1 ppm) as a yellow solid. LCMS: Rt=0.821 min, m/z=459.2 $(M+H)^+$. HPLC: Rt=1.839 min. $^1H$ NMR: 400 MHz DMSO-$d_6$ δ 11.1 (br s, 1H), 7.39 (br s, 1H), 6.95 (br s, 1H), 6.58 (s, 1H), 6.25 (s, 1H), 4.26 (br s, 1H), 3.59 (br s, 1H), 3.47 (br d, J=8.2 Hz, 1H), 2.47 (s, 3H), 2.18-2.02 (m, 1H), 1.87 (br s, 3H), 1.51 (s, 6H).

Alternate Experimental Procedures for the Preparation of Compound (14)

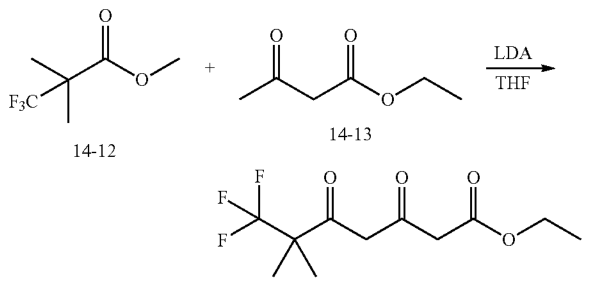

14-12
14-13
14-14

To a solution of diisopropyl amino lithium (2 M, 59 mL) in tetrahydrofuran (40 mL) was added a solution of compound 14-13 (6.12 g, 47.02 mmol, 5.94 mL) in tetrahydrofuran (40 mL) at −78° C. under nitrogen atmosphere. The mixture was stirred at −78° C. for 30 min, then compound 14-12 (8 g, 47.02 mmol) was added. The reaction mixture was stirred at −78° C. for 2 hours. LCMS showed the starting material was consumed. Saturated ammonium chloride (100 mL) was added, extracted with ethyl acetate (50 mL×2). The combined organic layer was washed with 1N hydrochloric acid (50 mL×2) and brine (50 mL×2), dried over anhydrous sodium sulfate, concentrated in vacuo to give compound 14-14 (11 g, 41.01 mmol, 87.22% yield) as a yellow oil, which was used for the next step without further purification. $^1H$ NMR ($CDCl_3$, 400 MHz) δ 4.05 (q, J=7.2 Hz, 2H), 3.38 (s, 2H), 3.31 (s, 2H), 2.27 (s, 3H), 1.97 (s, 3H), 1.20 (t, J=7.2 Hz, 3H).

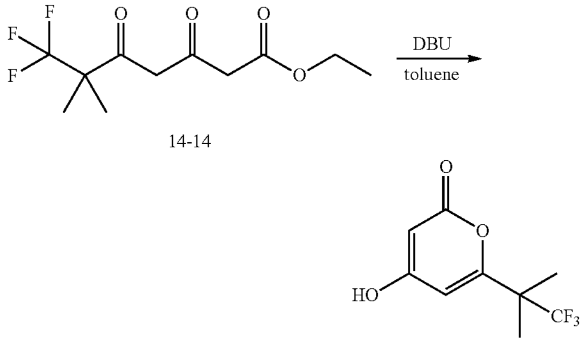

14-14
14-15

To a solution of compound 14-14 (11 g, 41.01 mmol) in toluene (100 mL) was added DBU (7.49 g, 49.21 mmol, 7.42 mL). The reaction mixture was stirred at 90° C. for 12 hours. LCMS showed starting material was consumed and the desired product was detected. After being cooled to 25° C., ethyl acetate (100 mL) was added, washed with 1N hydrochloric acid (100 mL×2) and brine (100 mL×2). The organic layer was dried over anhydrous sodium sulfate, concentrated in vacuo to give a residue. The residue was purified by MPLC to afford compound 14-15 (2 g, 8.73 mmol, 21.29% yield, 97% purity) as a yellow solid. LCMS: RT=0.710 min, m/z 223.0$[M+H]^+$. $^1H$ NMR ($CDCl_3$, 400 MHz) δ: 6.27 (s, 1H), 5.69 (s, 1H), 1.50 (s, 6H).

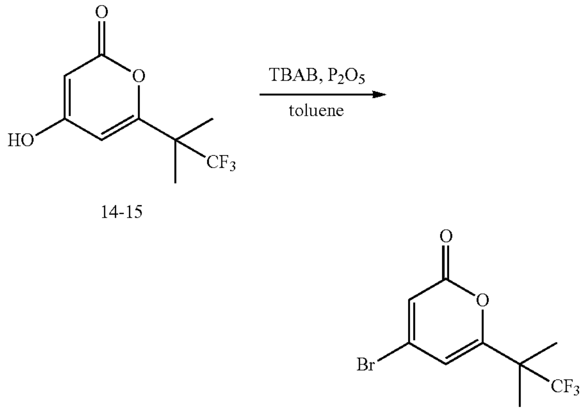

14-15
14-16

To a mixture compound 14-15 (2 g, 9.00 mmol) and phosphorus pentoxide (3.19 g, 22.50 mmol, 1.39 mL) in toluene (30 mL) was added tetrabutylammonium bromide (4.35 g, 13.50 mmol). The mixture was stirred at 90° C. for 1 hour. TLC (petroleum ether:ethyl acetate=5/1) and LCMS showed the starting material was consumed and the desired product was detected. After being cooled to 25° C., the reaction mixture was poured into saturate sodium bicarbonate (50 mL), extracted with ethyl acetate (50 mL×2). The combined organic layer was washed with brine (50 mL×2), dried over anhydrous sodium sulfate, concentrated in vacuo to give a residue. The residue was purified by column (petroleum ether:ethyl acetate=10:1~5:1) to afford compound 14-16 (2 g, 7.02 mmol, 77.96% yield) as a yellow solid. LCMS: RT=0.824 min, m/z 286.9$[M+H]^+$. $^1H$ NMR ($CDCl_3$, 400 MHz) δ: 6.59 (d, J=1.6 Hz, 1H), 6.43 (d, J=1.6 Hz, 1H), 1.51 (s, 6H).

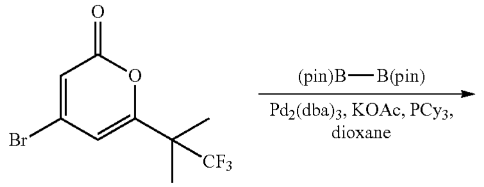

14-16

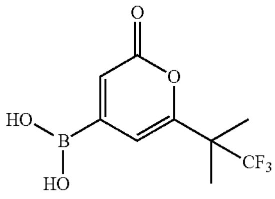

14-17

To a mixture of compound 14-16 (500 mg, 1.75 mmol) and bi(pinacolato)diboron (1.11 g, 4.38 mmol) in toluene (5 mL) was added potassium acetate (258 mg, 2.63 mmol). The mixture was degassed with nitrogen for 3 times. Phosphorus tricyclohexyl (59 mg, 210.00 umol, 67.69 uL) and $Pd_2(dba)_3$ (80.13 mg, 87.50 umol) was added to the above mixture under nitrogen atmosphere. Then the mixture was stirred at 50° C. for 1 hour. LCMS showed the starting material was consumed and the desired product was detected. The reaction mixture was filtered through a celite pad, the filtrate was concentrated in vacuo to give compound 14-17 (900 mg, crude) as a yellow solid, which was used directly without further purification. LCMS: RT=0.700 min, m/z 251.0 $[M+H]^+$.

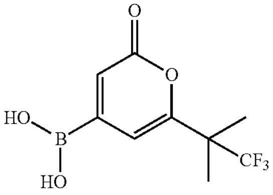

14-17

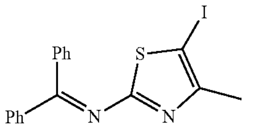

14-7

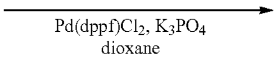

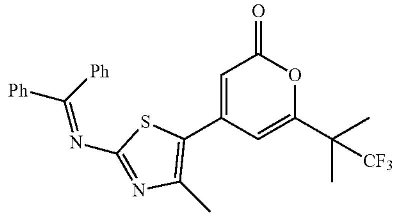

14-18

To a solution of compound 14-17 (450 mg, 900.07 umol) and compound 14-7 (364 mg, 900.07 umol) in dioxane (5 mL) was added a solution of potassium phosphate (287 mg, 1.35 mmol) in water (0.5 mL), the mixture was degassed with nitrogen for three times, $Pd(dppf)Cl_2$ (74 mg, 90.01 umol) was added under nitrogen atmosphere, the mixture was stirred at 90° C. for 18 hours. TLC (petroleum ether: ethyl acetate=5:1) and LCMS showed the starting material was consumed and the desired product was detected. The reaction mixture was filtered through a celite pad and the filtrate was concentrated in vacuo. The residue was purified by column (petroleum ether:ethyl acetate=20:1~10:1) to afford compound 14-18 (300 mg, crude) as a yellow solid. LCMS: RT=1.032 min, m/z 483.0 $[M+H]^+$. $^1H$ NMR ($CDCl_3$, 400 MHz) δ 7.86 (d, J=7.2 Hz, 2H), 7.57-7.42 (m, 7H), 7.30-7.29 (br. s, 1H), 6.28 (d, J=1.2 Hz, 1H), 6.12 (d, J=1.2 Hz, 1H), 2.53 (s, 3H), 1.51 (s, 6H).

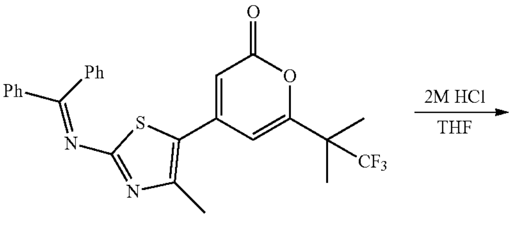

14-18

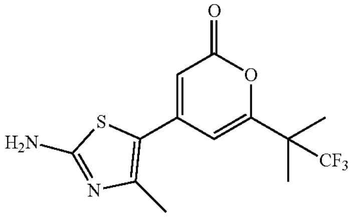

14-19

To a solution of compound 14-18 (300 mg, 621.74 umol) in tetrahydrofuran (1 mL) was added hydrochloric acid (2 M, 2.7 mL) dropwise. The reaction mixture was stirred at 25° C. for 1 hour. TLC (petroleum ether:ethyl acetate=1:2) showed the starting material was consumed completely, and two new spots was formed. The reaction mixture was poured into water (50 mL), and extracted with n-hexane (10 mL×2). The aqueous layer was basified to pH~7 with saturate sodium bicarbonate, then the precipitate was collected by filtration to give compound 14-19 (138 mg, 433.54 umol, 69.73% yield) as a light yellow solid. $^1H$ NMR ($CDCl_3$, 400 MHz) δ 6.37 (d, J=1.6 Hz, 1H), 6.14 (d, J=1.6 Hz, 1H), 5.29 (br. s, 2H), 2.43 (s, 3H), 1.25 (s, 6H).

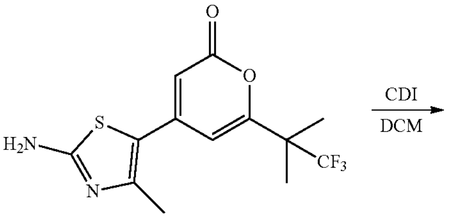

14-19

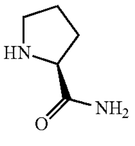

14-11

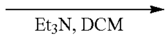

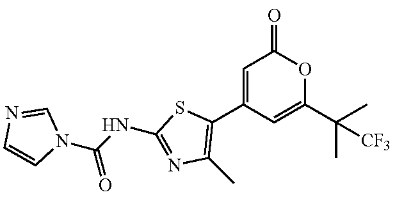

14-20

-continued

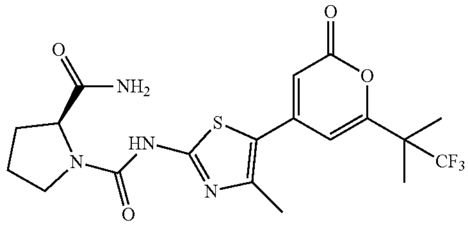

Compound (14)

To a solution of compound 14-19 (130 mg, 408.39 umol) in tetrahydrofuran (1 mL) and dichloromethane (2 mL) was added CDI (99 mg, 612.59 umol). The reaction mixture was warmed to 50° C. and stirred at 50° C. for 20 hours. LCMS showed the starting material was consumed. The solvent was evaporated. A solution of (2S)-pyrrolidine-2-carboxamide (93 mg, 816.78 umol) in DMF (2 mL) was added to the residue, the mixture was stirred at 25° C. for 4 hours. LCMS showed the starting material was consumed and the desired product was detected. The reaction mixture was poured into water (30 mL), extracted with ethyl acetate (10 mL×2). The combined organic layer was washed with brine (20 mL×2), dried over anhydrous sodium sulfate, concentrated in vacuo. The residue was purified by trituration with ethyl acetate (5 mL) to afford Compound (14) (50.00 mg, 109.06 umol, 100% purity, 26.71% yield) as a yellow solid. LCMS: RT=1.786 min, m/z 459.0 $[M+H]^+$. $^1H$ NMR ($CD_3OD$, 400 MHz) δ 6.61 (d, J=1.2 Hz, 1H), 6.27 (d, J=1.2 Hz, 1H), 4.45 (d, J=9.6 Hz, 1H), 3.71-3.67 (m, 1H), 3.60-3.54 (m, 1H), 2.48 (s, 3H), 2.30-2.25 (m, 1H), 2.01-2.04 (m, 3H), 1.56 (s, 6H).

Synthetic Preparation of Compound (15)

A synthetic route to Compound (15) is shown in the scheme below.

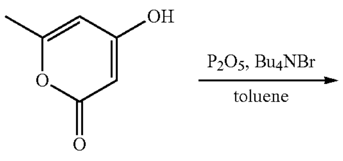

15-15

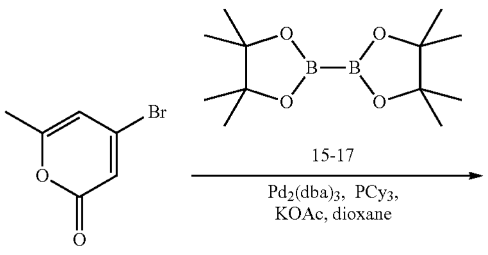

15-16

-continued

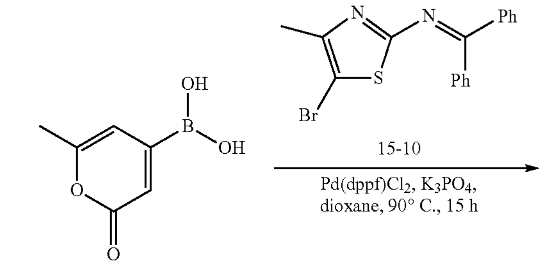

15-18

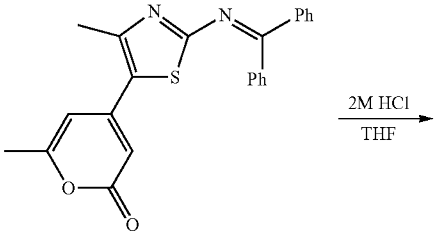

15-19

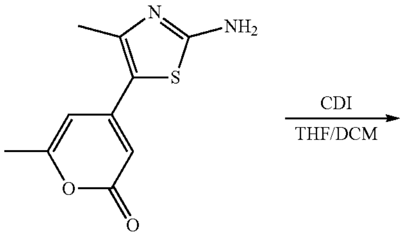

15-20

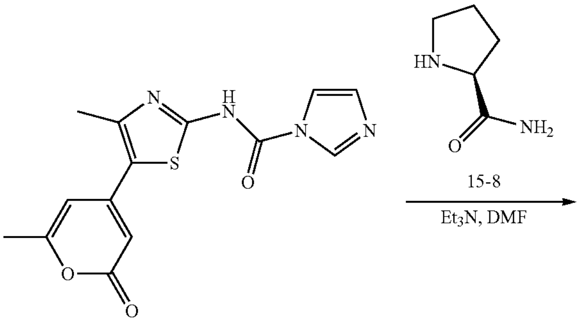

15-21

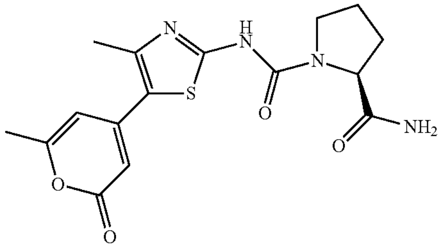

Compound (15)

Experimental Procedures for Compound (15)

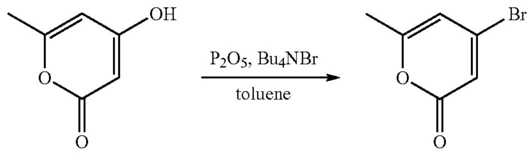

15-15 15-16

To a solution of compound 15-15 (5.00 g, 39.65 mmol, 1.00 eq) in toluene (160 mL) was added tetrabutylammonium bromide (14.83 g, 45.99 mmol, 1.16 eq) and phosphorus pentoxide (13.51 g, 95.16 mmol, 5.87 mL, 2.40 eq) at 25° C. Then the reaction mixture was stirred at 100° C. for 3 hrs. TLC (petroleum ether:ethyl acetate=3:1) showed the material was consumed and one new spot was detected. The reaction mixture was cooled to room temperature and the mixture was layered. The toluene layer was collected and washed with water (30 mL), saturated sodium bicarbonate solution (30 mL×2), brine (30 mL×2) and concentrated in vacuum to give compound 15-16 (7.49 g, 31.82 mmol, 80.26% yield) as a yellow solid, which used directly for next step without further purification. LCMS: RT=0.466, 0.478 min, m/z 188.9, 190.9 $[M+H]^+$. $^1$H NMR ($CDCl_3$, 400 MHz) δ 6.48 (s, 1H), 6.21 (s, 1H), 1.61 (s, 1H).

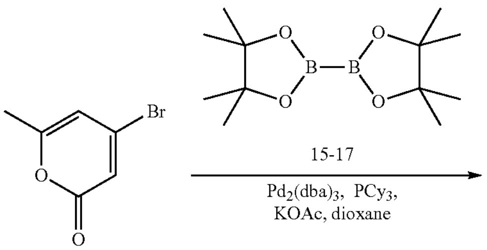

15-16

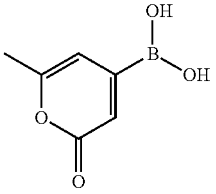

15-18

To a solution of compound 15-16 (4.00 g, 21.16 mmol, 1.00 eq), compound 15-17 (5.91 g, 23.28 mmol, 1.10 eq) and potassium acetate (3.11 g, 31.74 mmol, 1.50 eq) in dioxane (100 mL) was added $Pd_2(dba)_3$ (969 mg, 1.06 mmol, 0.05 eq) and tricyclohexylphosphine (712 mg, 2.54 mmol, 818.59 uL, 0.12 eq) respectively. The mixture was degassed with nitrogen for 3 times and stirred at 80° C. for 2 hrs. TLC (petroleum ether:ethyl acetate=10:1) showed the reaction was completed. The mixture was cooled to room temperature and filtered through a celite pad. The filtrate was concentrated under vacuum to give the crude product 15-18 (8.5 g) as brown liquid, which used directly for next step without further purification. LCMS: RT=0.164 min, m/z 155.1 $[M+H]^+$.

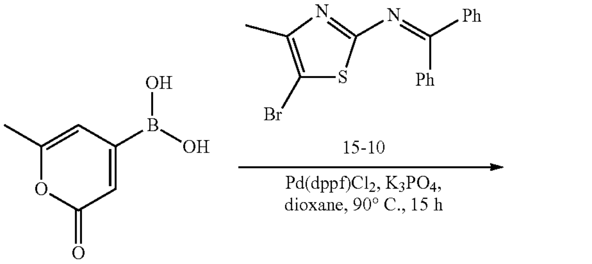

15-18

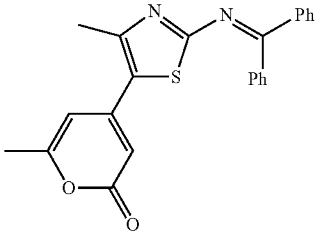

15-19

To a solution of compound 15-18 (3.03 g, 5.82 mmol, 1.30 eq), compound 15-10 (1.60 g, 4.48 mmol, 1.00 eq), potassium phosphate (1.43 g, 6.72 mmol, 1.50 eq) in dioxane (40 mL) was added $Pd(dppf)Cl_2$ (327.81 mg, 448.00 umol, 0.10 eq) under nitrogen atmosphere. The mixture was degassed with $N_2$ for three times and then stirred at 90° C. for 15 hrs. LCMS showed most of the starting material was consumed. The reaction mixture was cooled to 25° C., filtered through a celite pad. The filtrate was concentrated under vacuum to give the residue. The residue was purified by chromatography column on silica gel (petroleum ether: ethyl acetate=30:1 to 3:1) to give the desired product 15-19 (1.15 g, 2.86 mmol, 63.76% yield, 95.99% purity) as a yellow solid. LCMS: RT=0.927 min, m/z 387.0 $[M+H]^+$. $^1$H NMR ($CDCl_3$, 400 MHz) δ 8.76 (br. s, 2H), 7.40-7.60 (m, 6H), 7.31 (br. s, 2H), 6.06 (s, 1H), 5.98 (s, 1H), 2.54 (s, 3H), 2.29 (s, 3H).

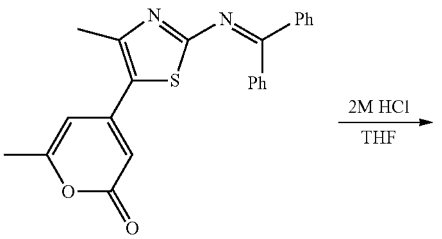

15-19

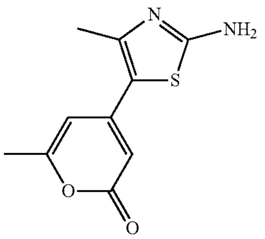

15-20

To a solution of compound 15-19 (1.15 g, 2.86 mmol) in tetrahydrofuran (30 mL) was added hydrochloric acid aqueous (2 M, 11.02 mL) at 25° C. Then the reaction mixture was stirred at 25° C. for 0.5 hour. TLC (petroleum ether:ethyl acetate=2:1) showed the material was consumed and two new spots was detected. The solvent was removed under vacuum at 40° C. The aqueous phase was extracted with n-hexane (5 mL×2). Then the aqueous phase was basified with 1N sodium hydroxide solution (10 mL) to pH=9, the aqueous was extracted with ethyl acetate (10 mL×3), dried over anhydrous sodium sulfate, concentrated under vacuum to give the desired product 15-20 (450 mg, 1.95 mmol, 68.42% yield, 96.31% purity) as a yellow solid, which used directly for next step without further purification. LCMS: RT=0.871 min, m/z 223.0 [M+H]+.

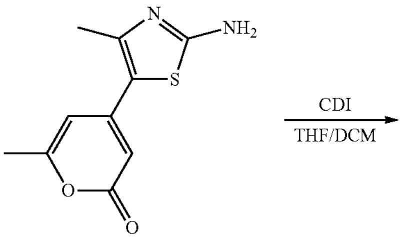

15-20

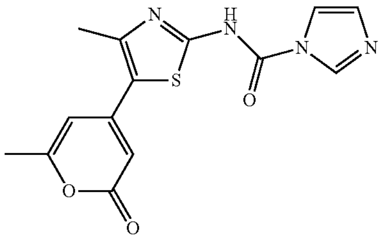

15-21

To a solution of compound 15-20 (400 mg, 1.80 mmol, 1.00 eq) in tetrahydrofuran (10 mL) and dichloromethane (20 mL) was added 1,1'-carbonyldiimidazole (467 mg, 2.88 mmol, 1.60 eq) at 50° C. The mixture was stirred at 50° C. for 15 hrs. LCMS and TLC (ethyl acetate) showed the material was consumed. The solvent was removed under vacuum to give the crude compound 15-21 (640 mg, crude), which was directly used in the next step without further purification. LCMS: RT=0.447, 0.504 min, m/z 339.0 [M+Na]+

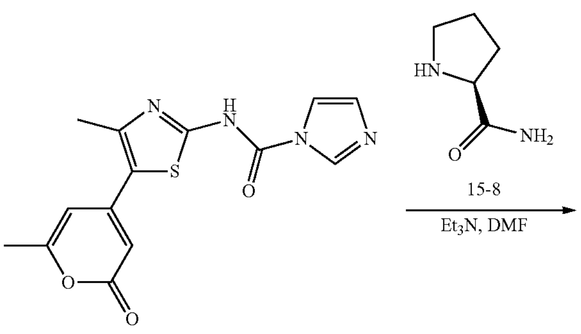

15-21

-continued

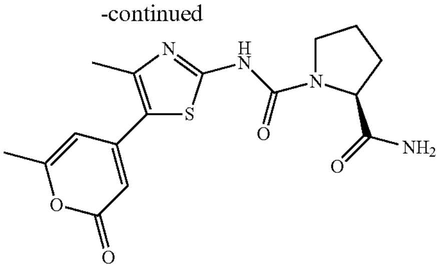

Compound (15)

To a solution of compound 15-21 (570 mg, 1.80 mmol, 1.00 eq) in dimethyl formamide (10 mL) was added triethylamine (546 mg, 5.40 mmol, 0.75 mL, 3.00 eq) and compound 15-8 (570 mg, 1.80 mmol, 1.00 eq) at 25° C. Then the reaction mixture was stirred at 25° C. for 1.5 h. LCMS showed the material was consumed and the desired compound was detected. The solvent was removed under vacuum to give the residue. The residue was dissolved in dichloromethane (100 mL), washed with water (80 mL). The aqueous phase was extracted with dichloromethane:methanol, v/v=10:1 (60 mL×5), dried over anhydrous sodium sulfate, concentrated under vacuum to give the crude product. The crude product was purified by prep-HPLC (base, column: PHENOMENEX® Gemini 150*25 mm*10 um; mobile phase: [water (0.05% ammonia hydroxide v/v)-ACN]; B %: 11%-41%, 10 min) to afford the desired product pure Compound (15) (72 mg; purity: 98.69%). LCMS: RT=2.223 min, m/z 363.1[M+H]+. $^1H$ NMR (MeOD, 400 MHz) δ 6.44 (s, 1H), 6.16 (s, 1H), 4.47 (d, J=10.4 Hz, 1H), 3.70-3.74 (m, 1H), 3.55-3.62 (m, 1H), 2.49 (s, 3H), 2.32 (s, 3H), 2.22-2.30 (m, 1H), 2.06-1.98 (m, 3H).

Synthetic Preparation of Compound (18), (19), and (22)

Synthetic routes to Compounds (18), (19), and (22) are shown in the scheme below.

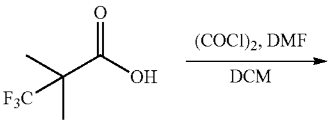

18-1

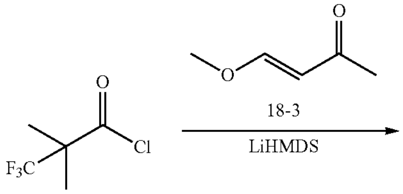

18-2

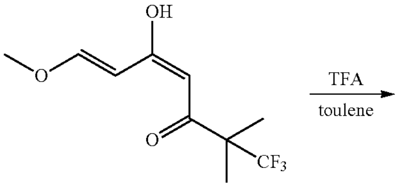

18-4

-continued
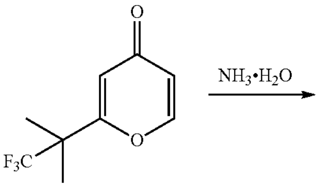
18-5
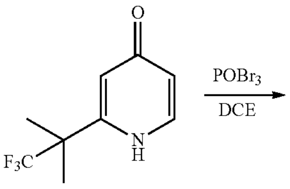
18-6
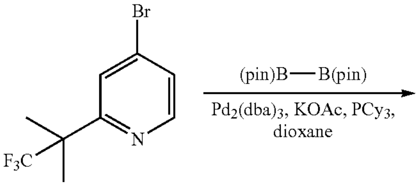
18-7
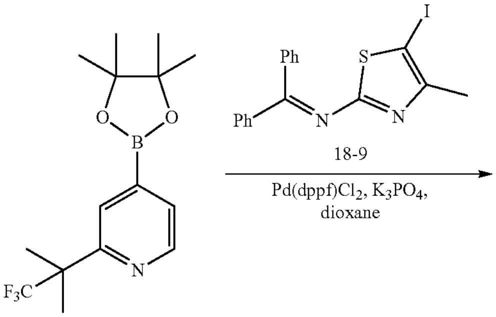
18-8
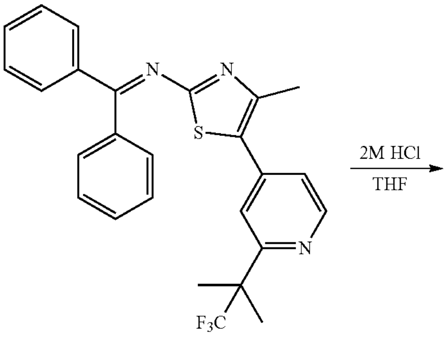
18-10
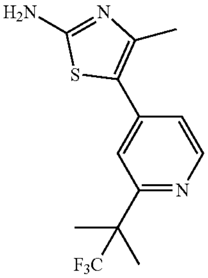
18-11
-continued
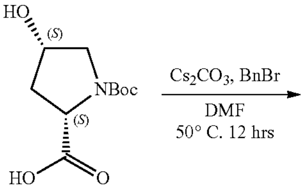
18-12
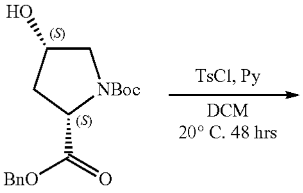
18-13
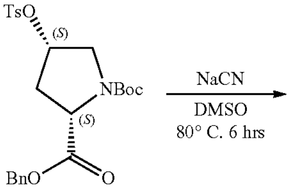
18-14
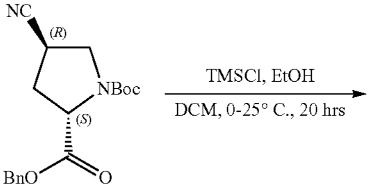
18-15
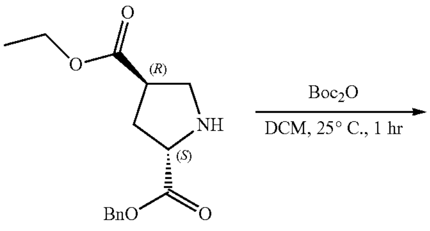
18-16
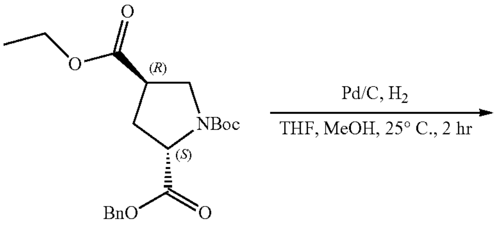
18-17
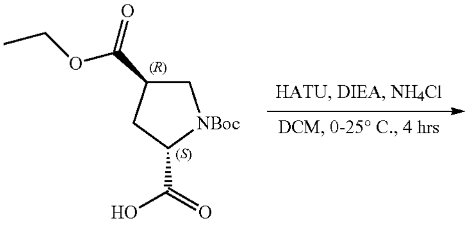
18-18

-continued
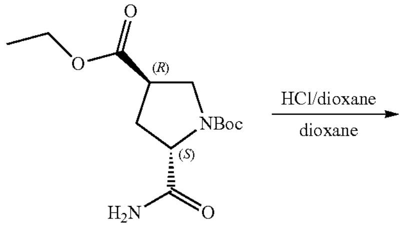
18-19
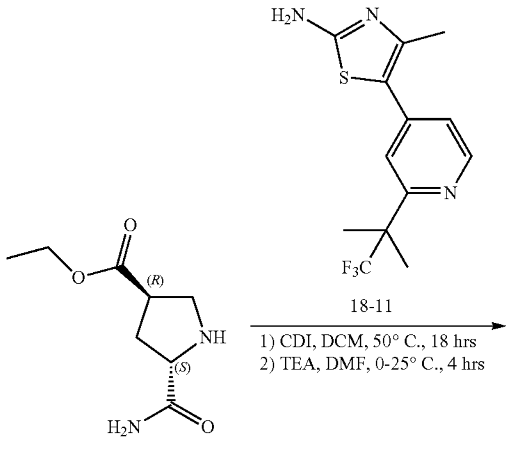
18-20
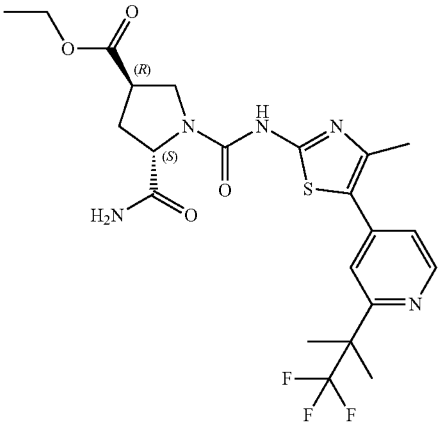
Compound (22)
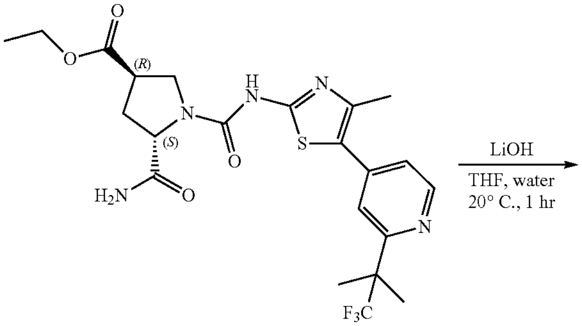
Compound (22)
-continued
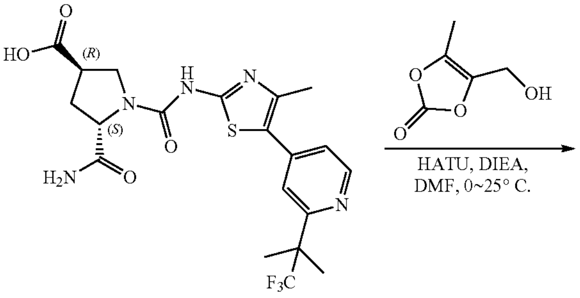
Compound (19)
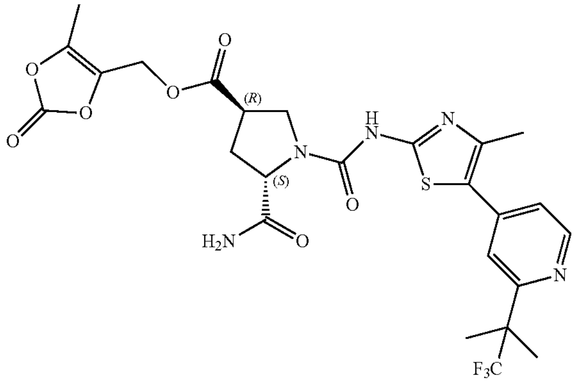
Compound (18)
Experimental Procedures for Compounds (18), (19), and (22)
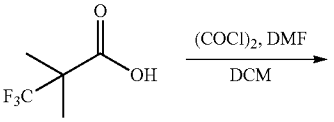
18-1
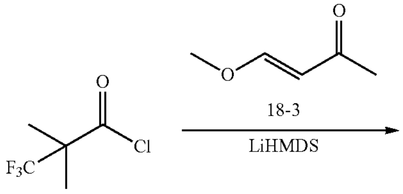
18-2
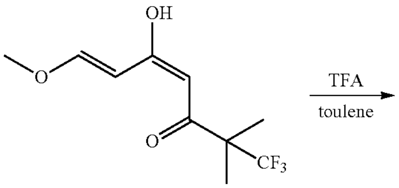
18-4

-continued

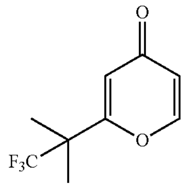

18-5

To a solution of 18-1 (20.0 g, 128.12 mmol, 1 eq) and N,N-dimethylformamide (187 mg, 2.56 mmol, 197.15 uL, 0.02 eq) in dichloromethane (200 mL) was added oxalyl chloride (24.4 g, 192.18 mmol, 16.82 mL, 1.5 eq) drop-wise at 0° C. The mixture was stirred at 20° C. for 3 hours. The mixture was concentrated in vacuum (at 0° C.) to give the crude 18-2 (17.2 g, crude) as colorless oil, which was used into the next step without further purification.

To a solution of LiHMDS (1 M, 157.66 mL, 1.6 eq) in tetrahydrofuran (170 mL) was drop-wise added compound 18-3 (14.80 g, 147.81 mmol, 14.84 mL, 1.5 eq) at −78° C. under nitrogen atmosphere. The mixture was stirred at −78° C. for 0.5 hour. A solution of compound 18-2 (17.2 g, 98.54 mmol, 1 eq) in tetrahydrofuran (50 mL) was drop-wise added into the mixture at −78° C. The reaction mixture was stirred at −78° C. for 1.5 hours and then stirred at 20° C. for 0.5 hour. TLC (petroleum ether:ethyl acetate=5:1) showed the new spots were detected. The mixture was quenched with ice saturated ammonium chloride solution (250 mL) and adjusted to pH=2-3 with 1N hydrochloric acid solution. The mixture was extracted with ethyl acetate (200 mL×3). The combined organic layers were washed with brine (200 mL), dried over anhydrous sodium sulfate, filtered, concentrated in vacuum to give the crude 18-4 (20.8 g, crude) as red gum, which was used into the next step without further purification.

To a solution of 18-4 (20.8 g, 87.32 mmol, 1 eq) in toluene (150 mL) was added trifluoroacetic acid (19.9 g, 174.64 mmol, 12.93 mL, 2 eq). The mixture was stirred at 20° C. for 18 hours under nitrogen atmosphere. TLC (petroleum ether: ethyl acetate=5:1) showed the starting material was consumed. The mixture was concentrated in vacuum. The residue was diluted with ethyl acetate (200 mL) and water (150 mL). The mixture was filtered. The filtrate was separated. The aqueous was extracted with ethyl acetate (150 mL×2). The combined organic layers were washed with brine (200 mL), dried over anhydrous sodium sulfate, filtered, concentrated in vacuum. The residue was purified by column chromatography ($SiO_2$, Petroleum ether:ethyl acetate=20:1 to 3:1) to give the 18-5 (10.94 g, 50.60 mmol, 57.95% yield, 95.36% purity) as red gum. LCMS: RT=0.713 min, m/z 207.1 $[M+H]^+$, purity: 95.36%. $^1H$ NMR ($CDCl_3$, 400 MHz) δ 7.77 (d, J=6.0 Hz, 1H), 6.44 (d, J=2.4 Hz, 1H), 6.33 (dd, J=6.0, 2.4 Hz, 1H), 1.49 (s, 6H).

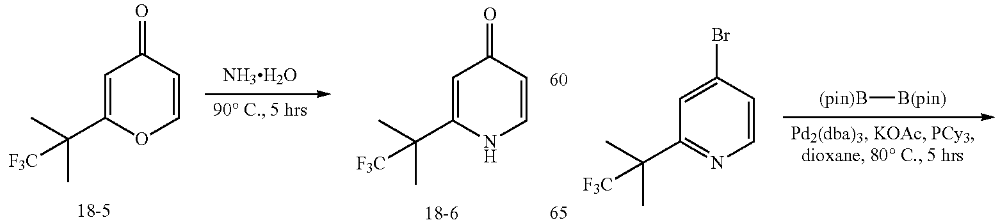

18-5 18-6 18-7

The mixture of 18-5 (10.94 g, 53.07 mmol, 1 eq) in ammonium hydroxide (100.10 g, 799.75 mmol, 110 mL, 28% purity in water, 15.07 eq) was heated to 90° C. for 6 hours. LCMS showed the starting material was consumed and desired product mass was detected. The mixture was concentrated in vacuum and the residue was purified by column chromatography ($SiO_2$, Petroleum ether:ethyl acetate:ethanol=40:3:1 to 12:3:1, monitoring by TLC Petroleum ether:ethyl acetate:ethanol=12:3:1) to give 18-6 (9.7 g, 46.61 mmol, 87.84% yield, 98.6% purity) as a yellow solid. LCMS: RT=0.263 min, m/z 206.2 $[M+H]^+$, purity: 98.60%. $^1H$ NMR: ($CDCl_3$, 400 MHz) δ 7.77 (d, J=6.8 Hz, 1H), 6.69 (d, J=1.6 Hz, 1H), 6.48 (dd, J=6.8, 1.6 Hz, 1H), 1.59 (s, 6H).

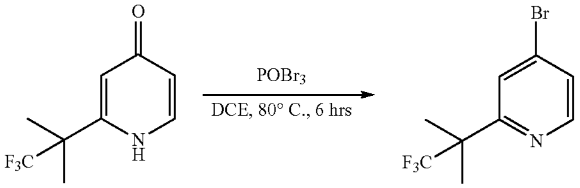

18-6 18-7

To a solution of 18-6 (8.7 g, 42.40 mmol, 1 eq) in 1,2-dichloroethane (90 mL) was added Phosphorus(V) oxybromide (18.23 g, 63.60 mmol, 6.47 mL, 1.5 eq). The mixture was stirred at 80° C. for 4 hours. TLC (Petroleum ether:Ethyl acetate:Ethanol=4:3:1) showed a part of starting material was remained. Another Phosphorus (V) oxybromide (6.08 g, 21.20 mmol, 2.16 mL, 0.5 eq) was added into the mixture. The reaction mixture was stirred at 80° C. for another 3 hours. TLC (Petroleum ether:ethyl acetate:ethanol=4:3:1) showed the starting material was consumed completely. The mixture was combined with another batch (1 g scale) and then poured into ice saturated sodium bicarbonate solution (300 mL) and adjust the pH=7-8. The mixture was extracted with ethyl acetate (100 mL×3). The combined organic layers were washed with brine (100 mL), dried over anhydrous sodium sulfate, filtered, concentrated in vacuum. The residue was purified by column chromatography ($SiO_2$, Petroleum ether:ethyl acetate=1:0 to 50:11) to give 18-7 (8.5 g, 31.71 mmol, 67.37% yield, 100% purity) as light yellow oil. LCMS: RT=0.966 min, m/z 268.0, 270.0 $[M+H]^+$, purity: 100.00%. $^1H$ NMR: ($CDCl_3$, 400 MHz) δ 8.44 (d, J=5.2 Hz, 1H), 7.67 (s, 1H), 7.44 (dd, J=5.3, 1.6 Hz, 1H), 1.61 (s, 6H).

-continued

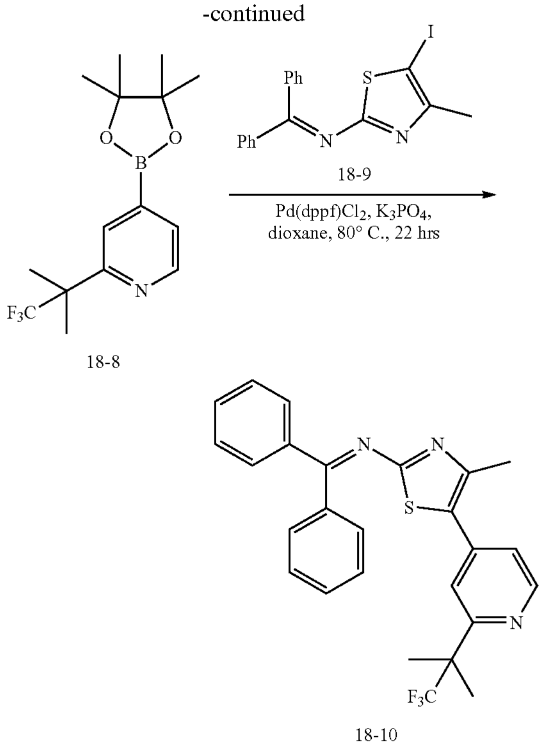

18-8

18-9

18-10

To a solution of 18-7 (8.5 g, 31.71 mmol, 1 eq) and 4,4,5,5-tetramethyl-2-(4,4,5,5-tetramethyl-1,3,2-dioxaborolan-2-yl)-1,3,2-dioxaborolane (9.66 g, 38.05 mmol, 1.2 eq) in dioxane (90 mL) was added tricyclohexylphosphine (889 mg, 3.17 mmol, 1.03 mL, 0.1 eq), Potassium acetate (4.67 g, 47.56 mmol, 1.5 eq), $Pd_2(dba)_3$ (1.45 g, 1.59 mmol, 0.05 eq) under nitrogen atmosphere. The mixture was degassed and then stirred at 80° C. for 4 hours under nitrogen atmosphere. TLC (petroleum ether:ethyl acetate=20:1) showed the starting material was consumed completely. LCMS showed the starting material was consumed and the mass of boric acid was detected. The mixture was diluted with ethyl acetate (20 mL). The mixture was filtered through celite pad. The solid was washed with ethyl acetate (20 mL×3) and the combined filtrates were concentrated in vacuum to give the crude 18-8 (19 g, crude) as red gum, which was used into the next step without further purification.

To a solution of 18-9 (8.5 g, 21.03 mmol, 1 eq), potassium phosphate (13.39 g, 63.08 mmol, 3 eq) and 18-8 (15.20 g, 25.23 mmol, 1.20 eq) in dioxane (100 mL) and water (10 mL) was added Pd(dppf)$Cl_2$ (769 mg, 1.05 mmol, 0.05 eq) under nitrogen atmosphere. The mixture was degassed and then the mixture was stirred at 80° C. for 16 hours under nitrogen atmosphere. TLC (petroleum ether:ethyl acetate=5:1) showed the most of starting material was consumed. The mixture was diluted with ethyl acetate (100 mL) poured into ice water (200 mL) and then filtered, the solid was washed with ethyl acetate (20*2 mL). The filtrate was extracted with ethyl acetate (100 mL×3). The combined organic layers were washed with brine (100 mL×2). The organic layer dried over anhydrous sodium sulfate, filtered, concentrated in vacuum. The residue was purified by column chromatography ($SiO_2$, Petroleum ether:ethyl acetate=30:1 to 10:1) to give 18-10 (6.27 g, 11.95 mmol, 56.84% yield, 88.74% purity) as a yellow solid. Another batch impure 2.5 g (purity:42.68%) was obtained as yellow gum. LCMS: RT=1.104 min, m/z 466.2 $[M+H]^+$, purity:88.74%. $^1H$ NMR: ($CDCl_3$, 400 MHz) δ 8.56 (d, J=4.8 Hz, 1H), 7.84-7.83 (m, 2H), 7.56-7.43 (m, 9H), 7.10 (dd, J=5.2, 1.6 Hz, 1H), 2.51 (s, 3H), 1.62 (s, 6H).

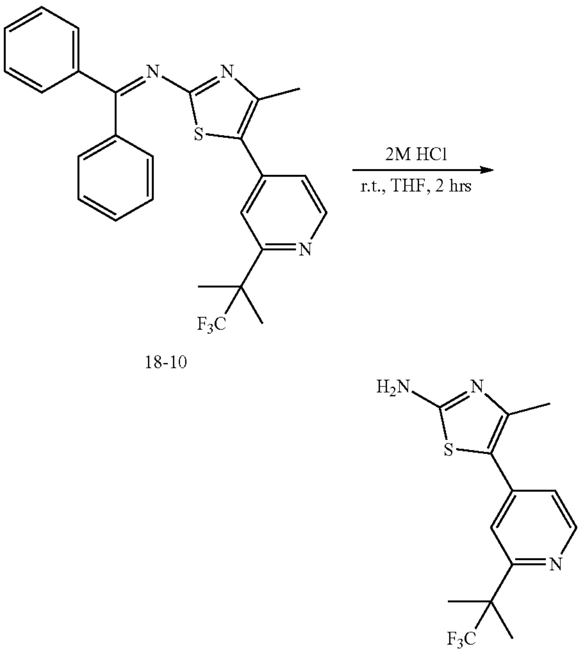

18-10

18-11

To a solution of 18-10 (6.27 g, 13.47 mmol, 1 eq) in tetrahydrofuran (63 mL) was added 2N hydrochloric acid solution (2 M, 31.5 mL, 4.68 eq) (in water). The mixture was stirred at 20° C. for 1 hour. TLC (petroleum ether:ethyl acetate=3:1) showed the starting material was consumed. The mixture was diluted with water (50 mL) and then extracted with ethyl acetate (50 mL×2). The combined organic layers were washed with 1N hydrochloric acid (50 mL×2). The aqueous layers were combined and then adjusted to pH=7-8 by sodium bicarbonate. The mixture was extracted with ethyl acetate (80 mL×3). The combined organic layers were washed with brine (80 mL), dried over anhydrous sodium sulfate, filtered, concentrated in vacuum. The residue was purified by column chromatography ($SiO_2$, Petroleum ether:ethyl acetate=4:1 to 3:1) to give 18-11 (2.7 g, 8.53 mmol, 63.37% yield, 95.25% purity) as a yellow solid. LCMS: RT=1.279 min, m/z 302.1 $[M+H]^+$, purity: 95.25%. $^1H$ NMR: ($CDCl_3$, 400 MHz) δ 8.57 (dd, J=5.6, 0.8 Hz, 1H), 7.46 (s, 1H), 7.18 (dd, J=5.6, 2.0 Hz, 1H), 5.14 (br.s, 2H), 2.39 (s, 3H), 1.64 (s, 6H).

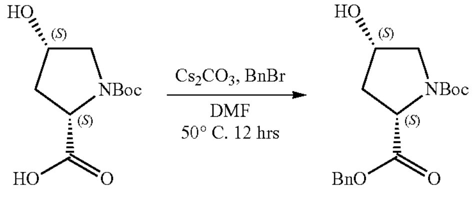

18-12

18-13

To a solution of 18-12 (10 g, 43.24 mmol, 1 eq) and cesium carbonate (14.09 g, 43.24 mmol, 1 eq) in dimethylformamide (100 mL) was added benzyl bromide (8.14 g, 47.57 mmol, 5.65 mL, 1.1 eq) drop-wise. The resulting mixture was stirred at 50° C. for 4 hours. LCMS showed part of the starting material remained and the mixture was stirred for another 5 hours at 50° C. TLC petroleum ether:ethyl acetate=1:1) showed the starting material was consumed. The reaction mixture was filtered. The aqueous phase was poured in to water (500 mL), extracted with ethyl acetate (200 mLx3). The combined organic phase was washed with brine (500 mLx2), dried over anhydrous sodium sulfate, filtered and concentrated in vacuo The residue was purified by column ($SiO_2$, petroleum ether:ethyl acetate=10:1 to 1:1) to afford 18-13 (13 g, 36.88 mmol, 85.28% yield, 91.17% purity) as colorless gum. LCMS: RT=0.79 min, m/z 222.2 $[M\text{-}Boc+H]^+$, purity: 91.17%. SFC: RT=0.567 min, de %=89.1%. $^1H$ NMR ($CDCl_3$, 400 MHz): δ 7.38-7.35 (m, 5H), 5.31-5.12 (m, 2H), 4.35-4.31 (m, 2H), 3.69-3.55 (m, 2H), 2.37-2.29 (m, 1H), 2.08-2.03 (m, 1H), 1.47 & 1.35 (s, 9H).

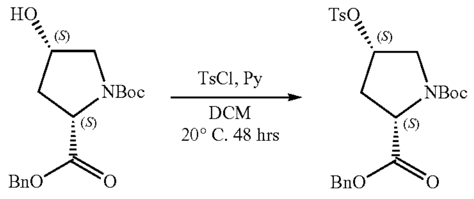

18-13 18-14

To a solution of 18-13 (20 g, 62.23 mmol, 1 eq) and pyridine (19.69 g, 248.94 mmol, 20.09 mL, 4 eq) in dichloromethane (200 mL) was added TosCl (35.59 g, 186.70 mmol, 3 eq). The mixture was stirred for 36 hours at 20° C. TLC (petroleum ether:ethyl acetate=2:1) showed most of the starting material was consumed and desired product was observed. The reaction mixture was concentrated in vacuo. The residue was dissolved in ethyl acetate (500 mL), washed with water (500 mLx2), saturated sodium bicarbonate (500 mLx2), 1N hydrochloric acid (500 mLx2), brine(500 mLx2), dried over anhydrous sodium sulfate, filtered and concentrated in vacuo. The residue was purified by column ($SiO_2$, petroleum ether:ethyl acetate=10:1 to 1:1) to afford 18-14 (20 g, 40.33 mmol, 64.80% yield, 95.894% purity) as colorless gum. LCMS: RT=0.918 min, m/z 376.0 $[M\text{-}Boc+H]^+$, purity: 95.84%. SFC: RT=1.068 min, de %=100%. $^1H$ NMR ($CDCl_3$, 400 MHz): δ 7.72 (d, J=8.0 Hz, 2H), 7.37-7.30 (m, 7H), 5.21-5.15 (m, 1H), 5.10-5.02 (m, 2H), 4.35-4.10 (m, 1H), 3.69-3.66 (m, 1H), 3.64-3.58 (m, 1H), 2.47-2.46 (m, 1H), 2.44 (s, 3H), 2.38-2.36 (m, 1H), 1.47& 1.32 (s, 9H).

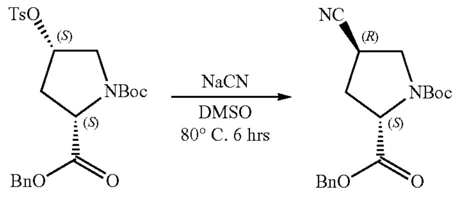

18-14 18-15

To a solution of 18-14 (20 g, 42.06 mmol, 1 eq, 1.2 batch) in dry dimethylsulfoxide (200 mL) was added sodium cyanide (3.10 g, 63.26 mmol, 1.5 eq). The mixture was stirred for 5 hours at 80° C. under nitrogen atmosphere. TLC (petroleum ether:ethyl acetate=3:1) showed starting material was consumed and desired mass was observed. The reaction mixture was poured into water (100 mL), extracted with ethyl acetate (100 mLx2). The combined organic phase was dried over anhydrous sodium sulfate, filtered and concentrated in vacuo. The residue was purified by column ($SiO_2$, petroleum ether:ethyl acetate=20:1 to 3:1) to afford 18-15 (10 g, 28.52 mmol, 56.52% yield, 94.24% purity) as white solid. LCMS: RT=0.932 min, m/z 353.1 [M+Na]+, purity: 94.23%. SFC: RT=0.617 min, de %=100%. $^1H$ NMR ($CDCl_3$, 400 MHz): δ 7.38-7.29 (m, 5H), 5.24-5.13 (m, 2H), 4.43& 4.45 (dd, $J_1$=3.2 Hz, $J_2$=8.8 Hz, 1H), 3.93-3.90 (m, 1H), 3.69-3.67 (m, 1H), 3.24-3.20 (m, 1H), 2.52-2.35 (m, 2H), 1.47& 1.36 (s, 9H).

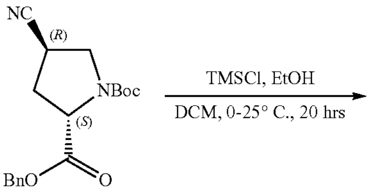

18-15

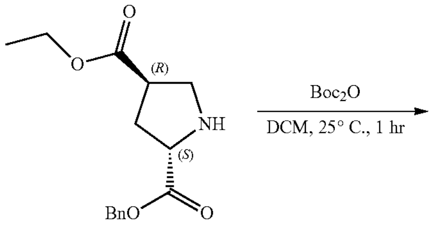

18-16

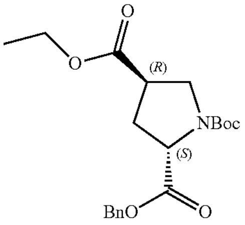

18-17

TMSCl (31.39 g, 288.91 mmol, 36.67 mL, 19.09 eq) was added dropwise to ethanol (36.77 g, 798.18 mmol, 46.66 mL, 52.74 eq) at 0° C. Then a solution of 18-15 (5 g, 15.13 mmol, 1 eq) in dichloromethane (20 mL) was added to the above mixture. The mixture was stirred at 25° C. for 15 hours under nitrogen atmosphere. LCMS showed the starting material was consumed and desired mass was observed. The mixture was quenched with ice-water (200 mL), adjusted to pH=7 with sodium bicarbonate solid and extracted with dichloromethane (300 mLx3). The organic layer was washed with brine (300 mL), dried over anhydrous sodium sulfate, filtered and concentrated in vacuo to afford 18-16 (7 g, crude) as yellow oil and used directly.

To a solution of 18-16 (7 g, 25.24 mmol, 1 eq) in dichloromethane (70 mL) was added di-tert-butyl dicarbonate (5.51 g, 25.24 mmol, 5.80 mL, 1 eq). The mixture was stirred for 1 hour at 25° C. LCMS showed the reaction worked well. The reaction mixture was concentrated in vacuo. The residue was purified by column ($SiO_2$, petroleum ether:ethyl acetate=50:1 to 5:1) to afford 18-17 (8.1 g, 20.18 mmol, 79.94% yield, 94.019% purity) as colorless oil. LCMS: RT=0.843 min, m/z 278.2 $[M\text{-}Boc+H]^+$, purity: 94.02%. $^1H$ NMR ($CDCl_3$, 400 MHz): δ 7.38-7.32 (m, 5H), 5.24-5.09 (m, 2H), 4.41-4.19 (m, 1H), 4.17-4.14 (m, 2H), 3.81-3.66 (m, 2H), 3.19-2.17 (m, 1H), 2.51-2.48 (m, 1H), 2.22-2.20 (m, 1H), 1.47 & 1.34 (s, 9H), 1.26 (t, J=7.2 Hz, 3H).

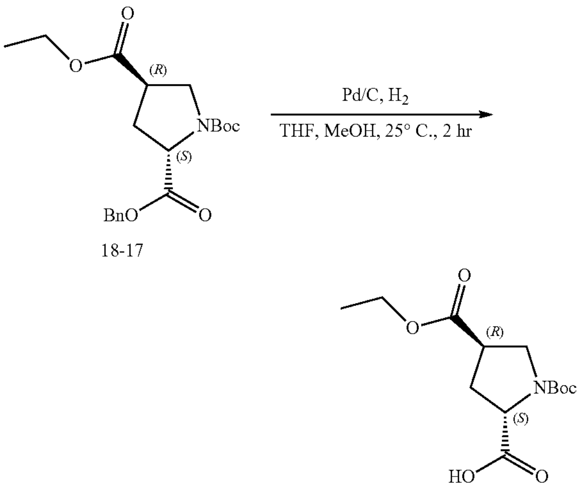

18-17

18-18

To a solution of 18-17 (8 g, 21.20 mmol, 1 eq) in methanol (40 mL) and tetrahydrofuran (40 mL) was added Pd/C (0.5 g, 5% purity) on carbon under nitrogen atmosphere. The suspension was degassed under vacuum and purged with hydrogen atmosphere several times. The mixture was stirred at 25° C. for 2 hours under hydrogen atmosphere (15 psi). LCMS showed the starting material was consumed and desired mass was observed. The reaction mixture was filtered and concentrated in vacuo to afford 18-18 (5.7 g, crude) as a colorless gum. LCMS: RT=0.68 min, m/z 188.0 $[M\text{-}Boc+H]^+$. $^1H$ NMR ($CDCl_3$, 400 MHz): δ 4.48-4.41 (m, 1H), 4.18 (q, J=7.2 Hz, 2H), 3.73-3.65 (m, 2H), 3.21-3.17 (m, 1H), 2.58-2.25 (m, 2H), 1.49-1.42 (m, 9H), 1.27 (t, J=7.2 Hz, 3H).

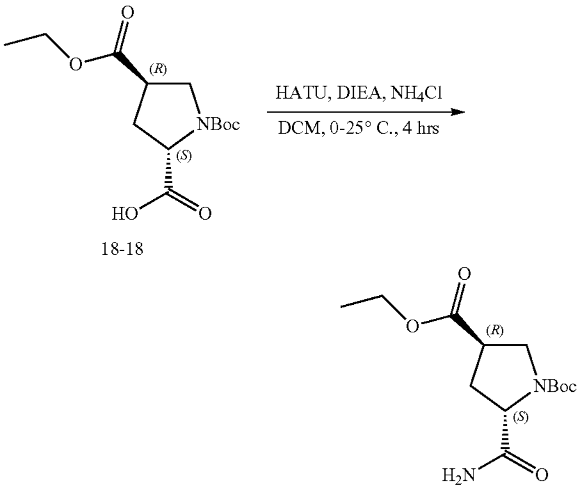

18-18

18-19

To a stirred solution of 18-18 (5.7 g, 19.84 mmol, 1 eq) in dimethylformamide (60 mL) was added HATU (9.05 g, 23.81 mmol, 1.2 eq), diisopropylethylamine (12.82 g, 99.20 mmol, 17.28 mL, 5.00 eq) and ammonium chloride (5.31 g, 99.20 mmol, 5 eq) at 0° C. under nitrogen atmosphere. The mixture was stirred for 2 hours at 0° C. under nitrogen atmosphere and LCMS indicated the reaction is completed. The reaction mixture was poured into water (100 mL), extracted with ethyl acetate (50 mL×3). The combined organic phase was washed with brine(100 mL), dried over anhydrous sodium sulfate, filtered and concentrated in vacuo. The residue was purified by column ($SiO_2$, petroleum ether:ethyl acetate=10:1 to ethyl acetate) to afford 18-19 (3.7 g, 11.63 mmol, 58.62% yield, 90% purity) as colorless gum. LCMS: RT=0.685 min, m/z 187.0 $[M\text{-}Boc+H]^+$, 309.1 $[M+23]^+$. $^1H$ NMR ($CDCl_3$, 400 MHz): δ6.94 (br. s, 1H), 5.39 (br. s, 1H), 4.43-4.41 (m, 1H), 4.17 (q, J=7.2 Hz, 2H), 3.72-3.56 (m, 2H), 3.24-3.11 (m, 1H), 2.63-2.11 (m, 2H), 1.48 (s, 9H), 1.26 (t, J=7.2 Hz, 3H).

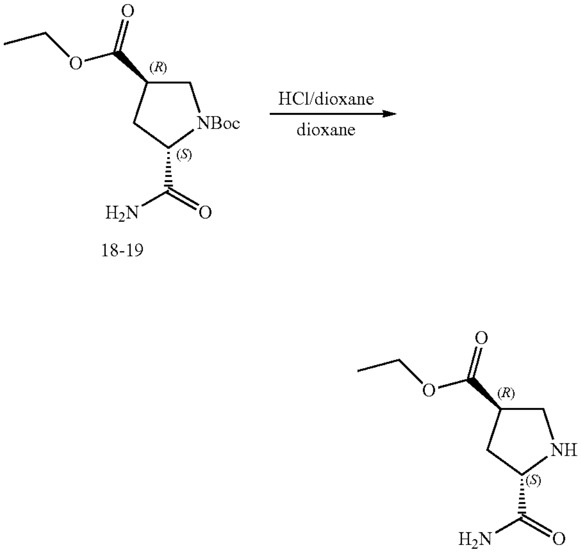

18-19

18-20

To a solution of 18-19 (3.7 g, 12.92 mmol, 1 eq) in dioxane (20 mL) was added HCl/dioxane (4 M, 30 mL) dropwise. The mixture was stirred for 2 hours at 20° C. TLC (ethyl acetate) showed most of the starting material was consumed. The reaction mixture was concentrated in vacuo to afford 18-20 (2.9 g, crude, HCl salt) as a white solid. $^1H$ NMR ($CD_3OD$, 400 MHz): δ 4.37 (t, J=8.0 Hz, 1H), 4.22 (q, J=7.2 Hz, 2H), 3.63-3.59 (m, 2H), 3.41-3.37 (m, 1H), 2.69-2.66 (m, 1H), 2.36-2.32 (m, 1H), 1.28 (t, J=7.2 Hz, 3H).

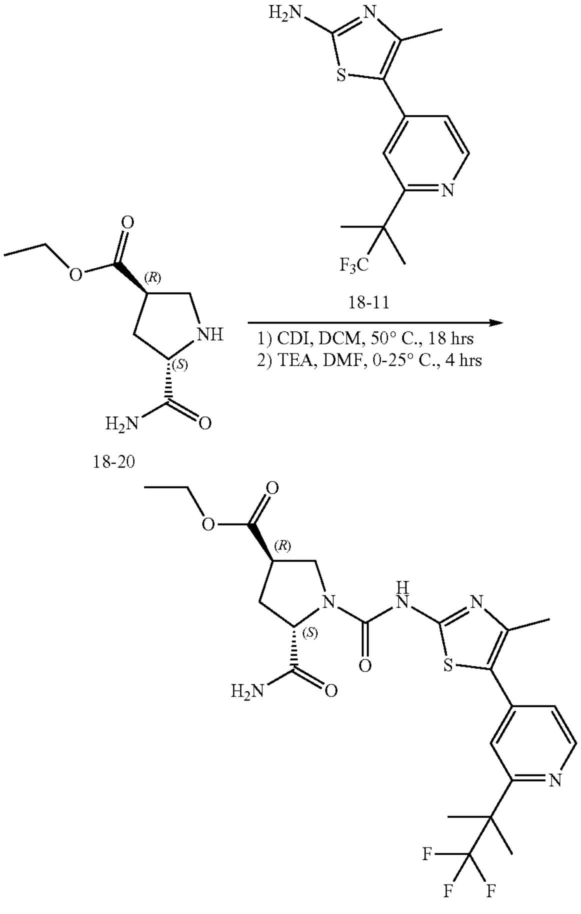

18-11

18-20

Compound (22)

To a solution of 18-11 (1.8 g, 5.97 mmol, 1 eq) in dichloromethane (30 mL) and tetrahydrofuran (15 mL) was added carbonyl diimidazole (1.00 g, 6.17 mmol, 1.03 eq) at 25° C. under nitrogen atmosphere. The mixture was stirred for 14 hours at 50° C. and LCMS showed that 20% starting material remained. Then additional 0.3 eq. of carbonyl diimidazole was added at 25° C. and continued to stir for 3 hours at 50° C. LCMS showed the reaction was completed. The mixture was concentrated in vacuo. The residue was redissolved in dimethylformamide (5 mL) and then added into a solution of 18-20 (1.40 g, 6.27 mmol, 1.05 eq, HCl salt) and triethylamine (1.81 g, 17.92 mmol, 2.49 mL, 3 eq) in DMF (15 mL) at 0° C. The mixture was stirred for 2 hours at 20° C. under nitrogen atmosphere. LCMS showed the reaction was completed. The reaction mixture was poured into water (50 ml), extracted with ethyl acetate (50 mL×3). The combined organic phase was washed with brine (50 mL×3), dried over anhydrous sodium sulfate, filtered and concentrated in vacuo. The residue was purified by column ($SiO_2$, petroleum ether:ethyl acetate=10:1 to ethyl acetate) to afford Compound (22) (1.5 g, 2.81 mmol, 47.05% yield, 96.21% purity) as a white solid. LCMS: RT=2.019 min, m/z 514.2 $[M+H]^+$, purity: 96.21%. SFC: RT=1.598 min, de %=89.48%. $^1H$ NMR ($CD_3OD$, 400 MHz): δ 8.62 (d, J=5.2 Hz, 1H), 7.52 (s, 1H), 7.26-7.25 (m, 1H), 6.72 (br. s, 1H), 4.75-4.73 (m, 1H), 4.21 (q, J=7.2 Hz, 2H), 3.88-3.82 (m, 2H), 3.50-3.46 (m, 1H), 2.68-2.64 (m, 1H), 2.49-2.11 (m, 4H), 1.65 (s, 6H), 1.29 (t, J=7.2 Hz, 3H).

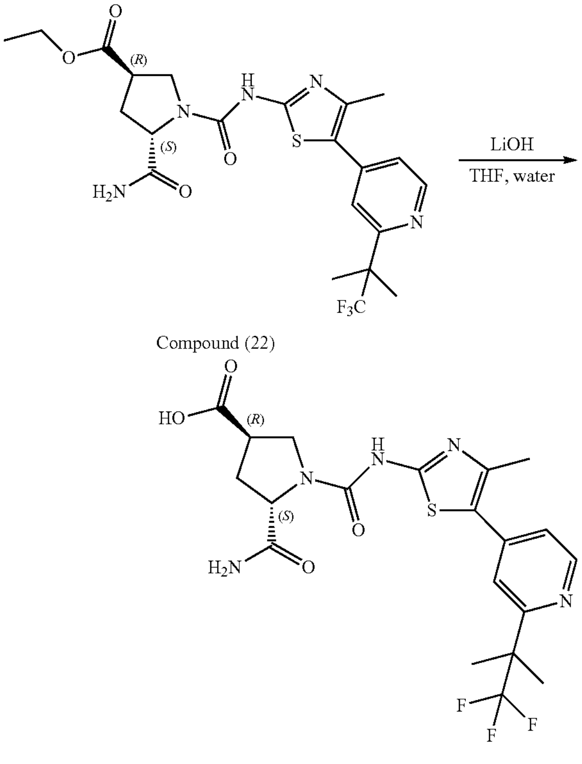

Compound (22)

Compound (19)

To a solution of Compound (22) (1.1 g, 2.14 mmol, 1 eq) in tetrahydrofuran (10 mL) was added lithium hydroxide monohydrate (270 mg, 6.43 mmol, 3 eq) in water (3 mL) dropwise at 0° C. The mixture was stirred at 25° C. for 1 hour. TLC (ethyl acetate) showed the starting material was consumed completely. The mixture was adjusted to pH=5 with 1N hydrochloric acid aqueous and concentrated in vacuum to remove tetrahydrofuran. The product was precipitated out and collected by filtration. The cake was washed with water (20 mL×3) and dried in vacuum at 45° C. The residue was triturated with acetonitrile (20 mL) to afford Compound (19) (1.1 g, crude) as a white solid. LCMS: RT=1.740 min, m/z 486.1 $[M+H]^+$, purity: 97.62%. SFC: RT=1.109 min, de %=98.61%. $^1H$ NMR ($CD_3OD$, 400 MHz) δ 8.55 (d, J=5.2 Hz, 1H), 7.60 (s, 1H), 7.40 (dd, $J_1$=2.0 Hz, $J_2$=7.6 Hz, 1H), 4.58-4.55 (m, 1H), 3.90-3.81 (m, 2H), 2.30-2.29 (m, 1H), 2.53-2.49 (m, 1H), 2.41 (s, 3H), 2.31-2.25 (m, 1H), 1.88-1.85 (m, 1H), 1.64 (s, 6H).

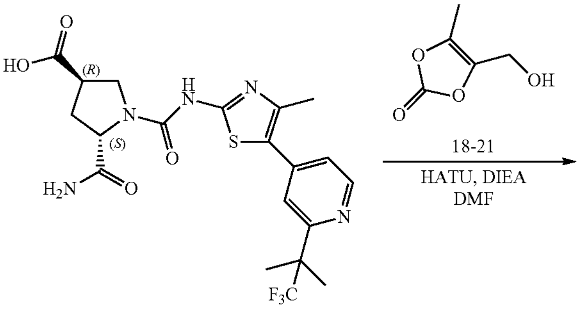

18-21

Compound (19)

-continued

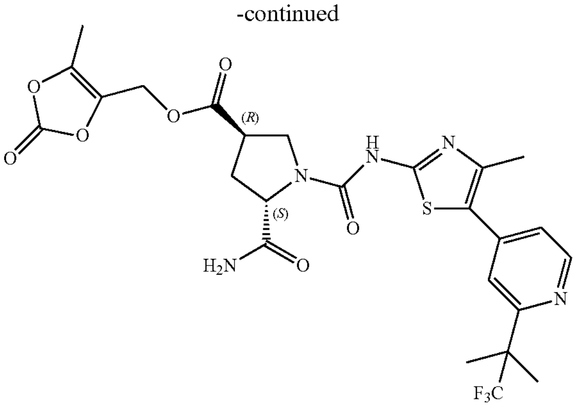

Compound (18)

To a solution of Compound (19) (240 mg, 494.36 umol, 1 eq) and HATU (226 mg, 593.23 umol, 1.2 eq) in N,N-dimethylformamide (5 mL) was added N,N-diisopropylethylamine (192 mg, 1.48 mmol, 258.32 uL, 3 eq) portion-wise at 0° C. The mixture was stirred for 10 min at 0° C. and then compound 18-21 (193 mg, 1.48 mmol, 3 eq) was added at 0° C. The mixture was stirred for 30 min at 0° C. LCMS showed the reaction worked well and completed. The reaction mixture was poured into water (50 mL), extracted with ethyl acetate (50 mL×3). The combined organic phase was washed with brine (100 mL), dried over anhydrous sodium sulfate, filtered and concentrated in vacuo. The residue was purified by prep-HPLC (column: PHENOMENEX® Synergi C18 150 mm*25 mm*0 um; mobile phase: [water (0.05% HCl)-ACN]; B %: 28%-48%, 10 min). The fraction was adjusted to pH=7 with saturated sodium bicarbonate aqueous, concentrated in vacuum to remove acetonitrile and extracted with dichloromethane (20 mL×3). The combined organic layers were washed with brine (20 mL), dried over anhydrous sodium sulfate, filtered and concentrated in vacuum. The residue was purified by column ($SiO_2$, ethyl acetate). The crude product was lyophilized twice to afford Compound (18) (241.22 mg, 403.67 umol, 48.24% yield, 100% purity) as a white solid. LCMS: RT=1.720 min, m/z 598.1 $[M+H]^+$, purity: 100%. SFC: RT=1.454 min, de %=100%. $^1H$ NMR ($CDCl_3$, 400 MHz): δ 8.62 (d, J=4.8 Hz, 1H), 7.52 (s, 1H), 7.26 (dd, $J_1$=1.2 Hz, $J_2$=5.2 Hz, 1H), 6.79 (br. s, 1H), 4.96-4.88 (m, 2H), 4.74 (dd, $J_1$=2.0 Hz, $J_2$=8.4 Hz, 1H), 3.92-3.84 (m, 2H), 3.53-3.50 (m, 1H), 2.70-2.65 (m, 1H), 2.42 (s, 3H), 2.38-2.28 (m, 1H), 2.19 (s, 3H), 1.65 (s, 6H).

Synthetic Preparation of Compound (20)

A synthetic route to Compound (20) is shown in the scheme below.

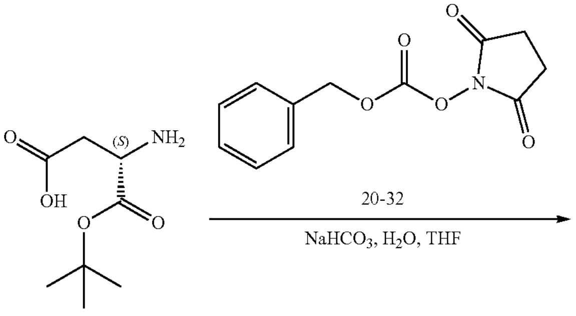

20-31

-continued

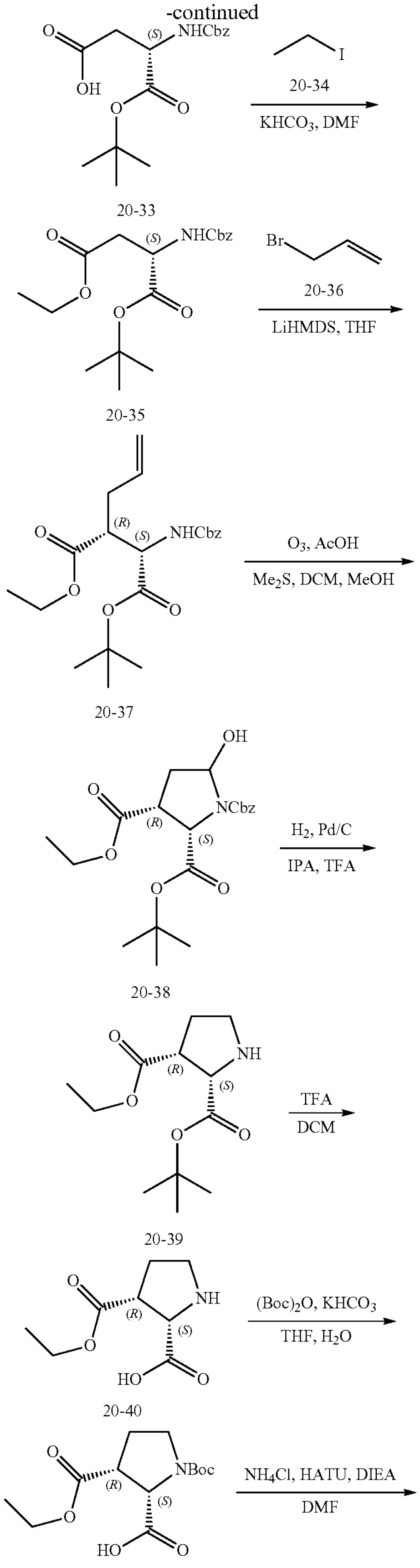

20-41

-continued

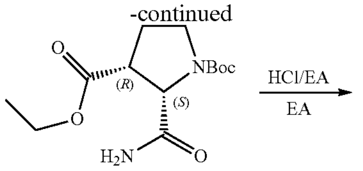

20-42

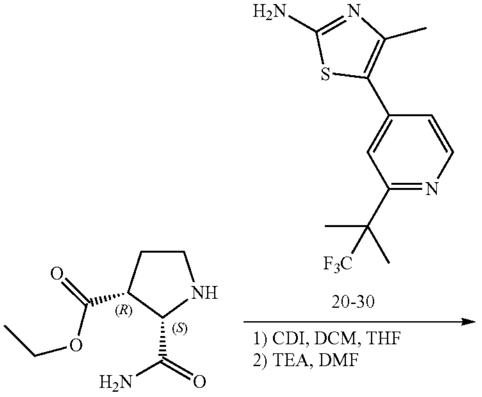

20-43

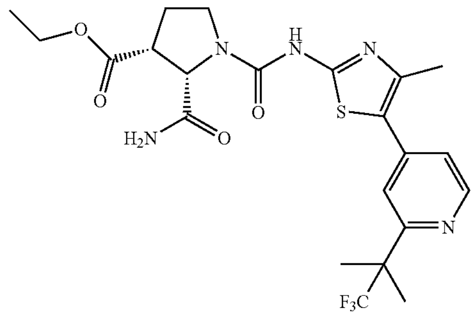

Compound (20)

Experimental Procedures for Compound (20)

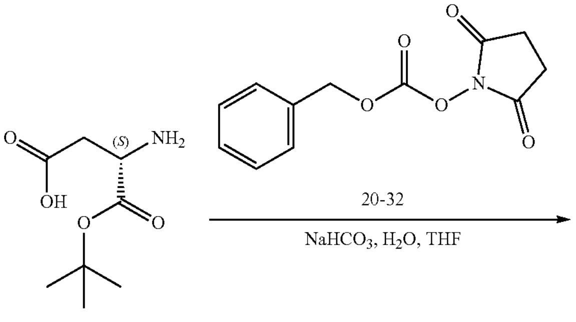

20-31

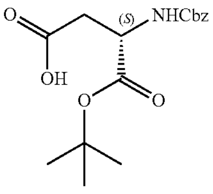

20-33

To a mixture of compound 20-31 (5 g, 26.43 mmol) in water (40 mL) was added sodium bicarbonate (6.66 g, 79.28 mmol) in one portion at 0° C., then a solution of compound 20-32 (6.59 g, 26.43 mmol) in tetrahydrofuran (10 mL) was added dropwise under nitrogen atmosphere. The mixture was stirred at 25° C. for 16 hours under nitrogen atmosphere. LCMS showed the starting material was consumed completely and the desired mass was detected. The mixture was washed with ethyl acetate (100 mL×2). The aqueous phase was adjusted to pH=4 with hydrochloric acid (1 M) and extracted with ethyl acetate (100 mL×3). The combined organic phase was washed with brine (30 mL×2), dried over anhydrous sodium sulfate, filtered and concentrated in vacuum to afford compound 20-33 (7 g, 21.65 mmol, 81.92% yield) as yellow oil, which was used directly in next step without purification. LCMS: RT=0.776 min, purity: 89.29%, m/z 346.0 $[M+Na]^+$. $^1H$ NMR ($CDCl_3$, 400 MHz): δ 7.38-7.33 (m, 5H), 5.74 (d, J=7.6 Hz, 1H), 5.14 (s, 2H), 4.56-4.54 (m, 1H), 3.05 (dd, $J_1$=4.4 Hz, $J_2$=17.6 Hz, 1H), 2.88 (dd, $J_1$=4.4 Hz, $J_2$=17.6 Hz, 1H), 1.46 (s, 9H).

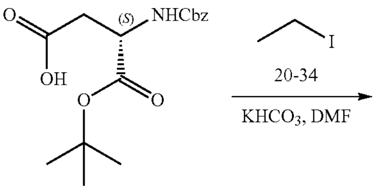

20-33

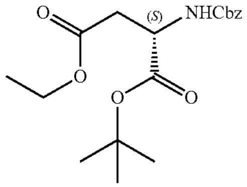

20-35

To a mixture of compound 20-33 (4 g, 12.37 mmol) and compound 20-34 (1.93 g, 12.37 mmol) in N,N-dimethylformamide (20 mL) was added potassium bicarbonate (3.10 g, 30.92 mmol) in one portion at 0° C. The mixture was stirred at 25° C. for 4 hours. TLC (petroleum ether:ethyl acetate=6:1) showed the starting material was consumed and the desired mass was observed. The mixture was poured into water (50 mL) and extracted with ethyl acetate (150 mL×2). The combined organic phase was washed with brine (50 mL×2) and dried over anhydrous sodium sulfate. After filtration and concentration, the crude product was purified by column chromatography ($SiO_2$, petroleum ether:ethyl acetate=100:1~10:1) to give compound 20-35 (3.3 g, 9.20 mmol, 74.40% yield) as yellow oil. LCMS: RT=0.887 min, purity: 98.34%, m/z 252.1 $[M-Boc+H]^+$; 296.1 $[M-tBu+H]^+$. $^1H$ NMR ($CDCl_3$, 400 MHz): δ 7.39-7.33 (m, 5H), 5.72 (d, J=8.0 Hz, 1H), 5.14 (s, 2H), 4.55-4.51 (m, 1H), 4.17-4.14 (m, 2H), 2.98 (dd, $J_1$=4.4 Hz, $J_2$=16.8 Hz, 1H), 2.81 (dd, $J_1$=4.4 Hz, $J_2$=16.8 Hz, 1H), 1.47 (s, 9H), 1.29-1.26 (m, 3H). SFC: RT=0.698 min, de %=100%

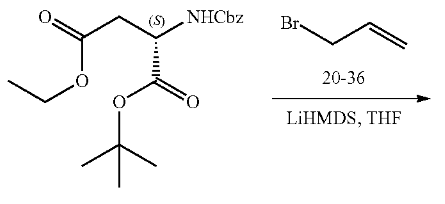

20-35

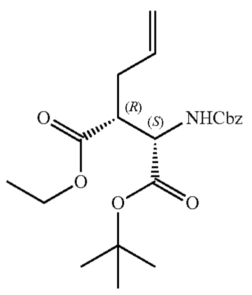

20-37

To a mixture of compound 20-35 (3.3 g, 9.39 mmol) in tetrahydrofuran (8 mL) was added LiHMDS (1 M, 23.48 mL) at −78° C. under nitrogen atmosphere. After stirring at −78° C. for 30 minutes, compound 20-36 (1.7 g, 14.09 mmol) was added and the mixture was stirred at 25° C. for another 1.5 hours. TLC (petroleum ether:ethyl acetate=8:1) showed the starting material was consumed and the desired mass was observed. The mixture was poured into hydrochloric acid (1 M, 40 mL) and extracted with ethyl acetate (150 mL×2). The combined organic phase was washed with brine (40 mL×2) and dried over sodium sulfate. After filtration and concentration, the crude product was purified by column chromatography ($SiO_2$, petroleum ether:ethyl acetate=100:1~20:1) to give compound 20-37 (1.05 g, 2.52 mmol, 26.88% yield) as colorless oil. LCMS: RT=0.966 min, purity: 94.11%, m/z 292.1[M-Boc+H]$^+$; 336.1 [M-t-Bu+H]$^+$. $^1$H NMR ($CDCl_3$, 400 MHz): δ 7.39-7.32 (m, 5H), 5.87-5.75 (m, 2H), 5.16 (s, 2H), 5.12-5.10 (m, 2H), 4.53 (dd, $J_1$=4.0 Hz, $J_2$=10.0 Hz, 1H), 4.18-4.15 (m, 2H), 3.14-3.11 (m, 1H), 2.54-2.48 (m, 1H), 2.34-2.30 (m, 1H), 1.46 (s, 9H), 1.27 (t, J=7.2 Hz, 3H). SFC: $RT_1$=1.008 min, $RT_2$=1.114 min, de %=97.8%.

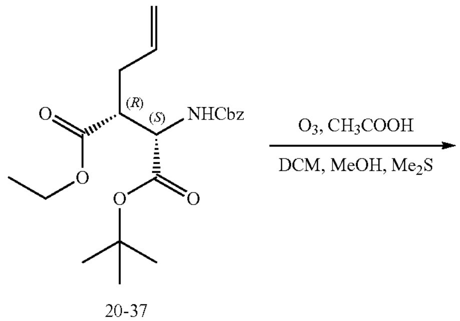

20-37

-continued

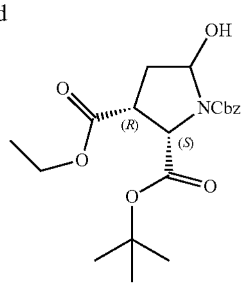

20-38

Ozone was bubbled into a solution of compound 20-37 (500 mg 1.02 mmol) and acetic acid (61 mg, 1.02 mmol) in methanol (24 mL) and dichloromethane (4 mL) at −78° C. for 30 minutes. Excess ozone was purged by nitrogen atmosphere, then dimethyl sulfide (63 mg, 1.02 mmol) was added and the mixture was stirred at 25° C. for 2.5 hours. LCMS showed the starting material was consumed completely and the desired mass was detected. The mixture was poured into dichloromethane (100 mL), washed with saturated sodium bicarbonate aqueous (15 mL×2), brine (10 mL×2) and dried over anhydrous sodium sulfate. After filtration and concentration, the crude product was purified by column chromatography ($SiO_2$, petroleum ether:ethyl acetate=100:1~2:1) to give compound 20-38 (380 mg, 0.869 mmol, 85.22% yield) as colorless oil. $^1$H NMR ($CDCl_3$, 400 MHz): δ 7.38-7.33 (m, 5H), 5.76-5.62 (m, 1H), 5.23-5.15 (m, 2H), 4.59-4.55 (m, 1H), 4.31-4.22 (m, 1H), 4.22-4.10 (m, 2H), 3.71-3.55 (m, 1H), 2.59-2.51 (m, 1H), 2.46-2.08 (m, 1H), 1.38 (s, 9H), 1.30-1.26 (m, 3H).

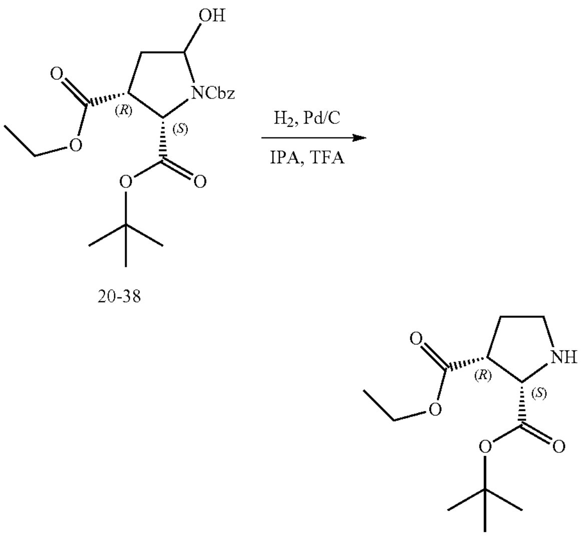

20-38

20-39

To a solution of compound 20-38 (280 mg, 0.711 mmol) and trifluoroacetic acid (122 mg, 1.07 mmol) in isopropanol (5 mL) was added Pd/C (10 mg, 10% purity on carbon) under nitrogen atmosphere. The suspension was degassed under vacuum and purged with hydrogen atmosphere several times. The mixture was stirred at 25° C. for 8 hours under hydrogen atmosphere (15 psi). LCMS showed the starting material was consumed completely and the desired mass was detected. The reaction mixture was filtered and the filtrate was concentrated to give compound 20-39 (254 mg, 0.710 mmol, 99.88% yield, TFA salt) as yellow gum, which was used directly for next step without purification. $^1H$ NMR ($CDCl_3$, 400 MHz): δ 4.66 (d, J=7.2 Hz, 1H), 4.26-4.20 (m, 2H), 3.77-3.68 (m, 1H), 3.66-3.57 (m, 2H), 2.63-2.51 (m, 1H), 2.35-2.28 (m, 1H), 1.49 (s, 9H), 1.34 (t, J=7.2 Hz, 3H).

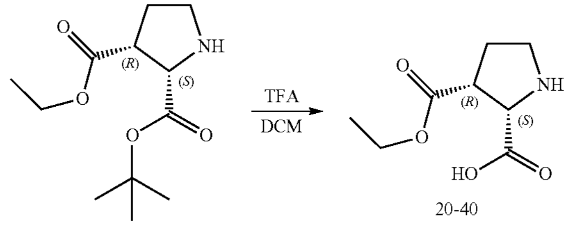

20-39 20-40

To a mixture of compound 20-39 (254 mg, 0.710 mmol, TFA salt) in dichloromethane (0.5 mL) was added trifluoroacetic acid (770 mg, 6.75 mmol). The mixture was stirred at 25° C. for 2 hours. TLC (dichloromethane:methanol=10:1) showed the starting material was consumed and the desired mass was observed. The reaction mixture was filtered and the filtrate was concentrated to give compound 20-40 (214 mg, 0.710 mmol, 99.95% yield, TFA salt) as yellow gum, which was used directly for next step without purification. $^1H$ NMR ($D_2O$, 400 MHz): δ 4.60-4.55 (m, 1H), 4.17-4.15 (m, 2H), 3.63-3.62 (m, 1H), 3.49-3.46 (m, 2H), 2.45-2.32 (m, 2H), 1.25-1.18 (m, 3H).

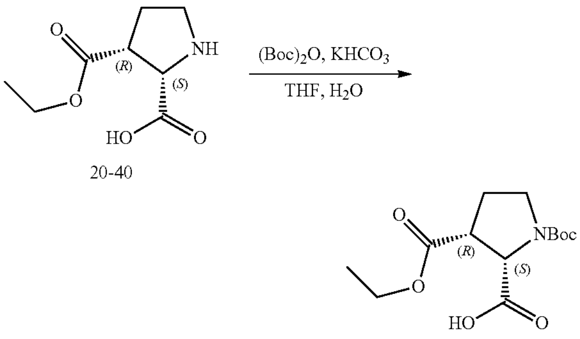

20-40 20-41

To a mixture of compound 20-40 (214 mg, 0.710 mmol, TFA salt) and di-tert-butyl dicarbonate (233 mg, 1.07 mmol) in tetrahydrofuran (1 mL) and water (1 mL) was added potassium bicarbonate (285 mg, 2.84 mmol). The mixture was stirred at 25° C. for 10 hours. LCMS showed the starting material was consumed completely and the desired mass was detected. The mixture was adjusted to pH=3 with hydrochloric acid (1 M) and extracted with ethyl acetate (20 mL×2). The combined organic phase was washed with brine (10 mL×2), dried over anhydrous sodium sulfate, filtered and concentrated in vacuum to give compound 20-41 (110 mg, 0.382 mmol, 53.89% yield) as yellow gum, which was used directly for next step without purification. LCMS: RT=0.582 min, purity: 62.89%, m/z 188.1 [M-Boc+H]$^+$. $^1H$ NMR ($CDCl_3$, 400 MHz): δ 4.57-4.45 (m, 1H), 4.17-4.05 (m, 2H), 3.49-3.42 (m, 1H), 3.35-3.32 (m, 1H), 3.08-3.03 (m, 1H), 2.38-2.31 (m, 1H), 2.12-2.08 (m, 1H), 1.41 (s, 9H), 1.18 (t, J=7.2 Hz, 3H).

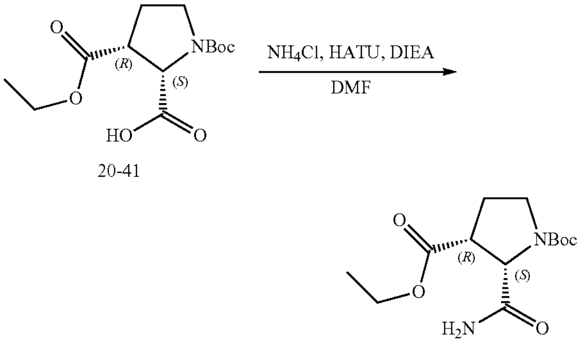

20-41 20-42

To a mixture of compound 20-41 (90 mg, 0.313 mmol) and N,N-diisopropylethylamine (101 mg, 0.783 mmol) in N,N-dimethylformamide (0.5 mL) was added HATU (179 mg, 0.469 mmol) in one portion followed by ammonium chloride (84 mg, 1.57 mmol) at 0° C. The mixture was stirred at 25° C. for 2 hours. TLC (petroleum ether:ethyl acetate=1:1) showed the starting material was consumed completely. The mixture was poured into ice-water (5 mL) and extracted with ethyl acetate (20 mL×2). The combined organic phase was washed with brine (10 mL×2), dried over anhydrous sodium sulfate. After filtration and concentration, the crude was purified by column chromatography ($SiO_2$, petroleum ether:ethyl acetate=100:1~1:1) to give compound 20-42 (89 mg, 310.84 umol, 99.23% yield) as yellow oil. $^1H$ NMR ($CDCl_3$, 400 MHz): δ 5.42 (br. s, 1H), 4.66-4.54 (m, 1H), 4.18 (q, J=7.2 Hz, 2H), 3.52-3.50 (m, 1H), 3.48-3.36 (m, 1H), 3.08-3.03 (m, 1H), 2.20-2.19 (m, 2H), 1.49 (s, 9H), 1.27 (t, J=7.2 Hz, 3H).

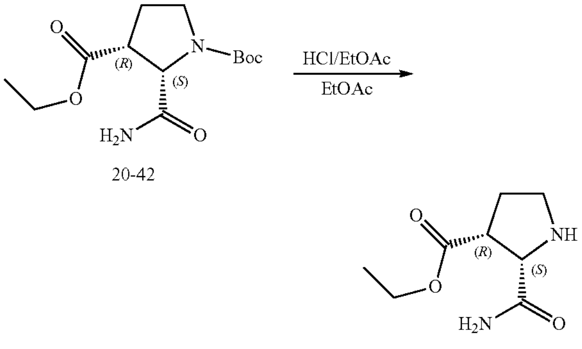

20-42 20-43

To a mixture of compound 20-42 (89 mg, 0.310 mmol) in ethyl acetate (2 mL) was added hydrogen chloride/ethyl acetate (4 M, 5 mL). The mixture was stirred at 25° C. for 1 hour. TLC (dichloromethane:methanol=10:1) showed the starting material was consumed and the desired mass was detected. The reaction mixture was filtered and the filtrate was concentrated to give compound 20-43 (60 mg, 0.269 mmol, 86.69% yield, HCl salt) as a white solid, which was used directly for next step without purification. $^1H$ NMR ($CD_3OD$, 400 MHz): δ 4.34 (d, J=7.2 Hz, 1H), 4.10-4.06 (m, 2H), 3.53-3.49 (m, 2H), 3.36-3.33 (m, 1H), 2.32-2.27 (m, 2H), 1.16 (t, J=7.2 Hz, 3H).

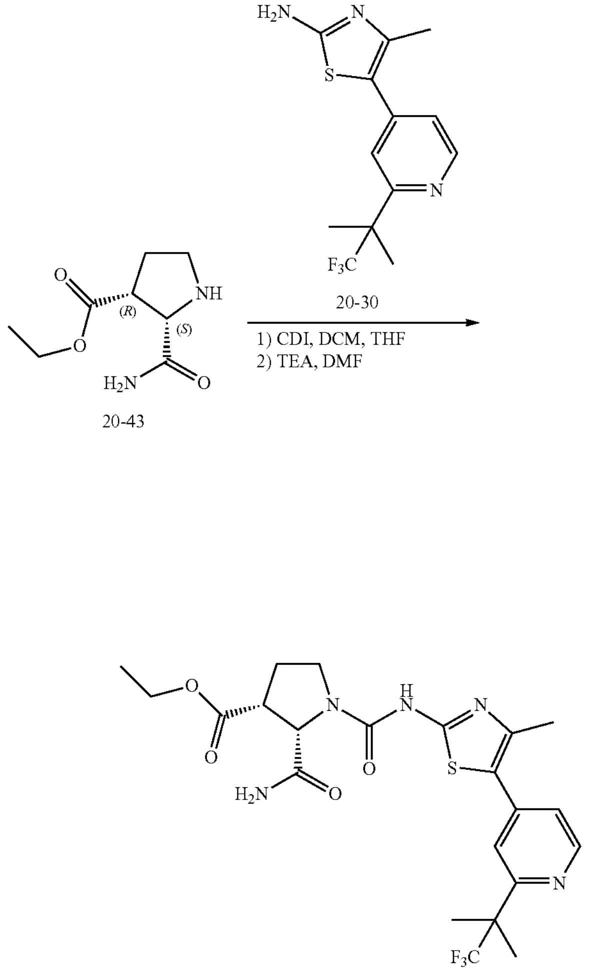

Compound (20)

A mixture of compound 20-30 (65 mg, 0.215 mmol) and 1,1'-carbonyldiimidazole (35 mg, 0.215 mmol) in tetrahydrofuran (0.1 mL) and dichloromethane (0.2 mL) was stirred at 50° C. for 20 hours. LCMS showed little of compound 20-30 remained, The mixture was concentrated in vacuum to give a residue which was dissolved in N,N-dimethylformamide (0.2 mL), then triethylamine (68 mg, 0.673 mmol) and compound 20-43 (60 mg, 0.269 mmol, HCl salt) were added. The mixture stirred at 25° C. for 6 hours. LCMS showed the starting material was consumed completely and the desired mass was detected. The mixture was poured into ice-water (10 mL) and extracted with ethyl acetate (20 mL×2). The combined organic phase was washed with brine (5 mL×2) and dried over anhydrous sodium sulfate. After filtration and concentration, the crude product was purified by prep-TLC ($SiO_2$, petroleum ether:ethyl acetate=0:1) to give Compound (20) (25.5 mg, 0.047 mmol, 17.56% yield) as a white solid. LCMS: RT=0.822 min, purity: 95.32%, m/z 514.2 $[M+H]^+$. $^1H$ NMR ($CDCl_3$, 400 MHz): δ 8.64 (d, J=5.2 Hz, 1H), 7.55 (d, J=7.2 Hz, 1H), 7.31-7.29 (m, 1H), 6.76 (br. s, 1H), 5.80 (br. s, 1H), 4.93-4.91 (m, 1H), 4.25-4.19 (m, 2H), 3.83-3.73 (m, 1H), 3.62-3.50 (m, 1H), 3.25-3.13 (m, 1H), 2.84-2.67 (m, 1H), 2.46 (s, 3H), 2.43-2.38 (m, 1H), 1.67 (s, 6H), 1.31-1.28 (m, 3H). SFC: $RT_1$=1.641 min, $RT_2$=1.906 min, de %=67.9%

Synthetic Preparation of Compound (21)

A synthetic route to Compound (21) is shown in the scheme below.

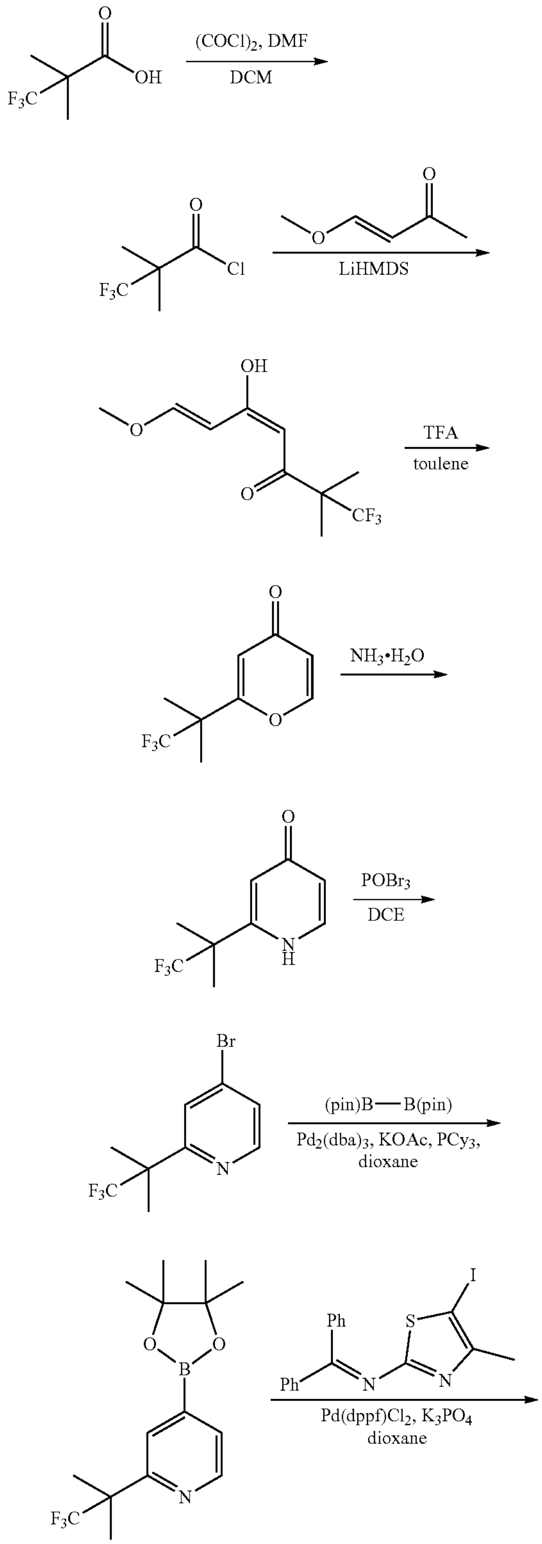

-continued

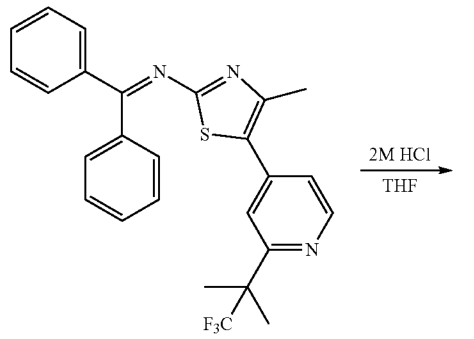

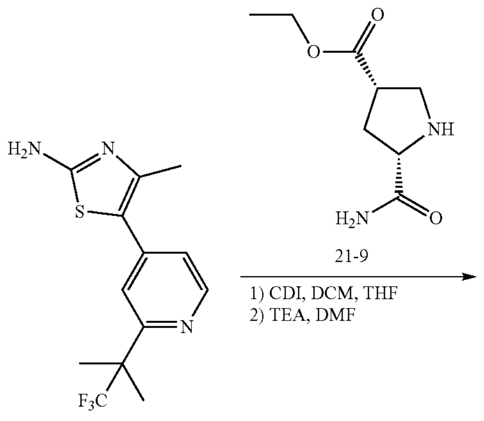

21-30

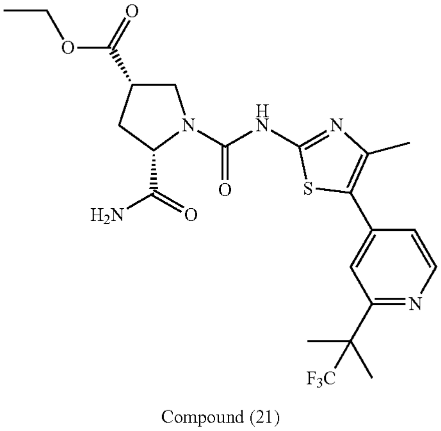

Compound (21)

Experimental Procedures for Compound (21)

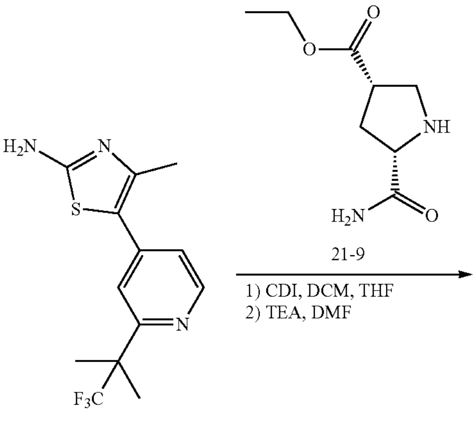

21-30

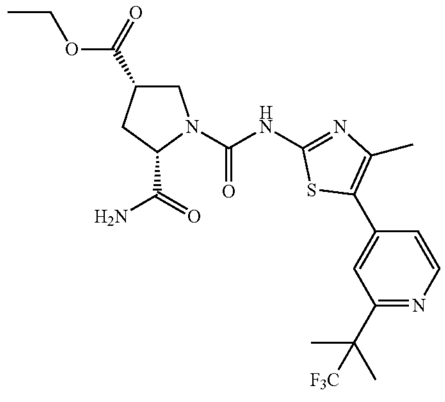

Compound (21)

To a solution of compound 21-30 (0.08 g, 216.45 umol, 1 eq) in dichloromethane (2 mL) and tetrahydrofuran (1 mL) was added 1,1'-carbonyldiimidazole (71 mg, 2 eq) at 25° C. The mixture was stirred for 42 hours at 50° C. under nitrogen atmosphere. TLC (petroleum ether:ethyl acetate=1:1, quenched with methanol) showed the reaction was completed. The mixture was concentrated in vacuo to give an intermediate, which was added to a solution of compound 21-9 (53 mg, 236.47 umol, 1.1 eq, HCl salt) and triethylamine (44 mg, 429.94 umol, 59.84 uL, 2 eq) in N,N-dimethylformamide (1 mL) at 0° C. The mixture was stirred at 25° C. for 1 hour under nitrogen atmosphere. LCMS showed the desired mass was detected. The mixture was quenched with water (5 mL) and extracted with ethyl acetate (10 mL×2). The organic layers were washed with brine (5 mL×3), dried over anhydrous sodium sulfate, filtered and concentrated in vacuo. The residue was purified by prep-HPLC (column: PHENOMENEX® Gemini C18 250*50 mm*10 um; mobile phase: [water (10 mM $NH_4HCO_3$)-ACN]; B %: 30%-60%, 3 min) to give Compound (21) (0.013 g, 24.18 umol, 11.25% yield) as a white solid. LCMS: RT=2.336 min, purity: 95.03%, m/z 514.1 $[M+H]^+$. $^1H$ NMR ($CD_3OD$, 400 MHz): δ 8.56 (d, J=5.2 Hz, 1H), 7.59 (s, 1H), 7.39 (dd, $J_1$=1.6 Hz, $J_2$=4.8 Hz, 1H), 4.50-4.48 (m, 1H), 4.17 (q, J=7.2 Hz, 2H), 3.96-3.89 (m, 2H), 3.26-3.25 (m, 1H), 2.62-2.56 (m, 1H), 2.41 (s, 3H), 2.36-2.34 (m, 1H), 1.65 (s, 6H), 1.27 (t, J=7.2 Hz, 3H). SFC: $RT_1$=1.567 min, $RT_2$=1.644 min, de %=88.9%

Development of PI3Kα Inhibitors

The design, synthesis and evaluation of Compound (14) and other PI3K inhibitors is described below. The scientific literature is replete with structurally diverse and biologically well-characterized PI3K inhibitors that have appeared over the past 2 decades as this pathway has been the focus of intense interest. As a consequence, the clinical utility of PI3K inhibitors in the treatment of cancer is well validated at this juncture. Due to its pivotal role, this pathway has been the focus of intense interest with drug discovery efforts culminating in the invention of over 50 new drugs inhibiting the PI3K/AKT/mTOR pathway advancing to different stages of development in this highly validated pathway.[7] Despite considerable resources directed towards the development of selective PI3K inhibitors only 2 inhibitors (idelalisib, a PI3Kδ inhibitor, FDA approved 2014; copanlisib, a PI3Kα/δ inhibitor, FDA approved 2017) have advanced successfully to registration, while numerous structurally diverse analogs remain under clinical investigation. For instance, the PI3Kα inhibitor BYL719 (alpelisib)[13] is currently under Phase 3 clinical investigation for metastatic breast cancer. Another PI3Kα inhibitor, GDC-0032 (taselisib), advanced to Phase 3 clinical trials for squamous cell lung cancer. Yet another PI3Kα antagonist exhibiting additional potent mTOR activity, GNE-317[37,38,39] was the focus of considerable preclinical scrutiny and served as the progenitor of at least one clinical candidate for brain cancers (GDC-0084, Phase 1).[39]

This comparative paucity of registered new chemical entities (relative to efforts expended) derives less from a dearth of efficacy than a repercussion from the well known PI3K-mediated systemic toxicities that pose significant challenges with respect to balancing on target efficacy in tumors versus mechanism-mediated toxicities. Described herein are PI3K inhibitors amenable to formulation in the furanoid nanoparticles to maximize efficacy with a commensurate reduction in mechanism-based liabilities. As detailed above, laboratories have established that IV-dosed, nanoformulated BYL719 was identical in efficacy at one seventh the dosage to orally delivered BYL719 while abrogating typical PI3K-mediated systemic liabilities.[23]

The strategy described herein involves molecules suitable for furanoid nanoformulation that functioned as antedrugs inhibiting the PI3K pathway. The antedrug concept originated in 1982, born of a strategy to design potent, yet safer medicines.[8] Antedrugs are bioactive derivatives that undergo a designed biotransformation yielding an inactive and/or cell impermeable form that is readily excreted from circulation, thereby minimizing systemic side effects and increasing therapeutic indices. Nanoformulation would permit these cell permeable compounds to be delivered in a targeted manner via the P-selectin pathway as before, but in principle they would be efficiently deactivated metabolically by enzymes in the blood and the liver to PI3K inactive or cell impermeable metabolites, thus mitigating PI3K systemic liabilities. Furthermore, to augment the potential TI of these novel analogs, high clearance properties are desirable, such that any PI3K inhibitor that prematurely leached from the nanoparticle or diffused from a tumor cell's milieu will manifest minimal potential for mechanism-based systemic toxicity.

Additional PI3K Inhibitors

Additional PI3K inhibitors have been developed (see Table 4, Table 5, and Table 6 for examples). Attempts to incorporate an antedrug into the BYL719 core proceeded via modification of its lipophilic —$C(CH_3)_2CF_3$ side chain. See, e.g., Table 4.

TABLE 4

Pyridine-Modified PI3Kα Inhibitors

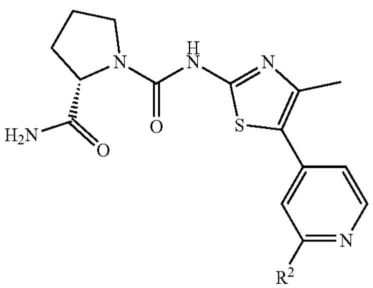

| Compound | $R^2$ | PI3Kα ($IC_{50}$, nM)** |
|---|---|---|
| (1) | 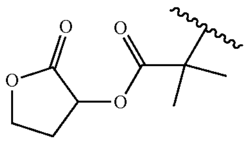 [SMILES: *C(C)(C)C(=O)OC1CCOC1=O] | (+++) |
| (2) | 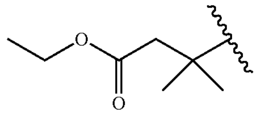 [SMILES: *C(C)(C)CC(=O)OCC] | (+++) |
| (3) | 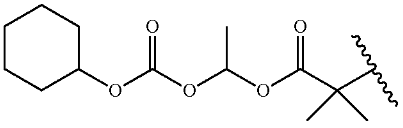 [SMILES: *C(C)(C)C(=O)OC(C)OC(=O)OC1CCCCC1] | (+++) |

TABLE 4-continued

Pyridine-Modified PI3Kα Inhibitors

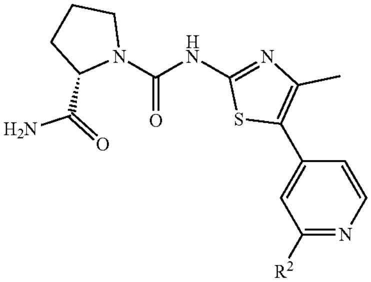

| Compound | $R^2$ | PI3Kα ($IC_{50}$, nM)** |
|---|---|---|
| (4) | 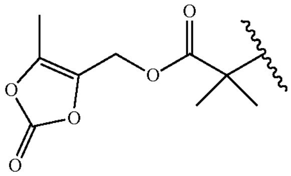 [SMILES: *C(C)(C)C(=O)OCc1oc(=O)oc1C] | (+++) |
| (5) | 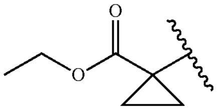 [SMILES: *C1(C(=O)OCC)CC1] | (+++) |
| (6) | 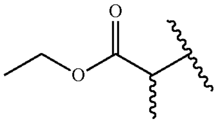 [SMILES: *C(C)C(=O)OCC] | (+++) |
| (7) | 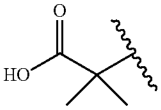 | (+++) |
| (8) | 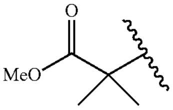 | (+++) |
| (9) | $MeO_2C$— | (+++) |

**$IC_{50}$ Activity Scale: <100 nM: (+++); <500 nM: (++); <1000 nM: (+)

A 2-pyrone ring could function as a viable bioisostere for the pyridine ring system, as in Compound (14) (Table 5). Compound (14) is a potent PJ3Kα inhibitor in biochemical assays and cellular assays (+++).

Additional metabolically labile functionality were incorporated in the molecule to increase the potential for ready degradation by enzymes in the blood and/or in the liver into biologically inactive and/or cell impermeable derivatives. Three additional analogs were synthesized by incorporating a carboethoxy group onto Compound (14)'s proline ring: Compound (10), Compound (11), and Compound (12). Submitting all three to the PI3Kα biochemical assay revealed that while all were active.

TABLE 5

Pyrone PI3Kα Inhibitors

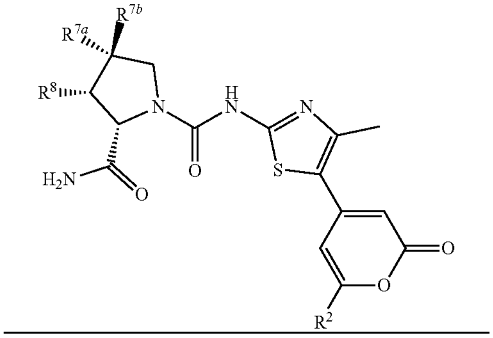

| Compound | $R^{7a}$ | $R^{7b}$ | $R^8$ | $R^2$ | PI3Kα ($IC_{50}$, nM)** |
|---|---|---|---|---|---|
| (10) | H | H | —$CO_2$Et | —C($Me_2$)$CF_3$ | (+++) |
| (11) | H | —$CO_2$Et | H | —C($Me_2$)$CF_3$ | (+++) |
| (12) | —$CO_2$Et | H | H | —C($Me_2$)$CF_3$ | (+++) |
| (13) | H | H | H | —$CHMe_2$ | (+++) |
| (14) | H | H | H | —C($Me_2$)$CF_3$ | (+++) |
| (15) | H | H | H | —Me | (++) |

**$IC_{50}$ Activity Scale: <100 nM: (+++); <500 nM: (++); <1000 nM: (+)

Similar attention was devoted to incorporating metabolically labile functionality onto the proline ring. These efforts served to identify 3 different ethyl esters (Compound (20), Compound (21), and Compound (22)), each of which retained good intrinsic PI3Kα potency (Table 13). The carboxylic acid analog of Compound (22) is Compound (19). Compound (18) incorporates an oxodioxolenylmethyl group cleaved by paraoxonase 1 (PON1), a liver produced esterase that also circulates in the blood.[42] Compound (18), like the related proline containing carboethoxy esters, is a potent PI3Kα inhibitor.

TABLE 6

Proline-Modified PI3Kα Inhibitors

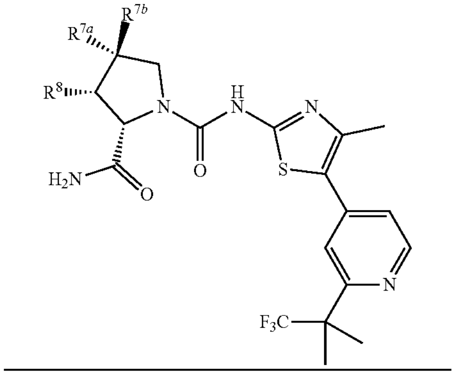

| Compound | $R^{7a}$ | $R^{7b}$ | $R^8$ | PI3Kα ($IC_{50}$, nM)** |
|---|---|---|---|---|
| (18) | H | 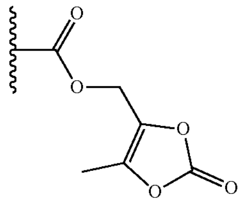 [SMILES: *C(=O)OCc1oc(=O)oc1C] | H | (+++) |
| (19) | H | —$CO_2$H | H | (+++) |
| (20) | H | H | —$CO_2$Et | (+++) |
| (21) | —$CO_2$Et | H | H | (+++) |
| (22) | H | —$CO_2$Et | H | (+++) |

**$IC_{50}$ Activity Scale: <100 nM: (+++); <500 nM: (++); <1000 nM: (+)

Compound (22), Compound (19), and Compound (18) were subjected to additional studies (Table 8). As noted previously, each of these analogs is potent in biochemical assays. Compound (22) and Compound (18) display permeability characteristics. Compound (22) was more labile in mouse microsomes than in human whereas Compound (18) exhibited a high metabolic rate in both mouse and human microsomes. This is consistent with mouse cassette PK data for Compound (18): no Compound (18) was detected either at $C_{max}$ (t=5 min) in the IV dosing arm or following oral administration (levels of Compound (19) were not measured in this study). Carboxylic acid Compound (19) was, as anticipated, very stable in microsomal incubations. The PK profile in mice for IV-dosed Compound (19) was generated; these results established that this compound exhibits much higher clearance and a shorter half-life relative to either BYL719 and Compound (14) (Table 7).

TABLE 7

Mouse Pharmakokinetic Properties of Cassette Dosed Free Compound (19) Compound (19)**

| $C5_{min}$ (ng/mL) | $AUC_{iv}$ (ng*h/mL) | $MRT_{iv}$ (h) | $VD_{ss}$ (mL/kg) | $Cl_{total}$ (mL/h/kg) |
|---|---|---|---|---|
| 55.7 | 9.6 | 0.19 | 2057 | 10662 |

**Dose: 0.1 mg/kg IV, 1 mL/kg (10-in-One)

Importantly, each of these 3 new derivatives shown in Table 8 were successfully encapsulated in fucoidan polysaccharide nanoparticles. Following nanoformulation, the drug loading in the nanoparticle for each analog was determined.

TABLE 8

Additional Profiling of Potential PI3K Antedrugs and Cell Impermeable Inhibitor

| ID | Compound (22) | | Compound (19) | | Compound (18) | |
|---|---|---|---|---|---|---|
| Class | Pyridine | | Pyridine | | Pyridine | |
| PAMPA pH 7.4 [nm/sec] | 155 | | <6 | | 172 | |
| Stability in blood (mouse/human) [% remaining @ 2 h] | 0.076 | 60 | 104 | 103 | 1.0 | 0.4 |
| Metabolic rate in microsome (mouse/human) [μL/min/mg] | 104 | 18 | −8 | 7 | 577 | 245 |
| Nanoparticle formulation | Yes | | Yes | | Yes | |
| Nanoparticle drug load, % | 39 | | 41 | | 34 | |

Development of P-Selectin Targeting Nanoparticles

Whereas P-selectin has been widely discussed as a clinical target, it has not been previously explored as a drug delivery target in cancer therapy. P-selectin, an inflammatory cell adhesion molecule responsible for leukocyte recruitment and platelet binding, is produced in endothelial cells where it is stored in intracellular granules known as Weibel-Palade bodies.[22] Upon endothelial activation with endogenous cytokines,[15] or exogenous stimuli such as RT,[43,44,45,46] P-selectin translocates to the cell membrane and into the lumen of blood vessels. Significantly elevated P-selectin expression has been found in the vasculature of human lung,[26] breast[27] and kidney cancers.[28] Moreover, P-selectin has been shown to facilitate metastasis by coordinating the interaction between cancer cells, activated platelets, and activated endothelial cells. P-selectin was, therefore, investigated as a target in tumors in part to exploit the same mechanism by which tumors metastasize in order to deliver drugs to the tumor/metastatic niche. These associations with tumors and micrometastases, as well its induction with radiation, suggest P-selectin as a possible target for cancer drug delivery and radiation-guided drug delivery.[22]

The clinical potential of nanomedicines has not yet been fulfilled[2] in part because of the endothelial barrier, which limits extravasation of nanoparticles at the sites of solid tumors.[29,30,31] Passive targeting mechanisms, such as the enhanced permeability and retention (EPR) effect[32] show some promise, but they have not yet demonstrated notable benefit in disseminated tumors or in patients.[22] Tumor vasculature, which is composed of smooth muscle cells, pericytes, extracellular matrix, and endothelial cells (ECs), is necessary for the growth and support of tumors. The EC component of tumor neovasculature is a promising target for antitumor therapy because of its genetic stability, exposure to the circulation, and direct access from the intravascular space. Nanoparticle drug carriers targeting the neovasculature are currently under clinical development;[18] however, targeted delivery of therapeutic agents to micrometastases or tumors lacking neovasculature remains a persistent challenge.[33]

P-selectin is a target for localized drug delivery to tumor sites, including metastases. Many human tumors express P-selectin on cells and in the vasculature, whereas normal tissues exhibit little expression. To target drugs to P-selectin-expressing tumors, the Heller team synthesized a nanoparticle carrier for chemotherapeutic drugs using the algae-derived polysaccharide fucoidan, which exhibits nanomolar affinity for P-selectin.[22] These fucoidan-based nanoparticles targeted activated endothelium, demonstrated penetration of endothelial barriers in vitro, and exhibited a therapeutic advantage over untargeted chemotherapeutic drugs or passively targeted nanoparticles in P-selectin-expressing tumors and metastases in vivo.

Expression of P-Selectin in Human Cancers

To determine the prevalence of P-selectin protein expression in cancer tissues, 420 clinical samples were assessed by immunohistochemistry (IHC).[22] This effort established that P-selectin is expressed within multiple tumor types, including lung (19%), ovarian (68%), lymphoma (78%), and breast (49%) (FIG. 2A). As expected, abundant expression of P-selectin was found in the vasculature surrounding the tumor cells but not in adjacent normal tissue. In a subset of cancers, P-selectin expression also was observed on tumor cells and/or stroma. To corroborate this finding, the Heller team interrogated The Cancer Genome Atlas (TCGA) for P-selectin (SELP) staining, RNA expression, and common SELP genomic alterations in tumor tissues. The TCGA database revealed elevated RNA expression in multiple tumors and amplifications in several human cancers such as melanoma (15.5%), liver cancer (15%), bladder urothelial carcinoma (13.4%) and lung adenocarcinoma (12.2%) (FIG. 2B).

P-Selectin-Targeted Nanoparticle Drug Carrier System

To design a P-selectin-targeted drug delivery system, nanoparticles composed of fucoidan (Fi) to encapsulate three different drugs were prepared. Fucoidan-encapsulated paclitaxel (FiPAX) nanoparticles were synthesized by coencapsulating paclitaxel and a near-infrared (NIR) fluorophore (IR-783) to facilitate imaging via nanoprecipitation (FIG. 18).[22] A specific inhibitor of MEK, MEK162, was similarly encapsulated in fucoidan nanoparticles (FiMEK) using the same method. Fucoidan-encapsulated doxorubicin (FiDOX) nanoparticles were synthesized via layer-by-layer assembly of a cationic doxorubicin-polymer conjugate [DOX-PEG- DOX (DPD)] and the anionic fucoidan. The DPD conjugate was synthesized with pH-cleavable hydrazone linkages to promote drug release within the acidic tumor microenvironment or within acidic organelles upon endocytosis. The FiPAX, FiMEK, and FiDOX nanoparticles measured 105±4.2, 85±3.6, and 150±8.1 nm in diameter, respectively, and they exhibited about −55 mV z potential (surface charge). Electron microscopy showed relatively uniform spherical morphologies. The nanoparticles exhibited good serum stability over 5 days and pH-dependent drug release rates, and they could be reconstituted after lyophilization.

Dyes are elements for generating stable, well-behaved nanoparticles and comprise approximately 6% of the total mass of a given nanoparticle (Table 9). IR820 and IR783 are particularly useful for preparing stable nanoparticles. Another dye, ICG, is FDA-approved for clinical uses and serves as a useful precedent for generating the data required for FDA registration.

TABLE 9

Near-Infrared Dyes Suitable for Nanoparticle Generation

IR820

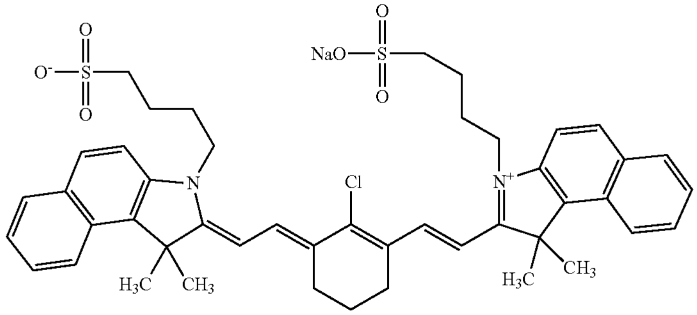

ICG (FDA-Approved)

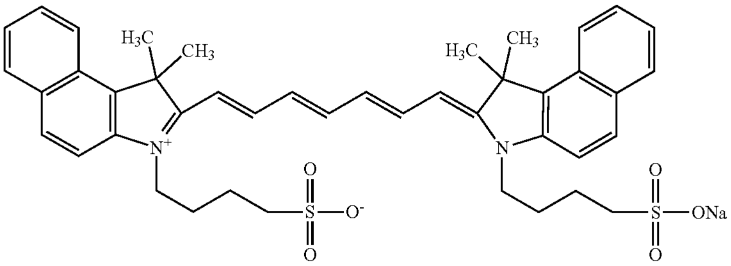

IR783

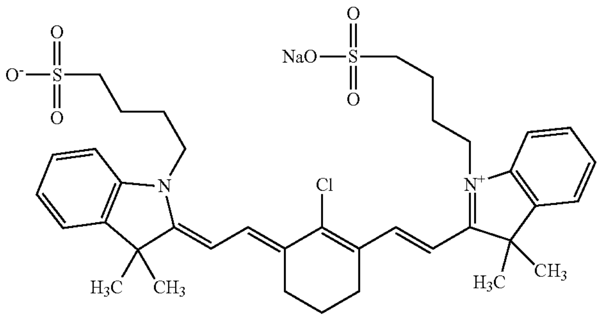

TABLE 9-continued

Near-Infrared Dyes Suitable for Nanoparticle Generation

IR806

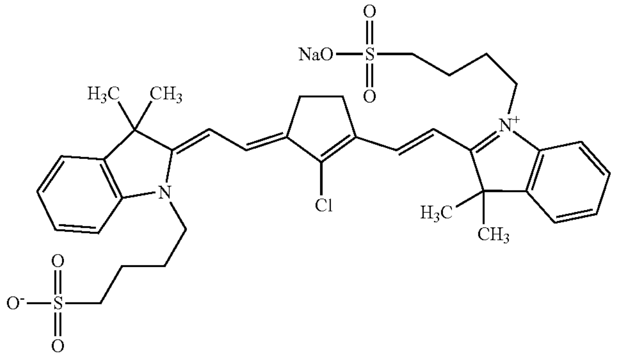

Brilliant Blue G

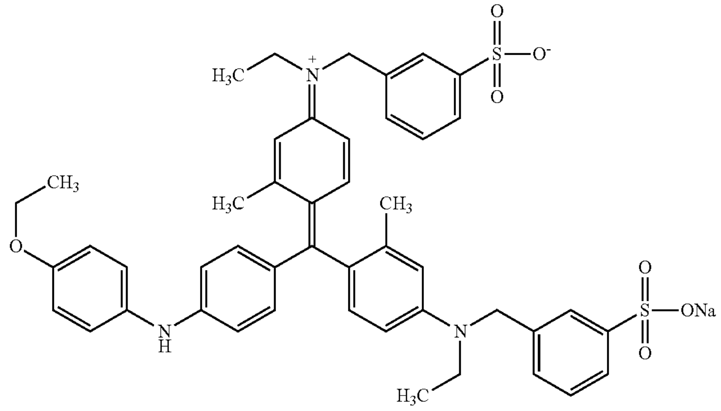

Nanoparticle Binding to P-Selectin

Figure 19:
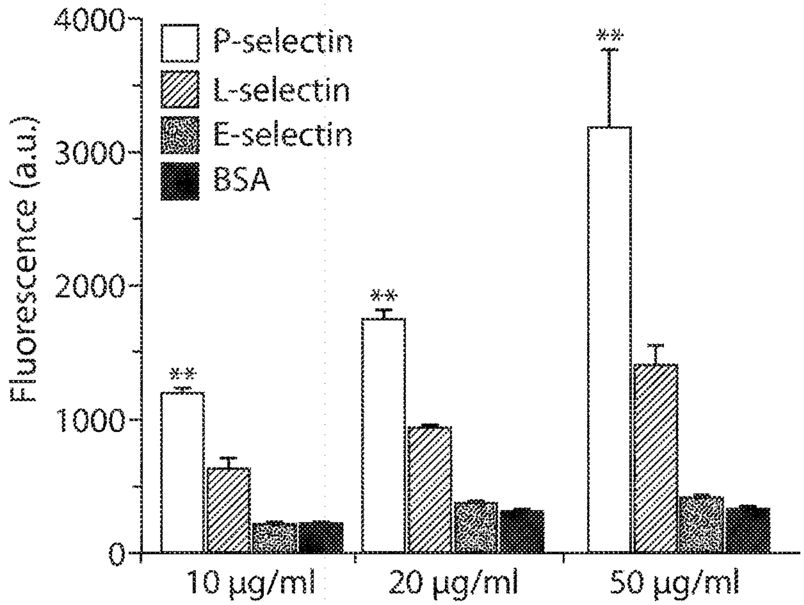
FIG. 19. Binding Studies to Reconstituted Proteins. Binding assay of FiPAX to immobilized recombinant proteins. Error bars are ±SD of the mean (n=4); from left to right, P=0.0062, 0.0028, 0.0022. *P<0.05, **P<0.01. a.u., arbitrary units.[22]

To assess the targeting selectivity to P-selectin, a drug-loaded nanoparticle lacking the fucoidan component was synthesized as a control. Dextran sulfate-based nanoparticles with comparable physical properties to those of FiPAX nanoparticles were similarly assembled (data not shown). The binding of fucoidan-based (FiPAX) and control (DexPAX) nanoparticles was assessed to immobilized human recombinant P-selectin, L-selectin, E-selectin, and bovine serum albumin (BSA). This experiment demonstrated selective dose-dependent binding of fucoidan-based nanoparticles to P-selectin and almost no binding to L-selectin, E-selectin, or BSA (FIG. 19).

Figure 20A:
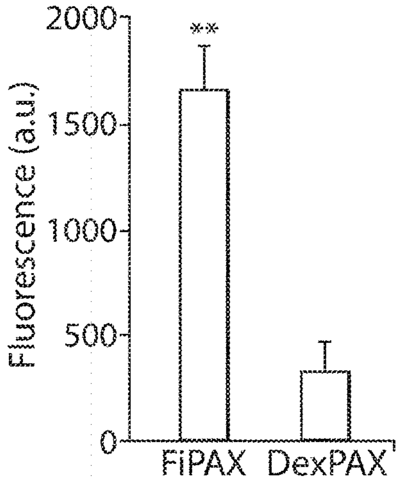
FIGS. 20A-20B. In Vitro Studies of Nanoparticle Penetration of Endothelium and Tumor.

To assess the binding of fucoidan-based nanoparticles to P-selectin-expressing tissues, the SK-136 murine cell line was used. This cell line formed multicellular tumor spheroids and constitutively expresses P-selectin.[22] Penetration of the nanoparticles into the tumor spheres was quantified by fluorescence microscopy. Upon incubation with the spheroids for 20 minutes, the FiPAX nanoparticle fluorescence was 5 times greater than the one of the DexPAX nanoparticle control (FIG. 20A; P=0.0042).

Figure 20B:
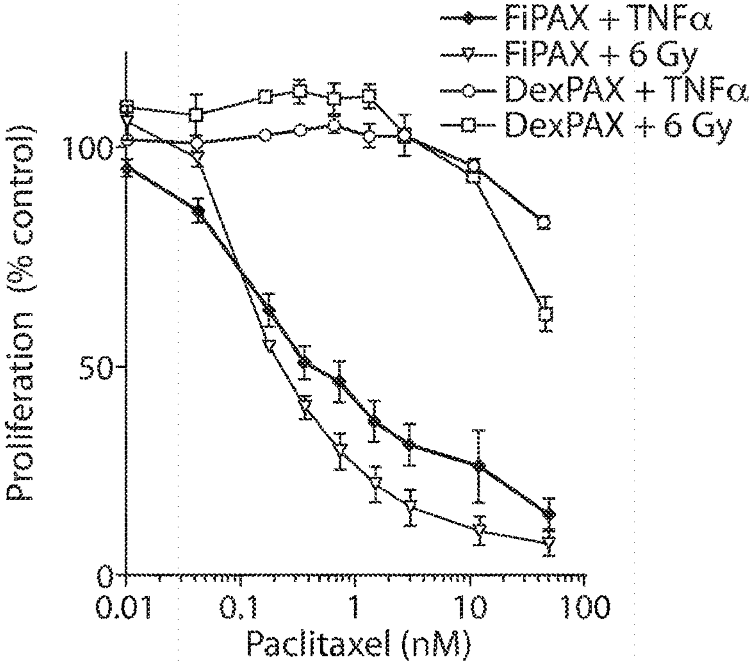

The binding of nanoparticles to a monolayer of ECs was measured under simulated inflammatory conditions to induce P-selectin expression.[22] Upon activation with tumor necrosis factor-α (TNFα) or ionizing radiation (6 Gy), FiPAX nanoparticles bound to EA.hy926 cells, as indicated by a large increase in fluorescence signal from the cells. All controls, including the TNFα-negative condition and DexPAX nanoparticles, exhibited virtually no signal. In addition, cells treated with short hairpin RNA to knock down P-selectin expression exhibited a marked decrease in particle binding. The nanoparticle-mediated cytotoxicity was evaluated under similar conditions of endothelial activation (FIG. 20B). The $IC_{50}$ of FiPAX was much lower, as compared to DexPAX, further confirming the selectivity of the fucoidan based nanoparticles to P-selectin.

In Vitro Assessment of Nanoparticle Penetration Through Endothelial Barriers

Figure 21A:
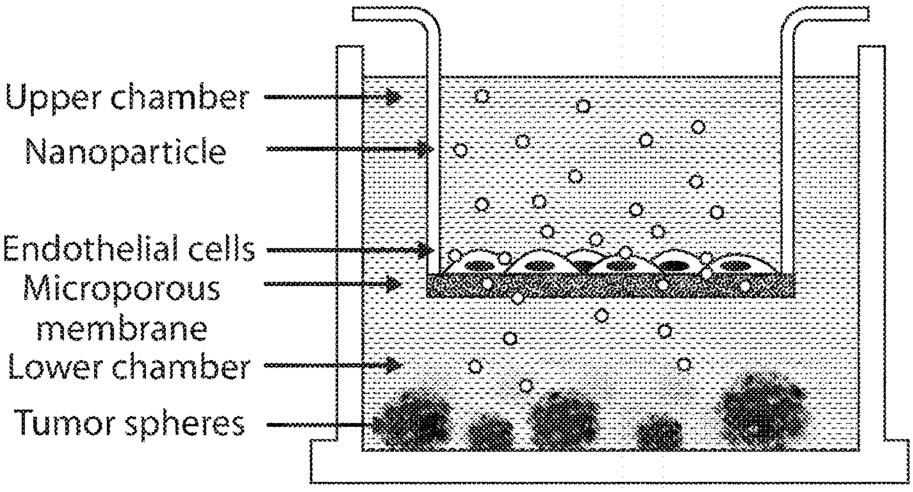
FIGS. 21A-21C. In Vitro Studies of Nanoparticle Penetration of Endothelium and Tumor.
Figure 21B:
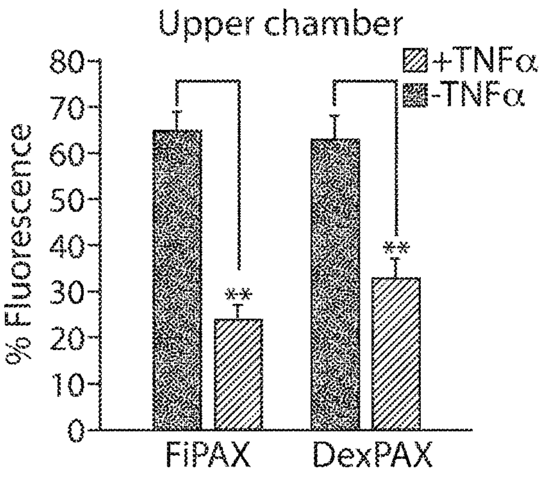
Figure 21C:
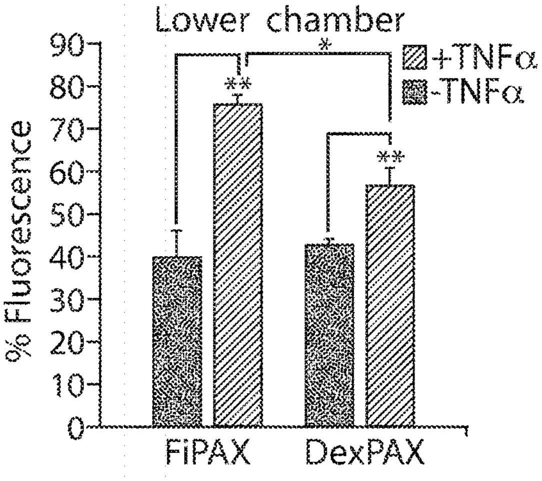

The ability of fucoidan nanoparticles to penetrate through activated endothelium and into tumor tissue was assessed using a modified Transwell assay.[22] Murine brain endothelial (bEnd.3) cells were grown on the membrane of the upper chambers. Tumor spheroids derived from P-selectin-expressing SK-136 cells were grown in the bottom chambers (FIG. 21A). The penetration of the nanoparticles through the bEnd.3 monolayers was measured under inflammatory conditions using TNFα activation, which induces P-selectin expression.[22] One hour after the addition of FiPAX nanoparticles to the top chambers, the quantity of FiPAX nanoparticles recovered from the bottom chamber increased by approximately 30% in the presence of TNFα (FIG. 21B, 21C), and recovery of DexPAX nanoparticles increased by 15% relative to nonactivated conditions. Penetration of the nanoparticles into the tumor spheres in the bottom well of the assay plates was quantified by fluorescence microscopy.

The FiPAX nanoparticles exhibited a 3 times higher signal in the tumor spheroids in the presence of TNFα, as well as greater penetration into the spheres, as compared to the controls. These observations suggest that endothelial activation mediated increased transport of P-selectin-targeted nanoparticles across the endothelial barrier, which resulted in greater penetration into solid tumor tissue.

In Vivo Targeting and Antitumor Efficacy Mediated by P-Selectin

Figure 22:
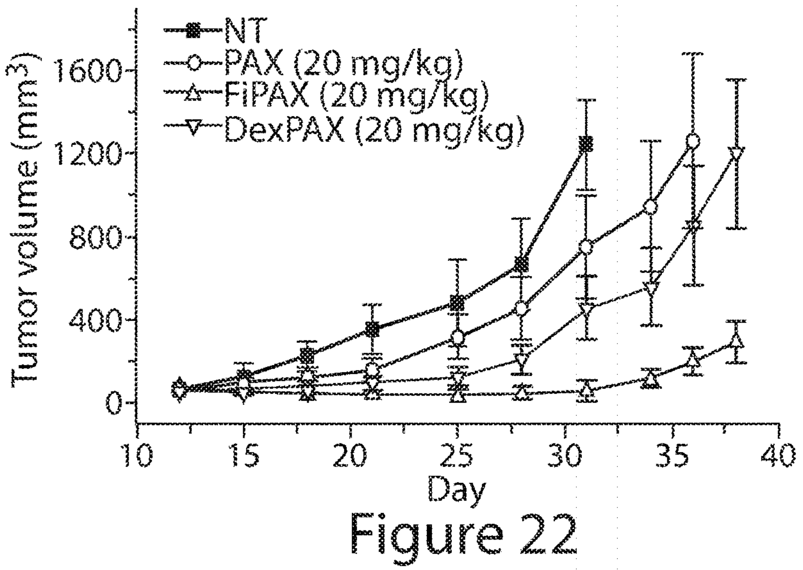
FIG. 22. Nanoparticle Treatment of P-Selectin-Expressing and Nonexpressing Tumors In Vivo. Tumor growth inhibition of PDX model after administration of a single dose of indicated treatments on Day 12. Plot shows means±SD (n=10 per group).[22]

Exploration of the penetration and antitumor activity of FiPAX in P-selectin-expressing tumors was explored in vivo.[22] To determine the efficacy of P-selectin targeting compared to passive mechanisms of drug delivery, the patient-derived xenograft (PDx) model of SCLC, JHU-LX33, was used. Based on IHC data, this xenograft expressed P-selectin in the tumor endothelium and moderately in the cancer cells. When tumors reached 70 $mm^3$, mice were randomized into 4 treatment arms: vehicle, FiPAX, DexPAX, and free paclitaxel (PAX). The average fluorescence intensity of FiPAX nanoparticles in the tumor, as measured by in vivo fluorescence imaging, reached 2.5-fold higher than that of passively targeted DexPAX nanoparticles at 24 hours after injection. The signal difference increased to 4.1-fold at 72 hours after injection (FIG. 22). The biodistribution, measured by fluorescence, showed substantial selective accumulation of FiPAX nanoparticles in the tumor over healthy organs, yielding a signal 3.6-fold higher in the tumor than the combined signal from all organs. For DexPAX nanoparticles, accumulation was only 1.3-fold, suggesting superior tumor targeting mediated by P-selectin with an improvement of 2.8-fold over passive targeting mechanisms. Improved tumor inhibition was observed upon administration of a single dose of FiPAX nanoparticles, as compared to free paclitaxel or DexPAX nanoparticles, all administered with equal drug concentrations (FIG. 22).

Radiation-Guided Drug Delivery Mediated by P-Selectin

Figure 23:
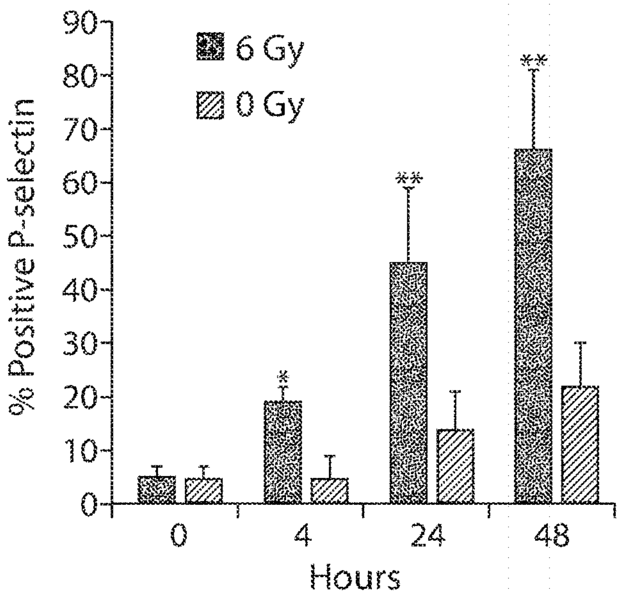
FIG. 23. Percentage of Blood Vessels Stained Positive for P-Selectin in Mouse Irradiated Tissue. Percentage of blood vessels stained positive for P-selectin in the irradiated tissue at 4, 24, and 48 hours (P values are 0.058, 0.0041, and 0.0076, respectively). Blood vessels were stained with a CD31 antibody.[22]

To study the effect of tumor irradiation on P-selectin targeting in vivo, the Lewis lung carcinoma model (i.e., a mouse tumor model that does not spontaneously express P-selectin), was employed. Immunocompetent, hairless SKH-1 mice were inoculated in both flanks with Lewis lung carcinoma (3LL) cells. The resulting tumor did not endogenously express P-selectin, as demonstrated by tissue staining (FIG. 23). The right flank tumor was irradiated with an x-ray dose of 6 Gy while the left flank tumor was left unirradiated. The appearance of P-selectin in the irradiated tumor was apparent by 4 hours, and the amount increased substantially by 24 hours (FIG. 23). Co-staining for P-selectin and CD31 shows that P-selectin was localized mainly to the endothelium after radiation treatment (data not shown) and also detected around vessels in smaller, scattered punctate patches, suggesting the presence of activated platelets.[47]

P-Selectin-Mediated Antitumor Efficacy in a Metastatic Model

Figure 24A:
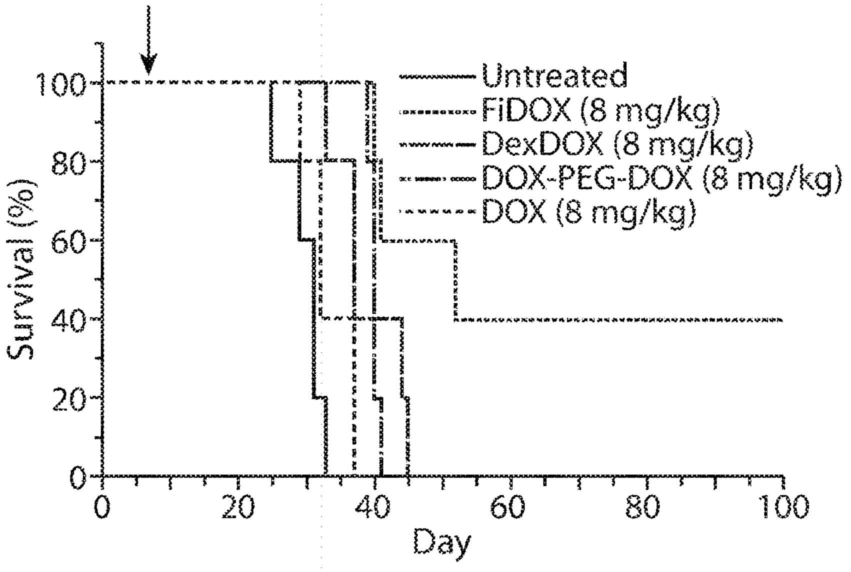
FIGS. 24A-24B. Survival Data from Experiment Using the B16F10 Model Treated 7 Days after Tumor Inoculation with a Single Intravenous Administration of the Indicated Treatments.

The antitumor efficacy of P-selectin-targeted drug carrier nanoparticles was evaluated against 2 aggressive experimental metastasis models of melanoma and breast cancer.[22] The IV injection of firefly luciferase-expressing B16F10 melanoma or firefly luciferase-expressing MDA-MB-231 cells resulted in lung metastases positive for P-selectin expression in the associated vasculature. Because melanoma shows little sensitivity to paclitaxel, the antitumor effects of doxorubicin (FiDOX) nanoparticles were compared to the passively targeted DexDOX nanoparticle control and drug-polymer conjugate, DPD, at equivalent doxorubicin doses of 8 mg/kg in the B16F10 model. The mean survival of the FiDOX group was significantly higher (68.8 days) with 40% complete and durable responses, compared to DexDOX (40.2 days) with no complete responses, DPD (39.2 days), or untreated controls (32.4 days) (FIG. 24A); log-rank test z=3.11, P=0.00184).

Figure 24B:
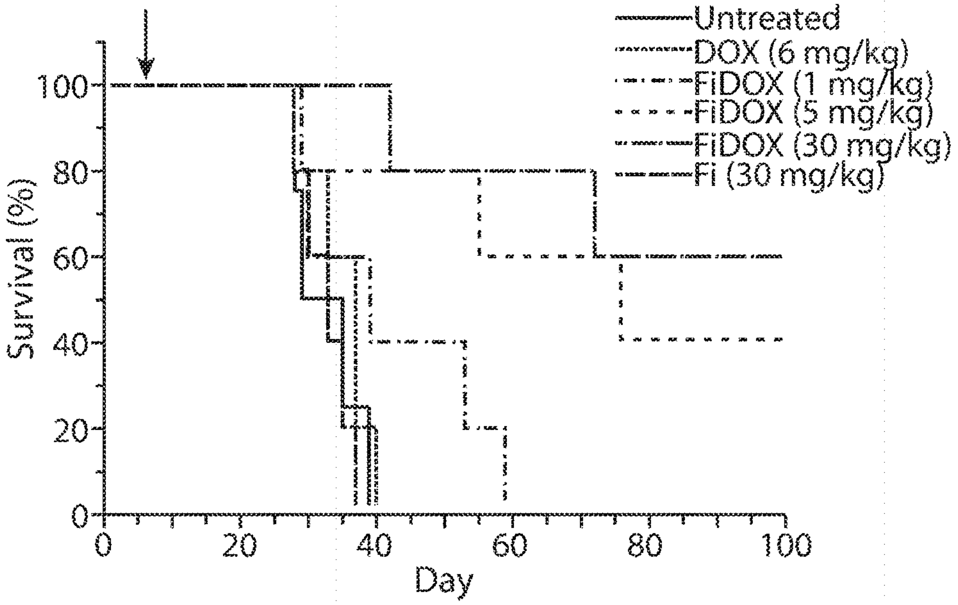
Figure 25:
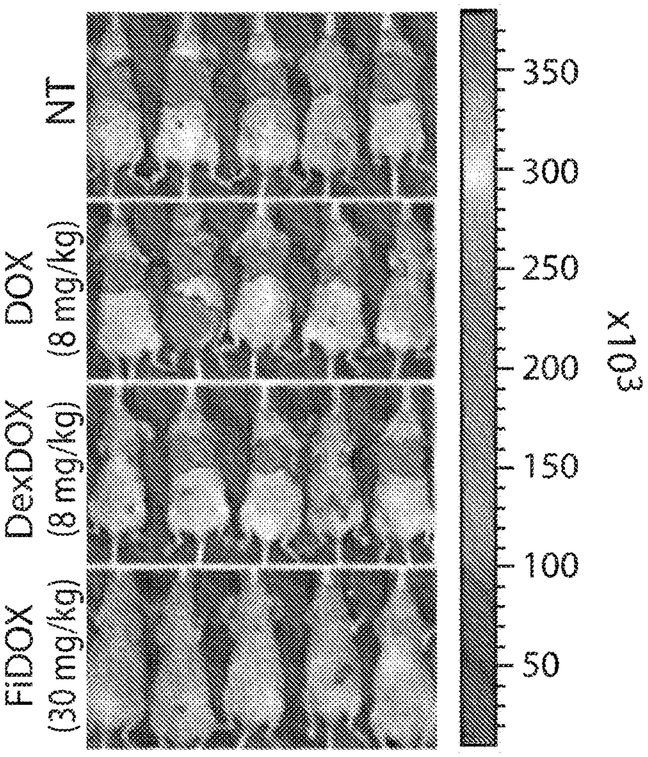
FIG. 25. P-Selectin-Targeted Nanoparticle Treatment of Metastatic Cancer Models. In vivo bioluminescence images acquired 21 days after a single administration of the indicated treatments to the luciferase-expressing MDA-MB-231 lung metastasis model.[22]

To investigate whether FiDOX nanoparticles exhibited an improved TI over free doxorubicin, 3 different doses of FiDOX nanoparticles were administered in the B16F10 model.[22] Mice bearing lung metastases were treated with a single dose of free doxorubicin (6 mg/kg), fucoidan (30 mg/kg) as a vehicle control, or FiDOX nanoparticles with several different doses of encapsulated doxorubicin (1, 5, and 30 mg/kg). The dose range explored the potential for both dose reduction due to improved tumor exposure and dose escalation due to reduced systemic exposure. All 3 FiDOX treatment arms resulted in decreased tumor burden and prolonged survival after a single injection, whereas an equivalent amount of free doxorubicin at its maximum tolerated dose did not have a significant effect, demonstrating the superiority of FiDOX over free doxorubicin (FIG. 24B). The fucoidan-only controls showed no survival benefit. Moreover, tumor bioluminescence 7 days after treatment with FiDOX showed a clear reduction in in the medium- and high-dose groups. Similar results were observed in an MDA-MB-231 breast cancer lung metastasis model, which showed a marked reduction of tumor bioluminescence and prolonged survival in FiDOX-treated mice (FIG. 25).

Organ biodistribution studies confirmed that FiDOX nanoparticles accumulated within areas of lung metastases, whereas DexDOX showed less accumulation in these regions.[22] Immunofluorescence microscopy of tumor tissue, resected 24 hours after treatment, revealed substantial increases in both tumor and EC apoptosis in FiDOX-treated mice. Notable signs of toxicity were not observed, as measured by weight loss, relative to the group receiving free doxorubicin. Complete blood count showed no deviations from the normal range.[22] A cytokine profile showed a slight increase 5 hours after FiDOX administration, and it reverted to baseline by 24 hours.[22]

P-Selectin Targeting Nanoparticles Containing MEK Inhibitor MEK162

To determine whether this approach was generalizable across a wide range of tumor types and pharmacophores, these investigations were extended to probe tumor-specific, kinase inhibition via nanoparticle-targeted delivery; the MAPK/ERK, fibroblast growth factor receptor family of receptor tyrosine kinase (FGFR3) and PI3K pathways were investigated.

Figure 18:
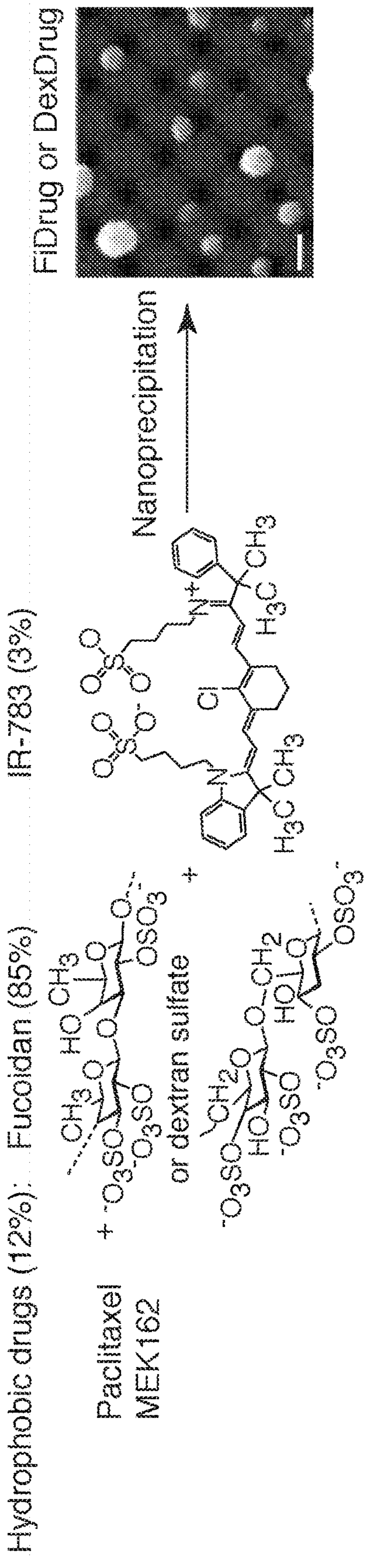
FIG. 18. Preparation of Targeted Nanoparticles. Synthesis scheme for P-selectin-targeted nanoparticles. Preparation of fucoidan-encapsulated paclitaxel (FiPAX) and MEK162 (FiMEK) nanoparticles and dextran sulfate-encapsulated controls by nanoprecipitation. Right panel: Scanning electron microscopy (SEM) images of FiPAX nanoparticles. Scale bars, 100 nm.[22]

The MAPK/ERK pathway is frequently hyperactive in several cancer types including melanoma, colorectal cancer, and lung cancer.[22] Several reversible MEK/ERK inhibitors are in clinical trials for RAS- and BRAF-mutated cancers; however, they have dose-limiting toxicities (including severe rash and chronic serous retinopathy).[48] Chronic administration is needed because of the temporary nature of the target inhibition.[49] It was hypothesized that delivery of a MEK inhibitor to the tumor microenvironment using P-selectin-targeted nanoparticles might increase drug exposure to tumor cells and prolong the duration of local inhibition while reducing systemic toxicities. Encapsulation of the MEK inhibitor MEK162[50] in fucoidan-based nanoparticles (FiMEK) (as shown in FIG. 18) served to test this hypothesis. In vitro, the FiMEK nanoparticles exhibited almost identical biochemical and antitumor activities as free MEK162 against BRAF-mutated melanoma (A375) and KRAS G12S homozygous mutant lung (A549) cancer cells.[22]

Figure 26A:
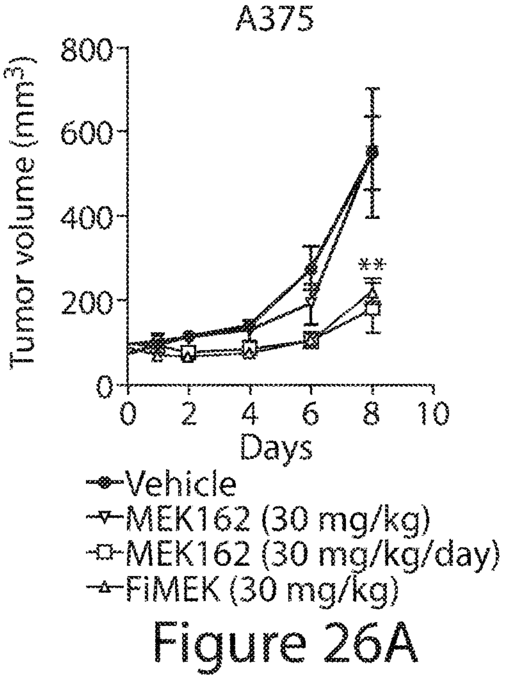
FIGS. 26A-26B. P-Selectin-Targeted Delivery of MEK162 (Inhibitor of the MEK/ERK Pathway). Growth of tumor xenografts after a single dose of vehicle, MEK162, and FiMEK or a daily dose of MEK162. X-axis represents days after first treatment; n=6 per group.
Figure 26B:
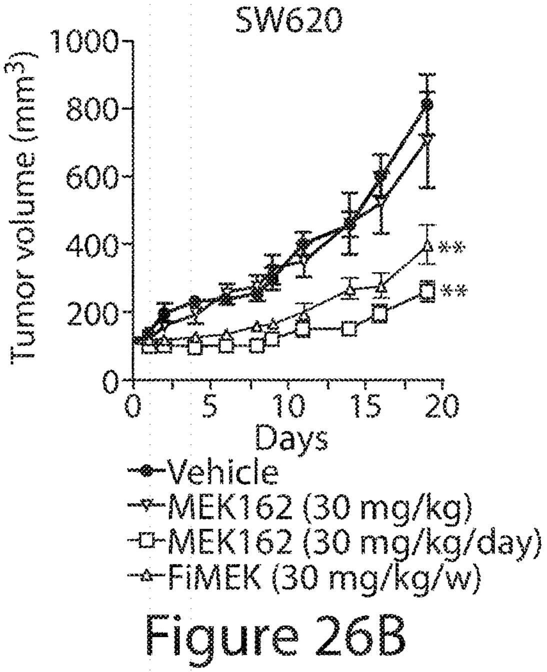

In vivo, FiMEK nanoparticles and free MEK162 were administered to mice bearing HCT116 and SW620 tumors, which express P-selectin in the vasculature (FIGS. 26A-26B). The nanoparticles were observed to accumulate in tumors and weekly FiMEK treatment resulted in enhanced efficacy as compared to a weekly dose of free MEK162 and comparable efficacy to daily administration of the free drug. These results were further validated in vivo using 2 additional models (LOVO and HCT116), both colorectal xenografts.

Figure 27A:
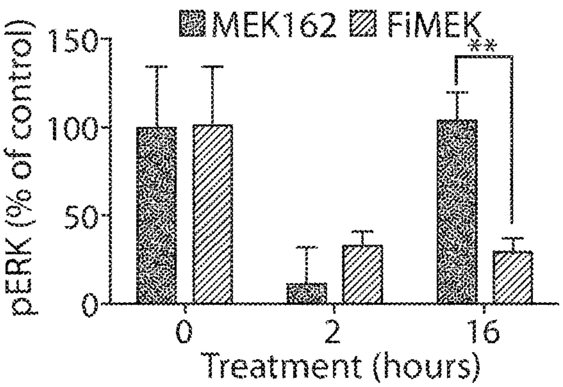
FIGS. 27A-27B. P-Selectin-Targeted Delivery of MEK162, an Inhibitor of the MEK/ERK Pathway. Biochemical quantification (Western blot) of pERK and PARP cleavage in xenografts of A375 tumors treated for 2 or 16 hours with MEK162 or FiMEK.
Figure 27B:
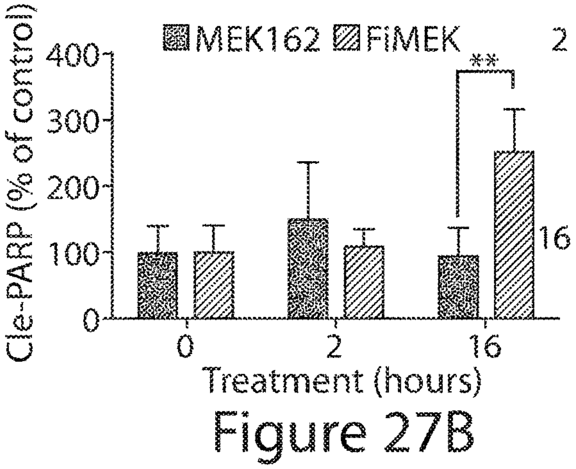
Figure 28:
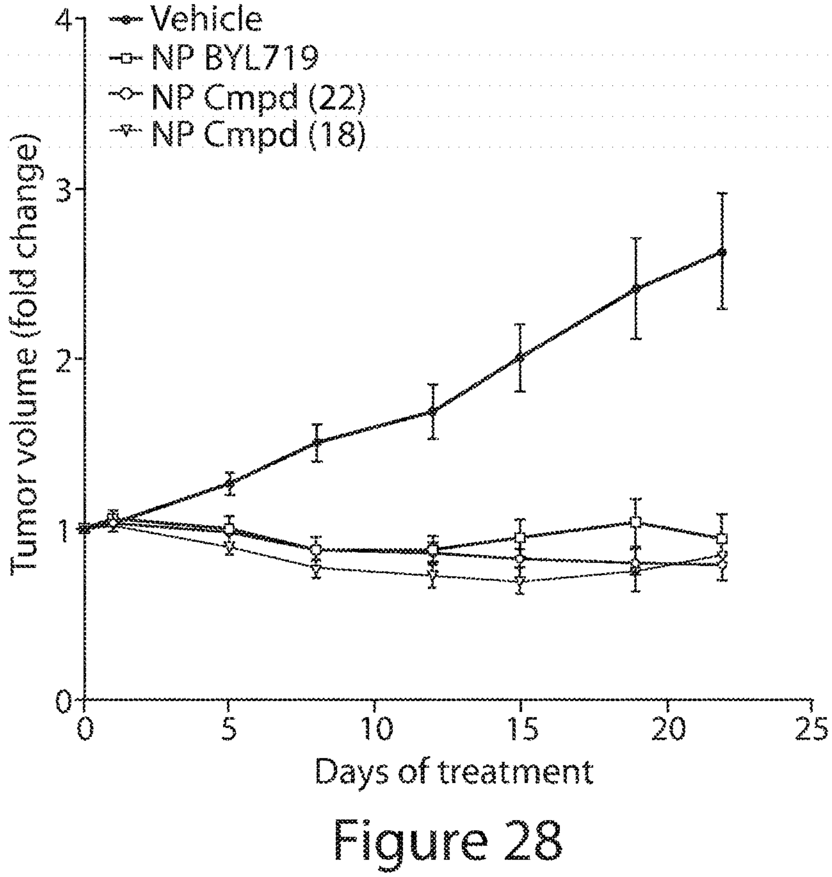
FIG. 28. Mice bearing MCF7-derived xenografts were treated with vehicle control, nanoparticle-delivered BYL719 (NP BYL719), nanoparticle-delivered Compound (22) (NP Cmpd (22)), or nanoparticle—delivered Compound 18 (NP Cmpd (18)) for three weeks. The graph shows relative tumor growth over time based on these treatments (25 mg/kg twice weekly).

ERK phosphorylation, measured to benchmark MEK activity, was inhibited similarly by both treatments after 2 hours, but significant (P=0.0089) inhibition was maintained after 16-hour time point only in mice treated with FiMEK (FIG. 27A). Apoptosis was assessed by IHC staining for cleaved poly[adenosine diphosphate-ribose]polymerase (PARP) and TUNEL in HCT116 xenografts treated with MEK162 and FiMEK. PARP and caspase 3 cleavage (FIG. 27B) as well as TUNEL staining at 16 hours after treatment were significantly higher (P=0.0053 for PARP cleavage) in the tumors treated with FiMEK.

Because the primary dose-limiting side effect of systemic MEK inhibition in humans is severe skin rash, MEK inhibition was assessed in both tumors and skin.[22] To benchmark MEK inhibition, the phosphorylation status of the downstream effector ERK was measured at numerous points. Administration of MEK162 inhibited ERK phosphorylation in the skin and tumor at 4 hours, but phosphorylation returned in both tissues after 24 hours. The FiMEK nanoparticles elicited prolonged pERK inhibition in the tumor after 24 hours but minimal inhibition in the skin at either time point. To further extend these findings, the standard 30 mg/kg dose of MEK162 was compared with 300 mg/kg. In this study, pERK inhibition was detected in both tumor and skin using the 300 mg/kg dose of free drug at 24 hours, whereas administration of FiMEK at one tenth of the MEK162 dose induced superior inhibition in the tumor with minimal inhibition in the skin.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Chow E K, Ho D. Cancer nanomedicine: from drug delivery to imaging. *Sci Transl Med.* 2013 Dec. 18; 5(216):216rv4.
2. Ferrari M. Cancer nanotechnology: opportunities and challenges. *Nat Rev Cancer.* 2005 March; 5(3):161-71.
3. Engelman J A. Targeting PI3K signalling in cancer: opportunities, challenges and limitations. *Nat Rev Cancer.* 2009 August; 9(8):550-62.
4. Fruman D A, Rommel C. PI3K and cancer: lessons, challenges and opportunities. *Nat Rev Drug Discov.* 2014 February; 13(2):140-56.
5. Vanhaesebroeck B, Stephens L, Hawkins P. PI3K signalling: the path to discovery and understanding. *Nat Rev Mol Cell Biol.* 2012 Feb. 23; 13(3):195-203.
6. Mayer I A, Arteaga C L. The PI3K/AKT Pathway as a Target for Cancer Treatment. *Annu Rev Med.* 2016; 67:11-28.
7. Rodon J, Dienstmann R, Serra V, Tabernero J. Development of PI3K inhibitors: lessons learned from early clinical trials. *Nat. Rev. Clin. Onc.* 2013, 10, 143-153.
8. Khan K H, Wong M, Rihawi K, Bodla S, Morganstein D, Banerji U, Molife L R.

Hyperglycemia and Phosphatidylinositol 3-Kinase/Protein Kinase B/Mammalian Target of Rapamycin (PI3K/AKT/mTOR) Inhibitors in Phase I Trials: Incidence, Predictive Factors, and Management. *Oncologist.* 2016 July; 21(7):855-60.

9. Crouthamel M C, Kahana J A, Korenchuk S, Zhang S Y, Sundaresan G, Eberwein D J, Brown K K, Kumar R. Mechanism and management of AKT inhibitor-induced hyperglycemia. *Clin Cancer Res.* 2009 Jan. 1; 15(1):217-25.
10. Samuel V T, Shulman G I. The pathogenesis of insulin resistance: integrating signaling pathways and substrate flux. *J Clin Invest.* 2016 January; 126(1):12-22.
11. Bernal-Mizrachi E, Fatrai S, Johnson J D, Ohsugi M, Otani K, Han Z, Polonsky K S, Permutt M A. Defective insulin secretion and increased susceptibility to experimental diabetes are induced by reduced Akt activity in pancreatic islet beta cells. *J Clin Invest.* 2004 October; 114(7):928-36.
12. Juric D, Castel P, Griffith M, Griffith O L, Won H H, Ellis H, Ebbesen S H, Ainscough B J, Ramu A, Iyer G, Shah R H, Huynh T, Mino-Kenudson M, Sgroi D, Isakoff S, Thabet A, Elamine L, Solit D B, Lowe S W, Quadt C, Peters M, Derti A, Schegel R, Huang A, Mardis E R, Berger M F, Baselga J, Scaltriti M. Convergent loss of PTEN leads to clinical resistance to a PI(3)Kα inhibitor. *Nature.* 2015 Feb. 12; 518(7538):240-4.
13. Furet P, Guagnano V, Fairhurst R A, Imbach-Weese P, Bruce I, Knapp M, Fritsch C, Blasco F, Blanz J, Aichholz R, Hamon J, Fabbro D, Caravatti G. Discovery of NVP-BYL719 a potent and selective phosphatidylinositol-3 kinase alpha inhibitor selected for clinical evaluation. *Bioorg Med Chem Lett.* 2013 Jul. 1; 23(13):3741-8.
14. Elkabets M, Vora S, Juric D, Morse N, Mino-Kenudson M, Muranen T, Tao J, Campos A B, Rodon J, Ibrahim Y H, Serra V, Rodrik-Outmezguine V, Hazra S, Singh S, Kim P, Quadt C, Liu M, Huang A, Rosen N, Engelman J A, Scaltriti M, Baselga J. mTORC1 inhibition is required for sensitivity to PI3K p110alpha inhibitors in PIK3CA-mutant breast cancer. *Sci Transl Med* 2013, 5 (196), 196ra99.
15. Clark A J, Wiley D T, Zuckerman J E, Webster P, Chao J, Lin J, Yen Y, Davis M E. CRLX101 nanoparticles localize in human tumors and not in adjacent, nonneoplastic tissue after intravenous dosing. *Proc Natl Acad Sci USA.* 2016 Apr. 5; 113(14):3850-4.
16. Ashton S, Song Y H, Nolan J, Cadogan E, Murray J, Odedra R, Foster J, Hall P A, Low S, Taylor P l, Ellston R, Polanska U M, Wilson J, Howes C, Smith A, Goodwin R J, Swales J G, Strittmatter N, Takits Z, Nilsson A, Andren P, Trueman D, Walker M, Reimer C L, Troiano G, Parsons D, De Witt D, Ashford M, Hrkach J, Zale S, Jewsbury P J, Barry S T. Aurora kinase inhibitor nanoparticles target tumors with favorable therapeutic index in vivo. *Sci Transl Med.* 2016 Feb. 10; 8(325):325ra17
17. Björnmalm M, Thurecht K J, Michael M, Scott A M, Caruso F. Bridging Bio-Nano Science and Cancer Nanomedicine. *ACS Nano.* 2017 Oct. 24; 11(10):9594-9613.
18. Hrkach J, Von Hoff D, Mukkaram Ali M, Andrianova E, Auer J, Campbell T, De Witt D, Figa M, Figueiredo M, Horhota A, Low S, McDonnell K, Peeke E, Retnarajan B, Sabnis A, Schnipper E, Song J J, Song Y H, Summa J, Tompsett D, Troiano G, Van Geen Hoven T, Wright J, LoRusso P, Kantoff P W, Bander N H, Sweeney C, Farokhzad O C, Langer R, Zale S. Preclinical development and clinical translation of a PSMA-targeted docetaxel nanoparticle with a differentiated pharmacological profile. *Sci Transl Med.* 2012 Apr. 4; 4(128):128ra39.
19. Wilczewska A Z, Niemirowicz K, Markiewicz K H, Car H. Nanoparticles as drug delivery systems. *Pharmacol* Rep. 2012; 64(5):1020-37.
20. Edgar J Y C, Wang H. Introduction for Design of Nanoparticle Based Drug Delivery Systems. *Curr Pharm Des.* 2017; 23(14):2108-2112.
21. Yu X, Trase I, Ren M, Duval K, Guo X, Chen Z. Design of Nanoparticle-Based Carriers for Targeted Drug Delivery. *J Nanomater.* 2016; 2016. pii: 1087250
22. Shamay Y, Elkabets M, Li H, Shah J, Brook S, Wang F, Adler K, Baut E, Scaltriti M, Jena P V, Gardner E E, Poirier J T, Rudin C M, Baselga J, Haimovitz-Friedman A, Heller D A. P-selectin is a nanotherapeutic delivery target in the tumor microenvironment. *Sci Transl Med.* 2016 Jun. 29; 8(345):345ra87.
23. Mizrachi A, Shamay Y, Shah J, Brook S, Soong J, Rajasekhar V K, Humm J L, Healey J H, Powell S N, Baselga J, Heller D A, Haimovitz-Friedman A, Scaltriti M. Tumour-specific PI3K inhibition via nanoparticle-targeted delivery in head and neck squamous cell carcinoma. *Nat Commun.* 2017 Feb. 13; 8:14292.
24. Zumsteg Z S, Morse N, Krigsfeld G, Gupta G, Higginson D S, Lee N Y, Morris L, Ganly I, Shiao S L, Powell S N, Chung C H, Scaltriti M, Baselga J. Taselisib (GDC-0032), a Potent β-Sparing Small Molecule Inhibitor of PI3K, Radiosensitizes Head and Neck Squamous Carcinomas Containing Activating PIK3C A Alterations. *Clin Cancer Res.* 2016 Apr. 15; 22(8):2009-19.
25. Chandarlapaty S, Sawai A, Scaltriti M, Rodrik-Outmezguine V, Grbovic-Huezo O, Serra V, Majumder P K, Baselga J, Rosen N. AKT inhibition relieves feedback suppression of receptor tyrosine kinase expression and activity. Cancer Cell. 2011 Jan. 18; 19(1):58-71.
26. Gong L, Mi H J, Zhu H, Zhou X, Yang H. P-selectin-mediated platelet activation promotes adhesion of non-small cell lung carcinoma cells on vascular endothelial cells under flow. *Mol Med* Rep. 2012 April; 5(4):935-42.
27. Gunningham S P, Currie M J, Morrin H R, Tan E Y, Turley H, Dachs G U, Watson A1, Frampton C, Robinson B A, Fox S B. The angiogenic factor thymidine phosphorylase up-regulates the cell adhesion molecule P-selectin in human vascular endothelial cells and is associated with P-selectin expression in breast cancers. *J Pathol.* 2007 July; 212(3):335-44.
28. Hemmerlein B, Scherbening J, Kugler A, Radzun H J. Expression of VCAM-1, ICAM-1, E- and P-selectin and tumour-associated macrophages in renal cell carcinoma. *Histopathology,* 2000 July; 37(1):78-83.
29. Lammers T, Kiessling F, Hennink W E, Storm G. Drug targeting to tumors: principles, pitfalls and (pre-) clinical progress. *J Control Release.* 2012 Jul. 20; 161(2):175-87.
30. Prabhakar U, Maeda H, Jain R K, Sevick-Muraca E M, Zamboni W, Farokhzad O C, Barry S T, Gabizon A, Grodzinski P, Blakey D C. Challenges and key considerations of the enhanced permeability and retention effect for nanomedicine drug delivery in oncology. *Cancer Res.* 2013 Apr. 15; 73(8):2412-7.
31. Grodzinski P, Farrell D. Future opportunities in cancer nanotechnology—NCI strategic workshop report. *Cancer Res.* 2014 Mar. 1; 74(5):1307-10.
32. Matsumura Y, Maeda H. A new concept for macromolecular therapeutics in cancer chemotherapy: mechanism of tumor tropic accumulation of proteins and the antitumor agent smancs. *Cancer Res.* 1986 December; 46(12 Pt 1):6387-92.

33. Schroeder A, Heller D A, Winslow M M, Dahlman J E, Pratt G W, Langer R, Jacks T, Anderson D G. Treating metastatic cancer with nanotechnology. *Nat Rev Cancer.* 2011 Dec. 23; 12(1):39-50.
34. Serra V, Scaltriti M, Prudkin L, Eichhorn P J, Ibrahim Y H, Chandarlapaty S, Markman B, Rodriguez O, Guzman M, Rodriguez S, Gili M, Russillo M, Parra J L, Singh S, Arribas J, Rosen N, Baselga J. PI3K inhibition results in enhanced HER signaling and acquired ERK dependency in HER2-overexpressing breast cancer. Oncogene, 2011 Jun. 2; 30(22):2547-57.
35. Mohan S, Vander Broek R, Shah S, Eytan D F, Pierce M L, Carlson S G, Coupar J F, Zhang J, Cheng H, Chen Z, Van Waes C. MEK Inhibitor PD-0325901 Overcomes Resistance to PI3K/mTOR Inhibitor PF-5212384 and Potentiates Antitumor Effects in Human Head and Neck Squamous Cell Carcinoma. *Clin. Cancer Res.* 2015 Sep. 1; 21(17):3946-56.
36. Fruman, D A, Rommel C. PI3K and Cancer: Lessons, Challenges and Opportunities. *Nat Rev Drug Discov.* 2014 February; 13(2): 140-156.
37. Salphati L, Heffron T P, Alicke B, Nishimura M, Barck K, Carano R A, Cheong J, Edgar K A, Greve J, Kharbanda S, Koeppen H, Lau S, Lee L B, Pang J, Plise E G, Pokorny J L, Reslan H B, Sarkaria J N, Wallin J J, Zhang X, Gould S E, Olivero A G, Phillips H S., Targeting the PI3K pathway in the brain—efficacy of a PI3K inhibitor optimized to cross the blood-brain barrier. *Clin Cancer Res.* 2012 Nov. 15; 18(22):6239-48.
38. Heffron T P, Salphati L, Alicke B, Cheong J, Dotson J, Edgar K, Goldsmith R, Gould S E, Lee L B, Lesnick J D, Lewis C, Ndubaku C, Nonomiya J, Olivero A G, Pang J, Plise E G, Sideris S, Trapp S, Wallin J, Wang L, Zhang X. The design and identification of brain penetrant inhibitors of phosphoinositide 3-kinase α. *J Med Chem.* 2012 Sep. 27; 55(18):8007-20.
39. Heffron T P, Ndubaku C O, Salphati L, Alicke B, Cheong J, Drobnick J, Edgar K, Gould S E, Lee L B, Lesnick J D, Lewis C, Nonomiya J, Pang J, Plise E G, Sideris S, Wallin J, Wang L, Zhang X, Olivero A G.) Discovery of Clinical Development Candidate GDC-0084, a Brain Penetrant Inhibitor of PI3K and mTOR. *ACS Med Chem Lett.* 2016 Feb. 16; 7(4):351-6.
40. Ndubaku C O, Heffron T P, Staben S T, Baumgardner M, Blaquiere N, Bradley E, Bull R, Do S, Dotson J, Dudley D, Edgar K A, Friedman L S, Goldsmith R, Heald R A, Kolesnikov A, Lee L, Lewis C, Nannini M, Nonomiya J, Pang J, Price S, Prior W W, Salphati L, Sideris S, Wallin J J, Wang L, Wei B, Sampath D, Olivero A G. Discovery of 2-{3-[2-(1-isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide (GDC-0032): a β-sparing phosphoinositide 3-kinase inhibitor with high unbound exposure and robust in vivo antitumor activity. *J Med Chem.* 2013 Jun. 13; 56(11):4597-610.
41. James A, Blumenstein L, Glaenzel U, Jin Y, Demailly A, Jakab A, Hansen R, Hazell K, Mehta A, Trandafir L, Swart P. Absorption, distribution, metabolism, and excretion of [(14)C]BYL719 (alpelisib) in healthy male volunteers. *Cancer Chemother Pharmacol.* 2015 October; 76(4):751-60.
42. Yang Y H, Aloysius H, Inoyama D, Chen Y, Hu L q. Enzyme-mediated hydrolytic activation of prodrugs. *Acta Pharmaceutica Sinica B,* 2011; 1(3):143-159.
43. Hallahan D E 1, Virudachalam S. Accumulation of P-selectin in the lumen of irradiated blood vessels. *Radiat Res.* 1999 July; 152(1):6-13.
44. Hallahan D E, Staba-Hogan M J, Virudachalam S, Kolchinsky A. X-ray-induced P-selectin localization to the lumen of tumor blood vessels. *Cancer Res.* 1998 Nov. 15; 58(22):5216-20.
45. Corso C D, Ali A N, Diaz R. Radiation-induced tumor neoantigens: imaging and therapeutic implications. *Am J Cancer Res.* 2011; 1(3):390-412.
46. (28) Wang A Z, Tepper J E. Nanotechnology in radiation oncology. *J Clin Oncol.* 2014 Sep. 10; 32(26):2879-85.
47. Amano H, Ito Y, Ogawa F, Eshima K, Suzuki T, Oba K, Matsui Y, Kato S, Fukui T, Nakamura M, Kitasato H, Fukamizu A, Majima M. Angiotensin II type 1A receptor signaling facilitates tumor metastasis formation through P-selectin-mediated interaction of tumor cells with platelets and endothelial cells. *Am J Pathol.* 2013 February; 182(2):553-64.
48. Wang D, Boerner S A, Winkler J D, LoRusso P M. Clinical experience of MEK inhibitors in cancer therapy. *Biochim Biophys Acta.* 2007 August; 1773(8):1248-55.
49. Fr6 min C, Meloche S. From basic research to clinical development of MEK1/2 inhibitors for cancer therapy. *J Hematol Oncol.* 2010 Feb. 11; 3:8.
50. Ascierto P A, Schadendorf D, Berking C, Agarwala S S, van Herpen C M, Queirolo P, Blank C U, Hauschild A, Beck J T, St-Pierre A, Niazi F, Wandel S, Peters M, Zubel A, Dummer R. MEK162 for patients with advanced melanoma harbouring NRAS or Val600 BRAF mutations: a non-randomised, open-label phase 2 study. *Lancet Oncol.* 2013 March; 14(3):249-56.
51. Khan M O, Park K K, Lee H J Antedrugs: an approach to safer drugs. *Curr Med Chem.* 2005; 12(19):2227-39)
52. Weigelt B, Downward J. Genomic Determinants of PI3K Pathway Inhibitor Response in Cancer *Front Oncol.* 2012; 2: 109, 1-16.

What is claimed is:

1. A compound of Formula (I):

(I)

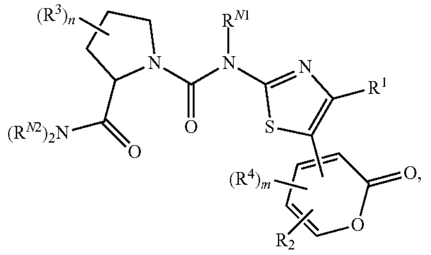

or a pharmaceutically acceptable salt thereof, wherein:

$R^1$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

$R^2$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, —$SR^S$, or is of the formula:

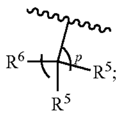

each instance of $R^3$ is independently halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, —$SR^S$, or is of the formula:

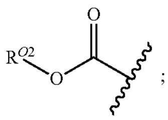

;

each instance of $R^4$ is independently halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^5$ is independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$, or two $R^5$ are joined together with the intervening atoms to form optionally substituted carbocyclyl or optionally substituted heterocyclyl;

$R^6$ is hydrogen, halogen, haloalkyl, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

$R^{N1}$ is hydrogen, optionally substituted alkyl, optionally substituted acyl, or a nitrogen protecting group;

each instance of $R^{N2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{N2}$ are joined together with the intervening atoms to form optionally substituted heterocyclyl or optionally substituted heteroaryl;

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are joined together with the intervening atoms to form optionally substituted heterocyclyl or optionally substituted heteroaryl;

each instance of $R^O$ and $R^{O2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group;

p is 0, 1, or 2;

n is 0, 1, 2, 3, 4, 5, 6, or 7; and m is 0, 1, or 2.

2. The compound of claim 1, wherein the compound is of the formula:

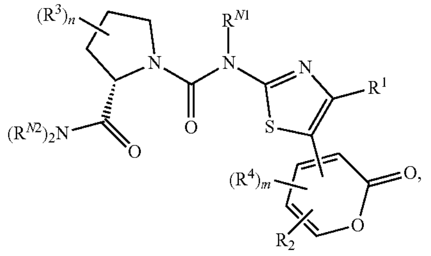

or a pharmaceutically acceptable salt thereof.

3. The compound of claim 1, wherein the compound is of the formula:

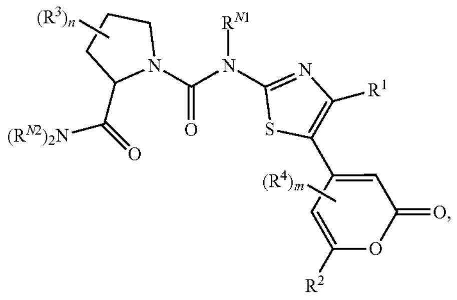

or a pharmaceutically acceptable salt thereof.

4. The compound of claim 1, wherein the compound is of the formula:

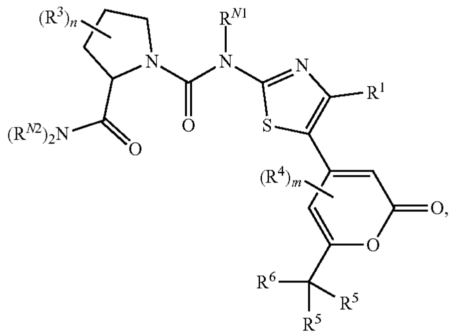

or a pharmaceutically acceptable salt thereof.

5. The compound of claim 1, wherein the compound is of the formula:

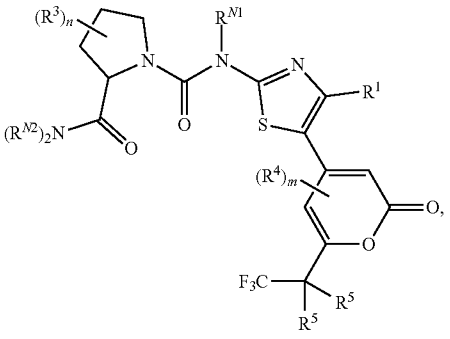

or a pharmaceutically acceptable salt thereof.

6. The compound of claim 1, wherein the compound is of the formula:

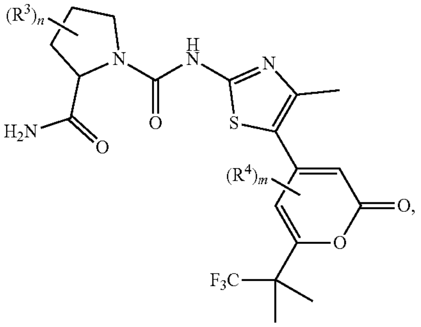

or a pharmaceutically acceptable salt thereof.

7. The compound of claim 1, wherein the compound is selected from the group consisting of:

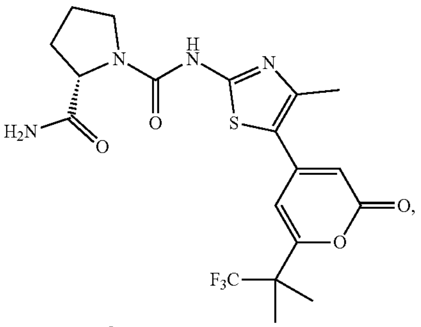

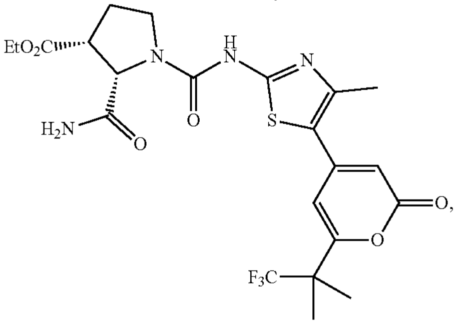

-continued

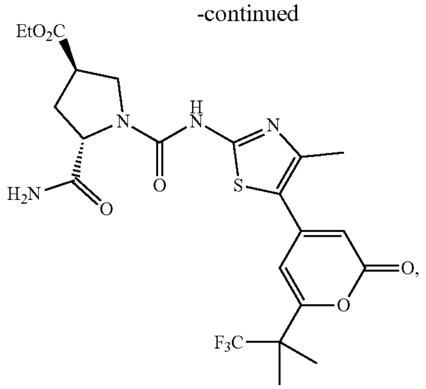

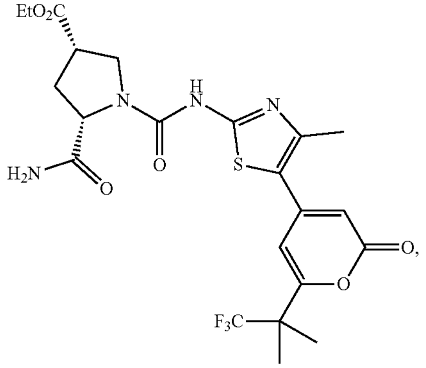

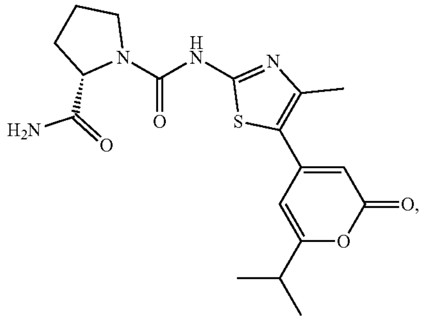

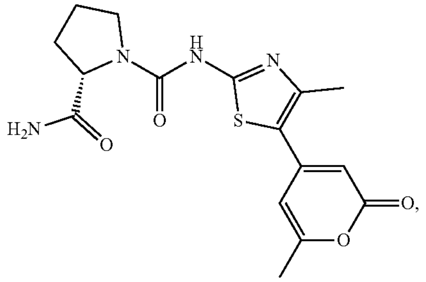

and pharmaceutically acceptable salts thereof.

8. The compound of claim 1, wherein $R^1$ is optionally substituted $C_{1-6}$ alkyl.

9. The compound of claim 4, wherein at least one instance of $R^5$ is optionally substituted $C_{1-6}$ alkyl.

10. The compound of claim 4, wherein $R^6$ is haloalkyl.

11. The compound of claim 1, wherein $R^{N1}$ is hydrogen.

12. The compound of claim 1, wherein at least one instance of $R^{N2}$ is hydrogen.

13. A pharmaceutical composition comprising a compound of claim 1, or a pharmaceutically acceptable salt thereof, and a pharmaceutically acceptable excipient.

14. A nanoparticle comprising a compound of claim 1, or a pharmaceutically acceptable salt thereof.

15. A nanogel comprising a plurality of nanoparticles of claim 14.

16. A method of treating cancer in a subject in need thereof, the method comprising administering to the subject a therapeutically effective amount of a compound of claim 1, or a pharmaceutically acceptable salt thereof, or a pharmaceutical composition thereof, wherein the cancer is head and neck cancer, brain cancer, breast cancer, ovarian cancer, cervical cancer, lung cancer, kidney cancer, bladder cancer, liver cancer, sarcoma, or a hematological cancer.

17. A method of inhibiting PI3Kα enzymatic activity in vitro comprising contacting a PI3Kα enzyme with an effective amount of a compound of claim 1, or a pharmaceutically acceptable salt thereof, or a pharmaceutical composition thereof.

18. A method of inducing apoptosis of a cancer cell comprising contacting the cancer cell with and effective amount of a compound of claim 1, or a pharmaceutically acceptable salt thereof, or a pharmaceutical composition thereof, wherein the cancer cell is a head and neck cancer, brain cancer, breast cancer, ovarian cancer, cervical cancer, lung cancer, kidney cancer, bladder cancer, liver cancer, sarcoma, or a hematological cancer cell.

19. The compound of claim 1, wherein the compound is of the formula:

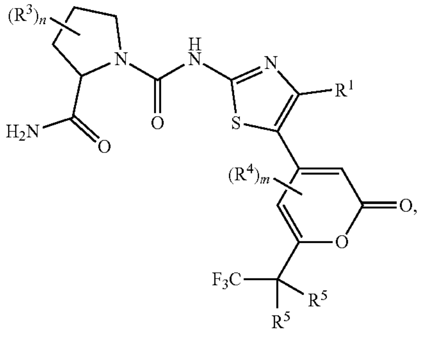

or a pharmaceutically acceptable salt thereof.

20. The compound of claim 1, wherein the compound is of the formula:

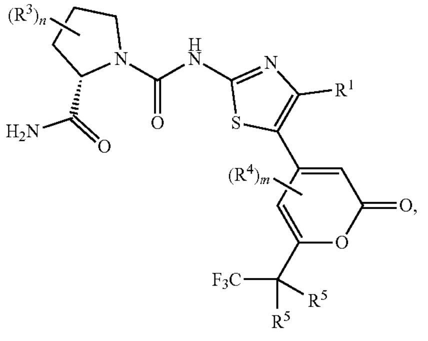

or a pharmaceutically acceptable salt thereof.

21. The method of claim 16, wherein the cancer is head and neck squamous cell carcinoma (HNSCC).

22. The method of claim 16, wherein the cancer is glioblastoma.

23. The method of claim 16, wherein the cancer is breast cancer.

24. A compound of Formula (II):

(II)

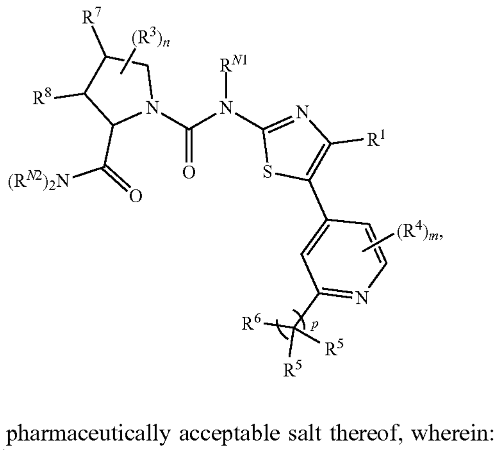

or a pharmaceutically acceptable salt thereof, wherein:

$R^1$ is hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^3$ is independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^4$ is independently hydrogen, halogen, —CN, —$N_3$, —$NO_2$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$;

each instance of $R^5$ is independently hydrogen, halogen, optionally substituted alkyl, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^O$, —$N(R^N)_2$, or —$SR^S$; or two $R^5$ are joined together with the intervening atoms to form optionally substituted carbocyclyl or optionally substituted heterocyclyl;

$R^{N1}$ is hydrogen, optionally substituted alkyl, optionally substituted acyl, or a nitrogen protecting group;

each instance of $R^{N2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{N2}$ are joined together with the intervening atoms to form optionally substituted heterocyclyl or optionally substituted heteroaryl;

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are joined together with the intervening atoms to form optionally substituted heterocyclyl or optionally substituted heteroaryl;

each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group;

n is 0, 1, 2, 3, 4, or 5;

m is 0, 1, 2, or 3;

p is 0, 1, or 2;

$R^6$ is haloalkyl, $-C(=O)OR^{O2}$, $-(C(R^5)_2)_pC(=O)OR^{O2}$, $-OR^O$, $-N(R^N)_2$, or $-SR^S$; and $R^7$ and $R^8$ are each independently hydrogen, halogen, —CN, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^O$, $-N(R^N)_2$, or $-SR^S$;

each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

provided that when $R^6$ is $-CF_3$, then $R^7$ is hydrogen or optionally substituted acyl, and at least one of $R^7$ or $R^8$ is not hydrogen; and provided that when $R^6$ is $-CF_3$, then $R^8$ and $R^7$ are independently hydrogen or optionally substituted acyl, and at least one of $R^7$ or $R^8$ is not hydrogen.

25. The compound of claim 24, wherein the compound is selected from the group consisting of:

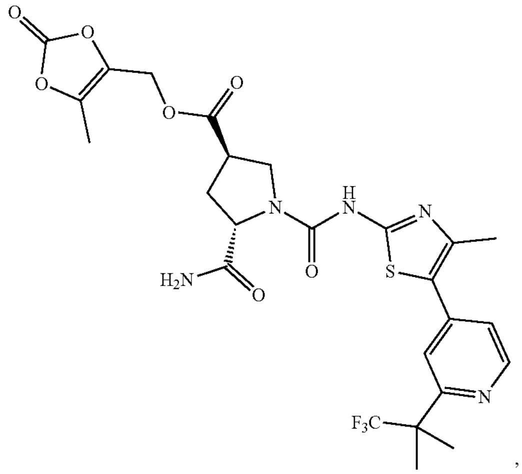

,

-continued

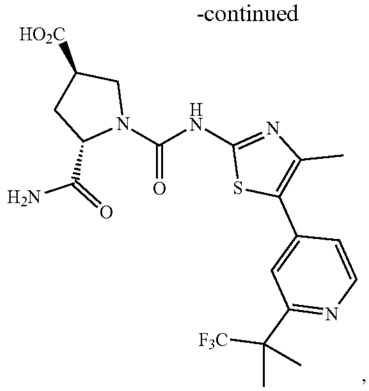

,

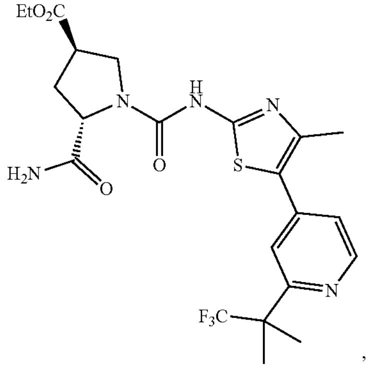

,

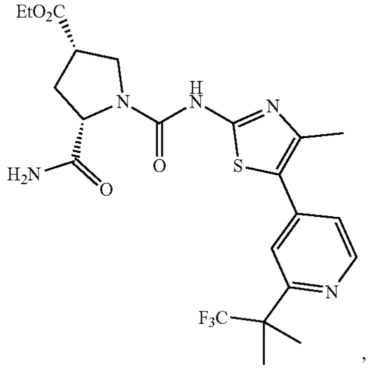

,

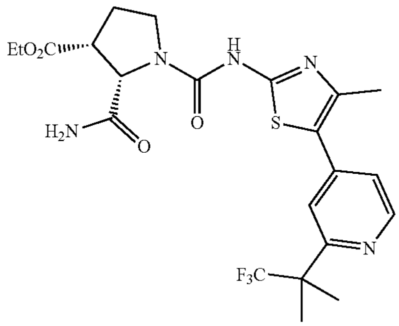

,

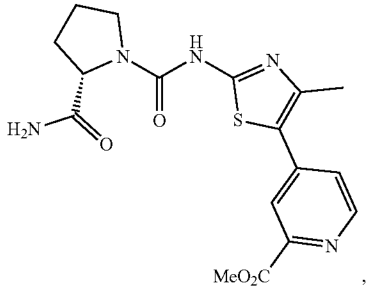

,

-continued
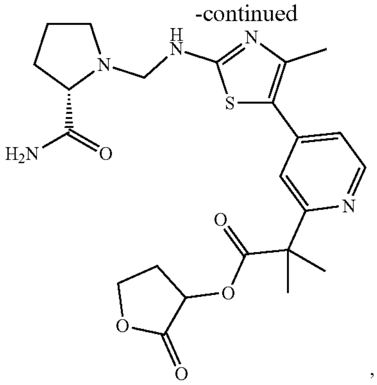
,
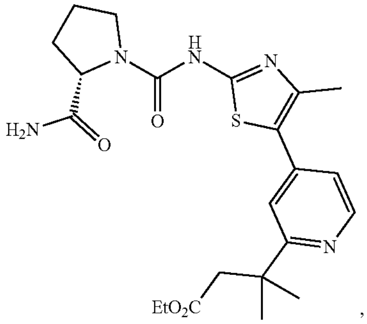
,
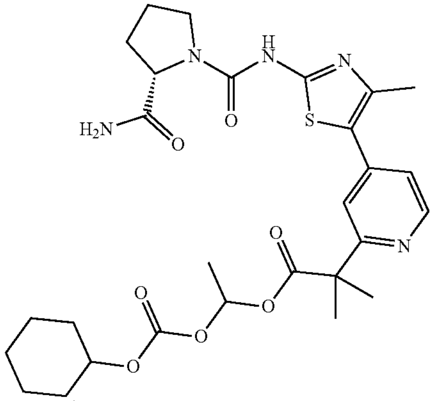
,
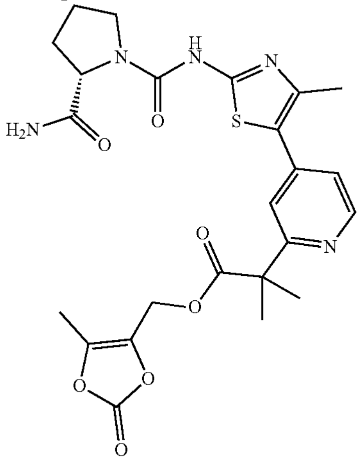
,
-continued
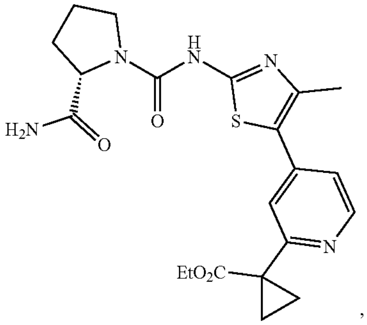
,
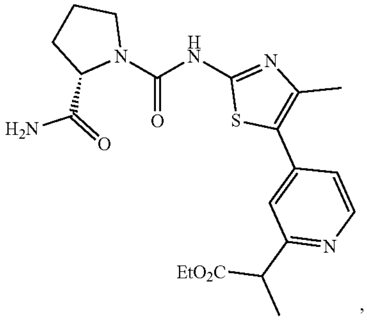
,
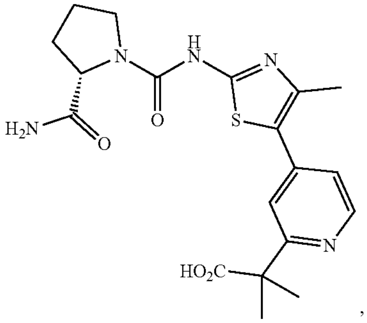
,
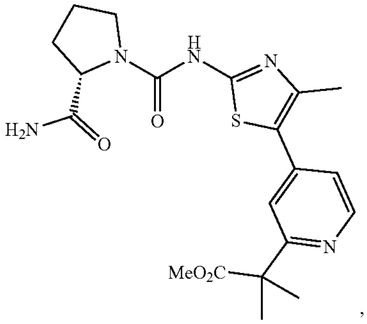
,
and pharmaceutically acceptable salts thereof.
* * * * *